(12) United States Patent
Kang et al.

(10) Patent No.: US 11,605,782 B2
(45) Date of Patent: *Mar. 14, 2023

(54) ORGANIC OPTOELECTRONIC DEVICE AND DISPLAY DEVICE

(71) Applicant: SAMSUNG SDI CO., LTD., Yongin-si (KR)

(72) Inventors: Giwook Kang, Yongin-si (KR); Dong Min Kang, Yongin-si (KR); Byungku Kim, Yongin-si (KR); Jun Seok Kim, Yongin-si (KR); Eun Sun Yu, Yongin-si (KR); Namheon Lee, Yongin-si (KR); Kipo Jang, Yongin-si (KR); Handong Chu, Yongin-si (KR); Jinhyun Lui, Yongin-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 308 days.

This patent is subject to a terminal disclaimer.

(21) Appl. No.: 16/701,838

(22) Filed: Dec. 3, 2019

(65) Prior Publication Data

US 2020/0176685 A1 Jun. 4, 2020

(30) Foreign Application Priority Data

Dec. 4, 2018 (KR) .................. 10-2018-0154654

(51) Int. Cl.
*H01L 51/00* (2006.01)
*H01L 51/50* (2006.01)

(52) U.S. Cl.
CPC ...... *H01L 51/0061* (2013.01); *H01L 51/0067* (2013.01); *H01L 51/0072* (2013.01);
(Continued)

(58) Field of Classification Search
CPC ............. H01L 51/0061; H01L 51/0067; H01L 51/0072; H01L 51/0073; H01L 51/0074;
(Continued)

(56) References Cited

U.S. PATENT DOCUMENTS 9,466,803 B1 10/2016 Park et al.
11,345,687 B2 * 5/2022 Parham ................ C07D 405/04
(Continued)

FOREIGN PATENT DOCUMENTS

CN 106029831 A 10/2016
CN 107155330 A 9/2017
(Continued)

OTHER PUBLICATIONS

Pending claims in U.S. Appl. No. 16/380,233, filed Mar. 18, 2022. (Year: 2022).*

Korean Office action dated Nov. 26, 2020.
Korean Office action dated Dec. 3, 2020.
Chinese Notice of Issuance dated Feb. 8, 2022 and Search Report dated Jan. 12, 2022.
Extended European Search Report dated Sep. 17, 2019, of the corresponding European Patent Application No. 19167152.8.
Office Action dated May 5, 2020, and the accompanying Search Report dated Apr. 20, 2020, of the corresponding Taiwanese Patent Application No. 108112164.
(Continued)

*Primary Examiner* — Douglas J Mc Ginty
(74) *Attorney, Agent, or Firm* — Lee IP Law, P.C.

(57) ABSTRACT

An organic optoelectronic device and a display device, the organic optoelectronic device including an anode and a cathode facing each other, a light emitting layer between the anode and the cathode, a hole transport layer between the anode and the light emitting layer, and a hole transport auxiliary layer between the light emitting layer and the hole transport layer, wherein the light emitting layer includes a first compound represented by a combination of Chemical Formula 1 and Chemical Formula 2, and a second compound represented by Chemical Formula 3, and the hole transport auxiliary layer includes a third compound represented by Chemical Formula 4:

[Chemical Formula 1]

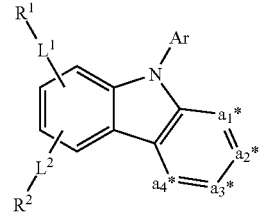

[Chemical Formula 2]

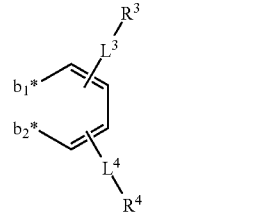

[Chemical Formula 3]

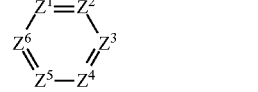

[Chemical Formula 4]

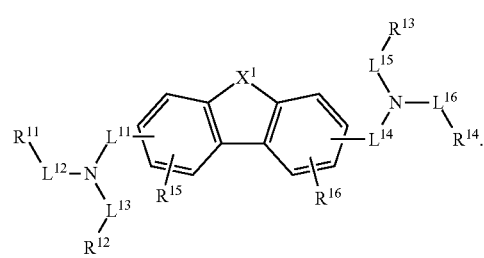

16 Claims, 1 Drawing Sheet

(52) U.S. Cl.
CPC ...... *H01L 51/0073* (2013.01); *H01L 51/0074* (2013.01); *H01L 51/5016* (2013.01); *H01L 51/5064* (2013.01); *H01L 2251/5384* (2013.01)

(58) Field of Classification Search
CPC ............ H01L 51/5016; H01L 51/5064; H01L 2251/5384; H01L 51/0052; H01L 51/0059; H01L 51/5012; H01L 51/0035; H01L 51/5056; H01L 51/0071; H01L 51/5024; H01L 51/5048; C07D 209/86; C07D 307/91; C07D 333/76; C07D 405/04; C07D 405/10; C07D 405/12; C07D 405/14; C07D 409/04; C07D 409/12; C07D 409/14
USPC ......................................................... 428/690
See application file for complete search history.

(56) References Cited

U.S. PATENT DOCUMENTS

| | | | |
|---|---|---|---|
| 2012/0302762 A1* | 11/2012 | Osaka | C07D 209/88 548/442 |
| 2015/0102301 A1 | 4/2015 | Cho et al. | |
| 2015/0349269 A1 | 12/2015 | Lee et al. | |
| 2017/0084845 A1 | 3/2017 | Kim et al. | |
| 2017/0104163 A1 | 4/2017 | Lee et al. | |
| 2017/0222158 A1 | 8/2017 | Jung et al. | |
| 2017/0237013 A1* | 8/2017 | Park | H01L 51/0061 257/40 |
| 2017/0288148 A1 | 10/2017 | Park et al. | |
| 2018/0301635 A1 | 10/2018 | Lee et al. | |
| 2019/0131543 A1 | 5/2019 | Lee et al. | |
| 2019/0165280 A1 | 5/2019 | Jang et al. | |
| 2019/0296244 A1* | 9/2019 | Mun | H01L 51/0054 |
| 2019/0296248 A1* | 9/2019 | Mun | H01L 51/5016 |
| 2019/0312215 A1* | 10/2019 | Kang | H01L 51/0074 |
| 2021/0328149 A1* | 10/2021 | Kim | H01L 51/0072 |
| 2022/0388976 A1* | 12/2022 | Kim | C07D 409/04 |

FOREIGN PATENT DOCUMENTS

| | | | |
|---|---|---|---|
| CN | 107531718 A | | 1/2018 |
| CN | 107635964 A | | 1/2018 |
| EP | 2860783 A1 | | 4/2015 |
| JP | 11-144866 A | | 5/1999 |
| JP | 2013-10749 | | 1/2013 |
| JP | 2016108292 A | * | 6/2016 |
| KR | 10-2010-0023783 | | 3/2010 |
| KR | 10-1074193 B1 | | 10/2011 |
| KR | 10-2014-0135524 | | 11/2014 |
| KR | 10-2014-0142923 A | | 12/2014 |
| KR | 10-2015-0077513 | | 7/2015 |
| KR | 10-2016-0011036 | | 1/2016 |
| KR | 10-1604647 B1 | | 3/2016 |
| KR | 10-2016-0044299 | | 4/2016 |
| KR | 10-2017-0005637 | | 1/2017 |
| KR | 10-2017-0048159 | | 5/2017 |
| KR | 10-2017-0089599 A | | 8/2017 |
| KR | 10-2017-0112913 | | 10/2017 |
| KR | 10-2017-0117775 A | | 10/2017 |
| KR | 10-1789998 | | 10/2017 |
| KR | 10-1804630 B1 | | 11/2017 |
| KR | 10-2018-0002351 | | 1/2018 |
| KR | 10-2018-0011429 | | 2/2018 |
| KR | 10-2018-0031874 | | 3/2018 |
| KR | 10-2018-0036529 A | | 4/2018 |
| KR | 10-2018-0069475 A | | 6/2018 |
| KR | 10-2018-0093354 | | 8/2018 |
| KR | 10-2019-0118392 | | 10/2019 |
| KR | 10-2018-0013449 A | | 12/2019 |
| WO | WO 2015/099486 A1 | | 7/2015 |
| WO | WO 2015/174792 A1 | | 11/2015 |
| WO | WO-2017076485 A1 * | 5/2017 | ........... C07D 209/82 |
| WO | WO-2017204556 A1 * | 11/2017 | ........... C07C 211/54 |
| WO | WO 2018/004096 A1 | | 1/2018 |
| WO | WO 2018-021663 A1 | | 2/2018 |
| WO | WO 2018-110958 A1 | | 6/2018 |
| WO | WO 2018-217067 A1 | | 11/2018 |
| WO | WO 2019-151682 A1 | | 8/2019 |

OTHER PUBLICATIONS

U.S. Office action received in co pending U.S. Appl. No. 16/672,880 dated Jul. 14, 2022.
U.S. Office action received in co pending U.S. Appl. No. 16/380,233 dated Oct. 21, 2021.
U.S. Office action received in co pending U.S. Appl. No. 16/380,233 dated May 24, 2022.
Chinese Notice of Allowance dated Jul. 26, 2022 and Search Report dated Jul. 14, 2022.
U.S. Appl. No. 16/380,233, filed Apr. 10, 2019.
U.S. Appl. No. 16/672,880, filed Nov. 4, 2019.
U.S. Advisory action dated Sep. 8, 2022, in copending U.S. Appl. No. 16/380,233.
U.S. Office action received in co pending U.S. Appl. No. 16/380,233, dated Dec. 5, 2022.
U.S. Office action received in co pending U.S. Appl. No. 16/672,880, dated Jan. 9, 2023.

* cited by examiner

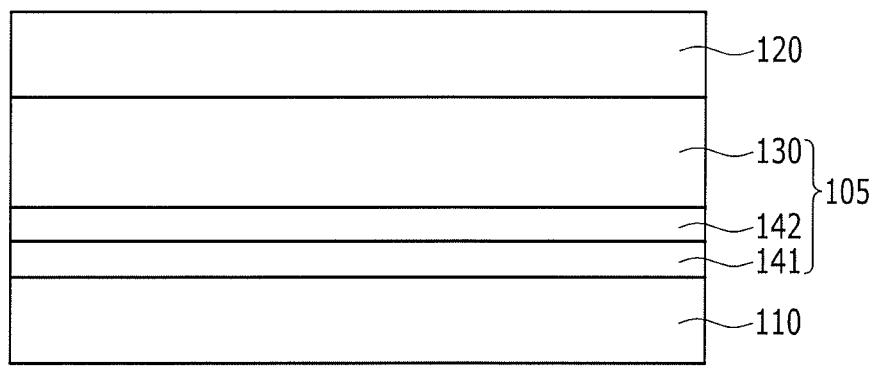

ORGANIC OPTOELECTRONIC DEVICE AND DISPLAY DEVICE

CROSS-REFERENCE TO RELATED APPLICATION

Korean Patent Application No. 10-2018-0154654, filed on Dec. 4, 2018, in the Korean Intellectual Property Office, and entitled: "Organic Optoelectronic Device and Display Device," is incorporated by reference herein in its entirety.

PARTIES TO A JOINT RESEARCH AGREEMENT

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are Samsung SDI Co., Ltd., and Samsung Electronics Co., Ltd.

BACKGROUND

1. Field

Embodiments relate to an organic optoelectronic device.

2. Description of the Related Art

An organic optoelectronic device is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device may include an organic photoelectric device, an organic light emitting diode, an organic solar cell, and an organic photo conductor drum.

Among them, the organic light emitting diode (OLED) has recently drawn attention due to an increase in demand for flat panel displays.

SUMMARY

The embodiments may be realized by providing a organic optoelectronic device including an anode and a cathode facing each other, a light emitting layer between the anode and the cathode, a hole transport layer between the anode and the light emitting layer, and a hole transport auxiliary layer between the light emitting layer and the hole transport layer, wherein the light emitting layer includes a first compound represented by a combination of Chemical Formula 1 and Chemical Formula 2, and a second compound represented by Chemical Formula 3, and the hole transport auxiliary layer includes a third compound represented by Chemical Formula 4,

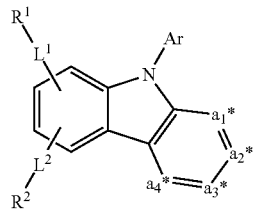

[Chemical Formula 1]

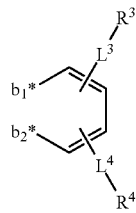

[Chemical Formula 2]

in Chemical Formula 1 and Chemical Formula 2, Ar is a substituted or unsubstituted C6 to C30 aryl group, a substituted or unsubstituted C2 to C30 heterocyclic group, or a combination thereof, adjacent two of $a_1^*$ to $a_4^*$ are carbon (C) linked at $b_1^*$ and $b_2^*$ respectively, the other two of $a_1^*$ to $a_4^*$ not linked at $b_1^*$ and $b_2^*$ are each independently $C-L^a-R^a$, $L^a$ and $L^1$ to $L^4$ are each independently a single bond, a substituted or unsubstituted C6 to C20 arylene group, a substituted or unsubstituted C2 to C20 heterocyclic group, or a combination thereof, $R^a$ and $R^1$ to $R^4$ are each independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^4$ is a group represented by Chemical Formula a,

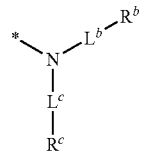

[Chemical Formula a]

in Chemical Formula a, $L^b$ and $L^c$ are each independently a single bond, a substituted or unsubstituted C6 to C20 arylene group, a substituted or unsubstituted C2 to C20 heterocyclic group, or a combination thereof, $R^b$ and $R^c$ are each independently a substituted or unsubstituted C6 to C30 aryl group, a substituted or unsubstituted C2 to C30 heterocyclic group, or a combination thereof, and * is a linking point with one of $L^a$ and $L^1$ to $L^4$;

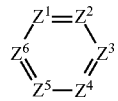

[Chemical Formula 3]

in Chemical Formula 3, $Z^1$ is N or $C-L^5-R^5$, $Z^2$ is N or $C-L^6-R^6$, $Z^3$ is N or $C-L^7-R^7$, $Z^4$ is N or $C-L^8-R^8$, $Z^5$ is N or $C-L^9-R^9$, $Z^6$ is N or $C-L^{10}-R^{10}$, at least two of $Z^1$ to $Z^6$ are N, $L^5$ to $L^{10}$ are each independently a single bond, a substituted or unsubstituted C6 to C20 arylene group, a substituted or unsubstituted C2 to C20 heterocyclic group, or a combination thereof, $R^5$ to $R^{10}$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, at least one of $R^5$ to $R^{10}$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and $R^5$ to $R^{10}$ are separately present or adjacent ones thereof are linked with each other to form a substituted or unsubstituted aliphatic, aromatic, or heteroaromatic monocyclic ring or a substituted or unsubstituted aliphatic, aromatic, or heteroaromatic polycyclic ring;

[Chemical Formula 4]

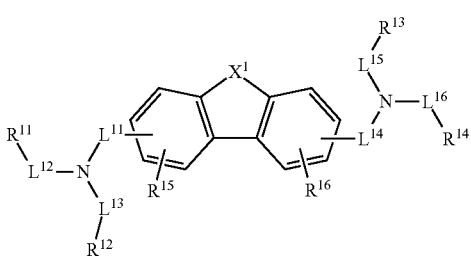

in Chemical Formula 4, $X^1$ is O or S, $L^{11}$ to $L^{16}$ are each independently a single bond, a substituted or unsubstituted C6 to C20 arylene group, a substituted or unsubstituted C2 to C20 heterocyclic group, or a combination thereof, $R^{11}$ to $R^{14}$ are each independently a substituted or unsubstituted C6 to C30 aryl group, a substituted or unsubstituted C2 to C30 heterocyclic group, or a combination thereof, and $R^{15}$ and $R^{16}$ are each independently hydrogen, deuterium, a cyano group, or a substituted or unsubstituted C1 to C10 alkyl group.

The embodiments may be realized by providing a display device comprising the organic optoelectronic device according to an embodiment.

BRIEF DESCRIPTION OF THE DRAWING

Features will be apparent to those of skill in the art by describing in detail exemplary embodiments with reference to the attached drawing in which:

The FIGURE illustrates a schematic cross-sectional view of an organic optoelectronic device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, "substituted" refers to replacement of at least one hydrogen of a substituent or a compound by deuterium, a C1 to C20 alkyl group, a C6 to C30 aryl group, or a C2 to C30 heteroaryl group. In addition, in specific examples, "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in specific examples, "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in specific examples, "substituted" refers to replacement of at least one hydrogen of a substituent or a compound by deuterium, a methyl group, an ethyl group, a propyl group, a butyl group, a phenyl group, a biphenyl group, a terphenyl group, a naphthyl group, a triphenyl group, a dibenzofuranyl group, or a dibenzothiophenyl group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, the description of adjacent groups being linked with each other to form a substituted or unsubstituted aromatic monocyclic or polycyclic ring, or a substituted or unsubstituted aromatic monocyclic or polycyclic heterocyclic ring refers to any two adjacent substituents directly substituting an aromatic ring or an aromatic heterocyclic ring with a single bond without a linking group being linked to form an additional ring.

For example, adjacent groups are linked with each other to form a substituted or unsubstituted aromatic monocyclic or polycyclic ring and examples may be a substituted or unsubstituted aromatic monocyclic ring.

For example, any two substituents directly substituting a pyrimidine ring are linked with each other to form an additional ring, and thereby a substituted or unsubstituted quinazolinyl group may be formed along with the pyrimidine ring.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, an organic optoelectronic device according to an embodiment is described.

The organic optoelectronic device may be a device to convert electrical energy into photoenergy and vice versa, e.g., an organic photoelectric device, an organic light emitting diode, an organic solar cell, or an organic photoconductor drum.

In an implementation, an organic light emitting diode as one examples of an organic optoelectronic device is described.

The FIGURE illustrates a cross-sectional view of an organic light emitting diode according to an embodiment.

Referring to the FIGURE, an organic light emitting diode 300 according to an embodiment may include an anode 110 and a cathode 120 facing each other and an organic layer 105 between the anode 110 and the cathode 120. The organic layer 105 may include a light emitting layer 130, a hole transport auxiliary layer 142, and a hole transport layer 141.

The anode 110 may be made of a conductor having a large work function to facilitate hole injection, and may be, e.g., a metal, a metal oxide and/or a conductive polymer. In an implementation, the anode 110 may be, e.g., a metal such as nickel, platinum, vanadium, chromium, copper, zinc, gold, and the like, or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline.

The cathode 120 may be made of a conductor having a small work function to facilitate electron injection, and may be, e.g., a metal, a metal oxide, and/or a conductive polymer. In an implementation, the cathode 120 may be, e.g., a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca.

The light emitting layer 130 may be between the anode 110 and the cathode 120 and may include a plurality of hosts and at least one type of a dopant.

The light emitting layer 130 may include a first compound having relatively strong hole characteristics and a second compound having relatively strong electron characteristics as a host.

In an implementation, the first compound may be a compound having relatively strong hole characteristics, and may be represented by, e.g., a combination of Chemical Formula 1 and Chemical Formula 2.

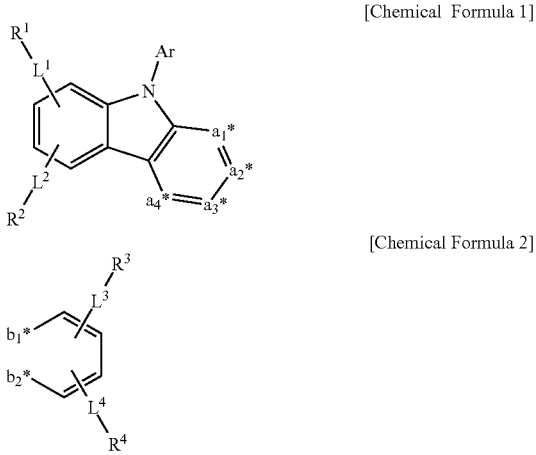

[Chemical Formula 1]

[Chemical Formula 2]

In Chemical Formula 1 and Chemical Formula 2,

Ar may be or may include, e.g., a substituted or unsubstituted C6 to C30 aryl group, a substituted or unsubstituted C2 to C30 heterocyclic group, or a combination thereof, adjacent two of $a_1^*$ to $a_4^*$ may be carbon (C) linked at or corresponding (e.g., coextensive) with $b_1^*$ and $b_2^*$ respectively, the remainders (e.g., other two) of $a_1^*$ to $a_4^*$ not linked at $b_1^*$ and $b_2^*$ may each independently be, e.g., $C-L^a-R^a$, $L^a$ and $L^1$ to $L^4$ may each independently be or include, e.g., a single bond, a substituted or unsubstituted C6 to C20 arylene group, a substituted or unsubstituted C2 to C20 heterocyclic group, or a combination thereof, $R^a$ and $R^1$ to $R^4$ may each independently be or include, e.g., hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

In an implementation, at least one of $R^a$ and $R^1$ to $R^4$ may be, e.g., a group represented by Chemical Formula a.

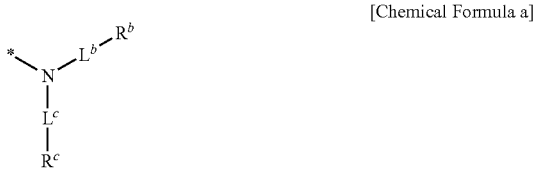

[Chemical Formula a]

In Chemical Formula a, $L^b$ and $L^c$ may each independently be or include, e.g., a single bond, a substituted or unsubstituted C6 to C20 arylene group, a substituted or unsubstituted C2 to C20 heterocyclic group, or a combination thereof, $R^b$ and $R^c$ may each independently be or include, e.g., a substituted or unsubstituted C6 to C30 aryl group, a substituted or unsubstituted C2 to C30 heterocyclic group, or a combination thereof, and

* is a linking point with one of $L^a$ and $L^1$ to $L^4$.

The first compound may have a structure in which benzocarbazole is substituted with an amine group, and may have high HOMO energy, as a HOMO electron cloud expands from the amine to the benzocarbazole, and may exhibit excellent hole injection and transfer characteristics.

In addition, the benzocarbazole may have relatively high HOMO energy compared with bicarbazole and indolocarbazole, and a device having a low driving voltage may be realized by applying the structure in which benzocarbazole is substituted with an amine group.

In addition, the bicarbazole and indolocarbazole may have high T1 energy and may not be appropriate as a red host. According to an embodiment, the structure the structure in which benzocarbazole is substituted with amine may have an appropriate T1 energy for a red host. For example, a device manufactured by applying the compound according to an embodiment may realize high efficiency/long life-span characteristics.

In an implementation, the first compound may be included with the second compound and may exhibit satisfactory interface characteristics and transportation capability of holes and electrons and accordingly, may help lower a driving voltage of a device manufactured by applying the same.

In an implementation, $L^b$ and $L^c$ may each independently be, e.g., a single bond or a substituted or unsubstituted C6 to C12 arylene group.

In an implementation, $L^b$ and $L^c$ may each independently be, e.g., a single bond, a substituted or unsubstituted phenylene group, or a substituted or unsubstituted biphenylene group.

In an implementation, $R^b$ and $R^c$ may each independently be, e.g., a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted arylamine group, a substituted or unsubstituted carbazolyl group, a substituted or unsubstituted dibenzofuranyl group, or a substituted or unsubstituted dibenzothiophenyl group.

In an implementation, $R^b$ and $R^c$ may each independently be, e.g., a substituted or unsubstituted, phenyl group, a substituted or unsubstituted biphenyl group, substituted or naphthyl group, a substituted or unsubstituted fluorenyl group, a substituted or unsubstituted dibenzofuranyl group, or a substituted or unsubstituted dibenzothiophenyl group. A substituent of the substituted groups may be, e.g., a phenyl group, a naphthyl group, an anthracenyl group, a phenanthrenyl group, a triphenylene group, a carbazolyl group, a dibenzofuranyl group, or a dibenzothiophenyl group.

In an implementation, Ar may be, e.g., a substituted or unsubstituted C6 to C20 aryl group, or a substituted or unsubstituted C2 to C20 heterocyclic group.

In an implementation, Ar may be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof.

In an implementation, Ar may be, e.g., a substituted or unsubstituted phenyl group, or a substituted or unsubstituted biphenyl group.

In an implementation, $L^a$ and $L^1$ to $L^4$ may each independently be, e.g., a single bond or a substituted or unsubstituted C6 to C20 arylene group.

In an implementation, $L^e$ and $L^1$ to $L^4$ may each independently be, e.g., a single bond, a substituted or unsubstituted phenylene group, a substituted or unsubstituted biphenylene group, a substituted or unsubstituted terphenylene group, or a substituted or unsubstituted naphthylene group.

In an implementation, $L^e$ and $L^1$ to $L^4$ may each independently be, e.g., a single bond, a substituted or unsubstituted m-phenylene group, a substituted or unsubstituted p-phenylene group, a substituted or unsubstituted o-phenylene group, a substituted or unsubstituted m-biphenylene group, a substituted or unsubstituted p-biphenylene group, a substituted or unsubstituted o-biphenylene group, a substituted or unsubstituted m-terphenylene group, a substituted or unsubstituted p-terphenylene group, or a substituted or unsubstituted o-terphenylene group. Herein, the substituted may for example refer to replacement of at least one hydrogen by deuterium, a C1 to C20 alkyl group, a C6 to C20 aryl group, a halogen, a cyano group, or a combination thereof.

In an implementation, $R^a$ and $R^1$ to $R^4$ may each independently be, e.g., hydrogen, deuterium, a cyano group, a substituted or unsubstituted C1 to C10 alkyl group, a substituted or unsubstituted C6 to C20 aryl group, a substituted or unsubstituted C2 to C20 heterocyclic group, or the group represented by Chemical Formula a.

In an implementation, $R^a$ and $R^1$ to $R^4$ may each independently be, e.g., hydrogen or the substituted amine group represented by Chemical Formula a.

In an implementation, the first compound may be represented by one of Chemical Formula 1A to Chemical Formula 1C according to a combination position of Chemical Formula 1 and Chemical Formula 2.

[Chemical Formula 1A]

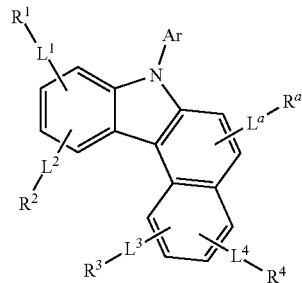

[Chemical Formula 1B]

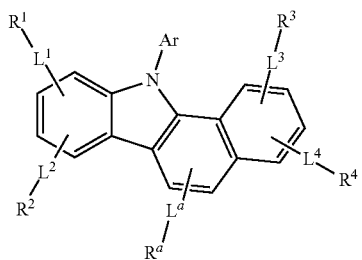

[Chemical Formula 1C]

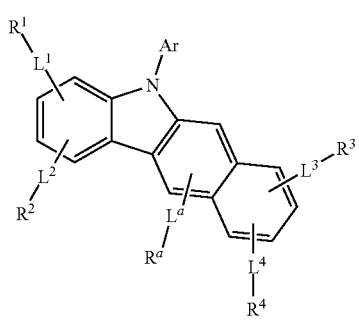

In Chemical Formula 1A to Chemical Formula 1C, Ar, $L^a$, $L^1$ to $L^4$, $R^a$, and $R^1$ to $R^4$ may be the same as described above.

In an implementation, Chemical Formula 1A may be represented by Chemical Formula 1A-1 to Chemical Formula 1A-3 according to a substitution position.

[Chemical Formula 1A-1]

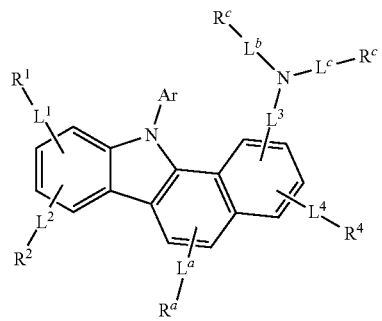

[Chemical Formula 1A-2]

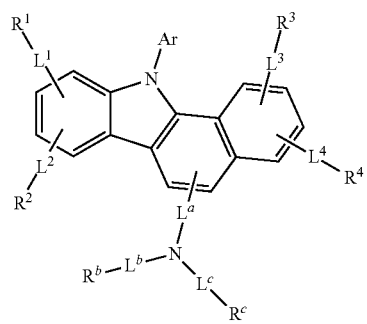

[Chemical Formula 1A-3]

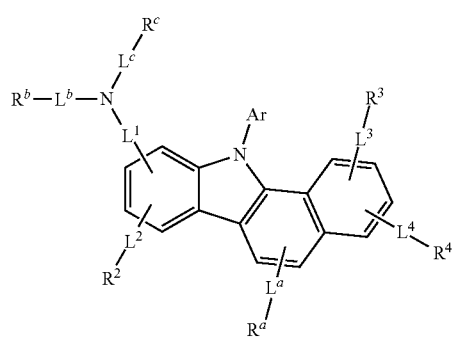

In an implementation, in Chemical Formula 1A-1 to Chemical Formula 1A-3, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1A-1 may be represented by one of Chemical Formula 1A-1-a to Chemical Formula 1A-1-d according to a specific substitution position of the group represented by Chemical Formula a.

In an implementation, Chemical Formula 1A-2 may be represented by one of Chemical Formula 1A-2-a or Chemical Formula 1A-2-b according to a specific substitution position of the group represented by Chemical Formula a.

[Chemical Formula 1A-1-a]

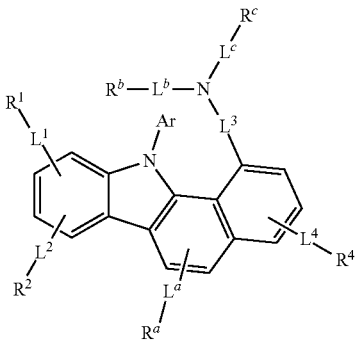

[Chemical Formula 1A-2-a]

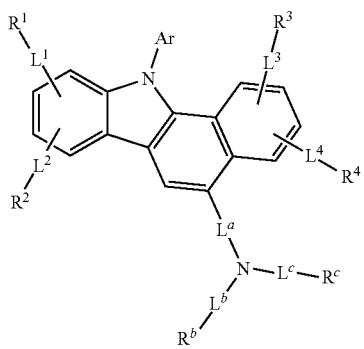

[Chemical Formula 1A-1-b]

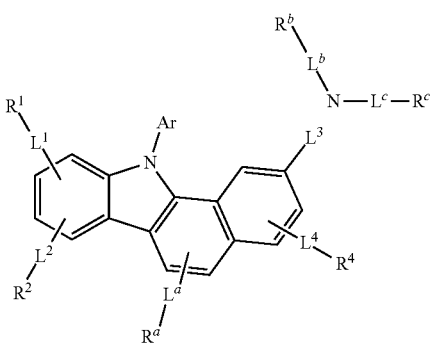

[Chemical Formula 1A-2-b]

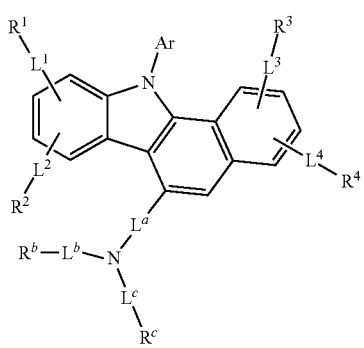

[Chemical Formula 1A-1-c]

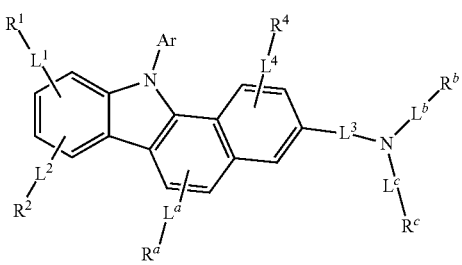

In Chemical Formula 1A-2-a and Chemical Formula 1A-2-b, Ar, $L^a$, $L^1$ to $L^4$, $R^1$ to $R^4$, $L^b$, $L^c$, $R^b$, and $R^c$ may be the same as described above.

In an implementation, Chemical Formula 1A-2 may be represented by Chemical Formula 1A-2-a.

In an implementation, Chemical Formula 1A-3 may be represented by one of Chemical Formula 1A-3-a to Chemical Formula 1A-3-d according to a specific substitution position of the group represented by Chemical Formula a.

[Chemical Formula 1A-1-d]

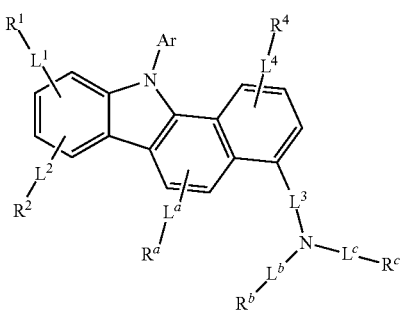

[Chemical Formula 1A-3-a]

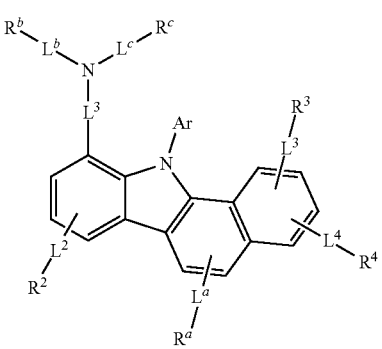

In Chemical Formula 1A-1-a to Chemical Formula 1A-1-d, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1A-1 may be represented by Chemical Formula 1A-1-b or Chemical Formula 1A-1-c.

[Chemical Formula 1A-3-b]

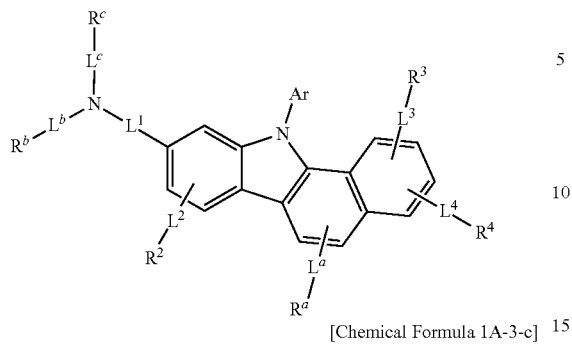

[Chemical Formula 1A-3-c]

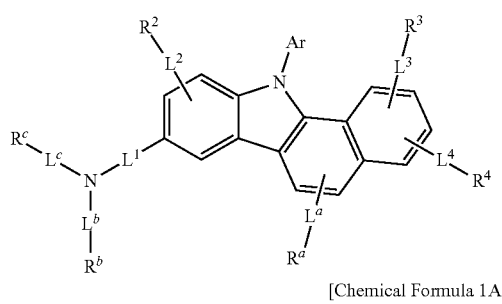

[Chemical Formula 1A-3-d]

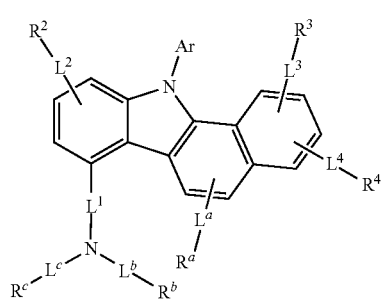

In Chemical Formula 1A-3-a to Chemical Formula 1A-3-d, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1A-3 may be represented by Chemical Formula 1A-3-b or Chemical Formula 1A-3-c.

In an implementation, Chemical Formula 1B may be represented by one of Formula 1B-1 to Chemical Formula 1B-3 according to a specific substitution position of the group represented by Chemical Formula a.

[Chemical Formula 1B-2]

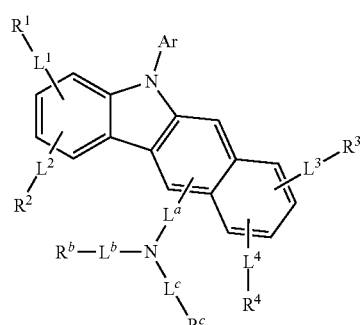

[Chemical Formula 1B-3]

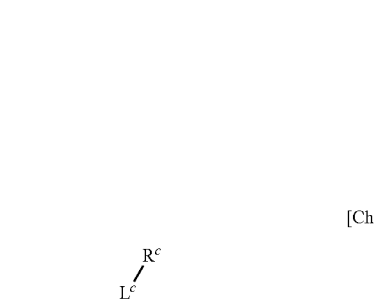

In Chemical Formula 1B-1 to Chemical Formula 1B-3, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1B-1 may be represented by one of Chemical Formula 1B-1-a to Chemical Formula 1B-1-d according to a specific substitution position of the group represented by Chemical Formula a.

[Chemical Formula 1B-1]

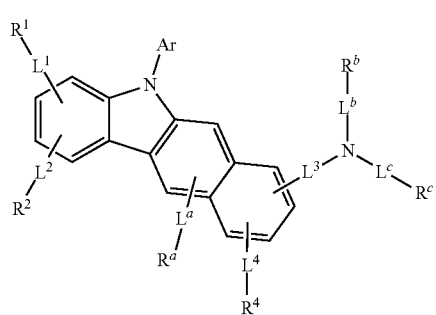

[Chemical Formula 1B-1-a]

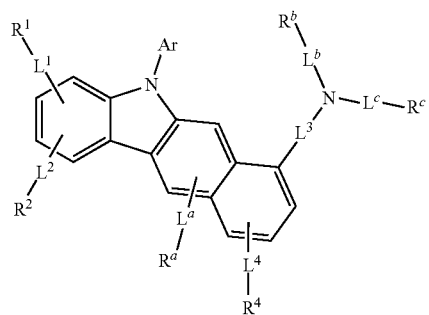

[Chemical Formula 1B-1-b]

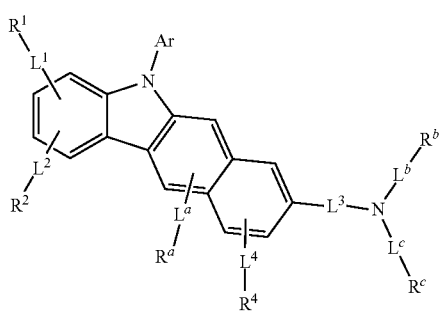

[Chemical Formula 1B-1-c]

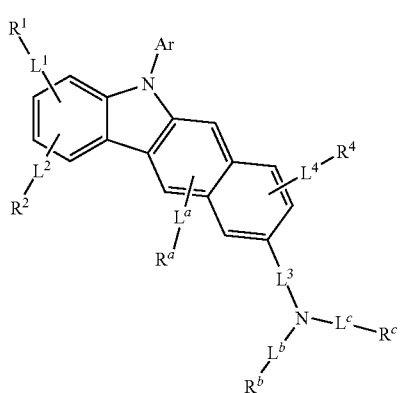

[Chemical Formula 1B-1-d]

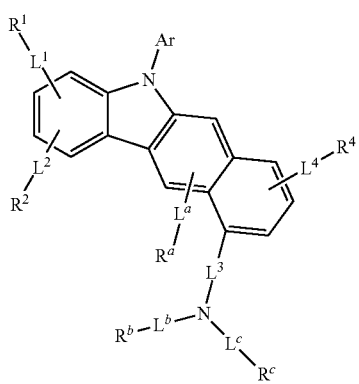

In Chemical Formula 1B-1-a to Chemical Formula 1B-1-d, Ar, Ar, $L^a$, $L^1$ to $L^4$, $R^a$, $R^1$ to $R^4$, $L^b$, L, $R^b$, and $R^c$ may be the same as described above.

For an implementation, Chemical Formula 1B-2 may be represented by one of Chemical Formula Chemical Formula 1B-2-a or Chemical Formula 1B-2-b according to a specific substitution position of the group represented by Chemical Formula a.

[Chemical Formula 1B-2-a]

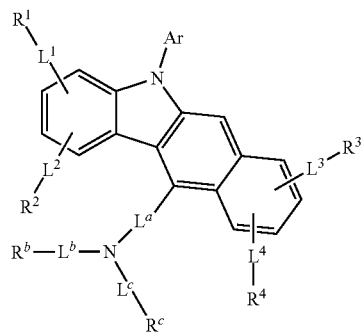

[Chemical Formula 1B-2-b]

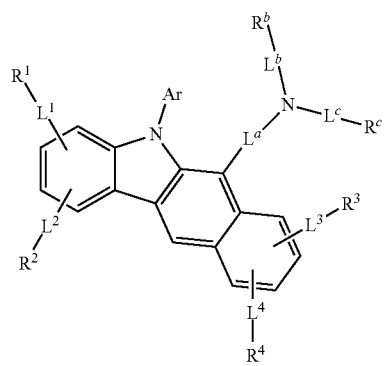

In Chemical Formula 1B-2-a and Chemical Formula 1B-2-b, Ar, $L^a$, $L^1$ to $L^4$, $R^1$ to $R^4$, $L^b$, $L^c$, $R^b$, and $R^c$ may be the same as described above.

In an implementation, Chemical Formula 1B-3 may be represented by one of Chemical Formula 1B-3-a to Chemical Formula 1B-3-d according to a specific substitution position of the group represented by Chemical Formula a.

[Chemical Formula 1B-3-a]

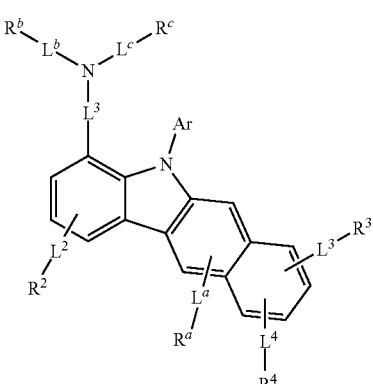

[Chemical Formula 1B-3-b]

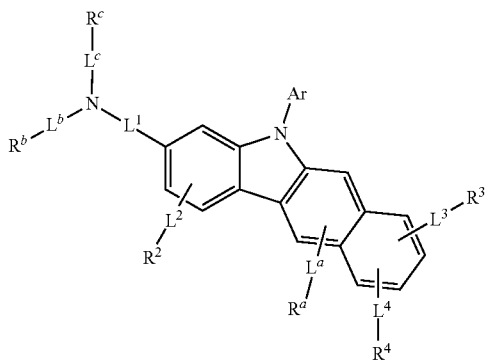

[Chemical Formula 1C-1]

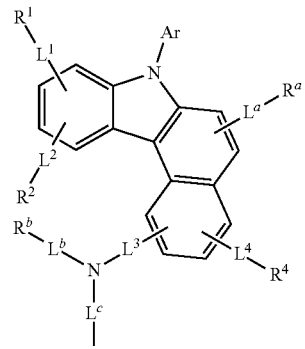

[Chemical Formula 1B-3-c]

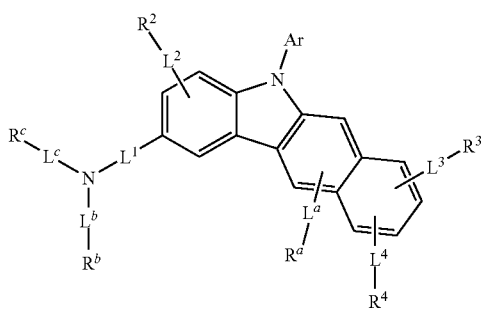

[Chemical Formula 1C-2]

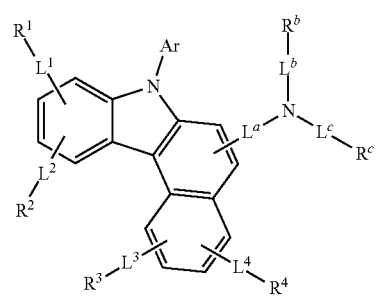

[Chemical Formula 1B-3-d]

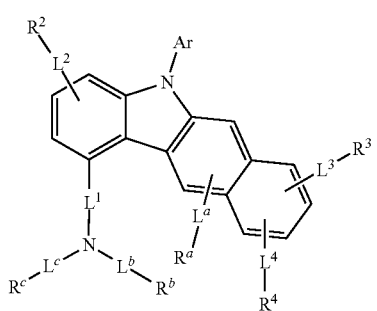

[Chemical Formula 1C-3]

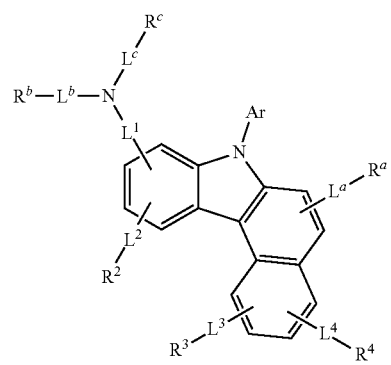

In Chemical Formula 1B-3-a to Chemical Formula 1B-3-d, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1B-3 may be represented by Chemical Formula 1B-3-b.

In an implementation, Chemical Formula 1C may be represented by one of Chemical Formula 1C-1 to Chemical Formula 1C-3 according to a specific substitution position of the group represented by Chemical Formula a.

In Chemical Formula 1C-1 to Chemical Formula 1C-3, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1C-1 may be represented by one of Chemical Formula 1C-1-a to Chemical Formula 1C-1-d according to a specific substitution position of the group represented by Chemical Formula a.

[Chemical Formula 1C-1-a]

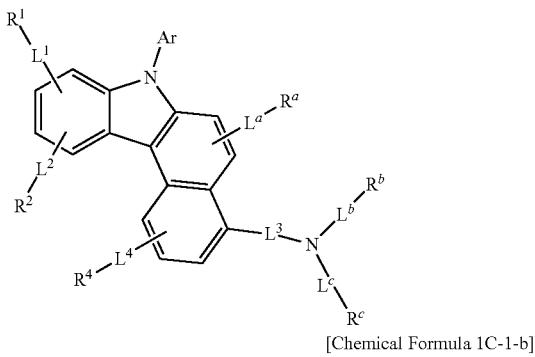

[Chemical Formula 1C-1-b]

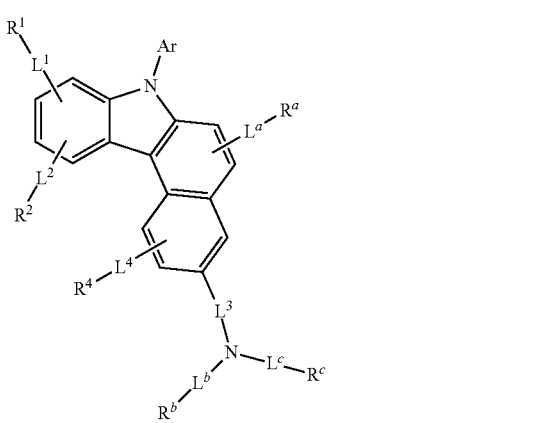

[Chemical Formula 1C-1-c]

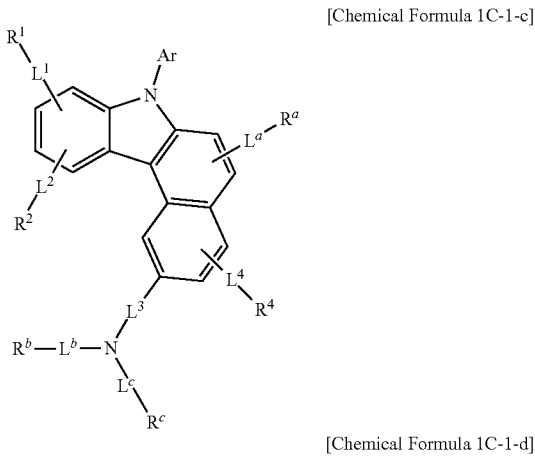

[Chemical Formula 1C-1-d]

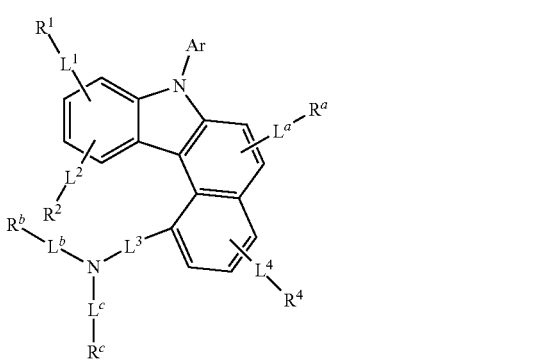

In Chemical Formula 1C-1-a to Chemical Formula 1C-1-d, Ar, $L^a$, $L^1$ to $L^4$, $R^a$, $R^1$ to $R^4$, $L^b$, L, $R^b$, and $R^c$ may be the same as described above.

In an implementation, Chemical Formula 1C-1 may be represented by Chemical Formula 1C-1-b.

In an implementation, Chemical Formula 1C-2 may be represented by Chemical Formula 1C-2-a or Chemical Formula 1C-2-b according to a specific substitution position of the group represented by Chemical Formula a.

[Chemical Formula 1C-2-a]

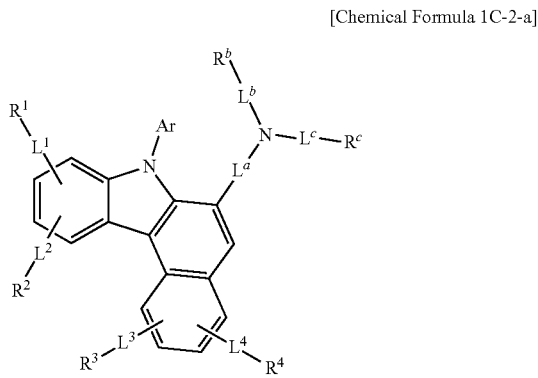

[Chemical Formula 1C-2-b]

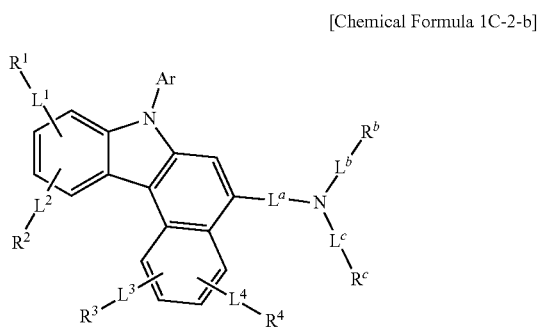

In Chemical Formula 1C-2-a and Chemical Formula 1C-2-b, Ar, $L^a$, $L^1$ to $L^4$, $R^1$ to $R^4$, $L^b$, $L^c$, $R^b$, and $R^c$ may be the same as described above.

In an implementation, Chemical Formula 1C-3 may be represented by one of Chemical Formula 1C-3-a to Chemical Formula 1C-3-d according to a specific substitution position of the group represented by Chemical Formula a.

[Chemical Formula 1C-3-a]

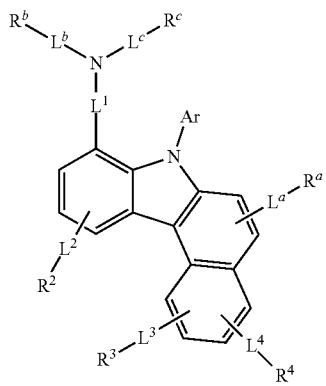

[Chemical Formula 1C-3-b]

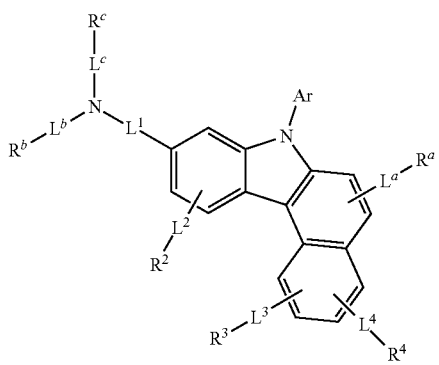

[Chemical Formula 1C-3-c]

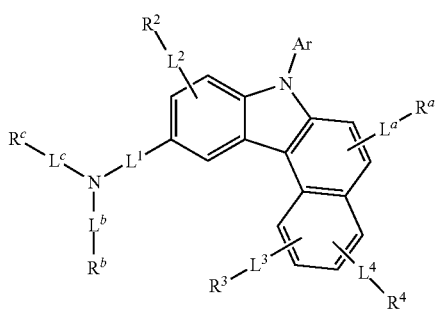

[Chemical Formula 1C-3-d]

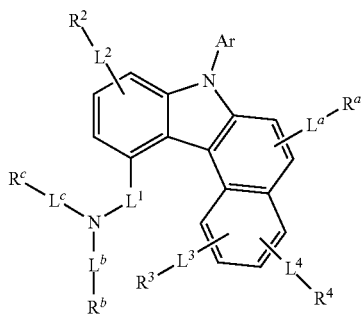

In Chemical Formula 1C-3-a to Chemical Formula 1C-3-d, Ar, $L^a$, $L^1$ to $L^4$, $R^a$, $R^1$ to $R^4$, $L^b$, $L^c$, $R^b$, and $R^c$ may be the same as described above.

In an implementation, Chemical Formula 1C-3 may be represented by Chemical Formula 1C-3-b.

In an implementation, the first compound may be represented by Chemical Formula 1A or Chemical Formula 1C, specifically one of Chemical Formulae 1A-1 to 1A-3 and 1C-1 to 1C-3, for example Chemical Formula 1A-1, Chemical Formula 1A-2 or Chemical Formula 1A-3.

In an implementation, the first compound may be represented by one of Chemical Formula 1A-1-b, Chemical Formula 1A-1-c. Chemical Formula 1A-2-a, 1A-3-b, and 1A-3-c.

In an implementation, the first compound may be, e.g., a compound of the following Group 1.

[Group 1]

A-1

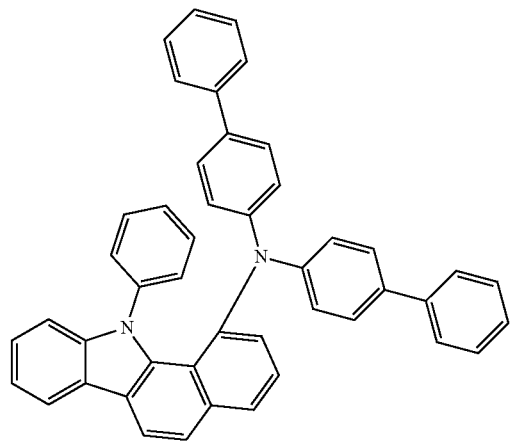

A-2

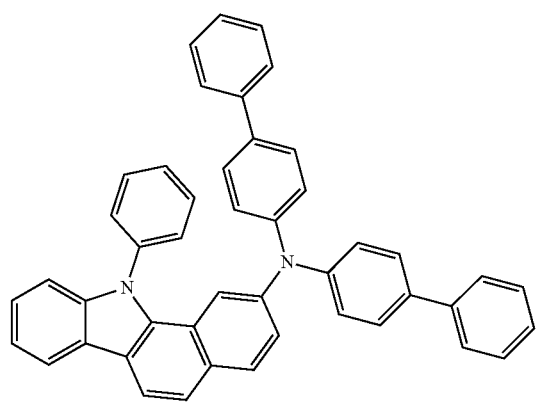

A-3

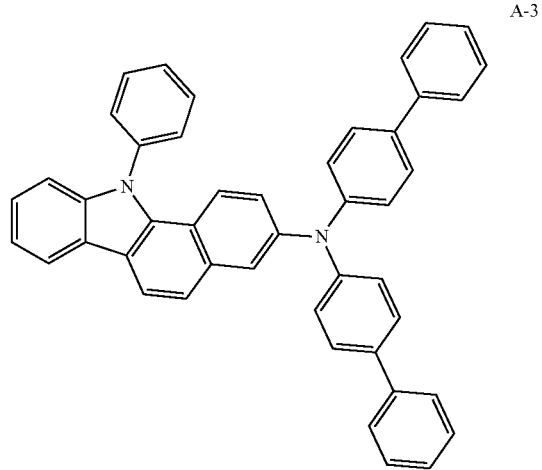

A-4
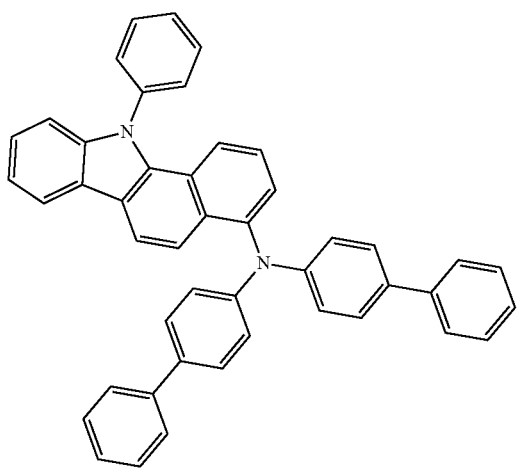
A-5
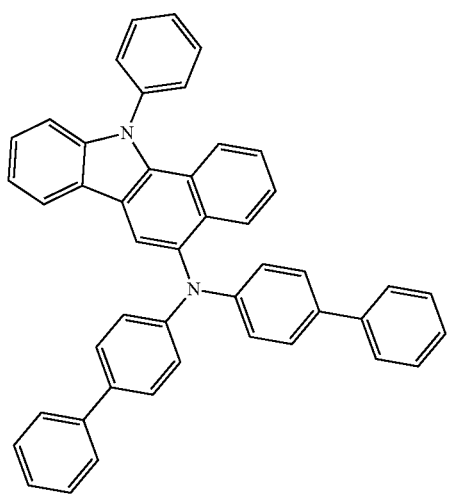
A-6
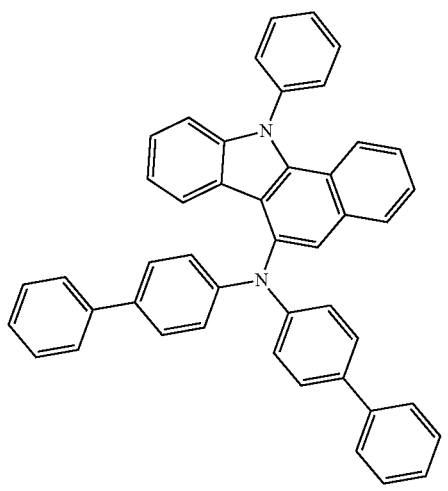
A-7
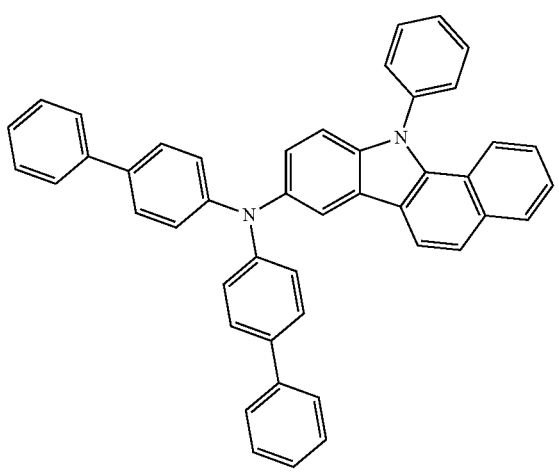
A-8
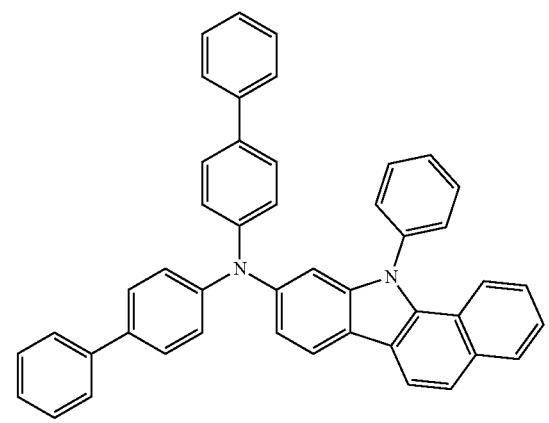
A-9
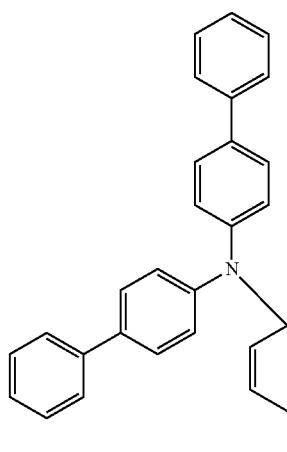

A-10
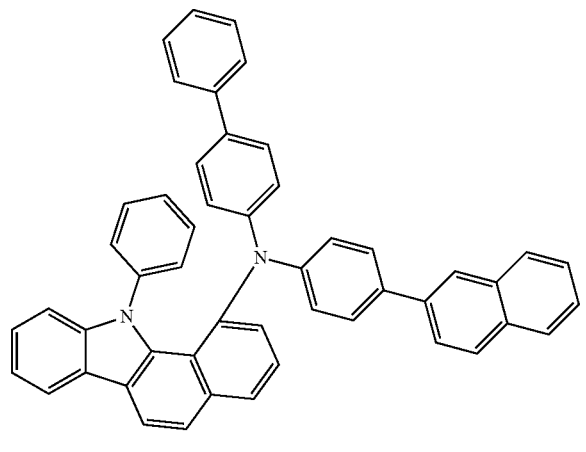
A-11
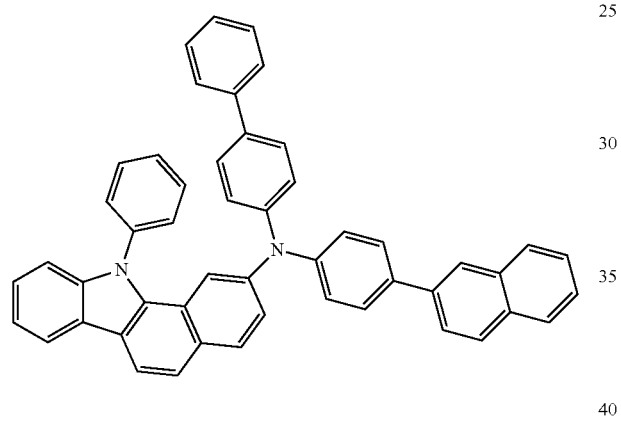
A-12
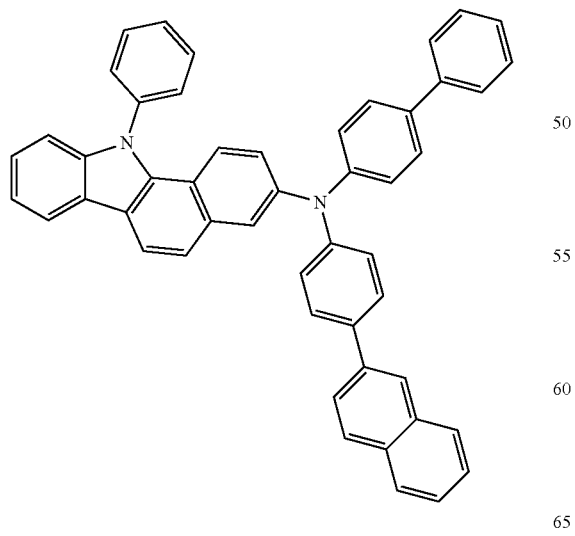
A-13
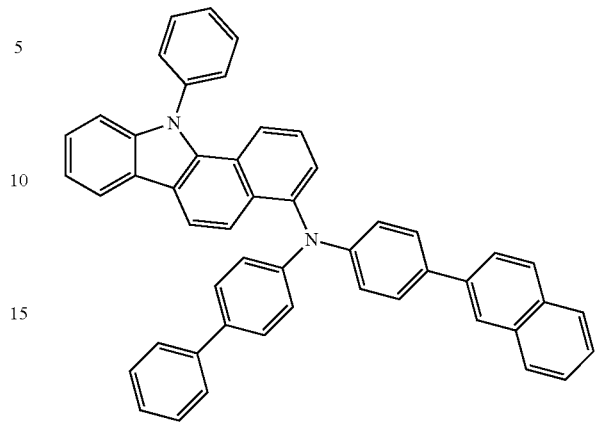
A-14
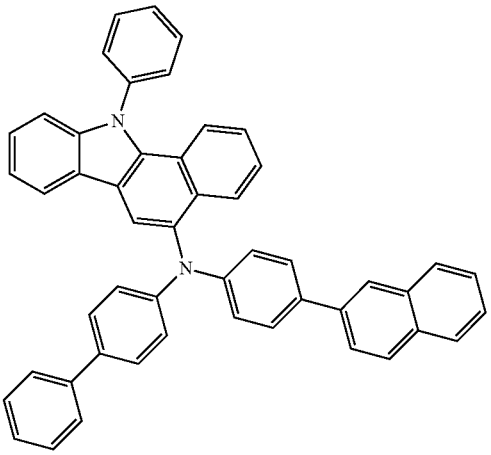
A-15
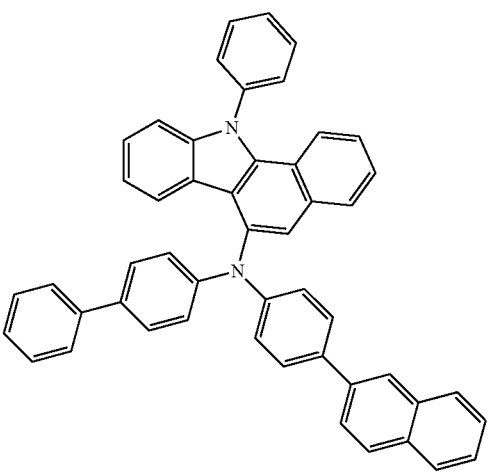

A-16
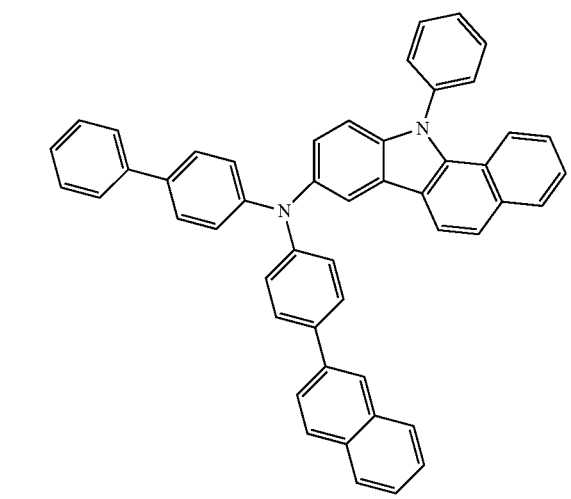
A-17
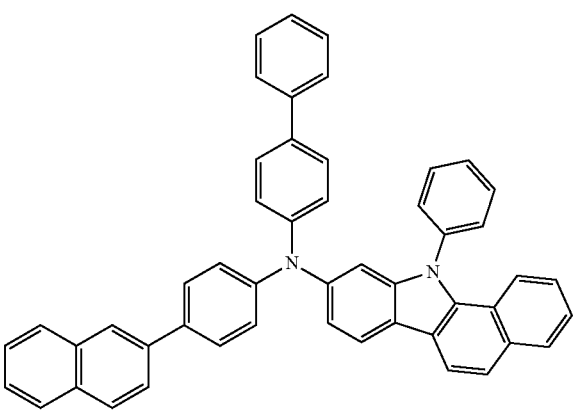
A-18
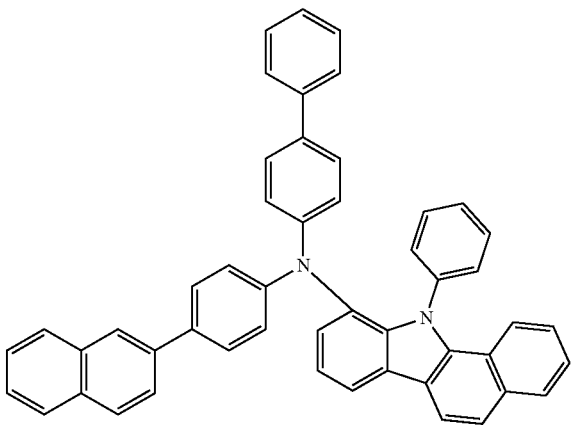
A-19
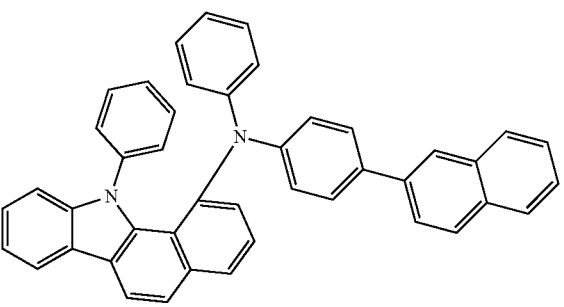
A-20
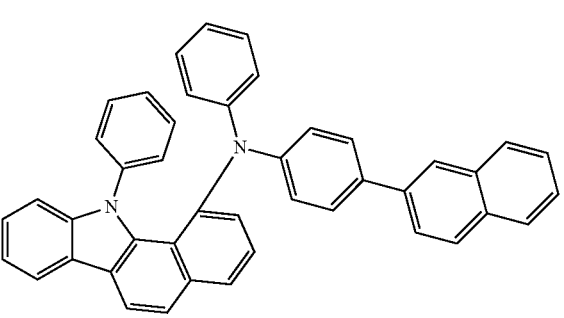
A-21
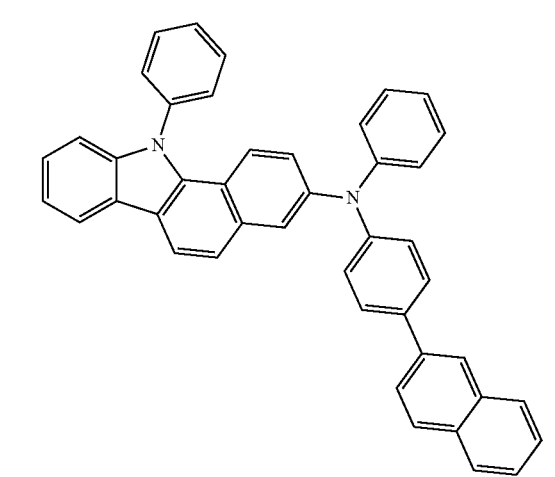
A-22
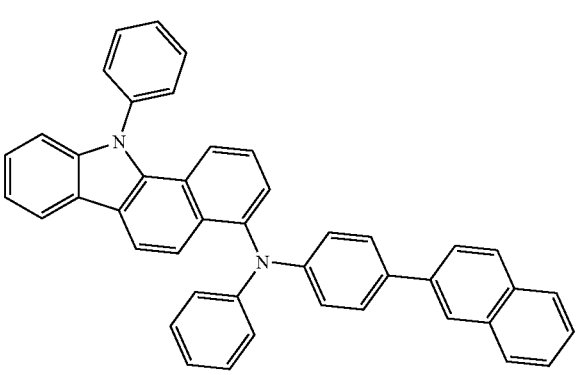

A-23
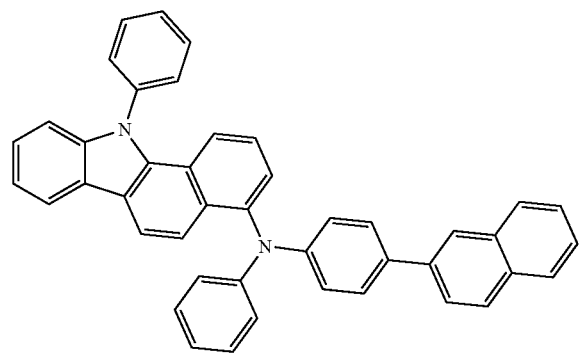
A-24
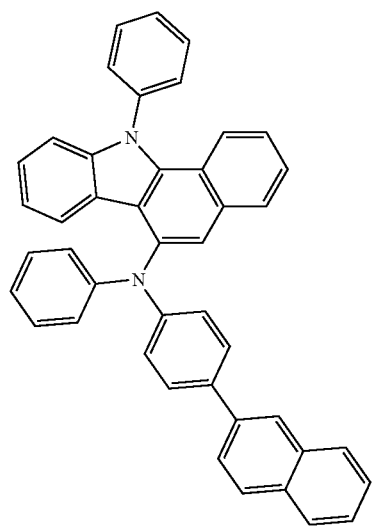
A-25
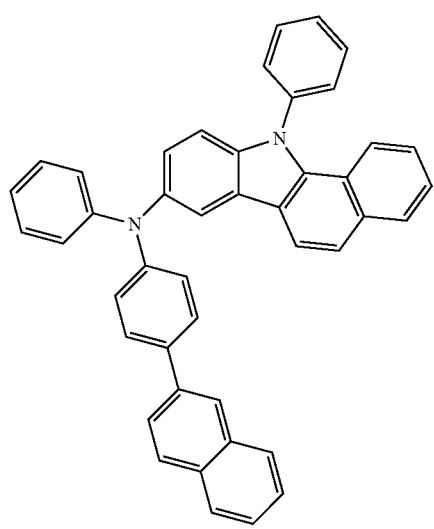
A-26
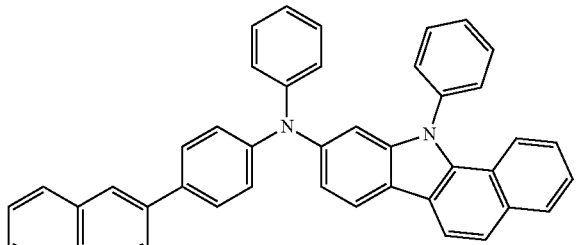
A-27
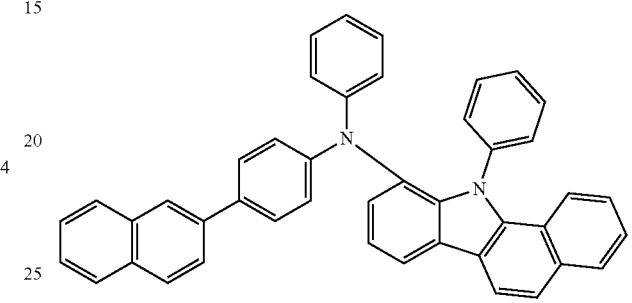
A-28

A-29

A-30
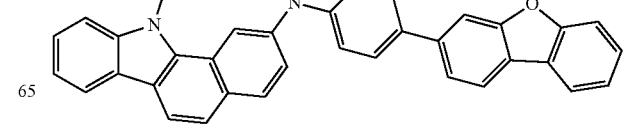

-continued
A-31
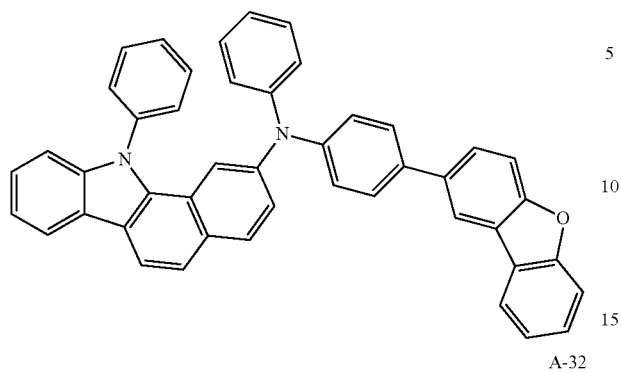
A-32
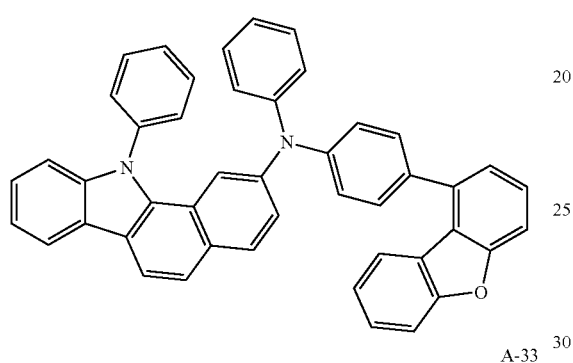
A-33
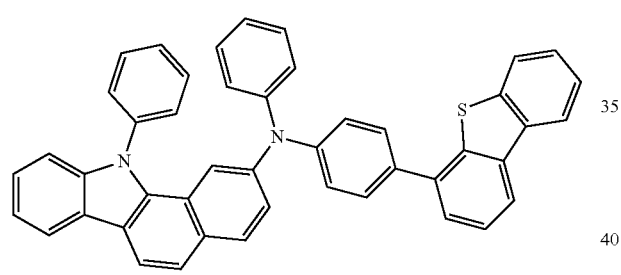
A-34
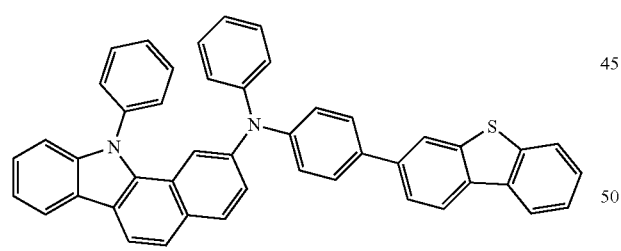
A-35
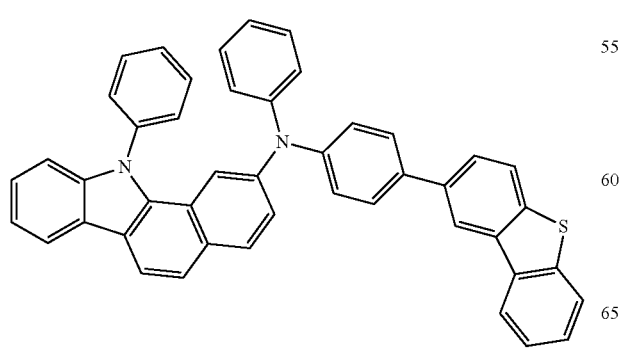
A-36
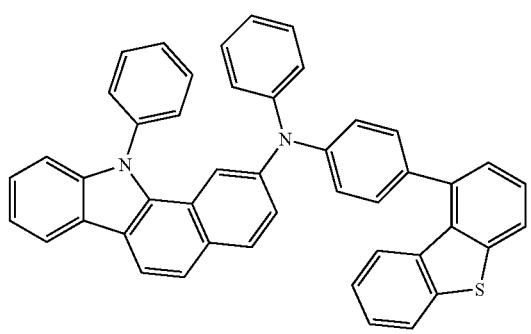
A-37
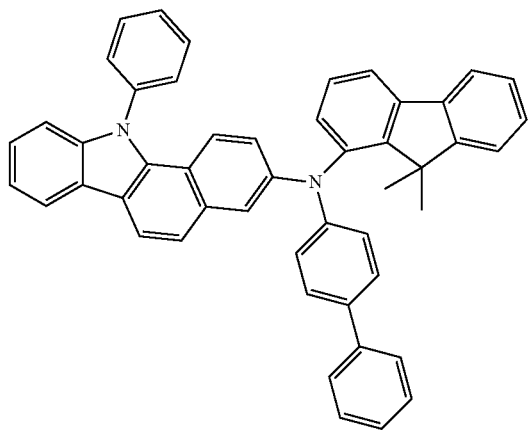
A-38
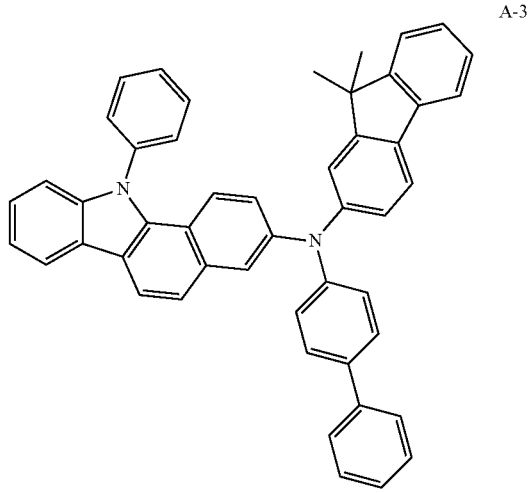

A-39
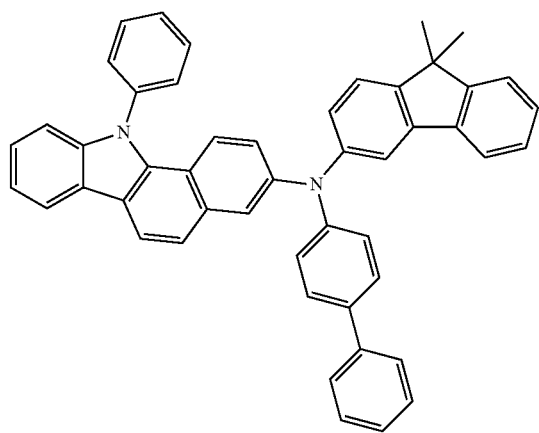
A-40
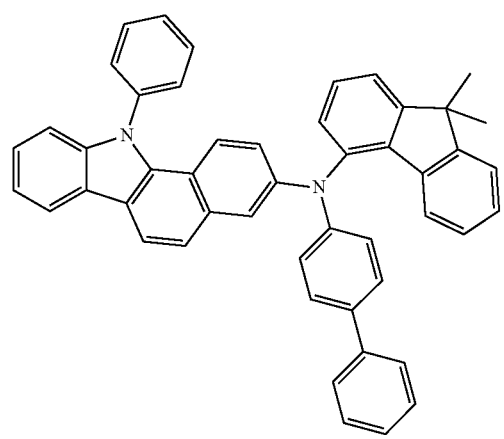
A-41
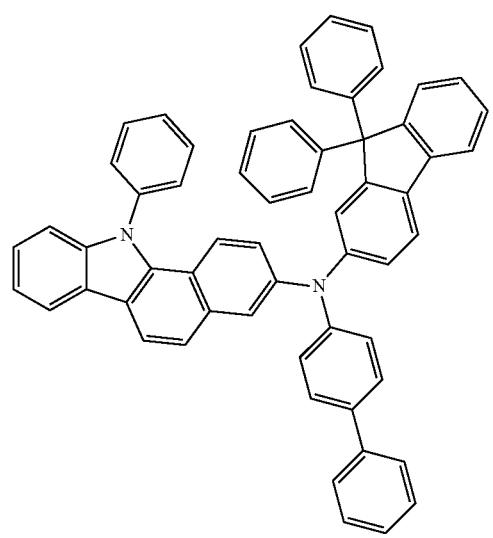
A-42
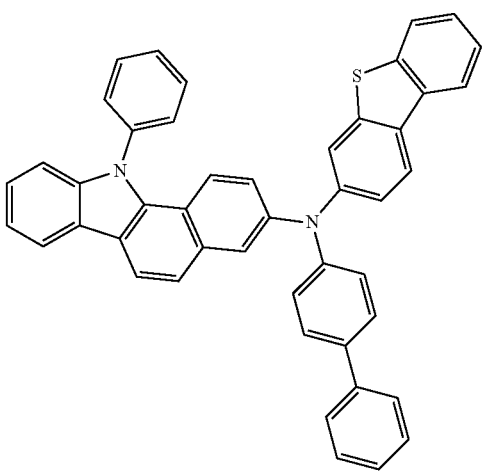
A-43
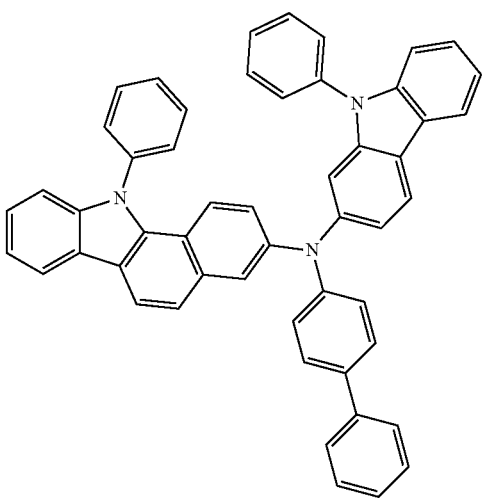
A-44
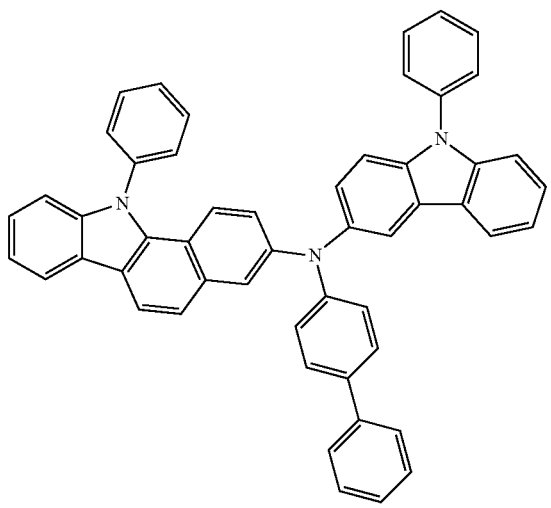

A-45
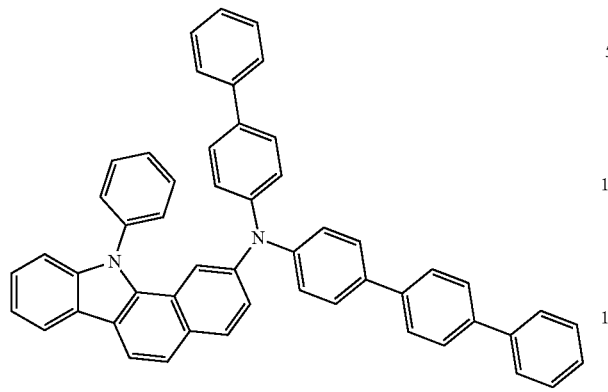
A-46
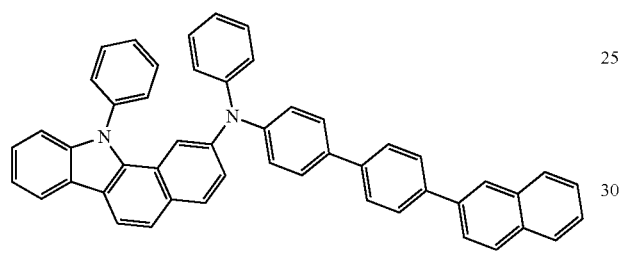
A-47
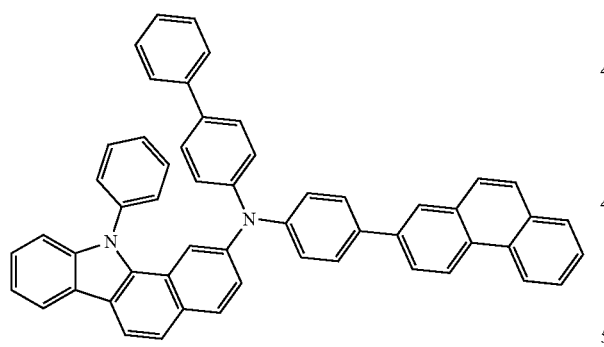
A-48
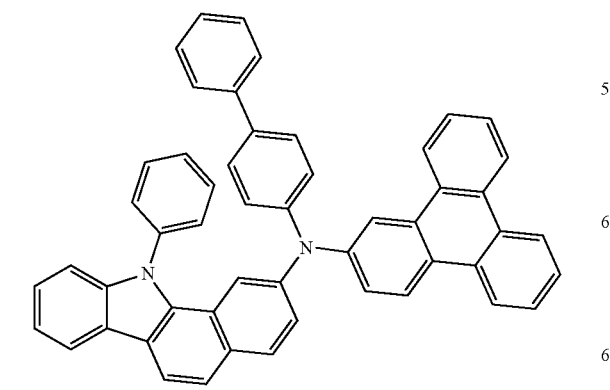
A-49
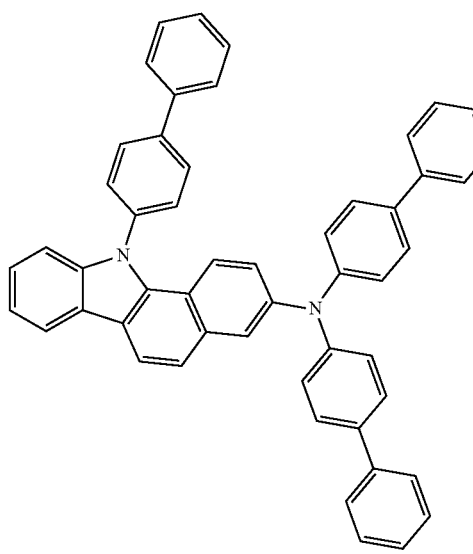
A-50
A-51
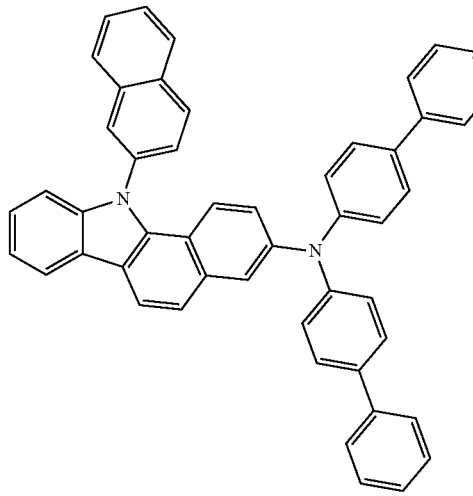

A-52
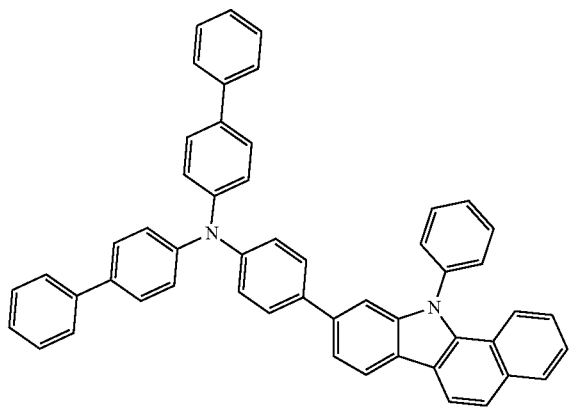
A-53
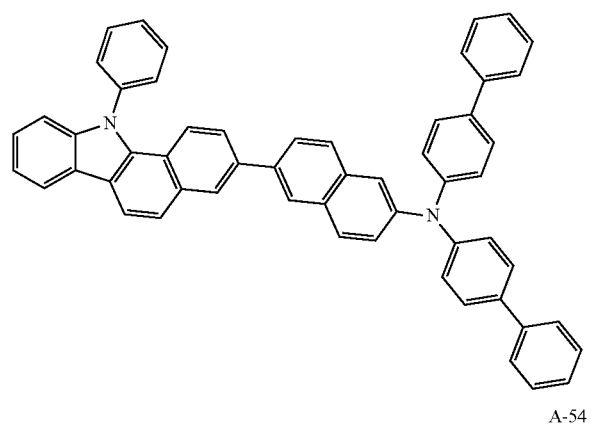
A-54
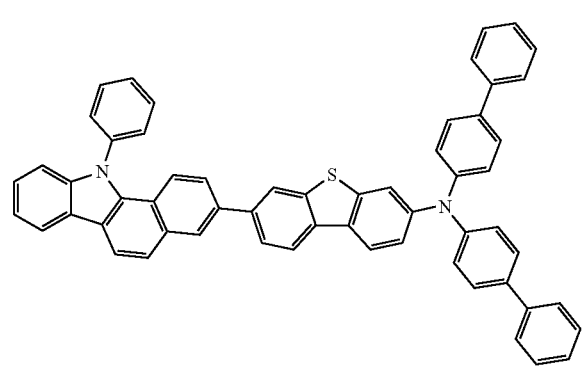
A-55
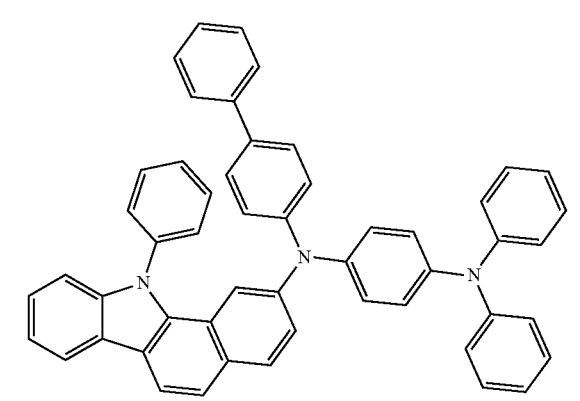
A-56
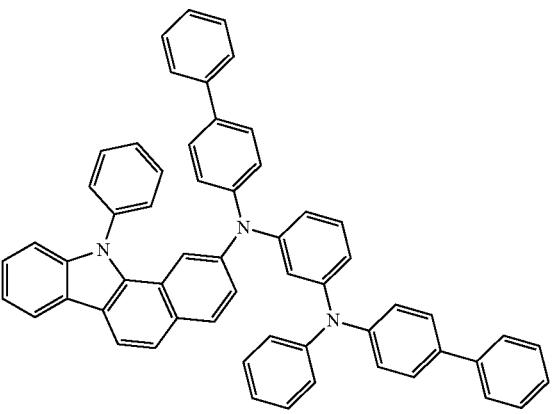
A-57
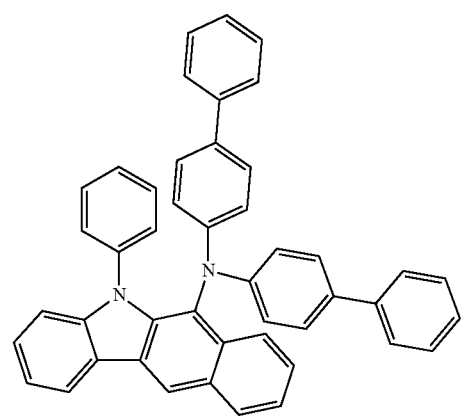
A-58
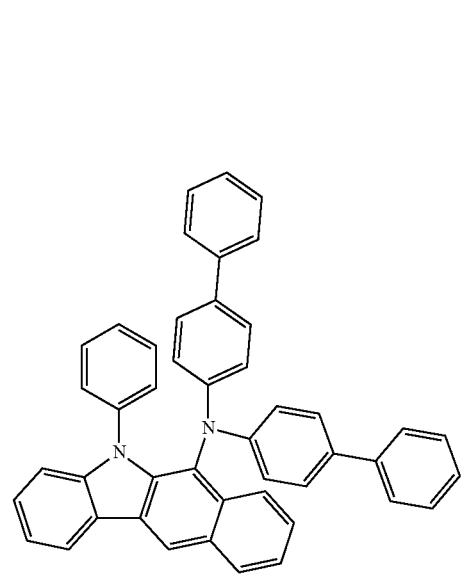

A-59
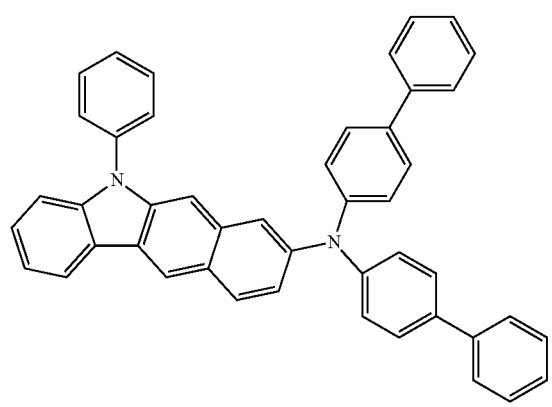
A-60
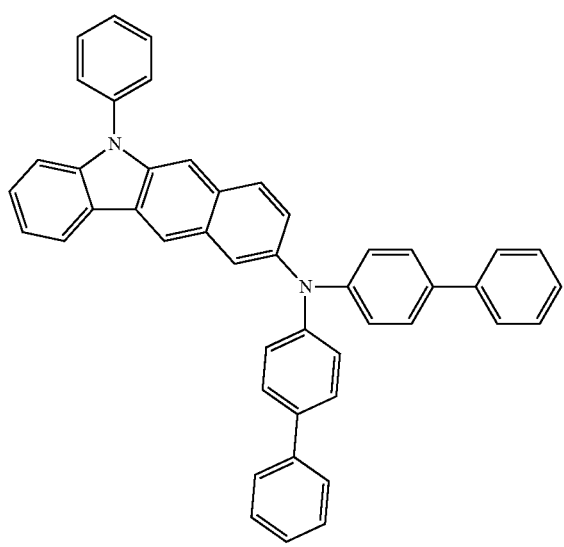
A-61
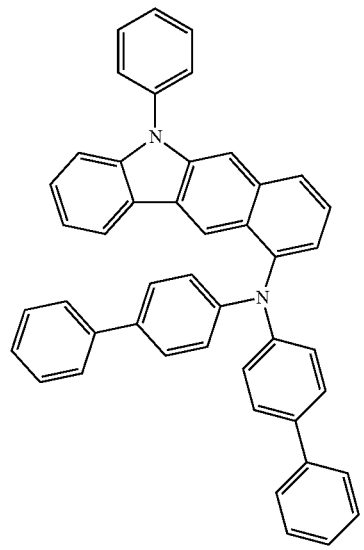
A-62
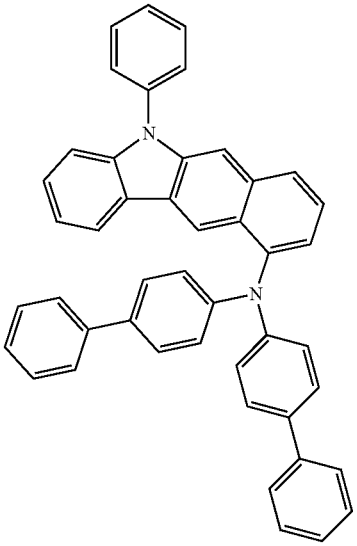
A-63
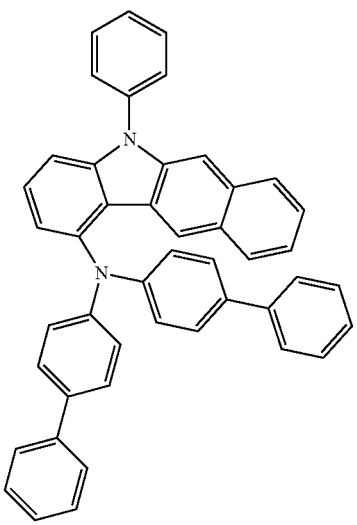
A-64
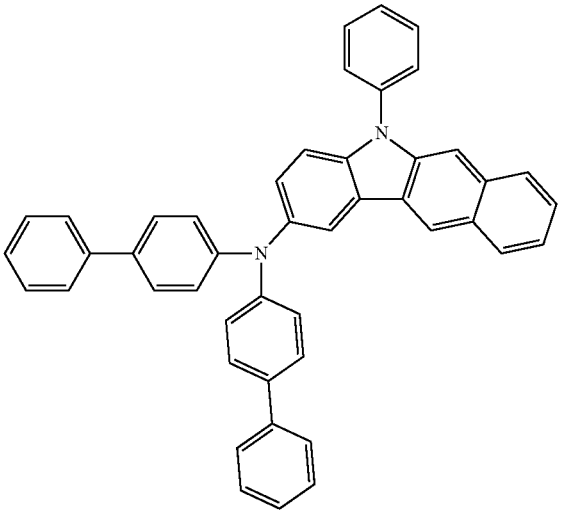

-continued
A-65
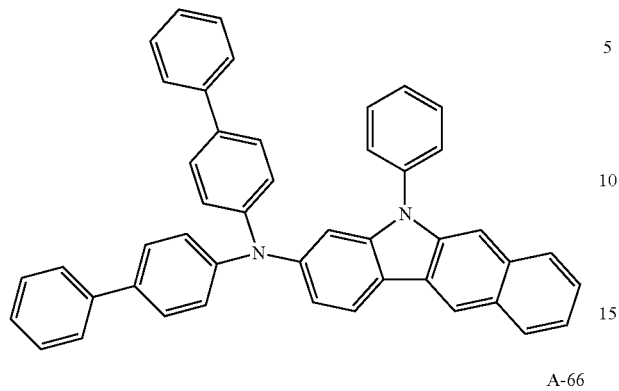
A-66
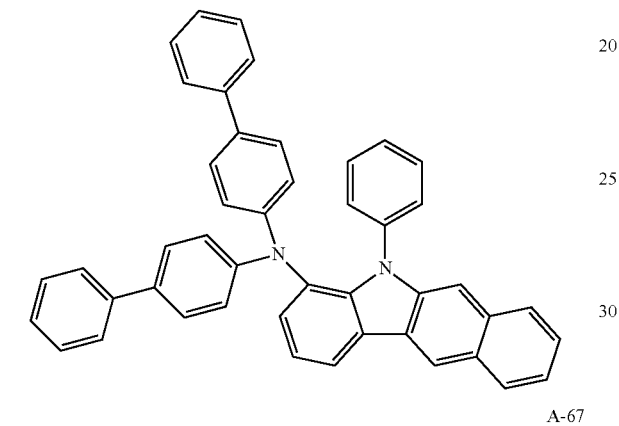
A-67
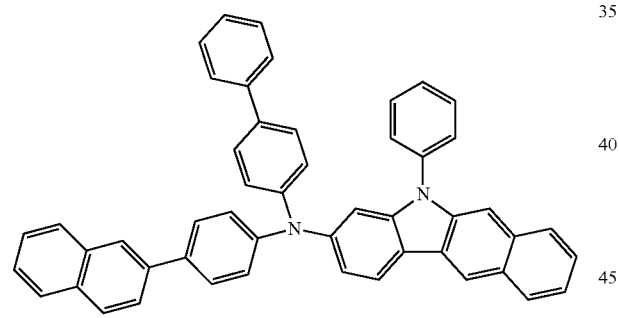
A-68
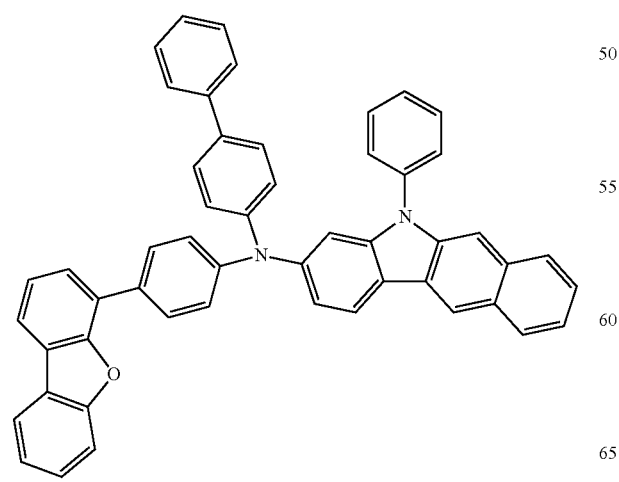
-continued
A-69
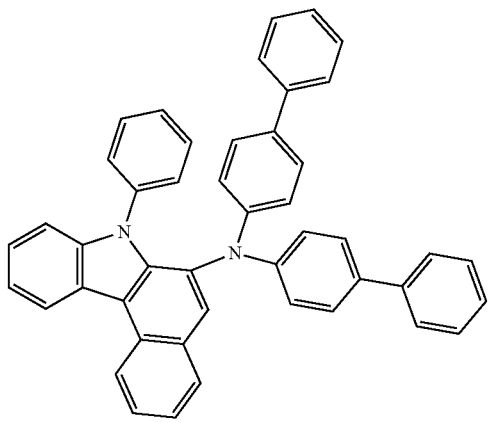
A-70
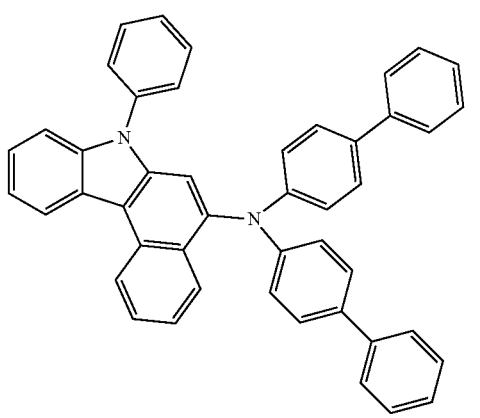
A-71
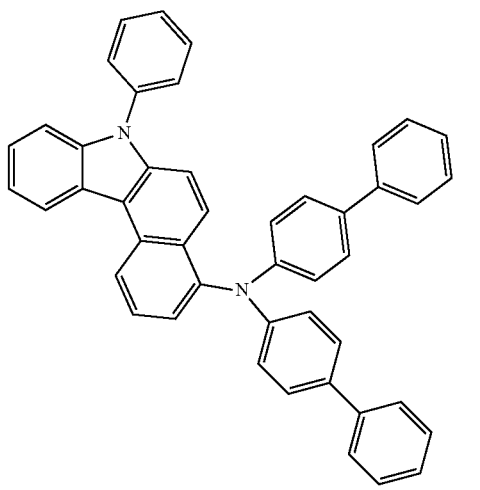

A-72
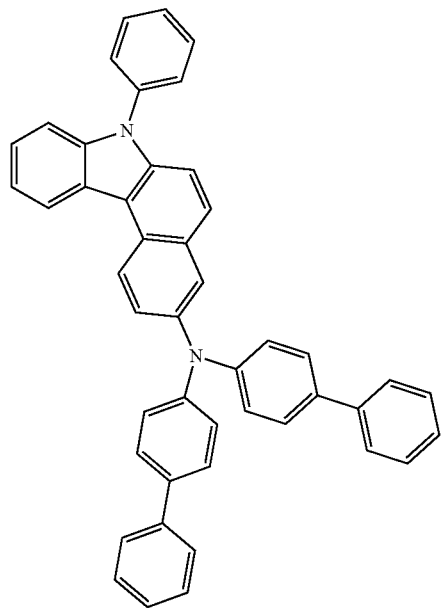
A-73
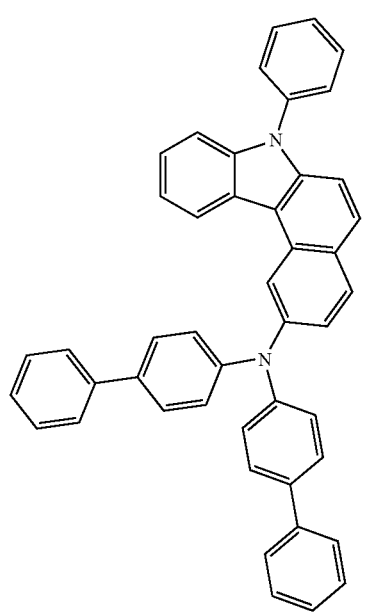
A-74
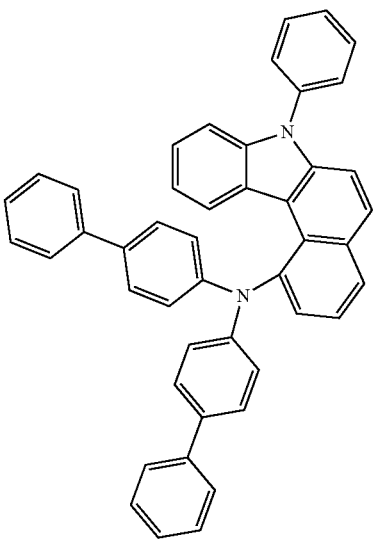
A-75
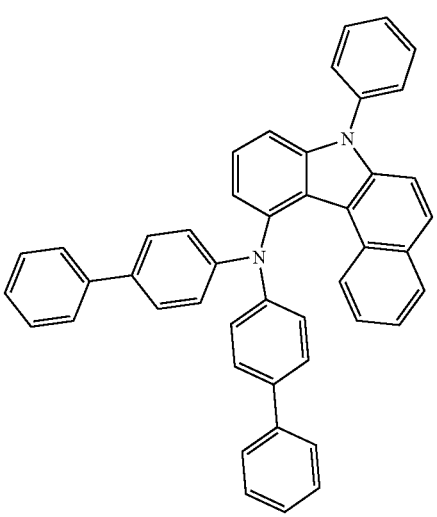
A-76
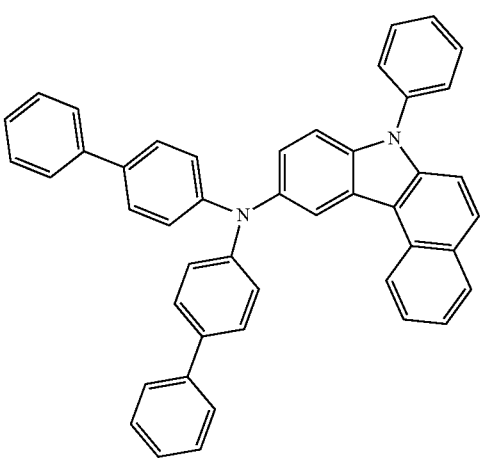

-continued
A-77
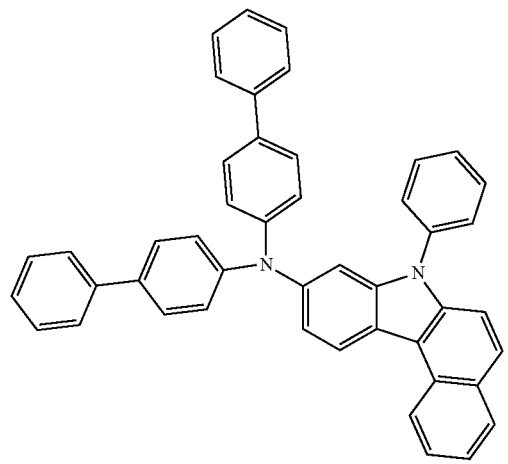
A-78
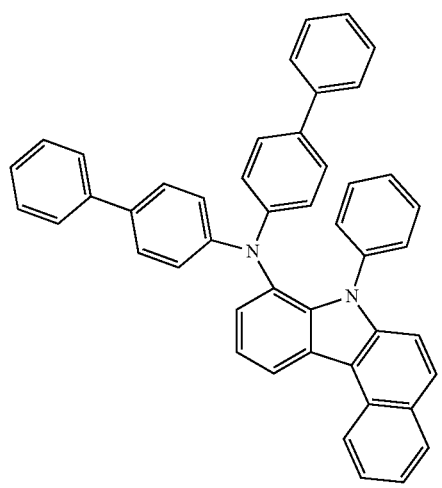
A-79
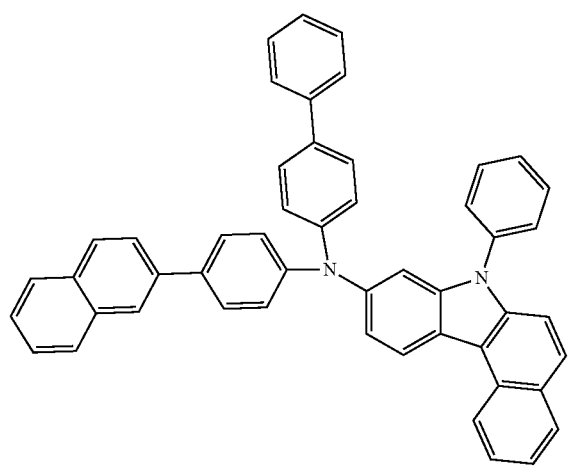
-continued
A-80
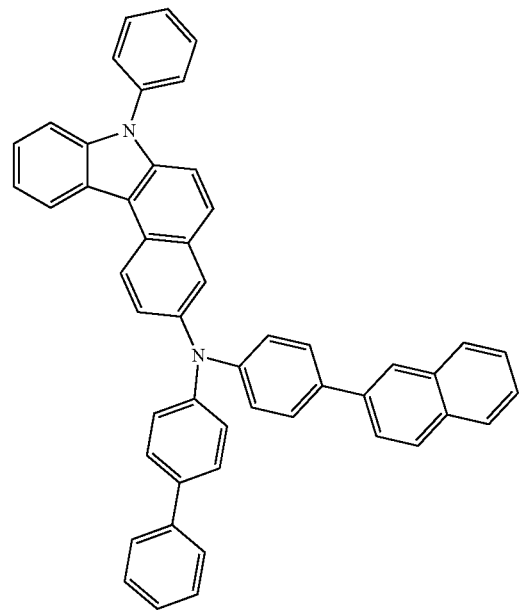
A-81
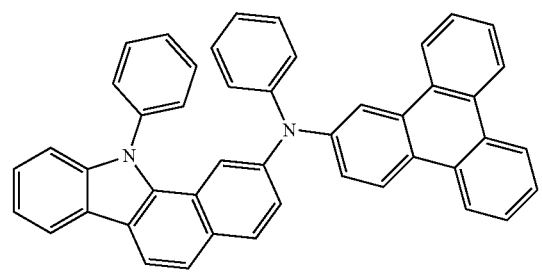
A-82
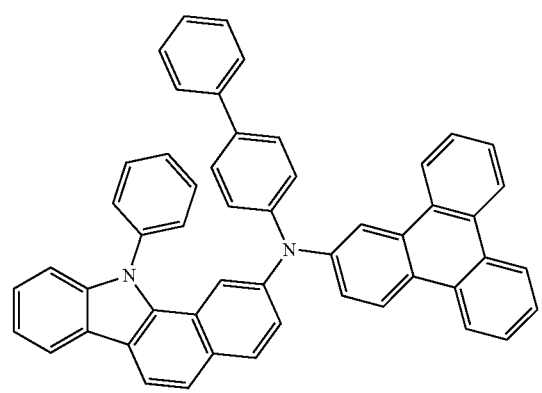

-continued
A-83
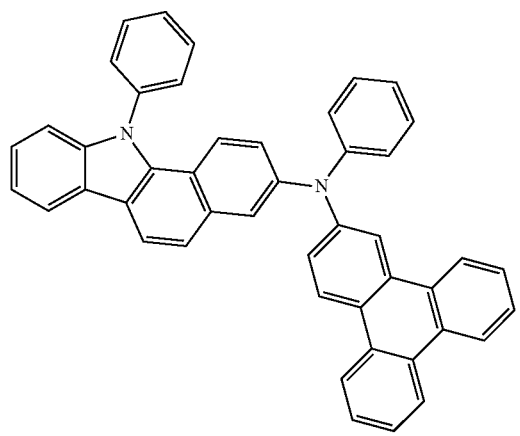
A-86
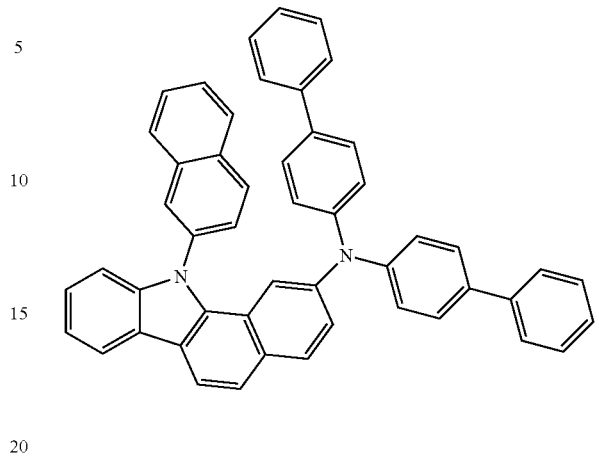
A-84
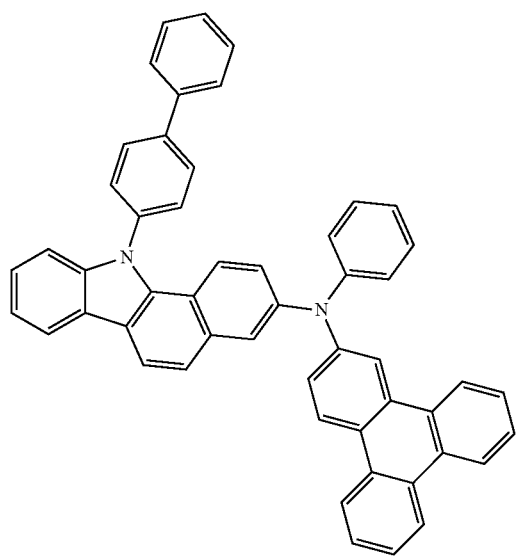
A-87
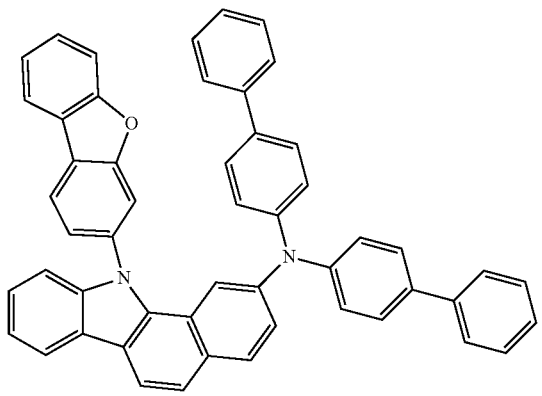
A-85
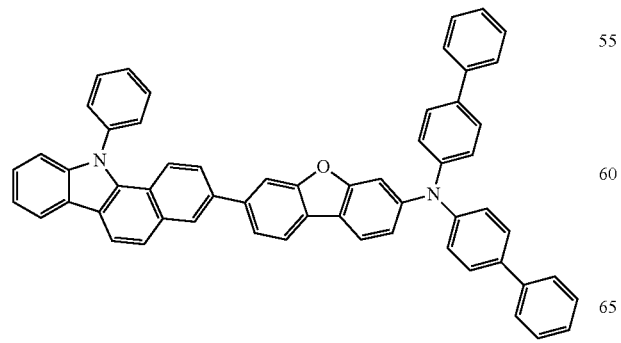
A-88
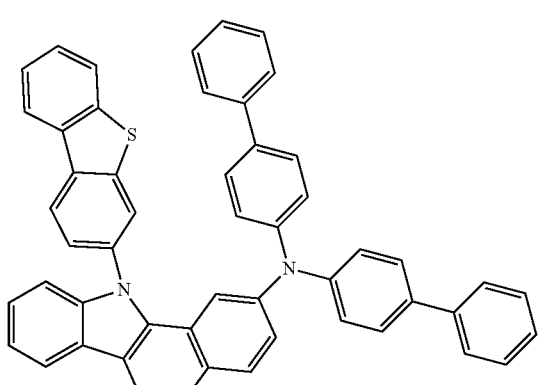

-continued

A-89

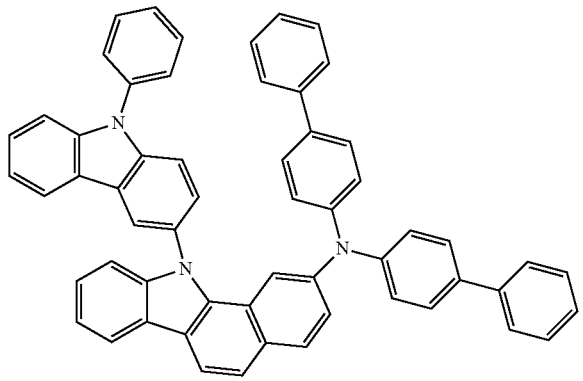

The second compound may be a compound having relatively strong electron characteristics and may be represented by Chemical Formula 3.

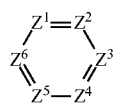

[Chemical Formula 3]

In Chemical Formula 3,
$Z^1$ may be, e.g., N or C-$L^5$-$R^5$,
$Z^2$ may be, e.g., N or C-$L^6$-$R^6$,
$Z^3$ may be, e.g., N or C-$L^7$-$R^7$,
$Z^4$ may be, e.g., N or C-$L^8$-$R^8$,
$Z^5$ may be, e.g., N or C-$L^9$-$R^9$, and
$Z^6$ may be, e.g., N or C-$L^{10}$-$R^{10}$.

In an implementation, at least two of $Z^1$ to $Z^6$ are N,
$L^5$ to $L^{10}$ may each independently be or include, e.g., a single bond, a substituted or unsubstituted C6 to C20 arylene group, a substituted or unsubstituted C2 to C20 heterocyclic group, or a combination thereof, $R^5$ to $R^{10}$ may each independently be or include, e.g., hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an implementation, at least one of $R^5$ to $R^{10}$ may be, e.g., a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

In an implementation, $R^5$ to $R^{10}$ may be separately present or adjacent groups thereof may be linked with each other to form a substituted or unsubstituted aliphatic, aromatic, or heteroaromatic monocyclic ring or a substituted or unsubstituted aliphatic, aromatic, or heteroaromatic polycyclic ring.

The second compound may effectively expand a LUMO energy band by including a nitrogen-containing six-membered (e.g., hexagonal) cyclic moiety, which may be included along with the aforementioned first compound to help greatly improve life-span characteristics of the device using it by increasing a balance of holes and electrons.

In an implementation, two of $Z^1$ to $Z^6$ may be nitrogen (N) and the remainders may be CR", in which R" refers to any substituent selected from $R^5$ to $R^{10}$.

In an implementation, $Z^1$ and $Z^3$ may be nitrogen, $Z^2$ may be N or C-$L^6$-$R^6$, may be N or C-$L^8$-$R^8$, $Z^5$ may be N or C-$L^9$-$R^9$, and $Z^6$ may be N or C-$L^{10}$-$R^{10}$.

In an implementation, at least one of $R^6$ and $R^8$ to $R^{10}$ may be a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

In an implementation, three of $Z^1$ to $Z^6$ may be nitrogen (N) and the remainders may be CR".

In an implementation, $Z^1$, $Z^3$, and $Z^5$ may be nitrogen, $Z^2$ may be N or C-$L^6$-$R^6$, $Z^4$ may be N or C-$L^8$-$R^8$, and $Z^6$ may be N or C-$L^{10}$-$R^{10}$.

In an implementation, at least one of $R^6$, $R^8$, and $R^{10}$ may be a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

In an implementation, $R^5$ to $R^{10}$ may be separately present, and the second compound may be represented by Chemical Formula 3-1.

[Chemical Formula 3-1]

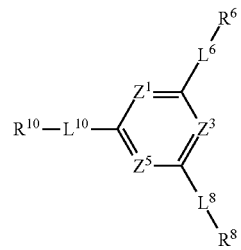

In Chemical Formula 3-1, $Z^1$, $Z^3$, and $Z^5$ may each independently be, e.g., N or CH, at least two of $Z^1$, $Z^3$, and $Z^5$ may be N, $L^6$, $L^8$, $L^{10}$, $R^6$, $R^8$, and $R^{10}$ may be the same as described above, and at least one of $R^6$, $R^8$, and $R^{10}$ may be, e.g., a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

In an implementation, Chemical Formula 3-1 may be represented by Chemical Formula 3-1a or Chemical Formula 3-1b.

[Chemical Formula 3-1a]

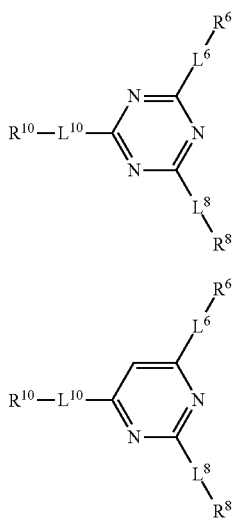

[Chemical Formula 3-1b]

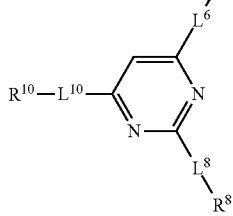

In Chemical Formula 3-1a and Chemical Formula 3-1b, $L^6$, $L^8$, $L^{10}$, $R^6$, $R^8$, and $R^{10}$ may be the same as described above.

In an implementation, adjacent groups of $R^5$ to $R^{10}$ may be linked with each other to form a substituted or unsubstituted aliphatic, aromatic, or heteroaromatic monocyclic ring or a substituted or unsubstituted aliphatic, aromatic, or heteroaromatic polycyclic ring, and at least one of $R^5$ to $R^{10}$ that does not form the ring may be, e.g., a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

As noted, above, in the present specification, the description of adjacent groups thereof being linked with each other to form a substituted or unsubstituted aliphatic, aromatic, or heteroaromatic monocyclic ring or a substituted or unsubstituted aliphatic, aromatic, or heteroaromatic polycyclic ring means that any two adjacent substituents are fused to form a ring. For example, adjacent $R^5$ and $R^6$, $R^6$ and $R^7$, $R^7$ and $R^8$, $R^8$ and $R^9$, or $R^9$ and $R^{10}$ in Chemical Formula 3 may be fused with each other to form a heteroaromatic polycyclic ring together with the nitrogen-containing hexagonal ring moiety substituted therewith. In an implementation, examples of the formed heteroaromatic polycyclic ring may be a substituted or unsubstituted quinazolinyl group, a substituted or unsubstituted quinoxalinyl group, a substituted or unsubstituted benzofuranpyrimidinyl group, a substituted or unsubstituted benzothiophenepyrimidinyl group, and the like, e.g., $R^6$ and $R^7$ of Chemical Formula 3 may be fused with each other to form a heteroaromatic polycyclic ring together with the nitrogen-containing hexagonal ring moiety, thereby providing a compound represented by Chemical Formula 3-2 or Chemical Formula 3-3.

[Chemical Formula 3-2]

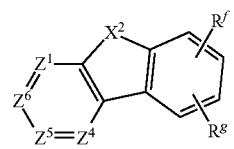

[Chemical Formula 3-3]

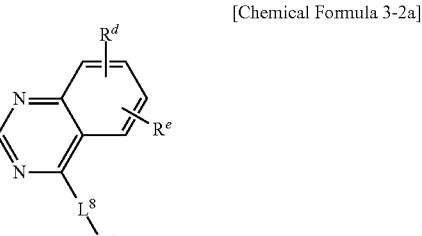

In Chemical Formula 3-2 and Chemical Formula 3-3, $Z^1$, $Z^4$, $Z^5$, $Z^6$, $L^{10}$, and $R^{10}$ may be the same as described above, $X^2$ is O or S, $R^d$, $R^e$, $R^f$, and $R^g$ may each independently be, e.g., hydrogen, deuterium, a halogen, a cyano group, a C1 to C20 alkyl group, a C6 to C30 aryl group, a C2 to C30 heteroaryl group, or a combination thereof.

In an implementation, $Z^1$ and $Z^5$ of Chemical Formula 3-2 may each be N.

In an implementation, $Z^1$ and $Z^4$ of Chemical Formula 3-2 may each be N.

In an implementation, Chemical Formula 3-2 may be represented by Chemical Formula 3-2a or Chemical Formula 3-2b.

[Chemical Formula 3-2a]

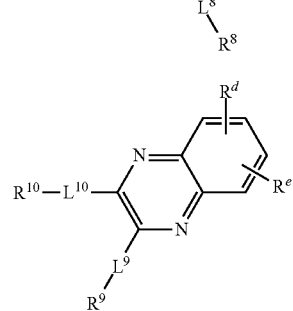

[Chemical Formula 3-2b]

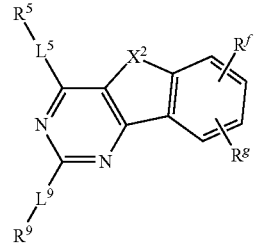

In Chemical Formula 3-2a and Chemical Formula 3-2b, $L^8$ to $L^{10}$, $R^8$ to $R^{10}$, $R^d$, and $R^e$ may be the same as described above.

In an implementation, $Z^1$ and $Z^5$ of Chemical Formula 3-3 may each be N.

In an implementation, $Z^4$ and $Z^6$ of Chemical Formula 3-3 may each be N.

In an implementation, Chemical Formula 3-3 may be represented by Chemical Formula 3-3a or Chemical Formula 3-3b.

[Chemical Formula 3-3a]

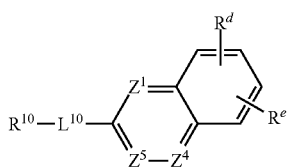

[Chemical Formula 3-3b]

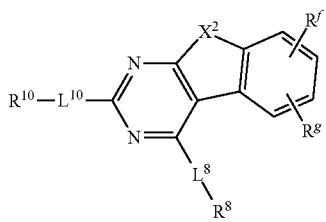

In Chemical Formula 3-3a and Chemical Formula 3-3b, $X^3$, $L^5$, $L^8$, $L^9$, $L^{10}$, $R^5$, $R^8$, $R^9$, $R^{10}$, $R^f$, and $R^g$ may be the same as described above.

In an implementation, $R^5$ to $R^{10}$ of Chemical Formula 3 may each independently be, e.g., hydrogen, a substituted or unsubstituted C6 to C30 aryl group, or a substituted or unsubstituted C2 to C30 heterocyclic group.

In an implementation, $R^5$ to $R^{10}$ may each independently be, e.g., hydrogen, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, a substituted or unsubstituted pyrimidinyl group, a substituted or unsubstituted triazinyl group, a substituted or unsubstituted benzofuranpyrimidinyl group, or a substituted or unsubstituted benzothiophenepyrimidinyl group.

In an implementation, at least one of $R^5$ to $R^{10}$ may be, e.g., a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

As noted above, "substituted" refers to replacement of at least one hydrogen by at least one of a phenyl group, a biphenyl group, a terphenyl group, a naphthyl group, a dibenzofuranyl group, and a dibenzothiophenyl group.

In an implementation, $R^5$ to $R^{10}$ may each independently be, e.g., a group of the following Group I and Group II. In an implementation, at least one of $R^5$ to $R^{10}$ may each be a group of the following Group II.

[Group I]

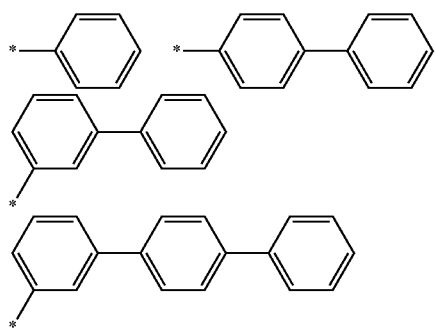

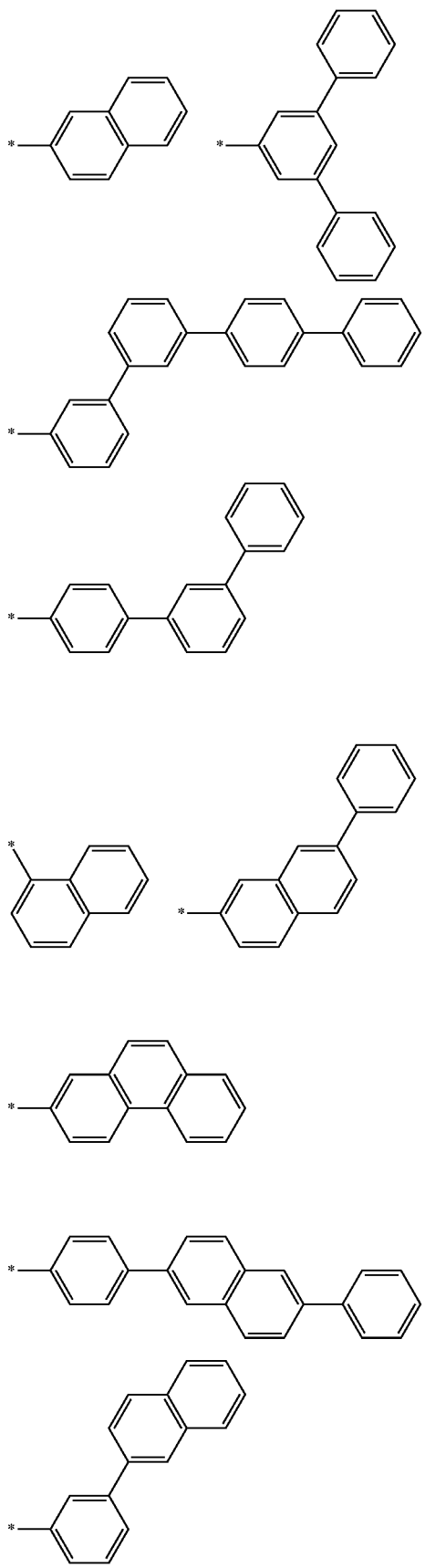

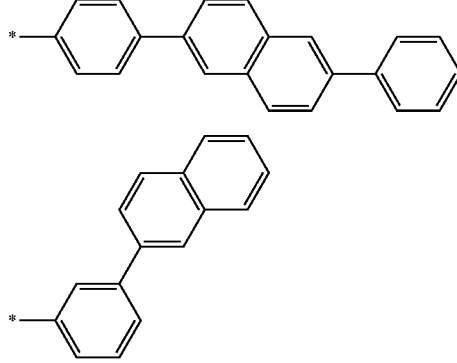

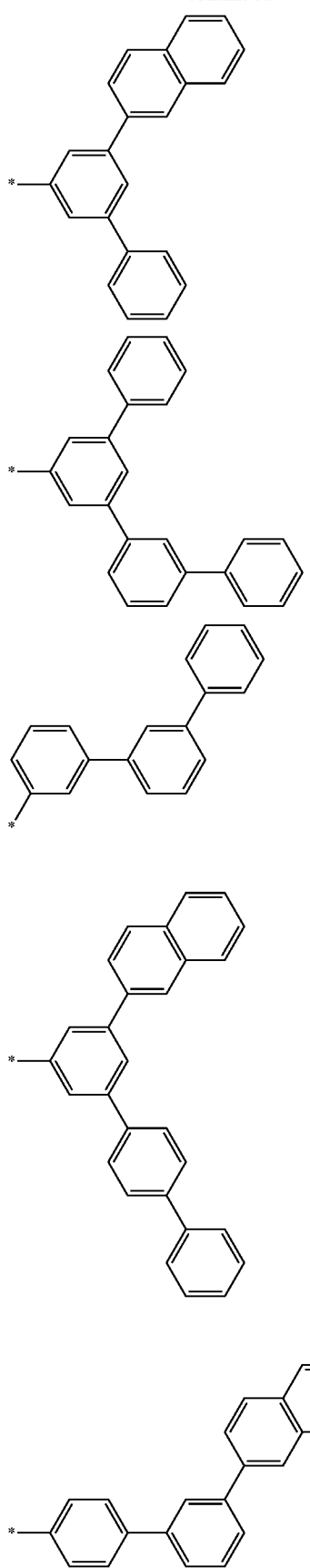
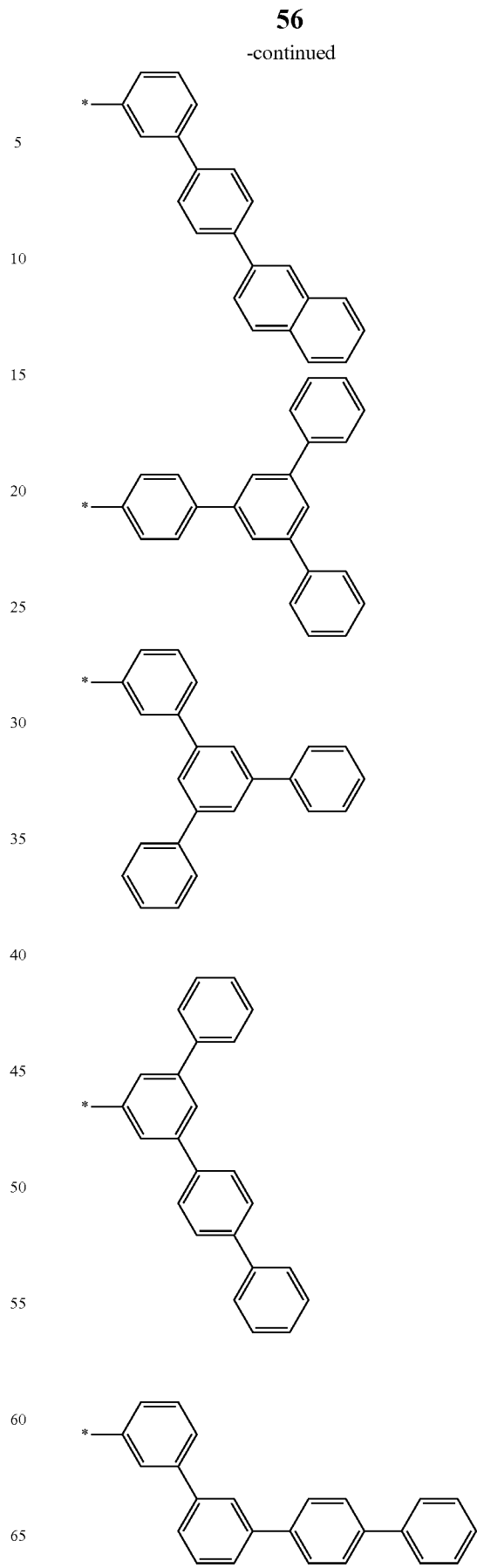

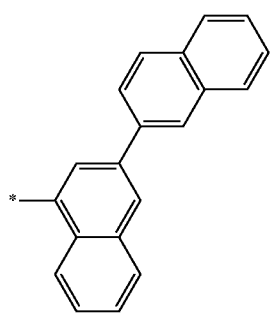
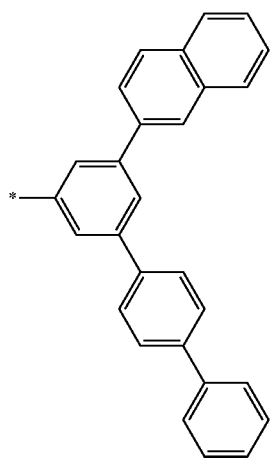
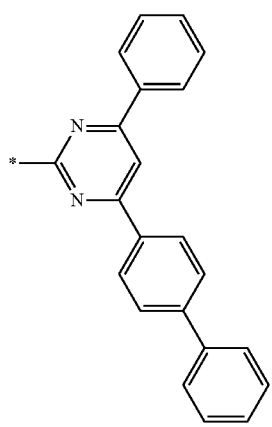
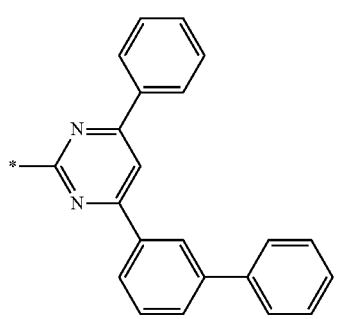
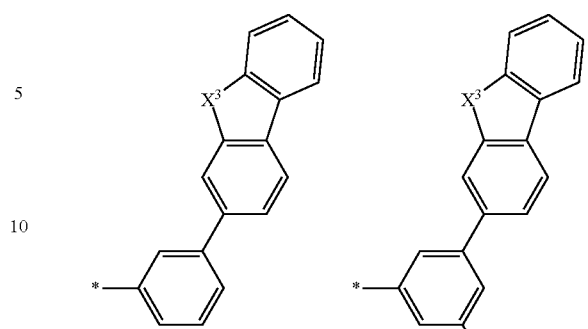
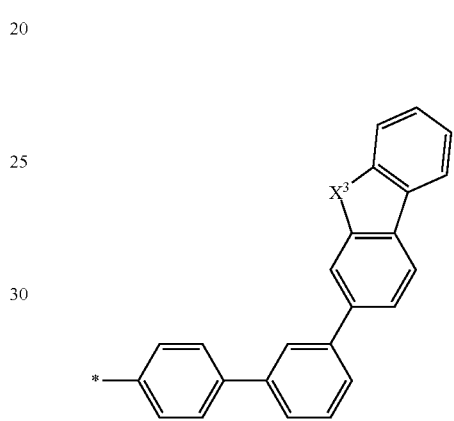
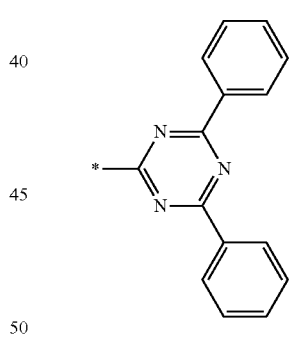
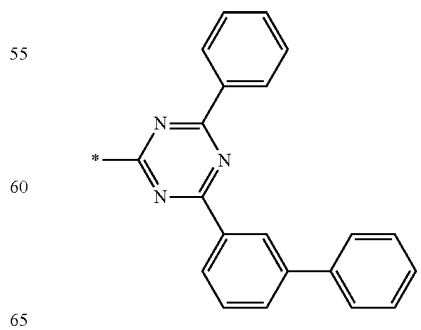

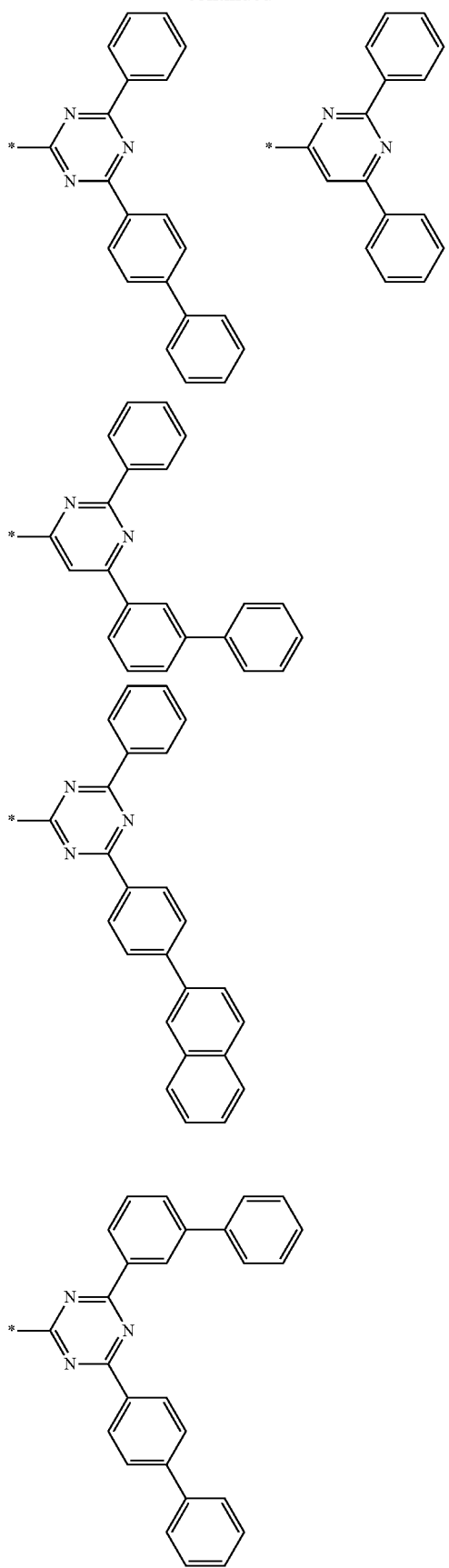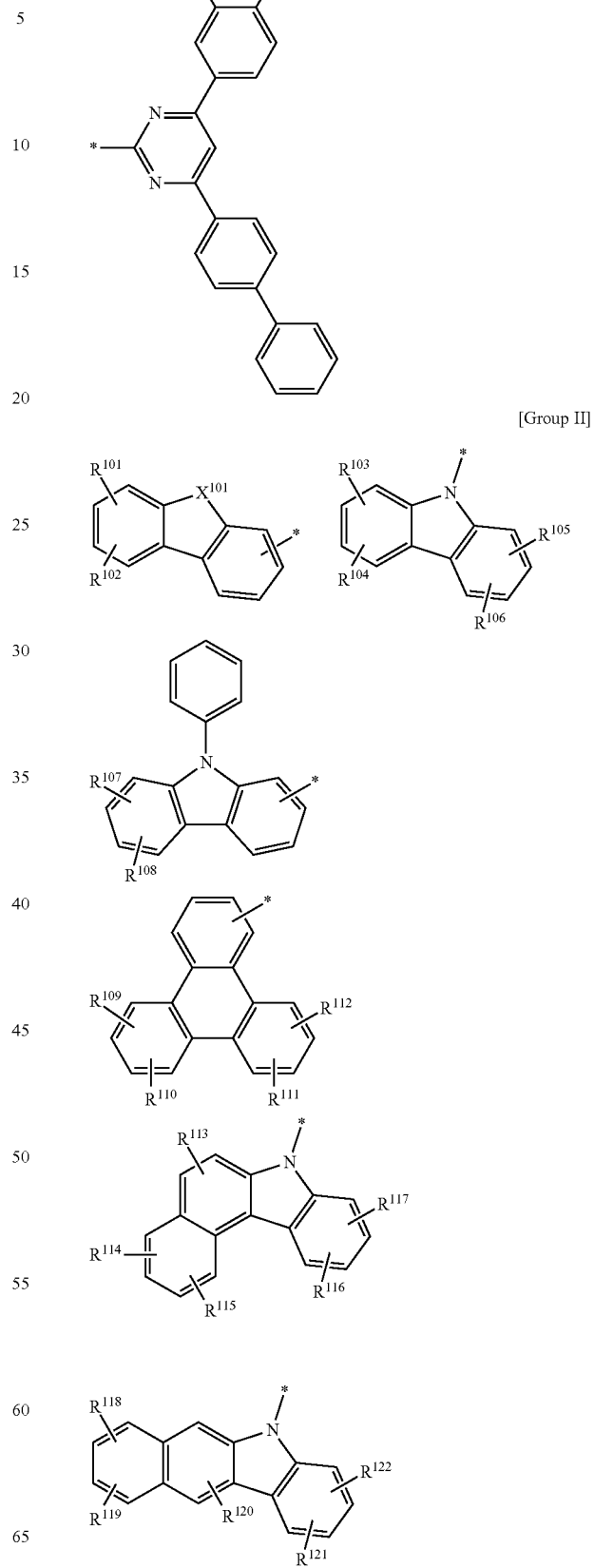
[Group II]

-continued

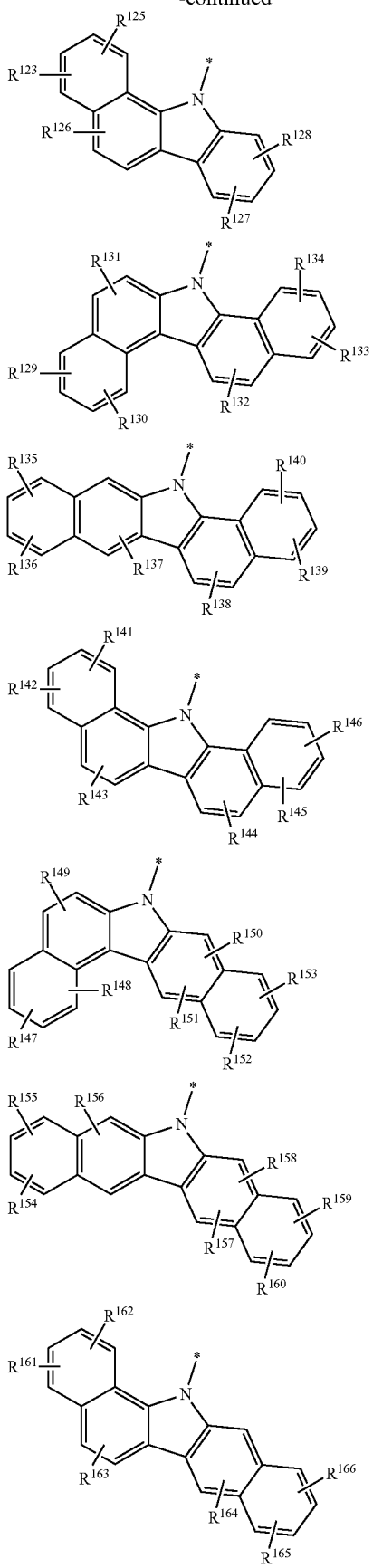

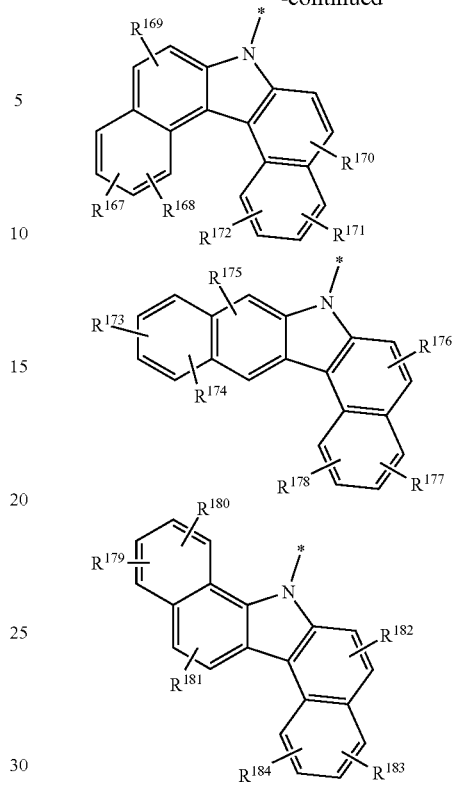

In Group I and Group II, $X^3$ and $X^{101}$ may each independently be, e.g., O or S, $R^{101}$ to $R^{123}$ and $R^{125}$ to $R^{184}$ may each independently be, e.g., hydrogen, deuterium, a halogen, a cyano group, a C1 to C20 alkyl group, a C6 to C30 aryl group, a C2 to C30 heteroaryl group, or a combination thereof, and

* is a linking point.

In an implementation, Chemical Formula 3 may be represented by Chemical Formula 3-1a or Chemical Formula 3-3a.

In an implementation, in Chemical Formula 3-1a, $L^6$, $L^8$, and $L^{10}$ may each independently be, e.g., a single bond or a substituted or unsubstituted phenylene group, $R^6$, $R^8$, and $R^{10}$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, and at least one of $R^6$, $R^8$ and $R^{10}$ may be, e.g., a substituted or unsubstituted triphenylene group, a substituted or unsubstituted carbazolyl group, a substituted or unsubstituted dibenzofuranyl group, or a substituted or unsubstituted dibenzothiophenyl group.

In an implementation, in Chemical Formula 3-3a, $L^5$ and $L^9$ may each independently be, e.g., a single bond or a substituted or unsubstituted phenylene group, $R^5$ and $R^9$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, at least one of $R^5$ and $R^9$ may be, e.g., a substituted or unsubstituted carbazolyl group, a substituted or unsubstituted dibenzofuranyl group, or a substituted or unsubstituted dibenzothiophenyl group, and $R^f$ and $R^g$ may each independently be, e.g., hydrogen, deuterium, a C1 to C10 alkyl group, a C6 to C12 aryl group, or a combination thereof.

In an implementation, the second compound may be, e.g., a compound of the following Group 2.

[Group 2]

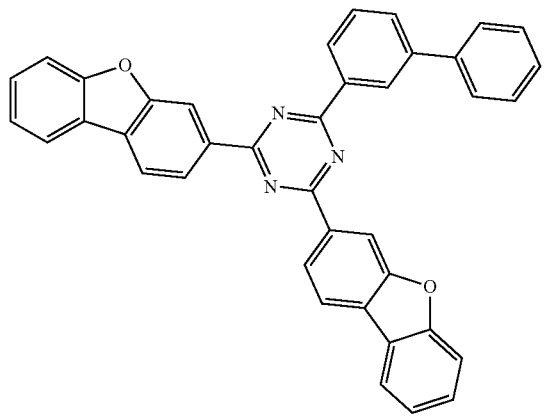

B-1

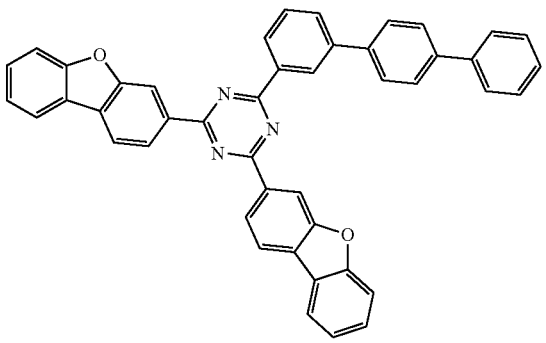

B-2

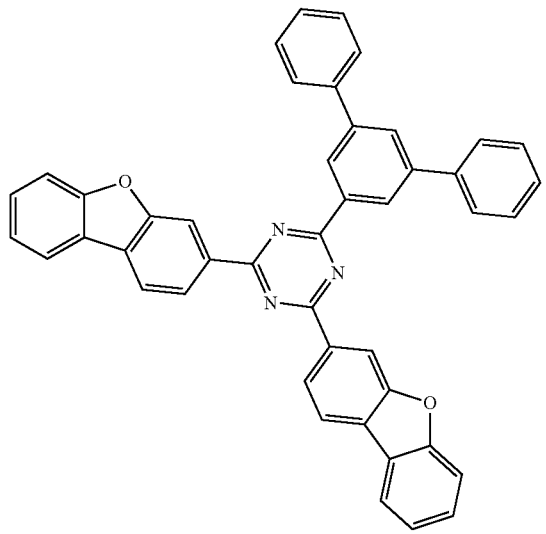

B-3

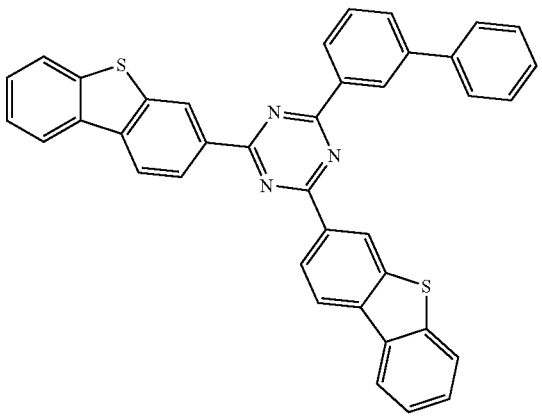

B-4

-continued
B-5
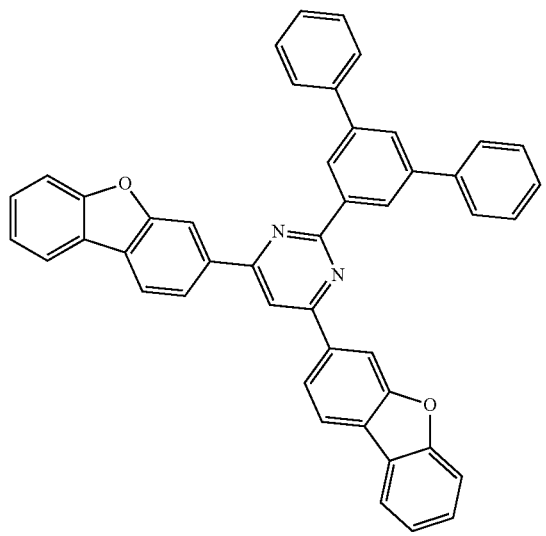
B-6
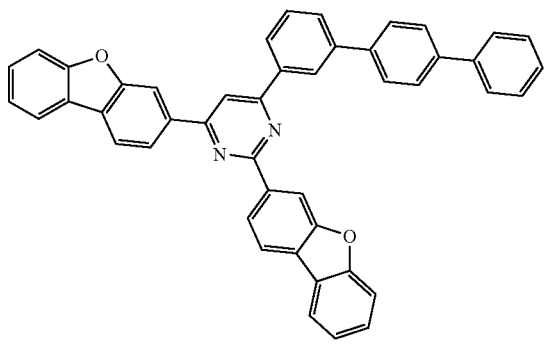
B-7
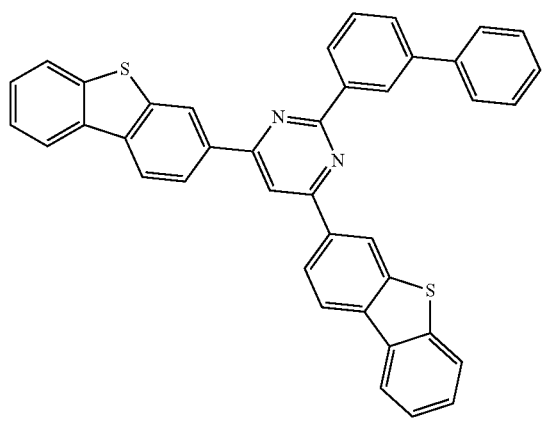
B-8
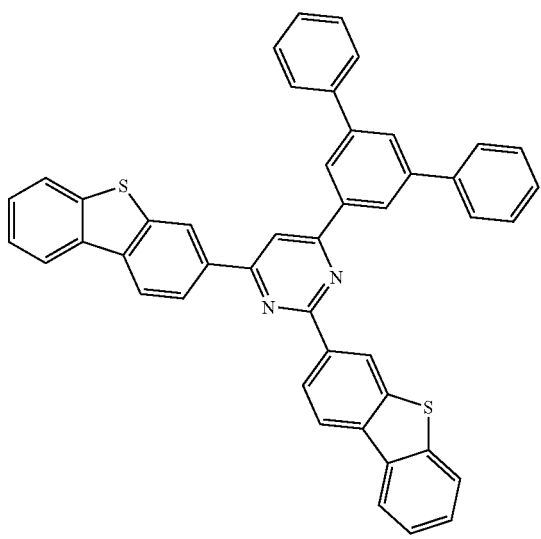
B-9
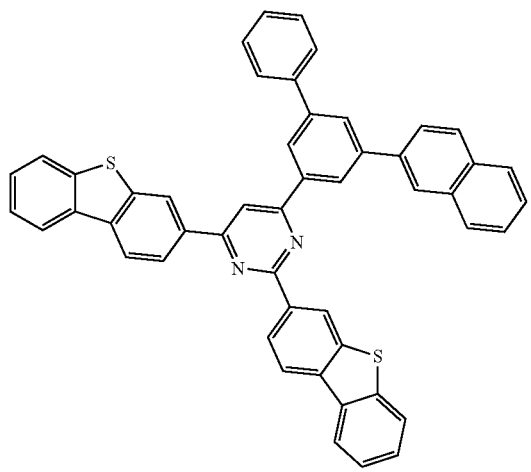
B-10
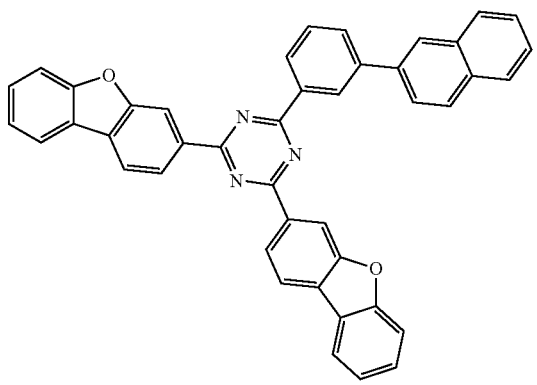

-continued
B-11
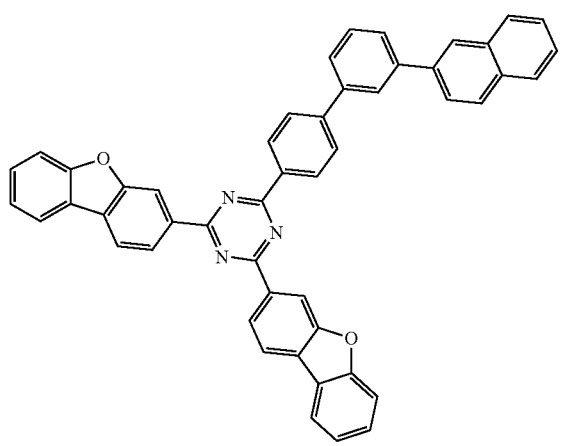
B-12
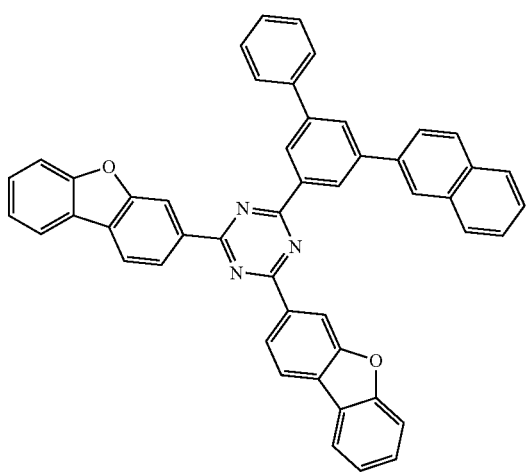
B-13
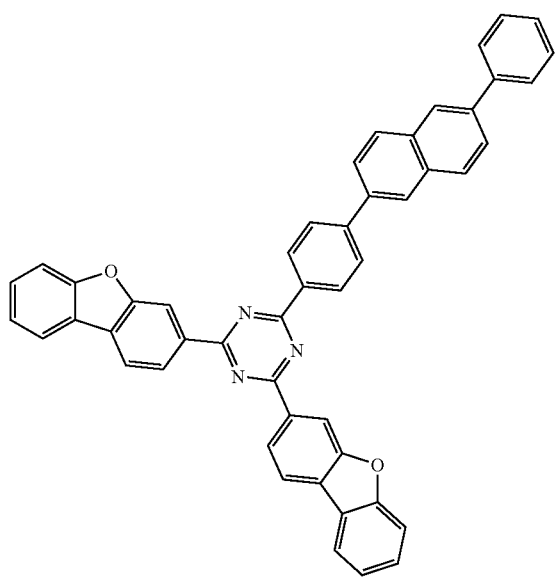
B-14
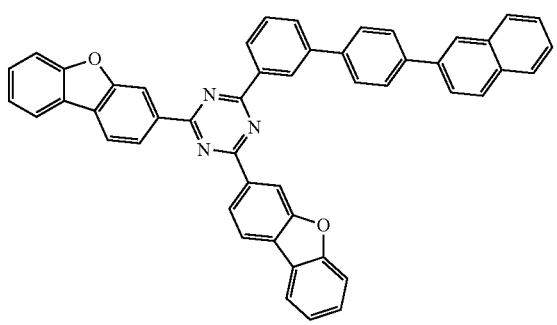
B-15
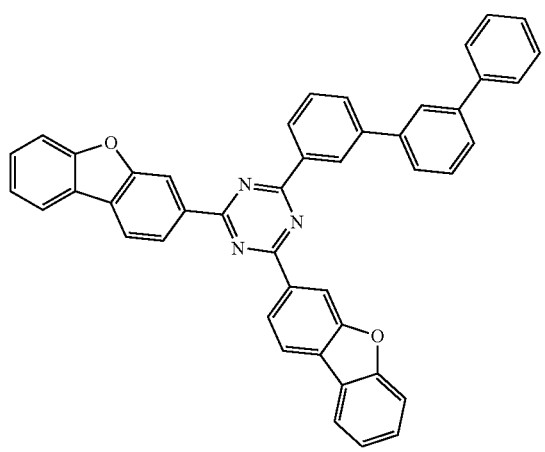
B-16
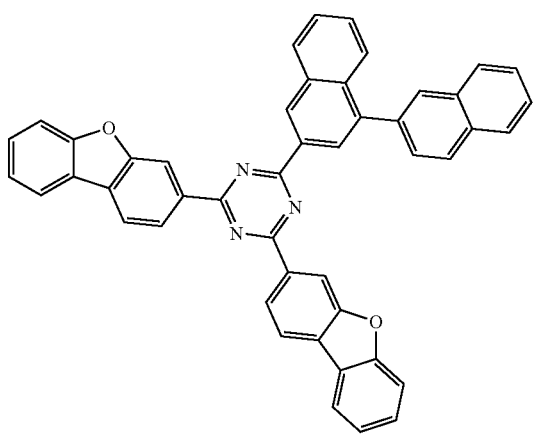

-continued
B-17
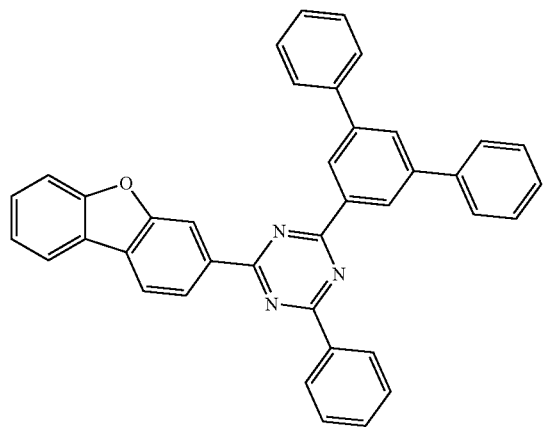
B-18
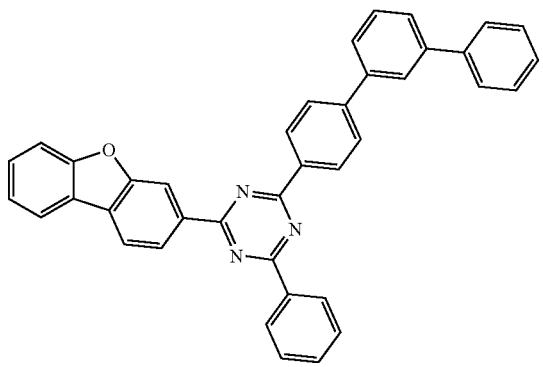
B-19
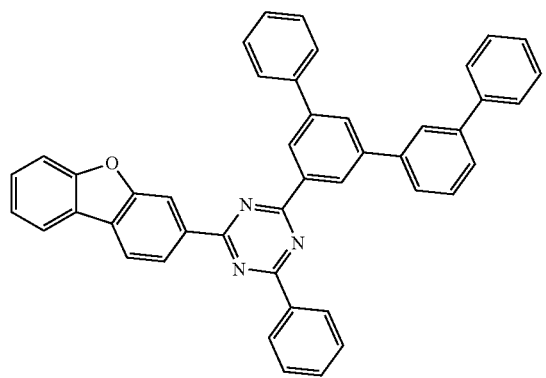
B-20
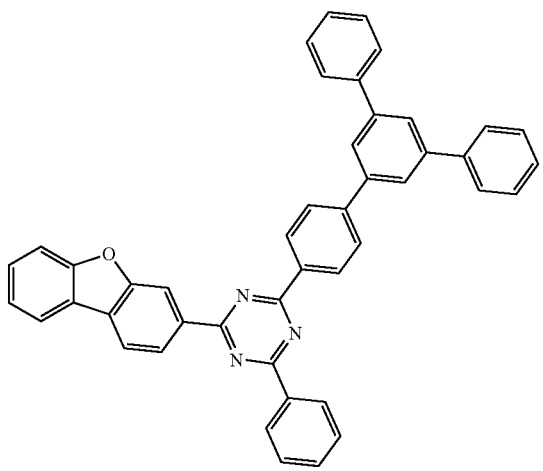
B-21
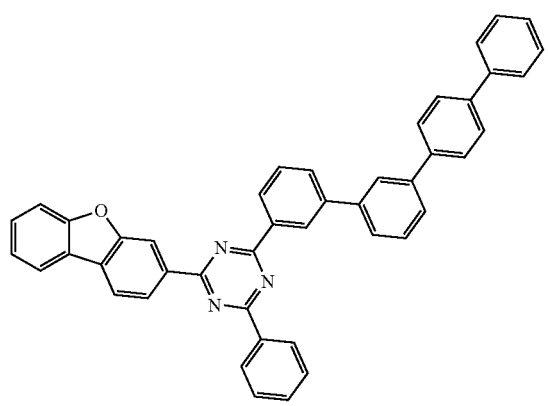
B-22
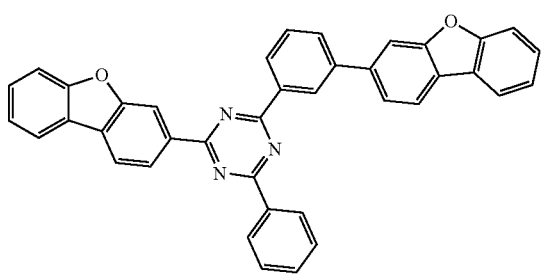

-continued
B-23
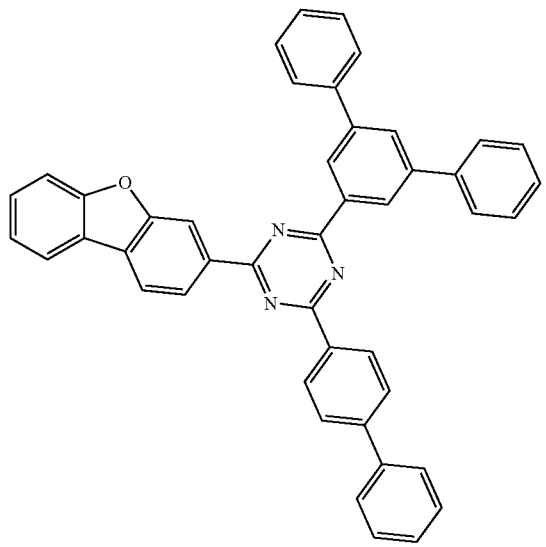
B-24
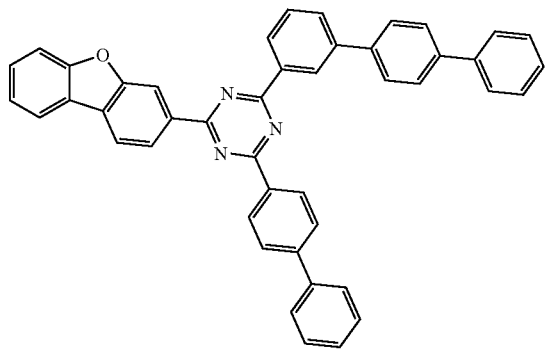
B-25
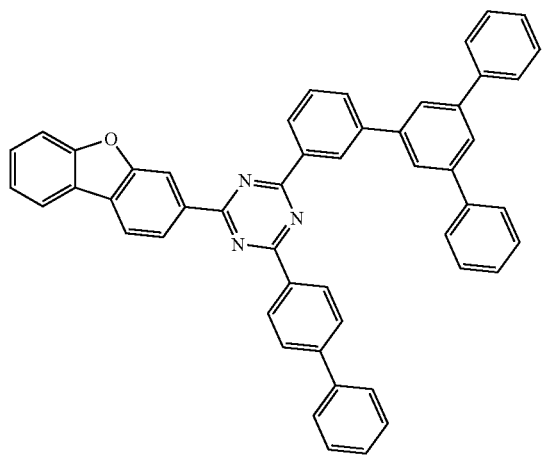
B-26
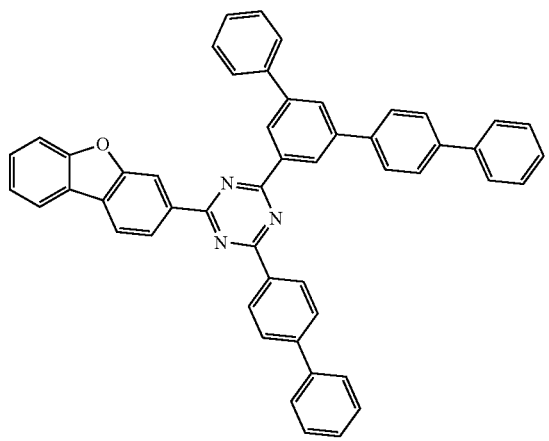
B-27
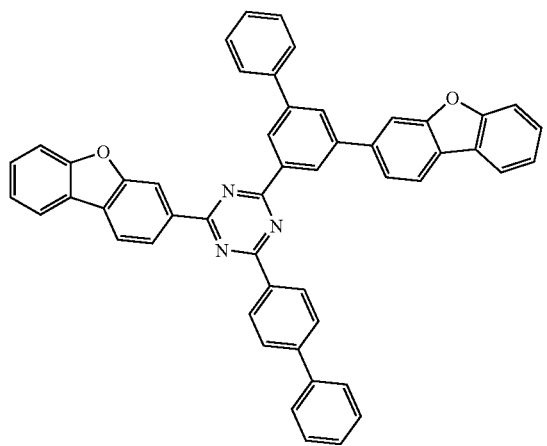
B-28
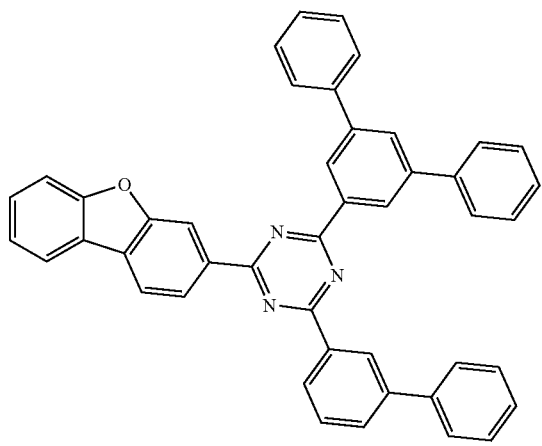

-continued
B-29
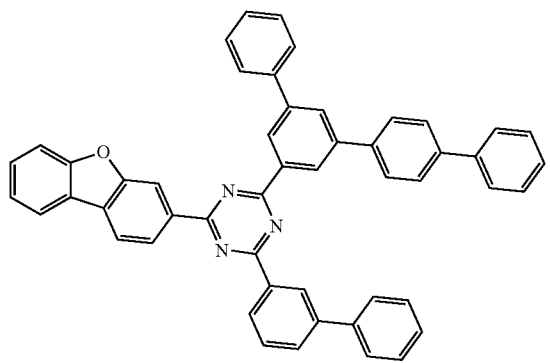
B-30
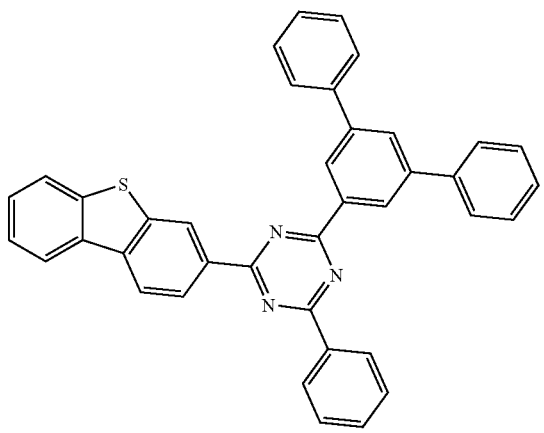
B-31
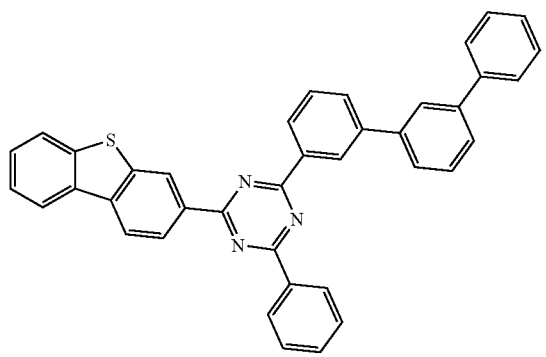
B-32
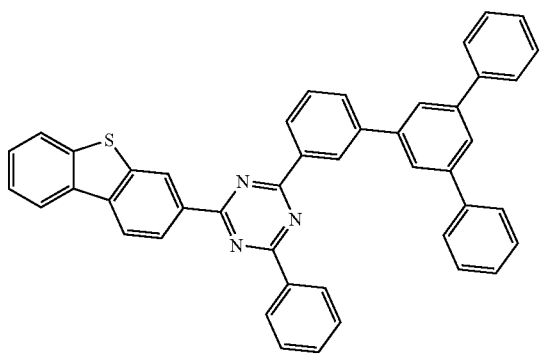
B-33
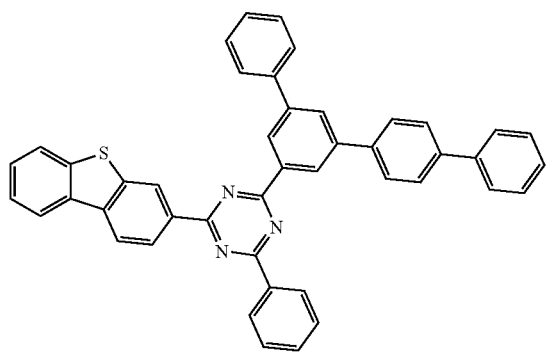
B-34
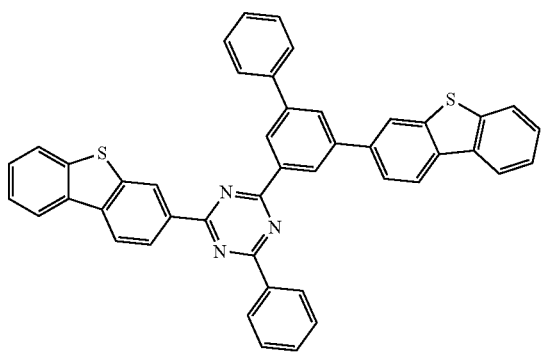

-continued
B-35
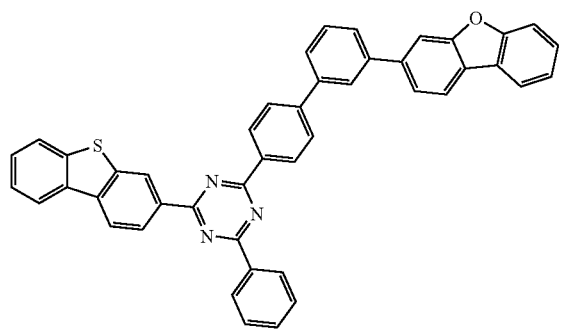
B-36
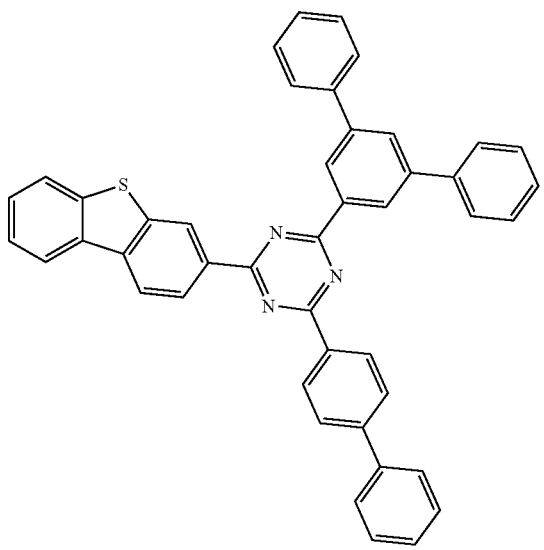
B-37
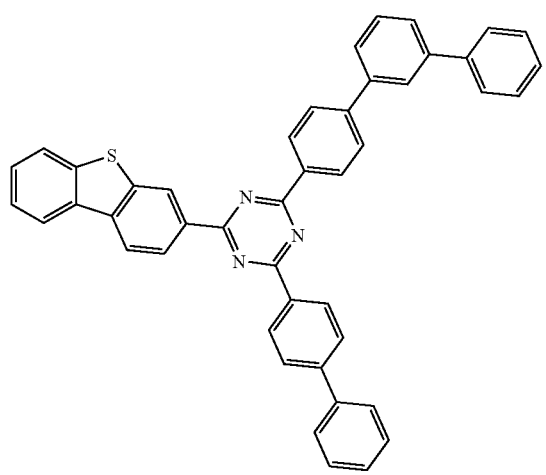
B-38
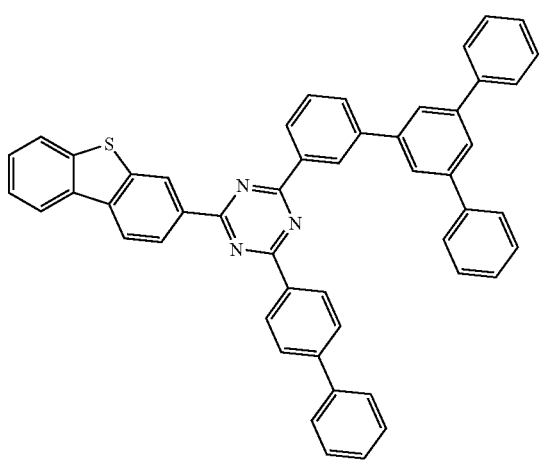
B-39
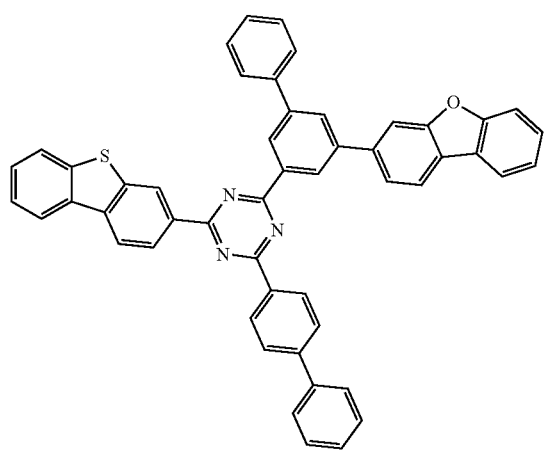
B-40
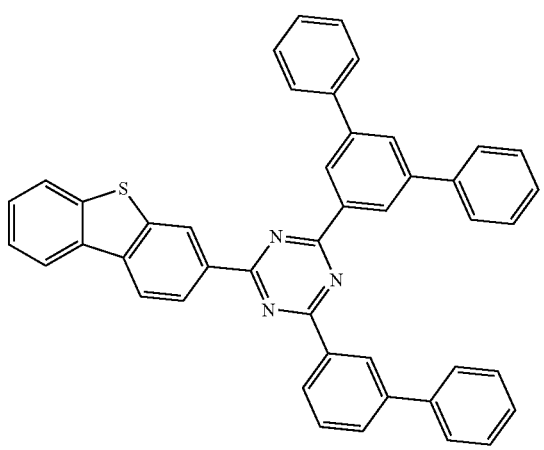

-continued
B-41
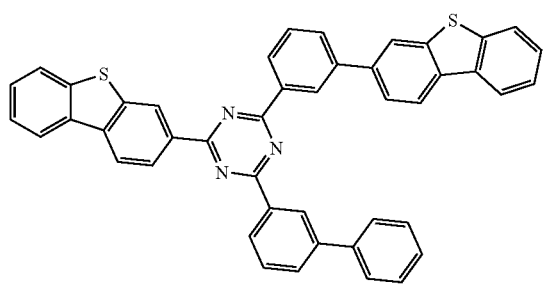
B-42
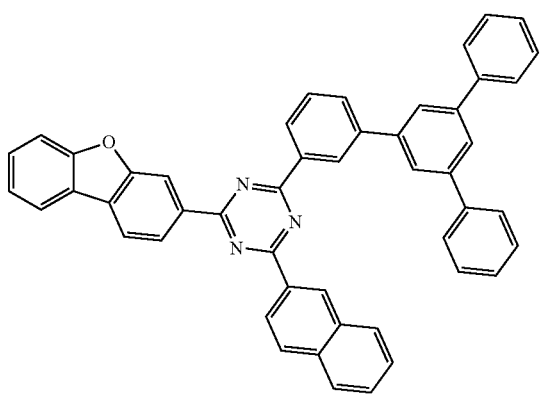
B-43
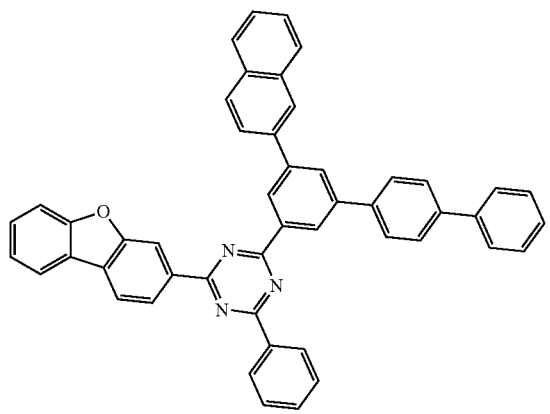
B-44
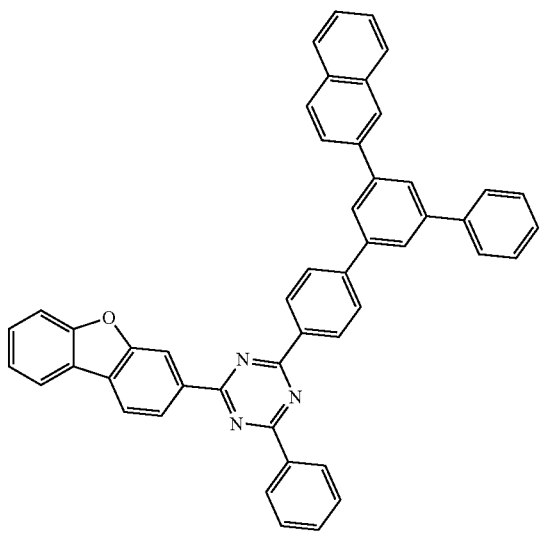
B-45
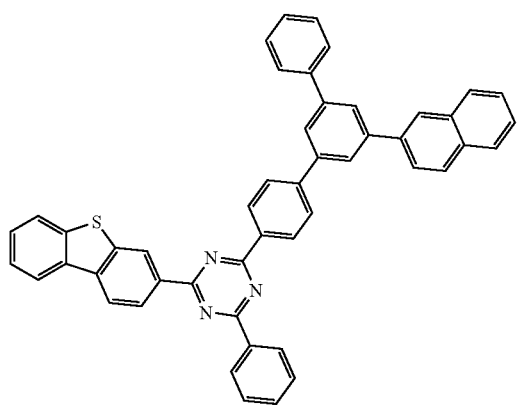
B-46
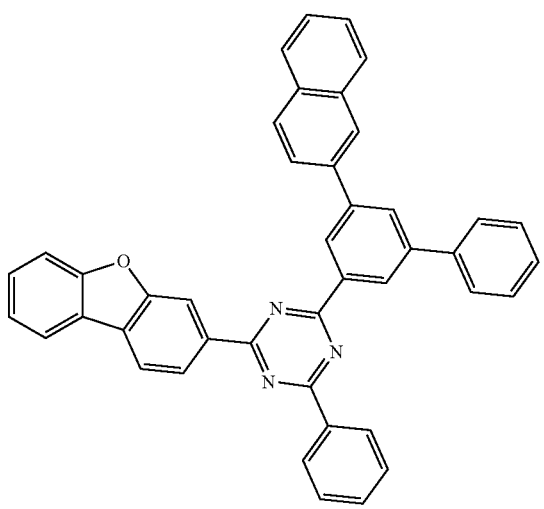

-continued
B-47
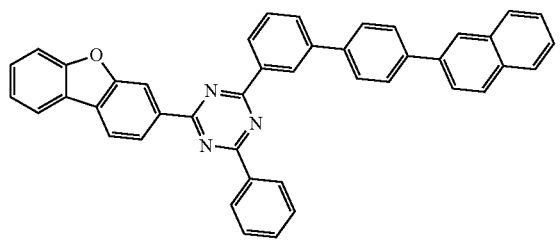
B-48
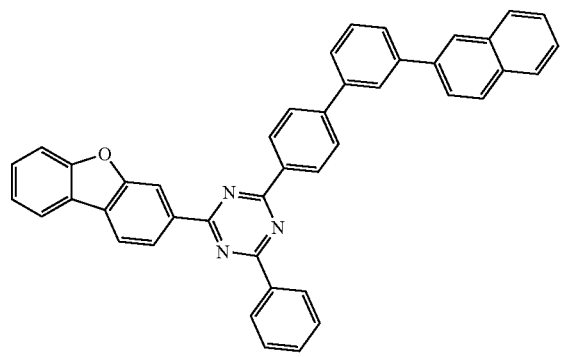
B-49
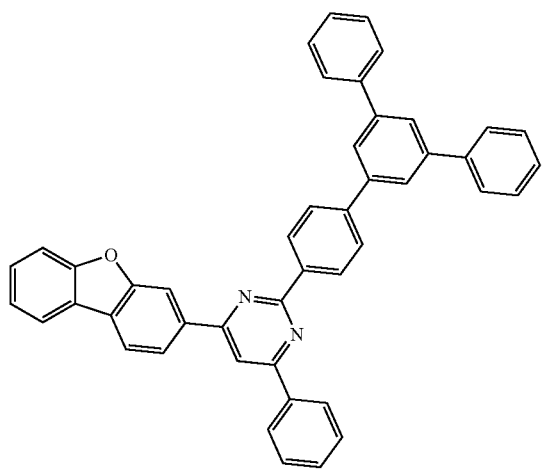
B-50
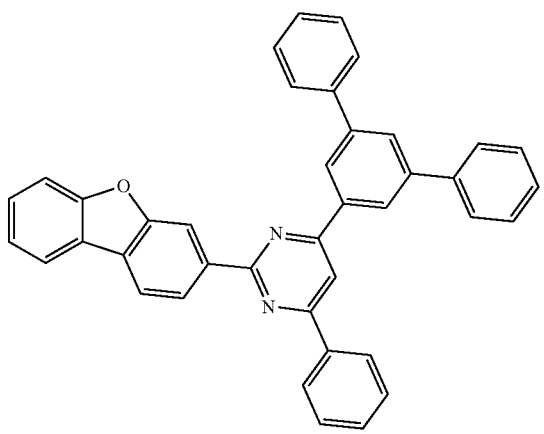
B-51
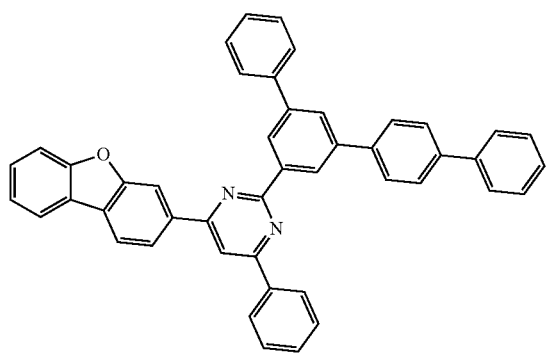
B-52
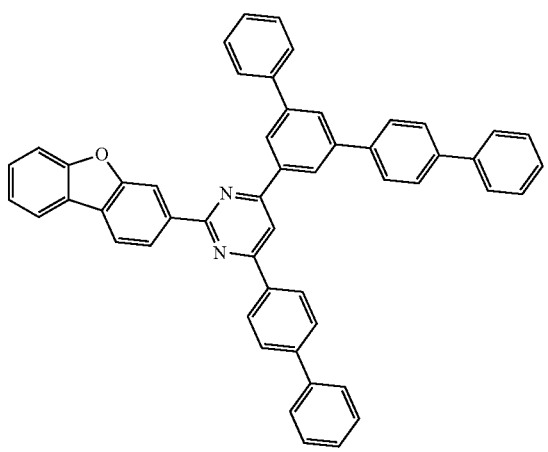

-continued
B-53
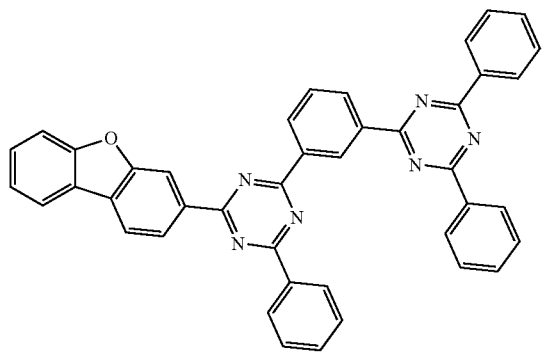
B-54
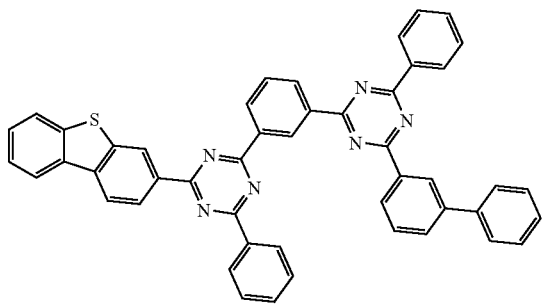
B-55
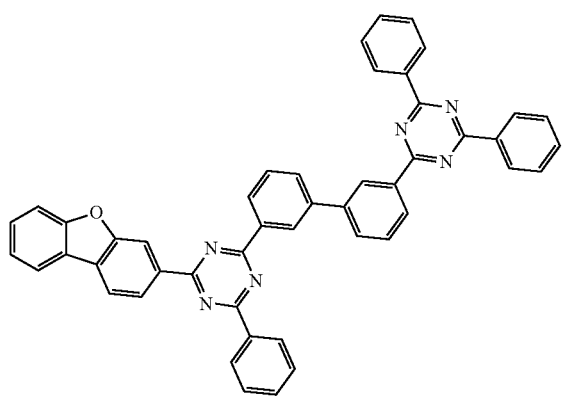
B-56
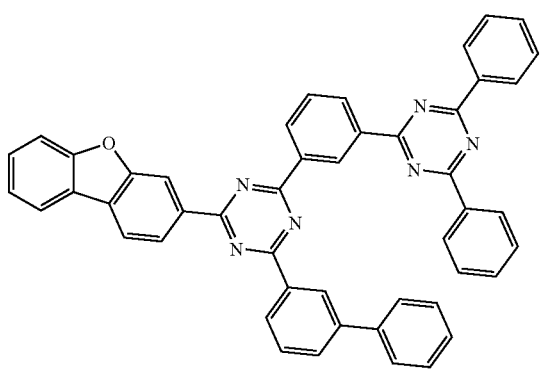
B-57
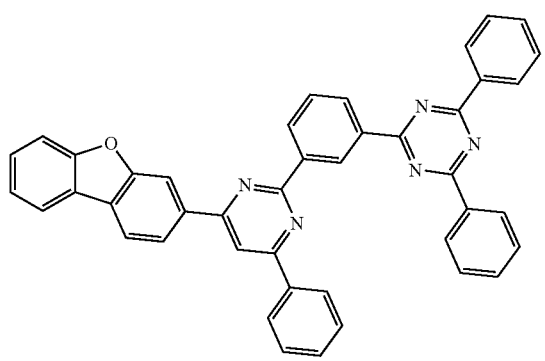
B-58
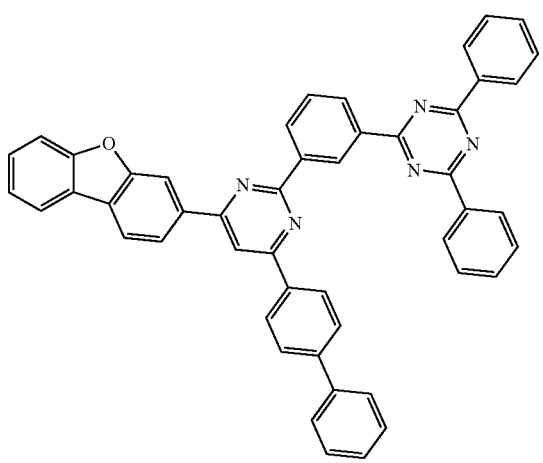
B-59
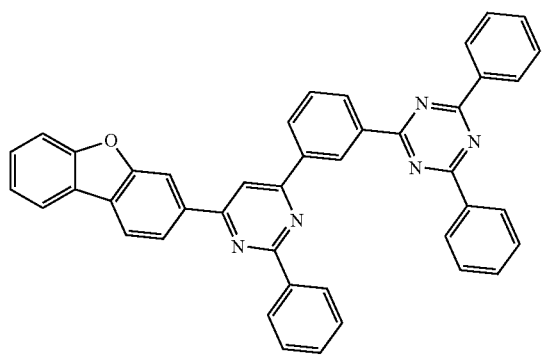
B-60
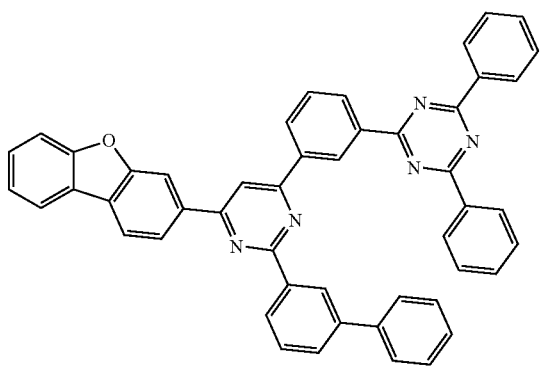

-continued
B-61
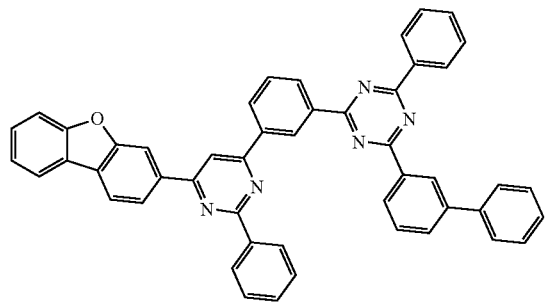
B-62
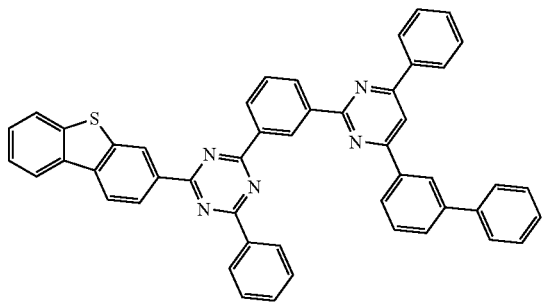
B-63
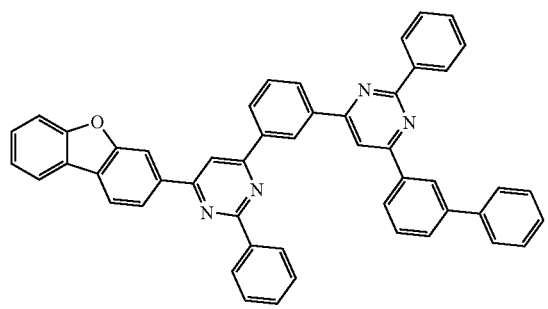
B-64
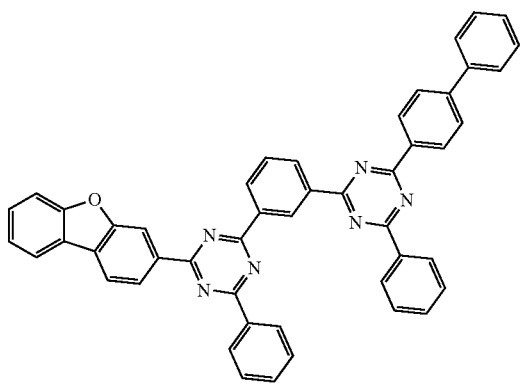
B-65
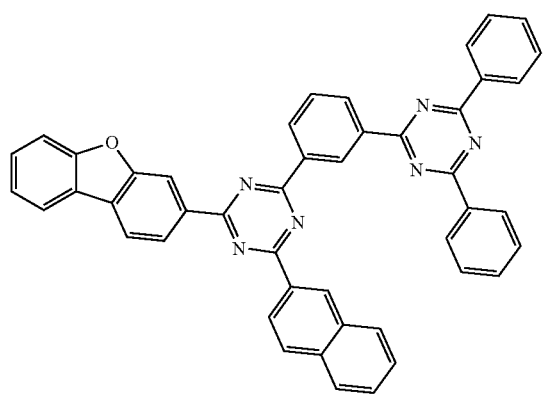
B-66
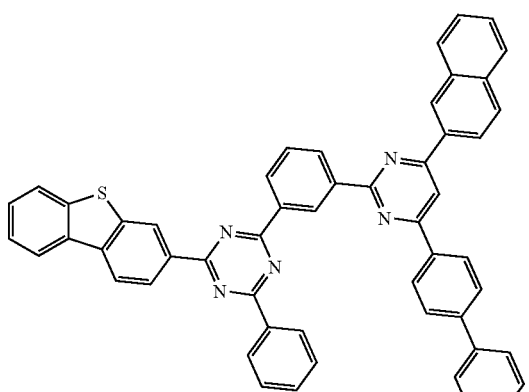

-continued
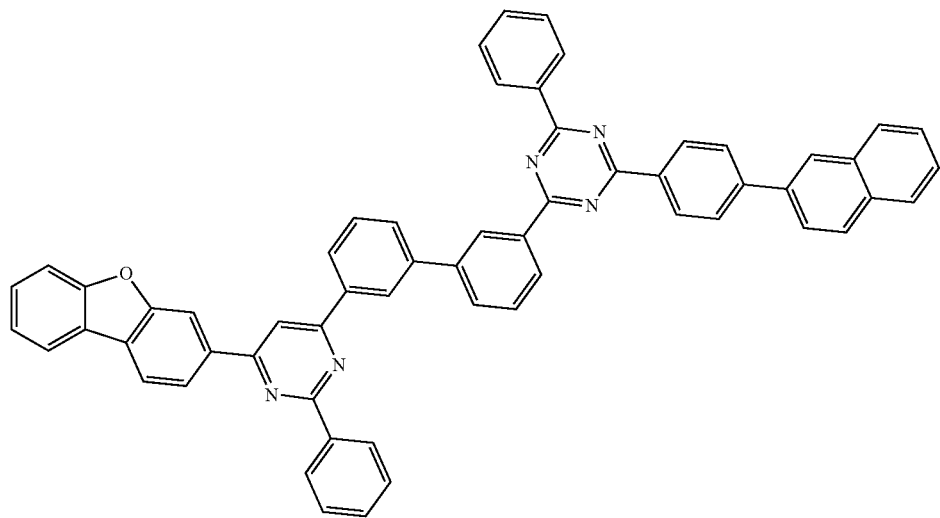
B-67
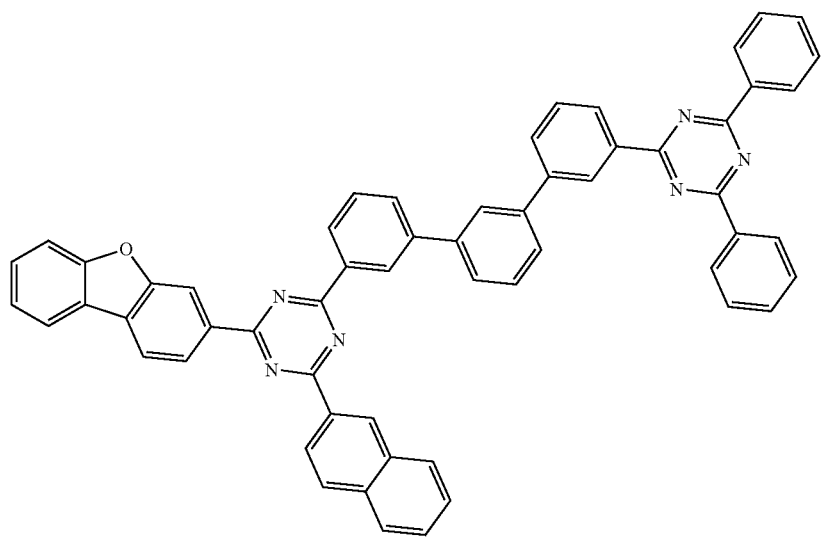
B-68
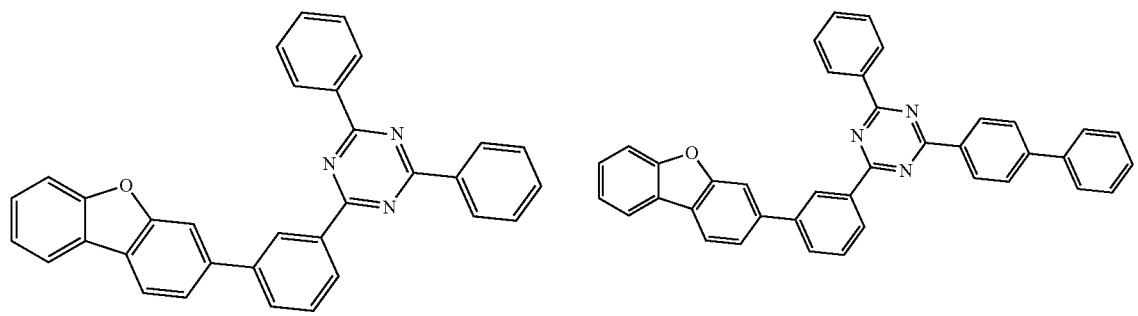
B-69    B-70

B-71
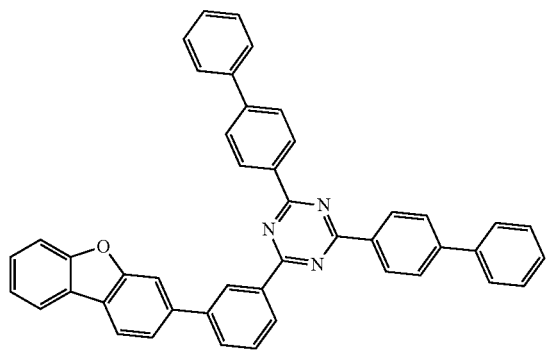
B-72
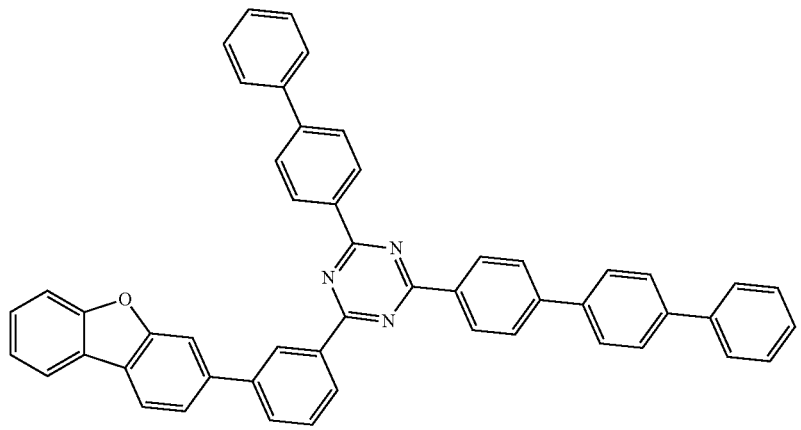
B-73
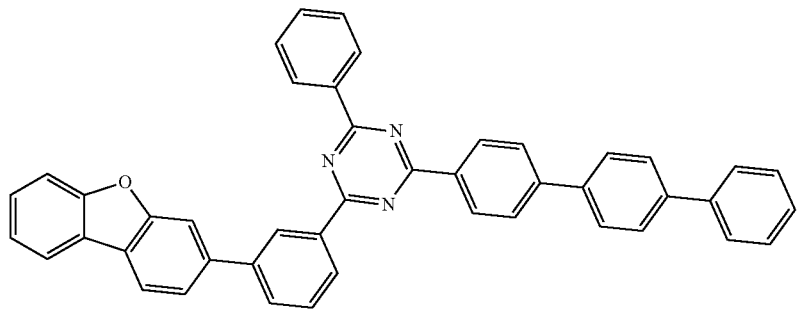
B-74
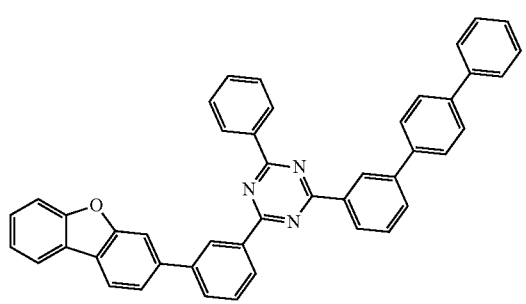
B-75
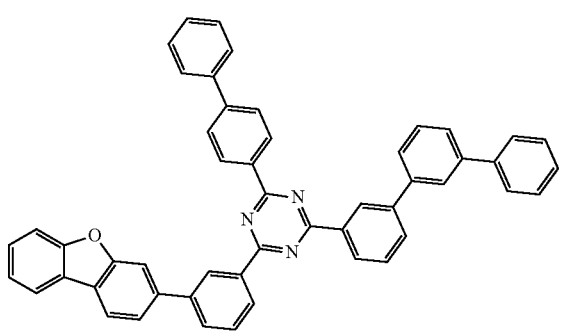

-continued
B-76
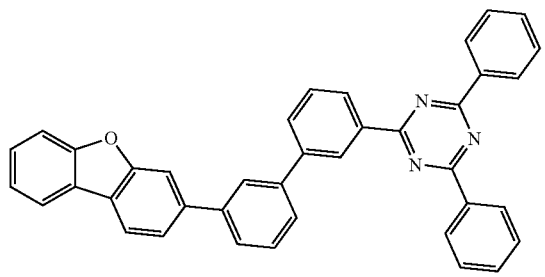
B-77
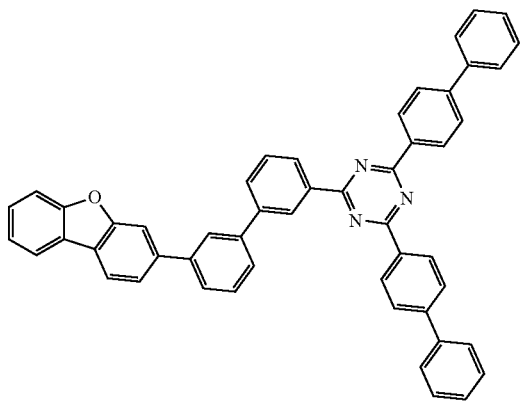
B-78
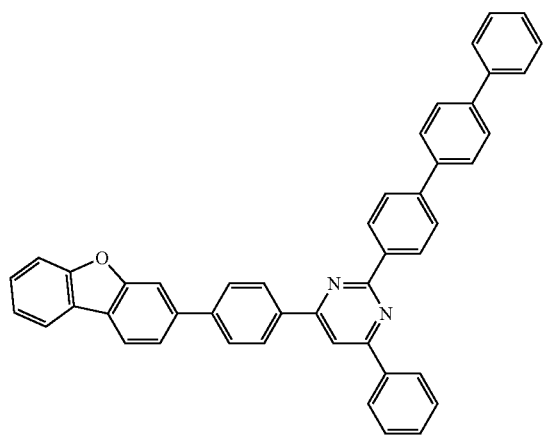
B-79
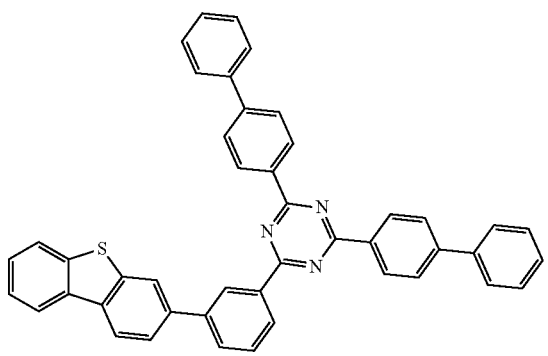
B-80
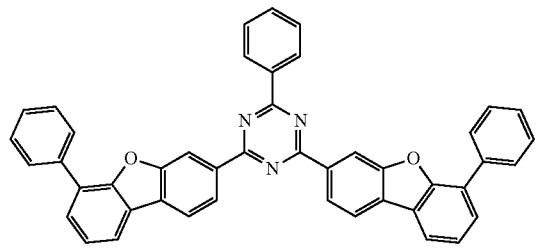
B-81
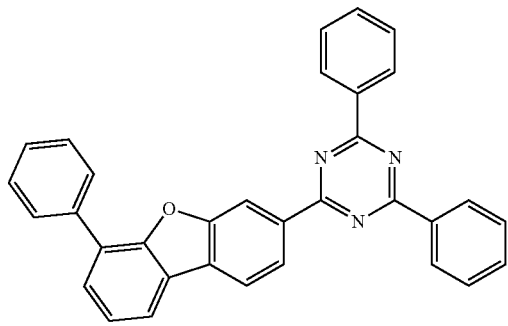
B-82
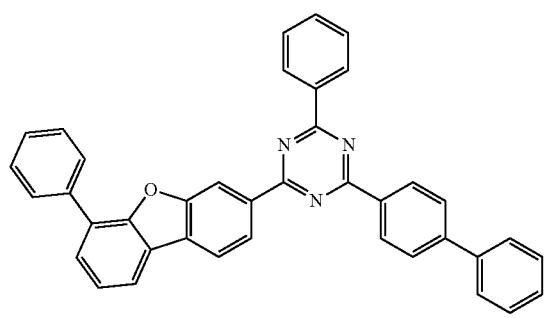
B-83
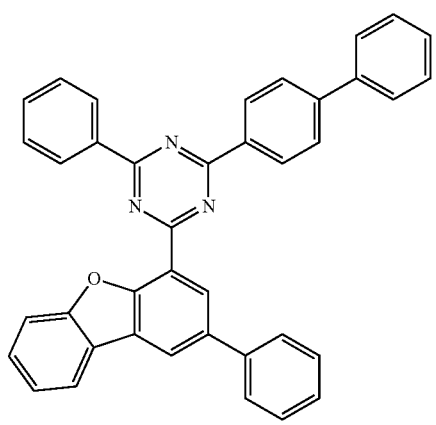

-continued
B-84
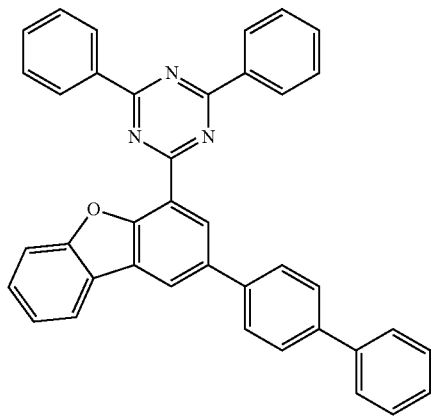
B-85
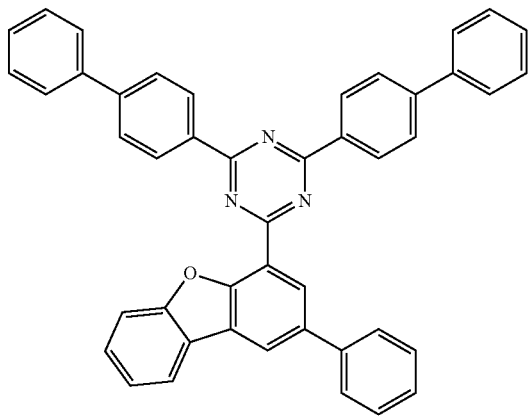
B-86
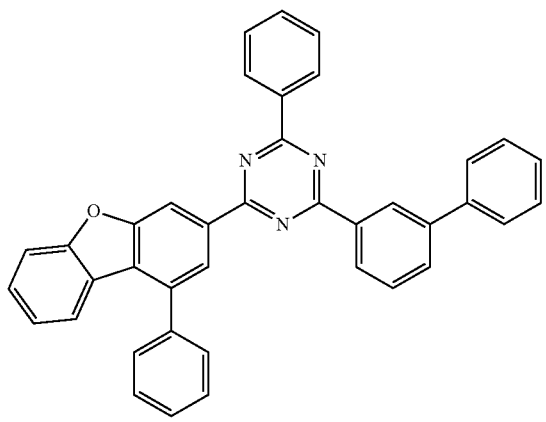
B-87
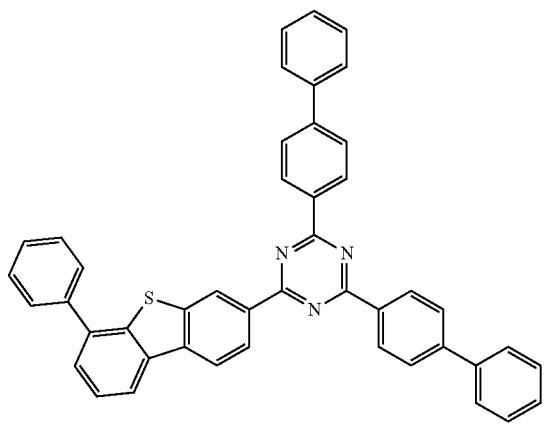
B-88
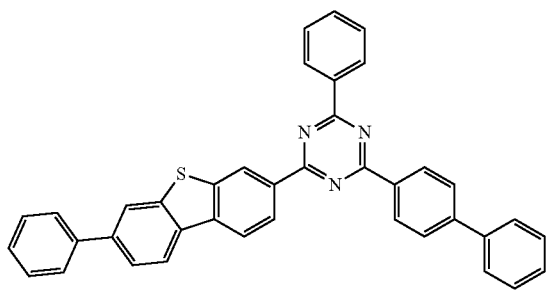
B-89
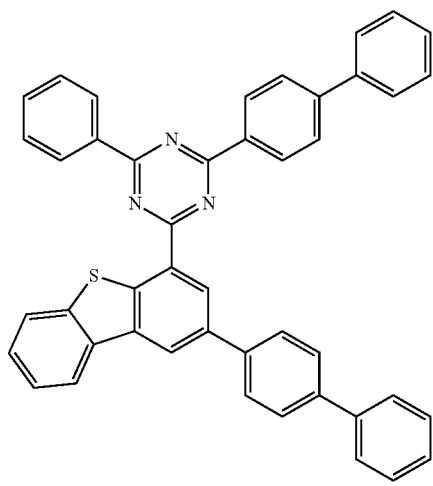

B-90
B-91
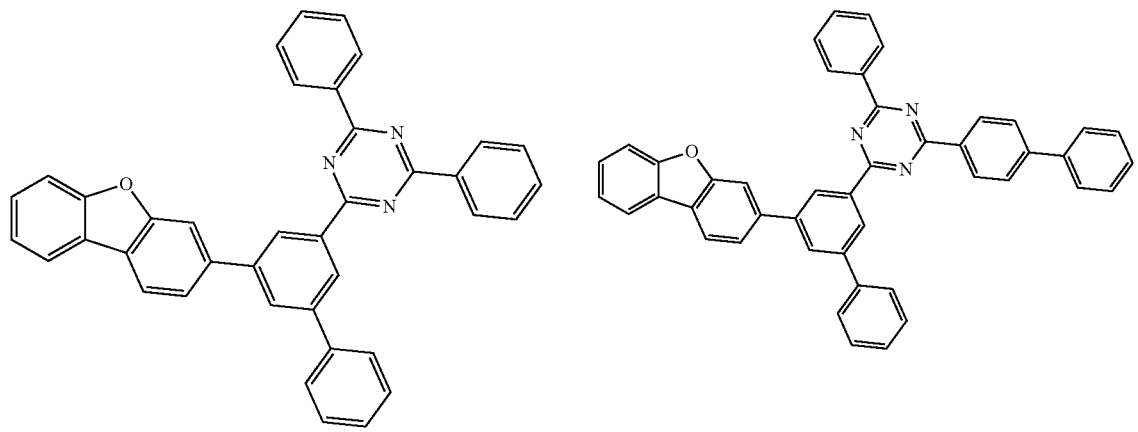
B-92
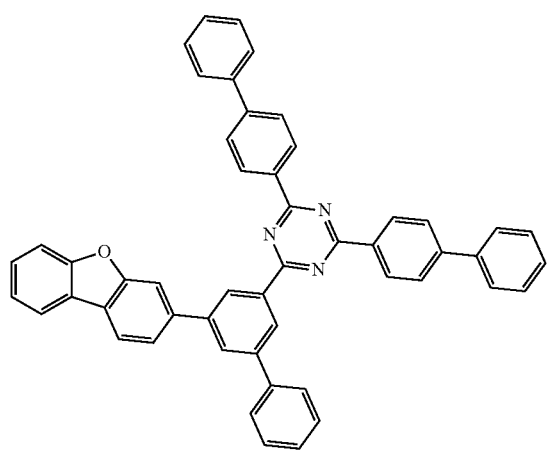
B-93
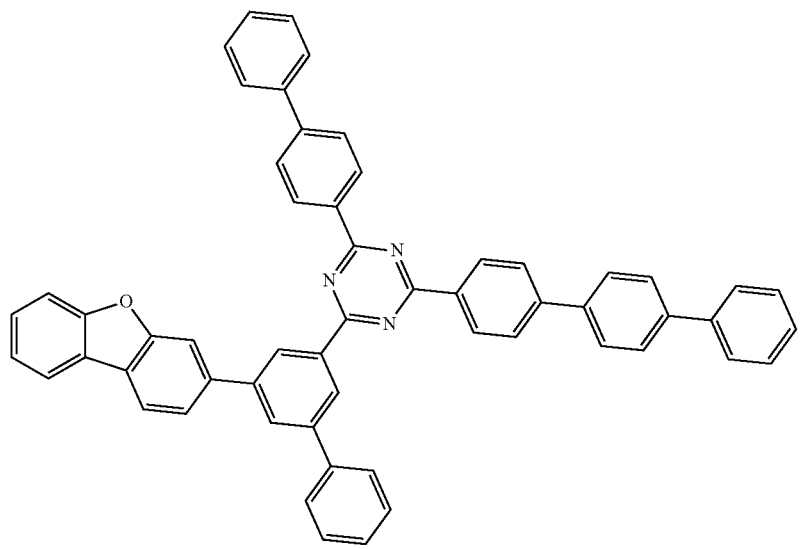

-continued
B-94
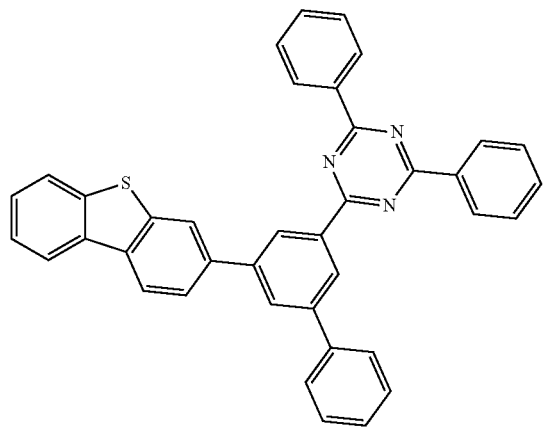
B-95
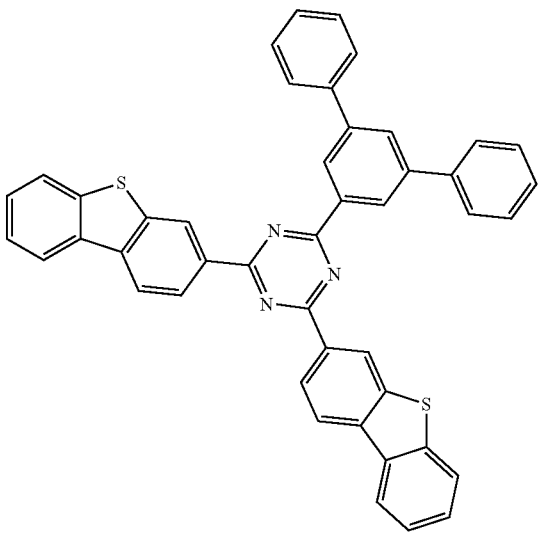
B-96
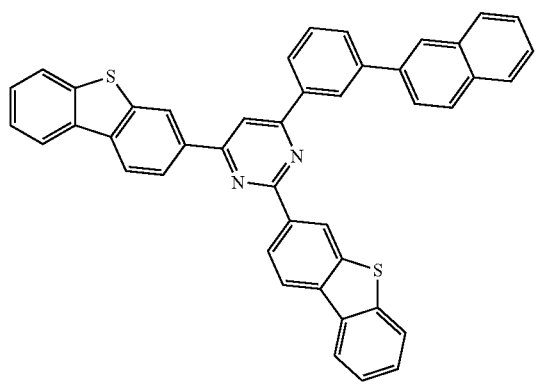
B-97
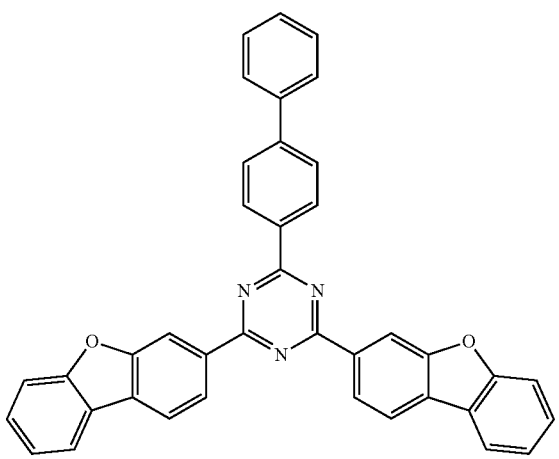
B-98
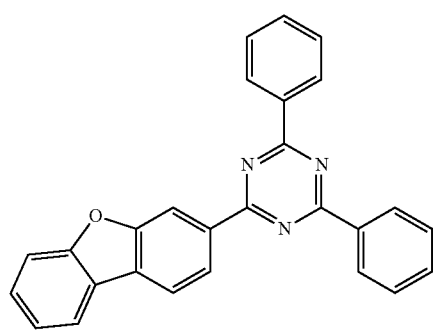
B-99
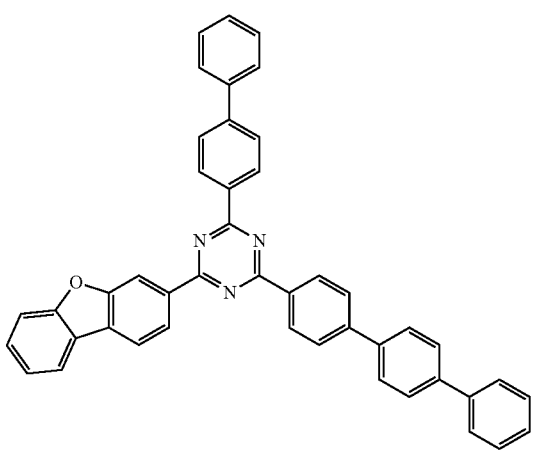

-continued
B-100
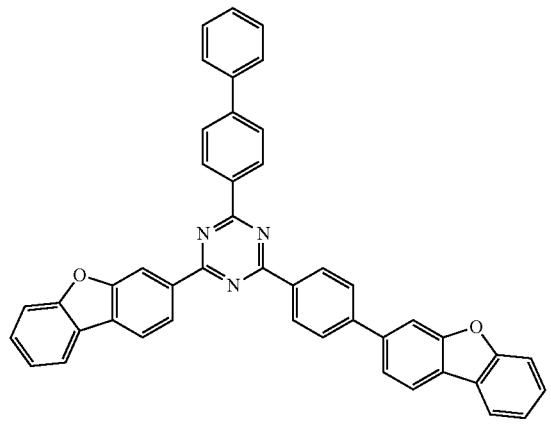
B-101
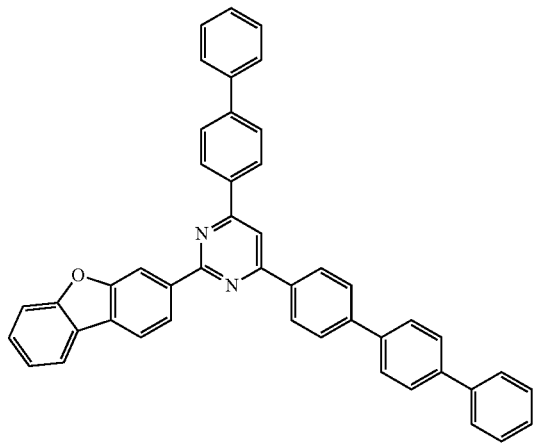
B-102
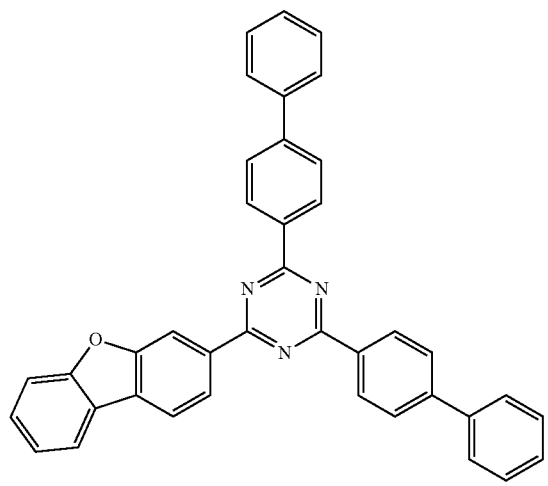
B-103
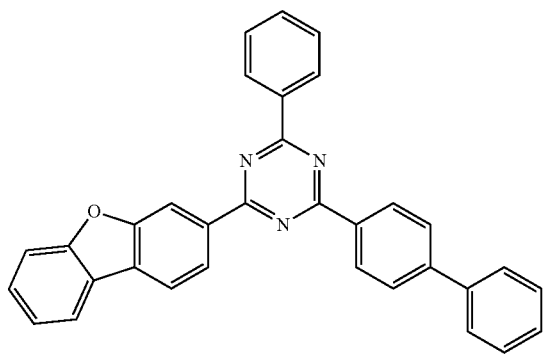
B-104
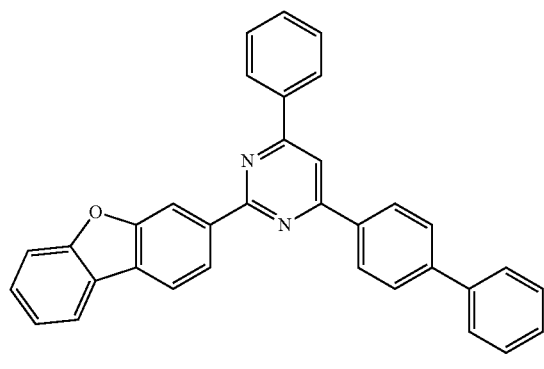
B-105
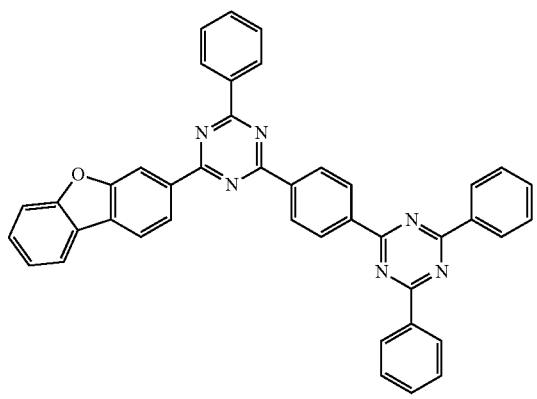

-continued
B-106
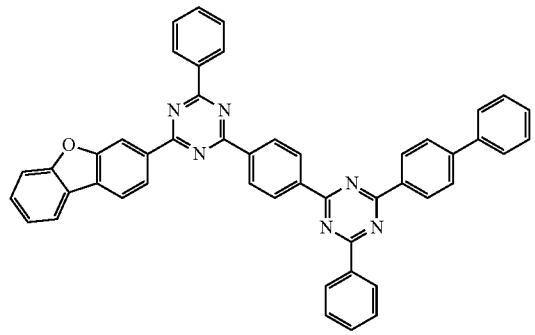
B-107
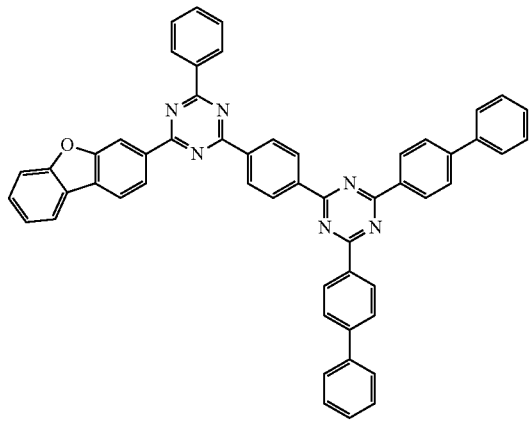
B-108
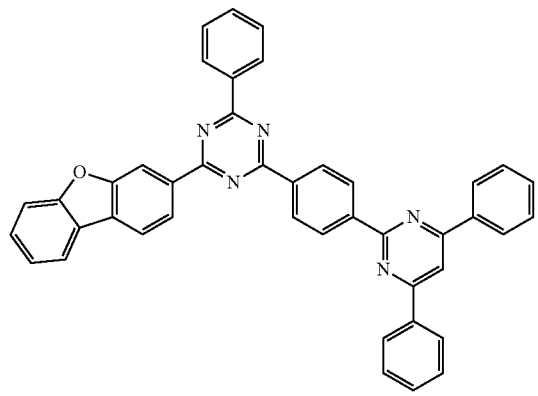
B-109
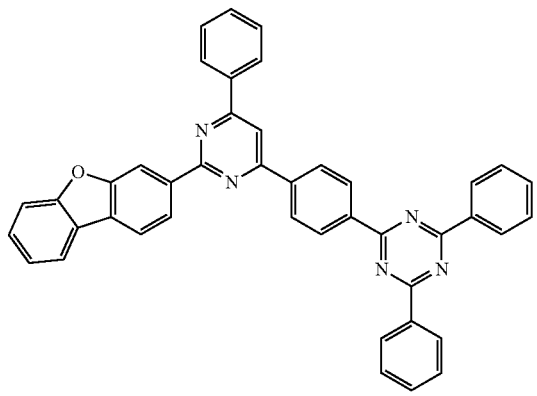
B-110
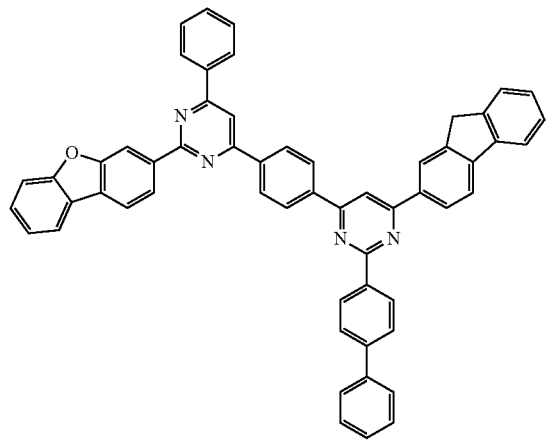
B-111
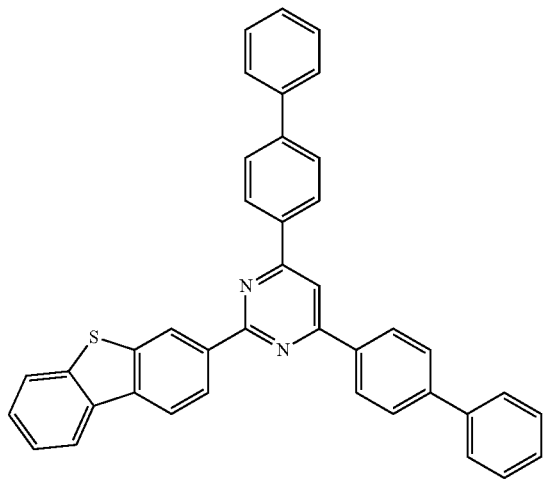

-continued
B-112
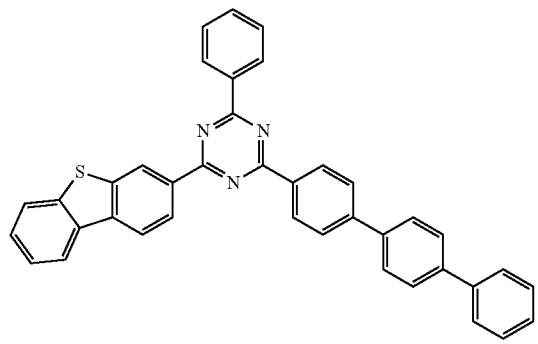
B-113
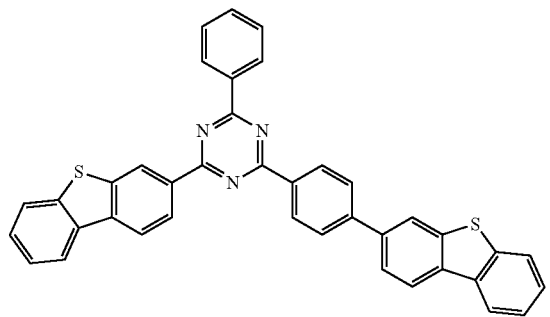
B-114
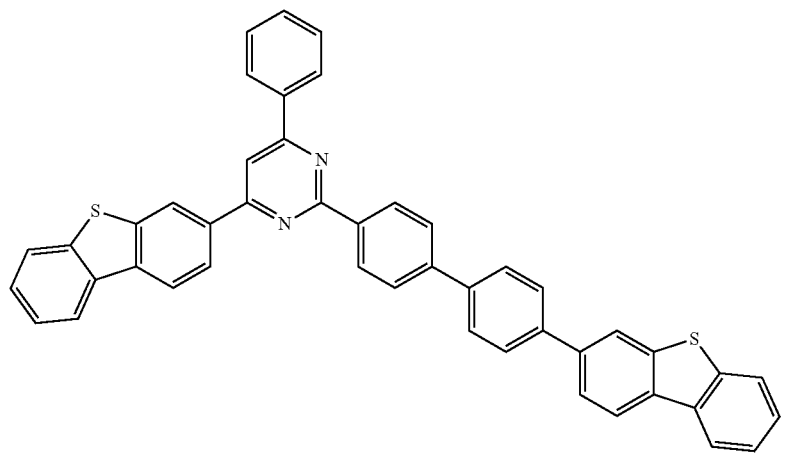
B-115
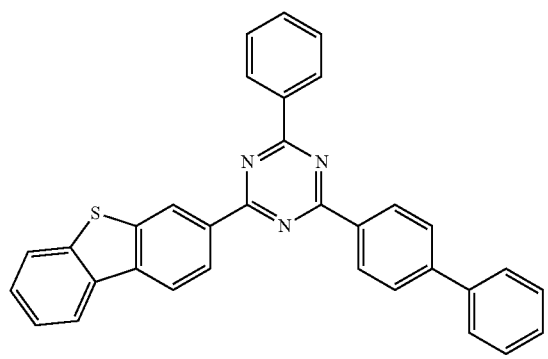
B-116
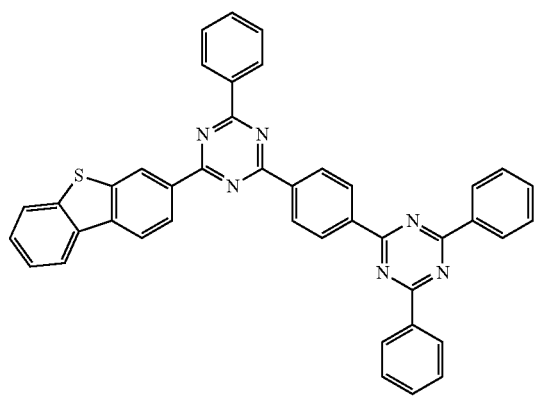

-continued
B-117
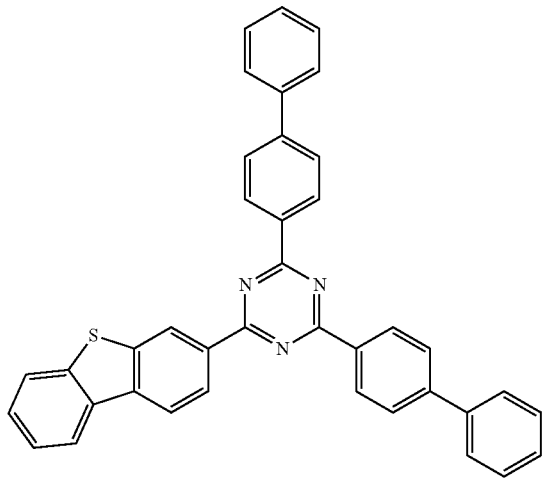
B-118
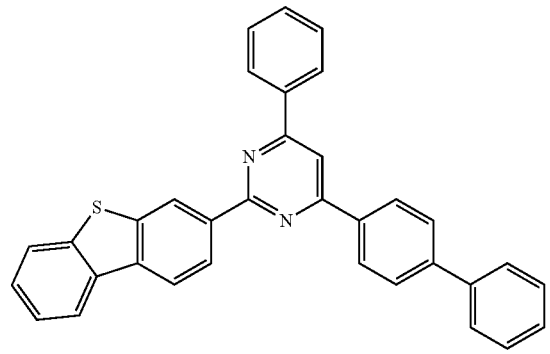
B-119
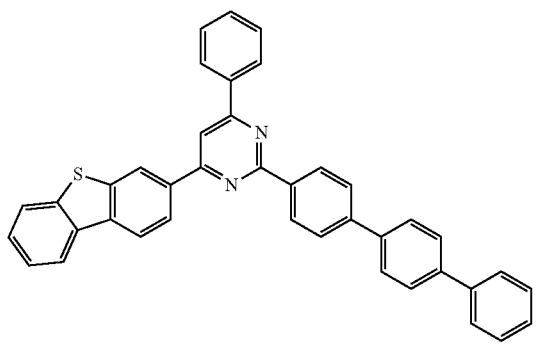
B-120
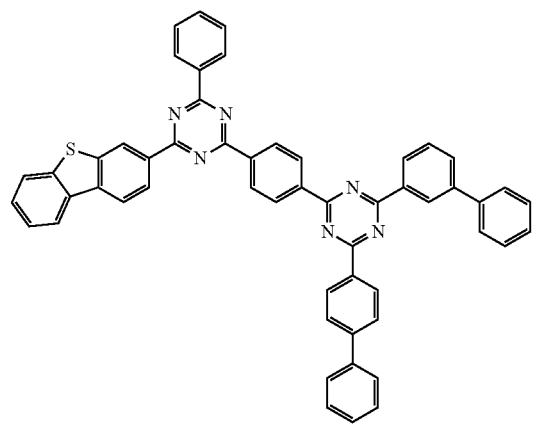
B-121
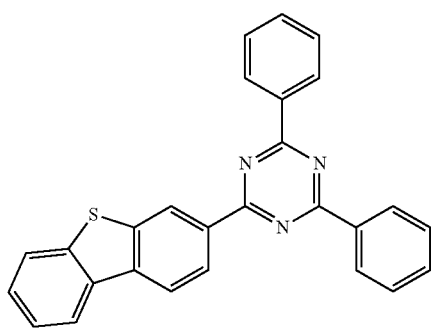
B-122
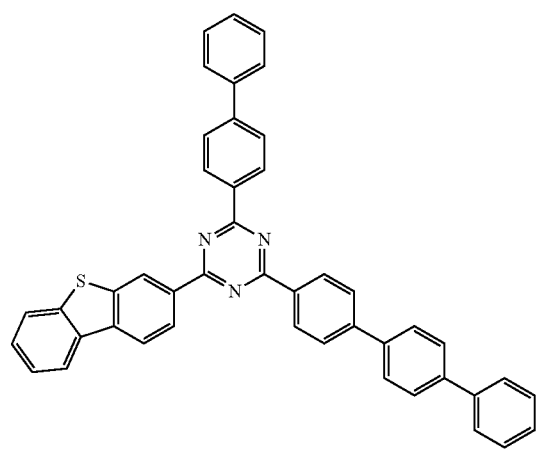

-continued
B-123
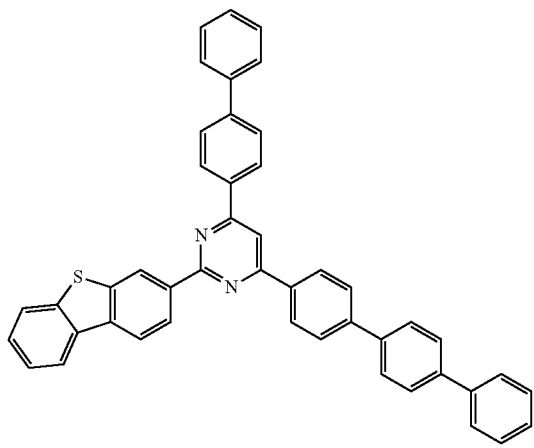
B-124
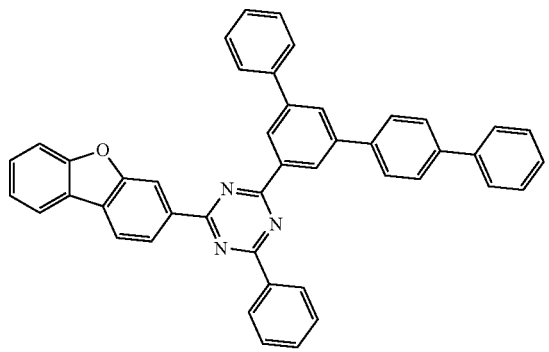
B-125
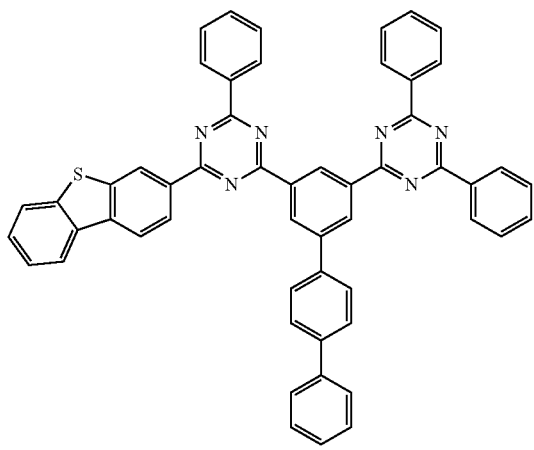
B-126
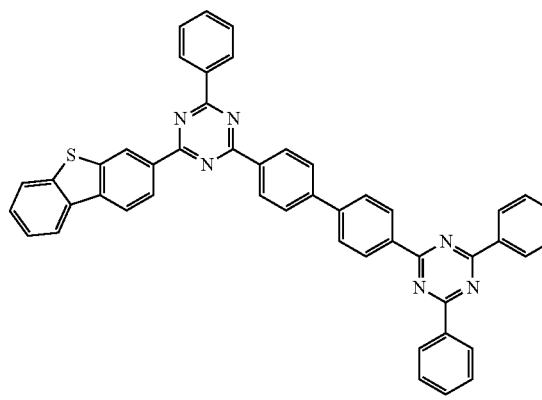
B-127
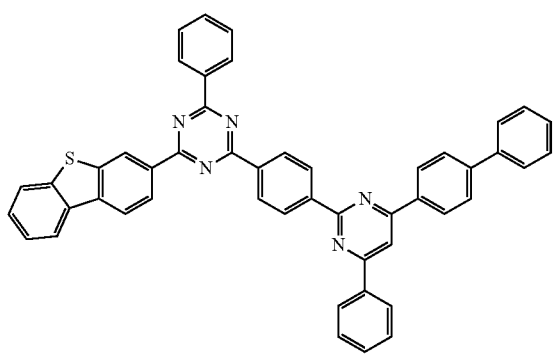
B-128
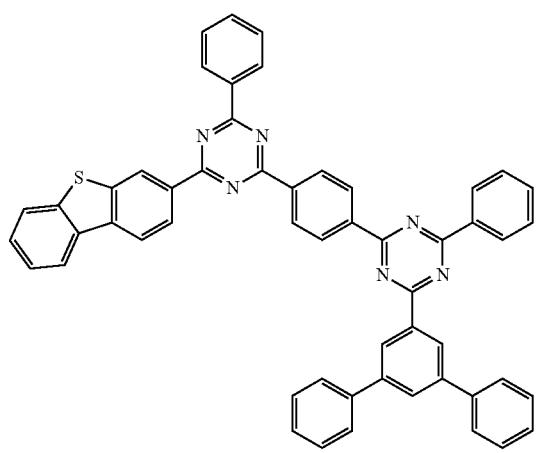

-continued
B-129
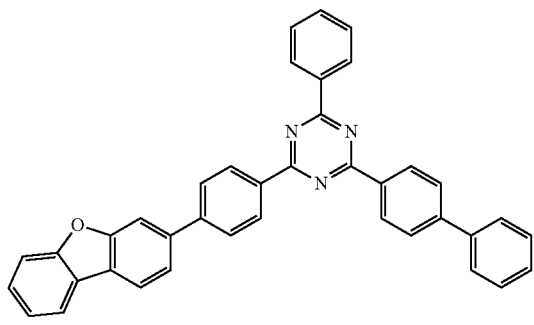
B-130
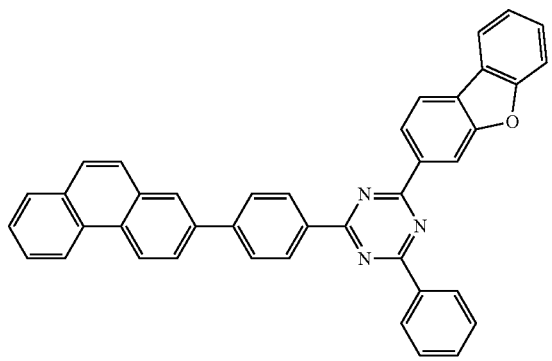
B-131
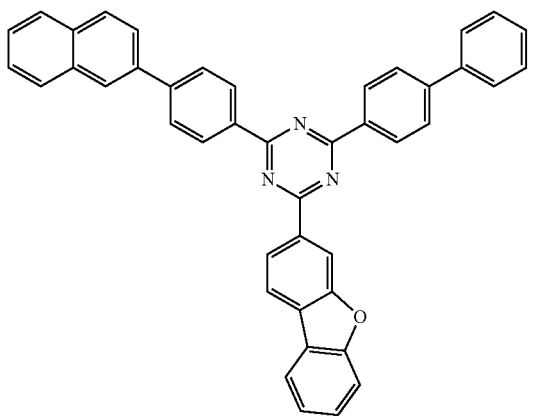
B-132
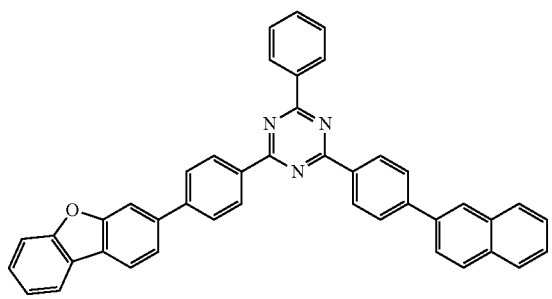
B-133
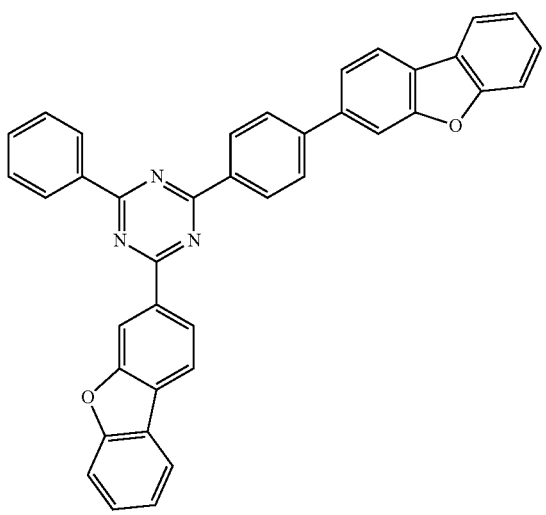
B-134
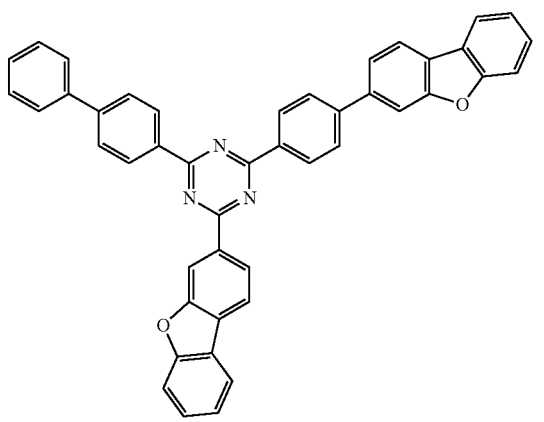

-continued
B-135
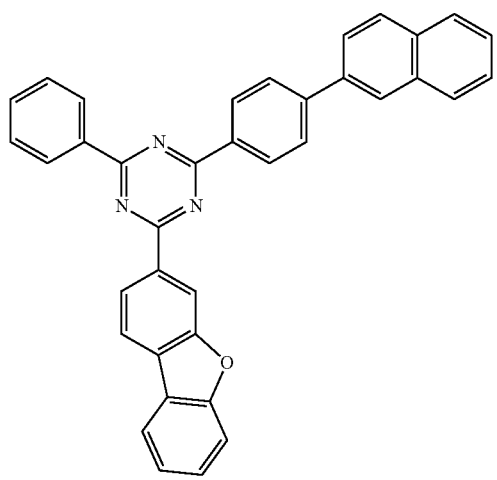
B-136
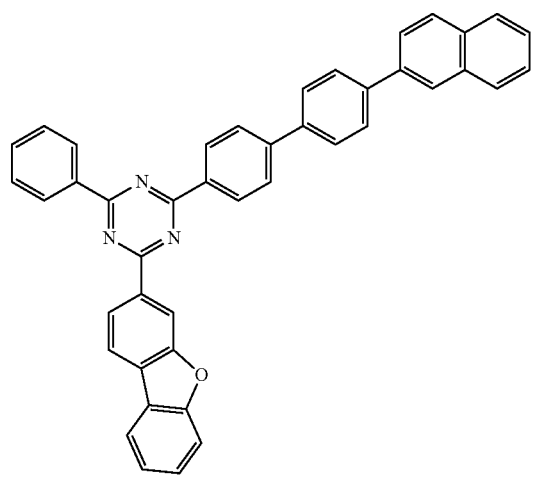
B-137
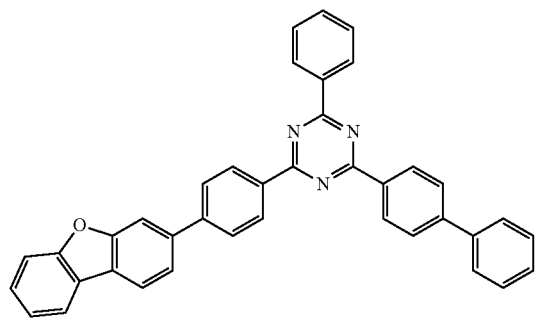
B-138
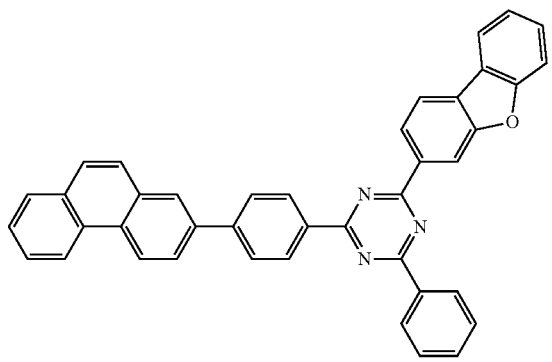
B-139
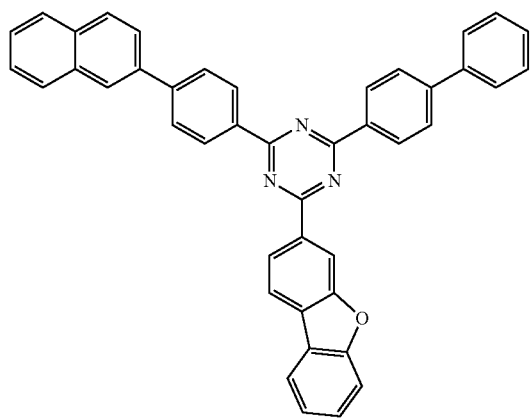
B-140
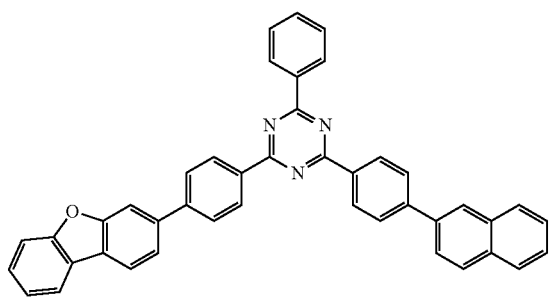

-continued
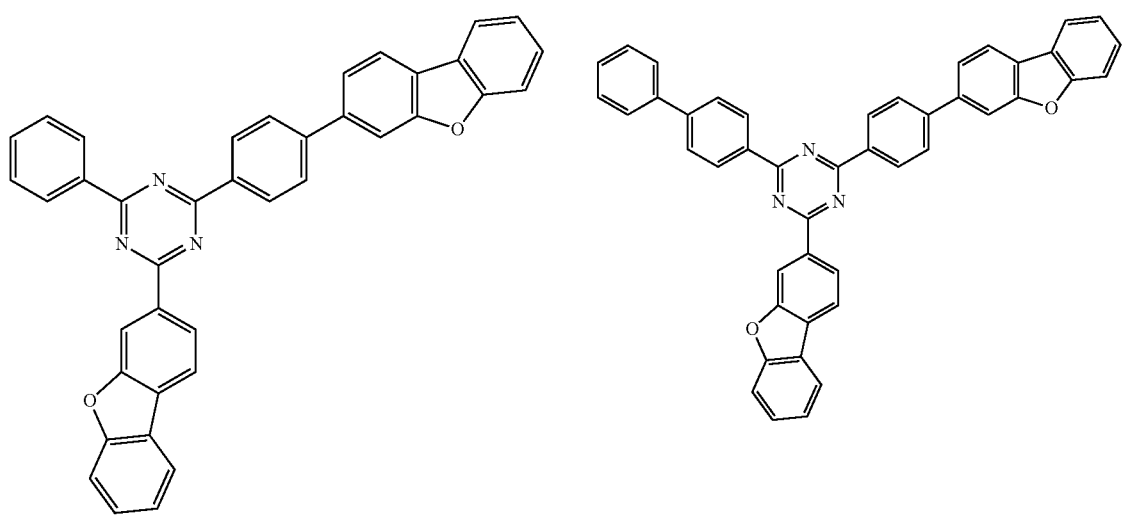
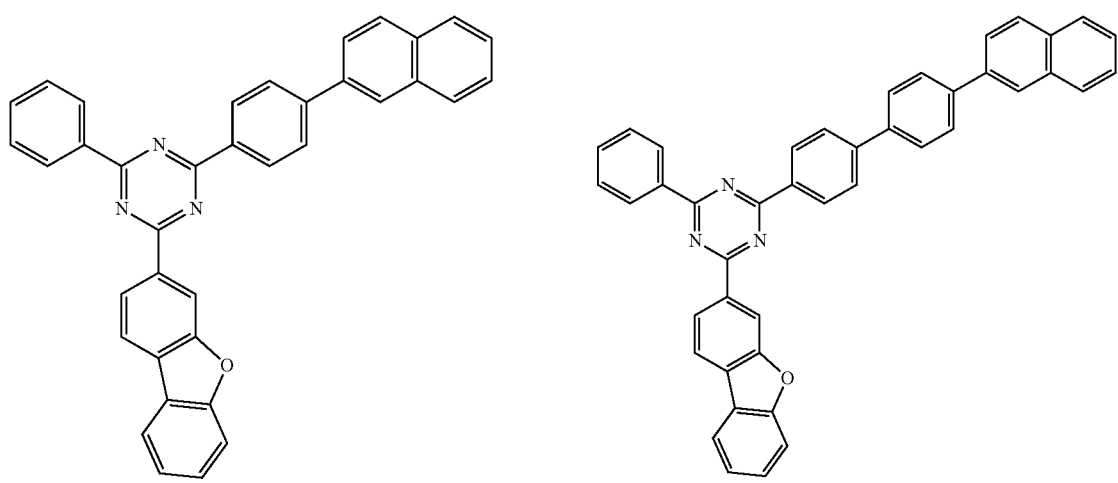
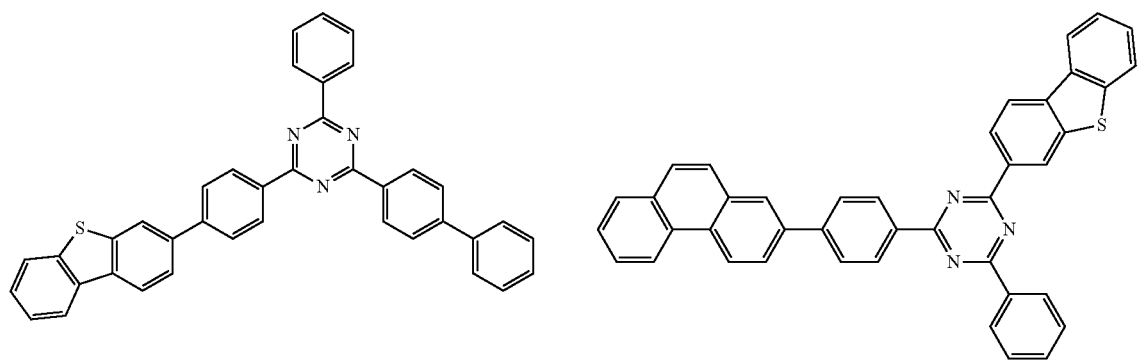

-continued
B-147
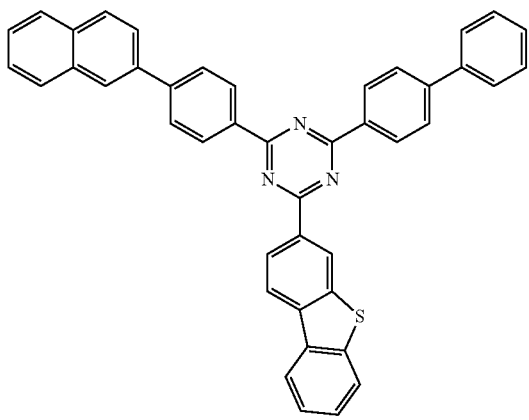
B-148
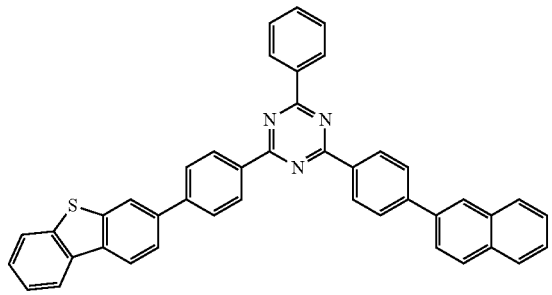
B-149
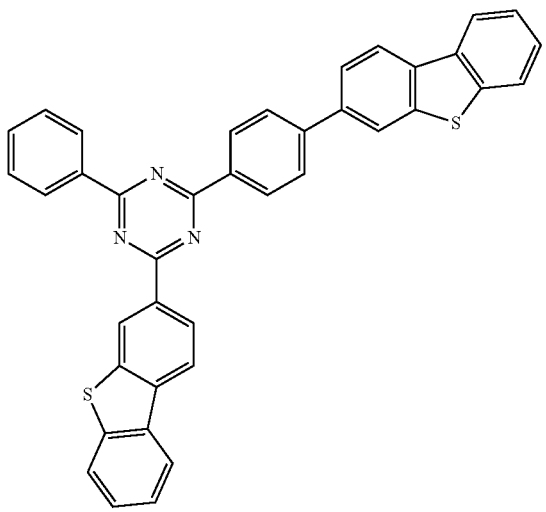
B-150
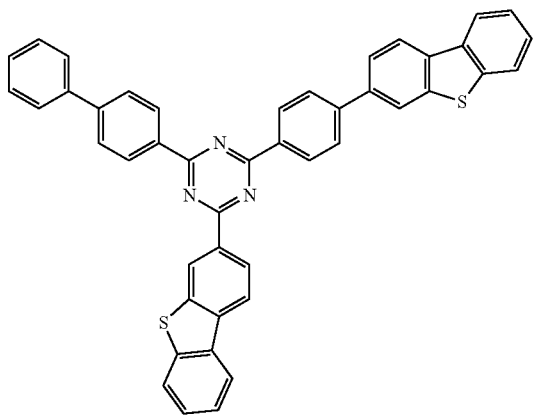
B-151
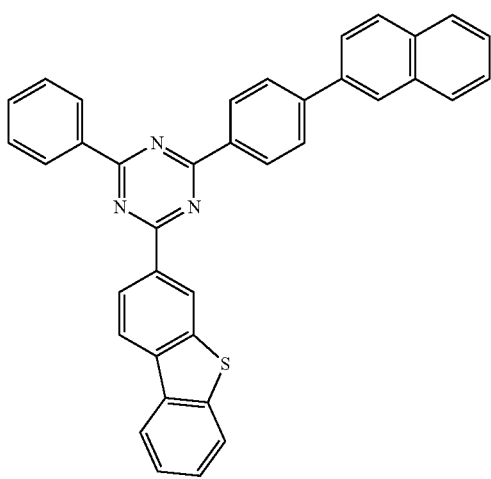
B-152
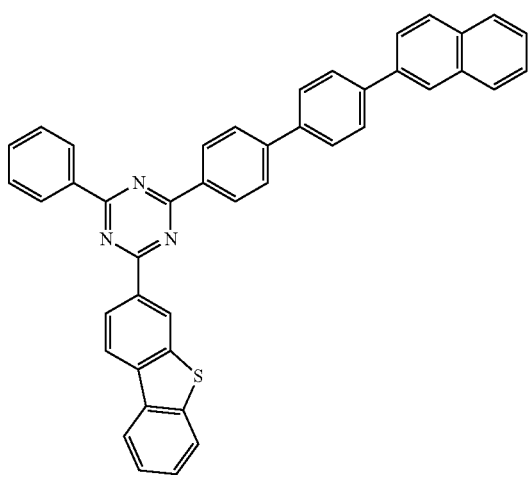

-continued
B-153
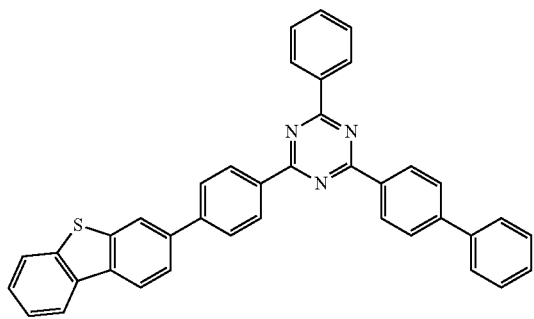
B-154
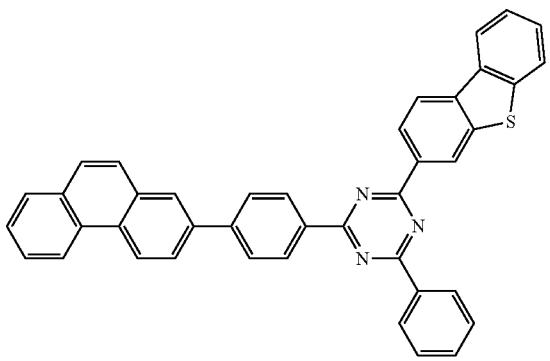
B-155
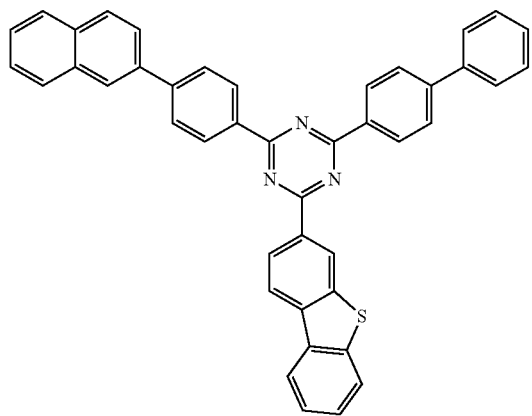
B-156
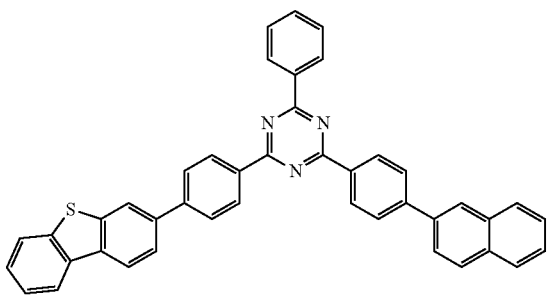
B-157
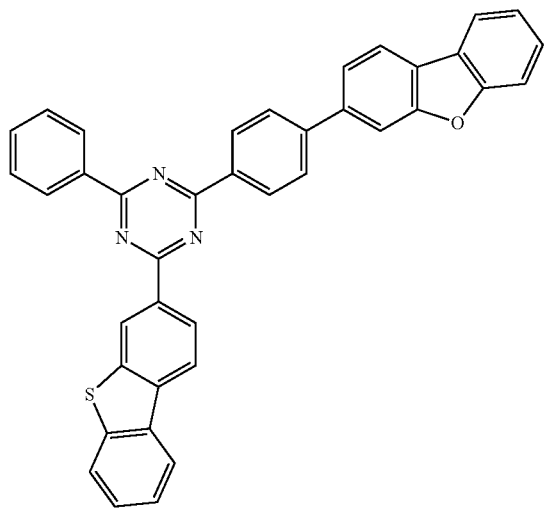
B-158
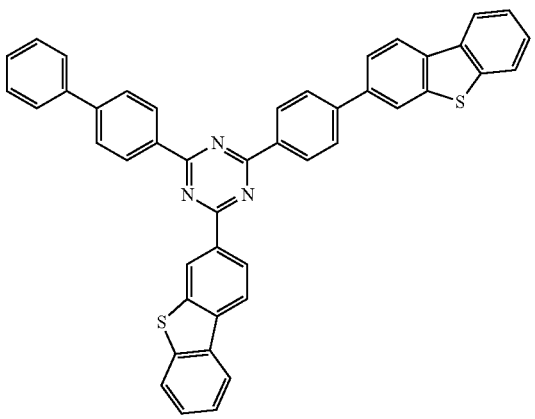

-continued
B-159
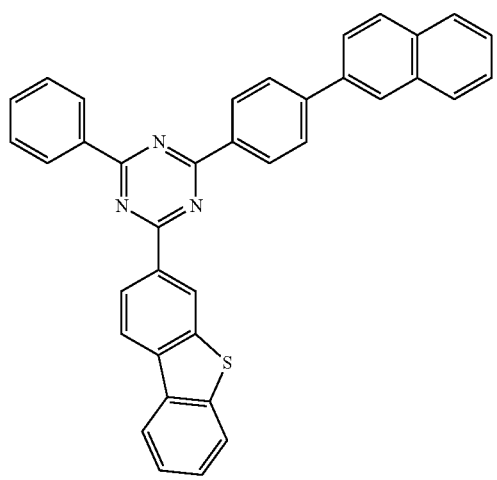
B-160
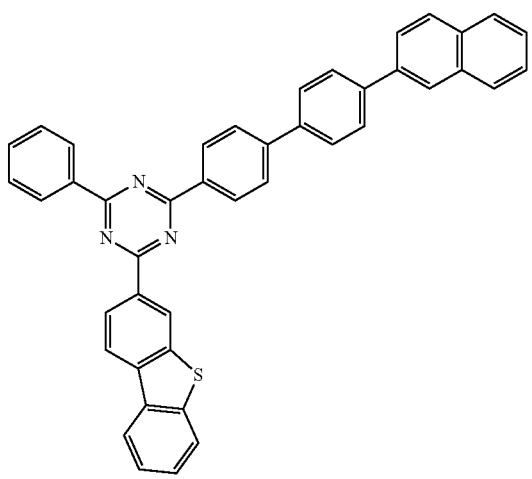
B-161
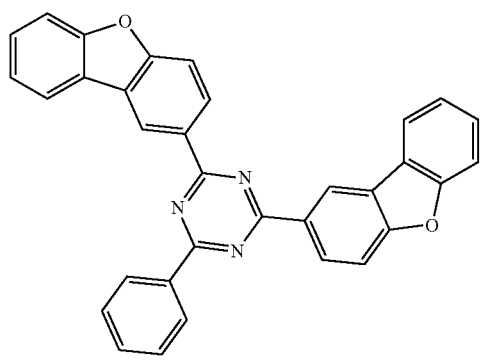
B-162
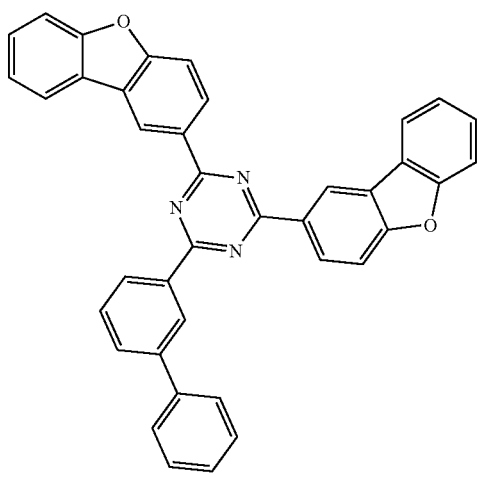
B-163
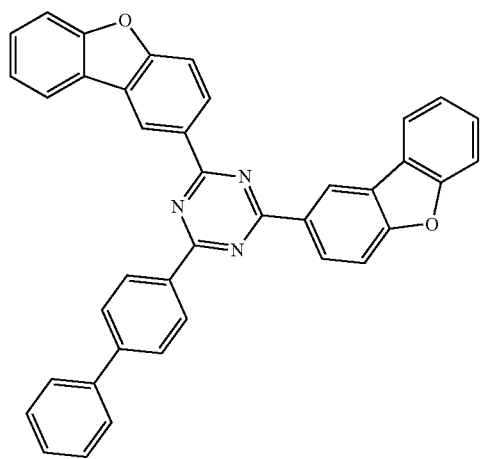
B-164
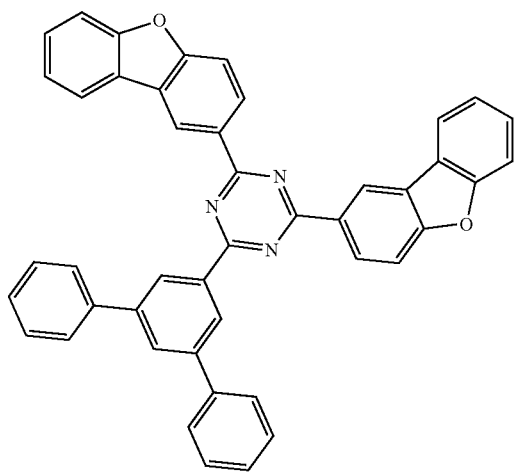

B-165
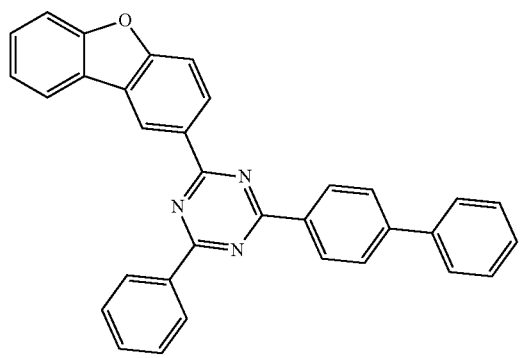
B-166
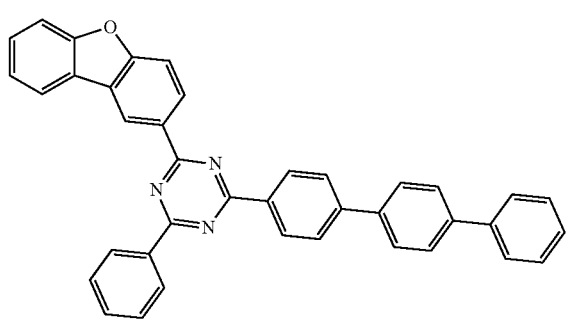
B-167
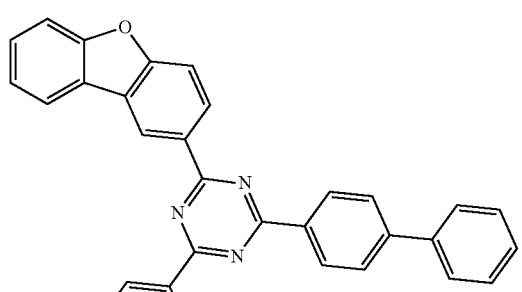
B-168
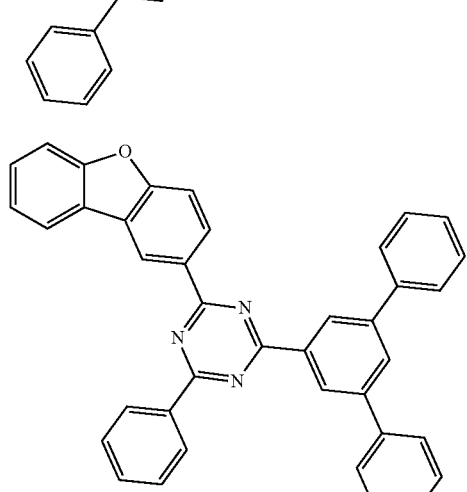
-continued
B-169
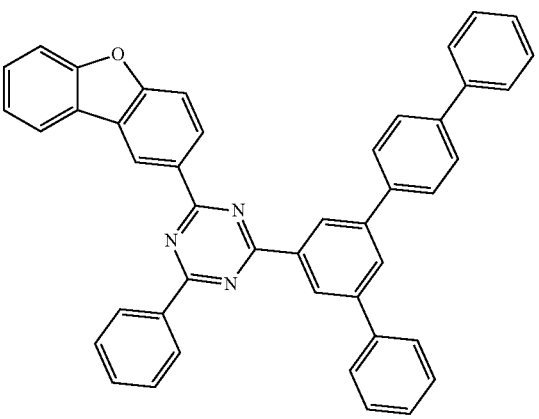
B-170
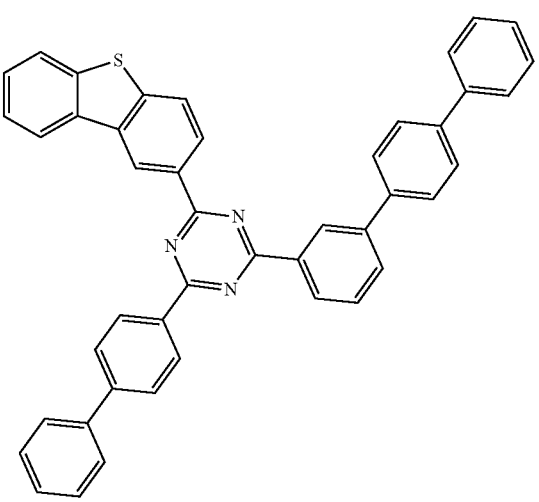
B-171
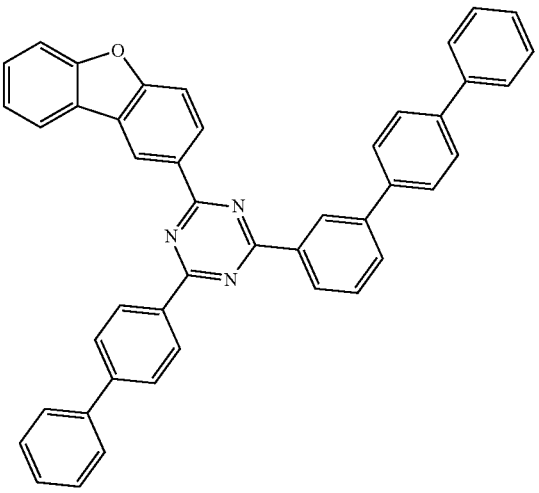

-continued
B-172
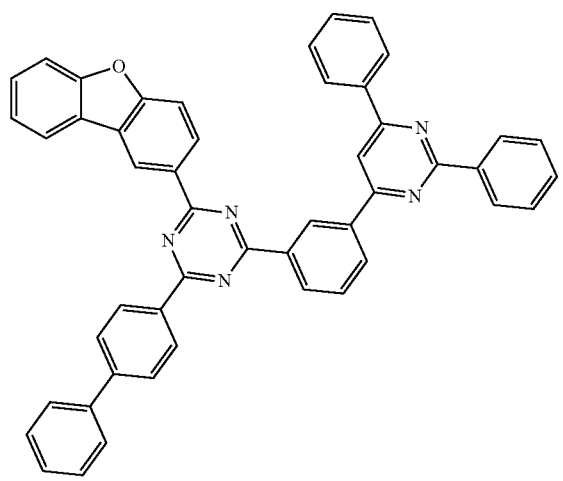
B-175
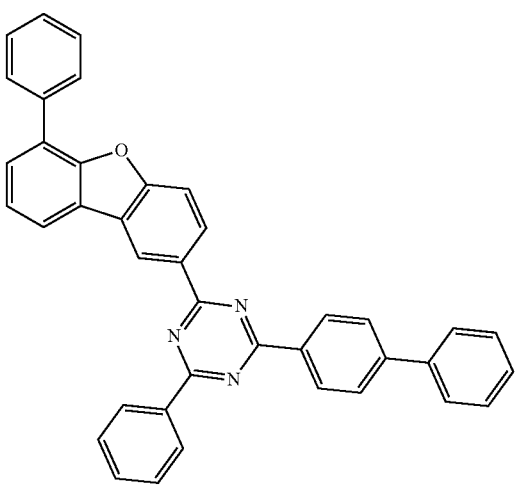
B-173
B-176
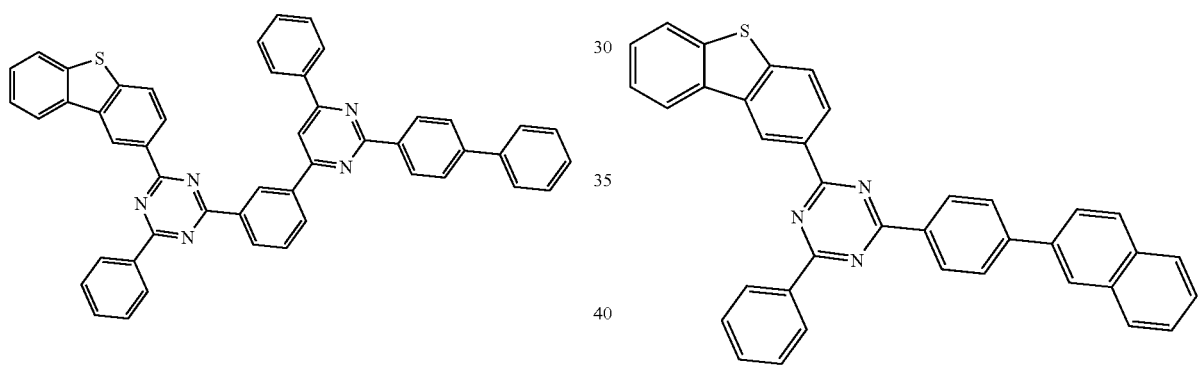
B-174
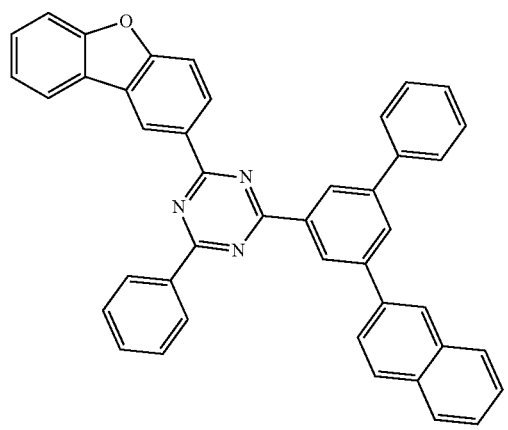
B-177
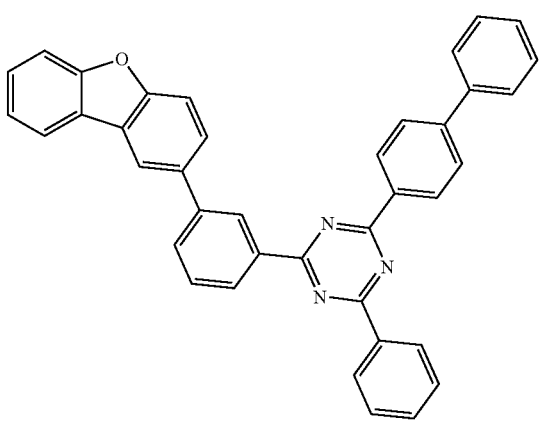

B-178
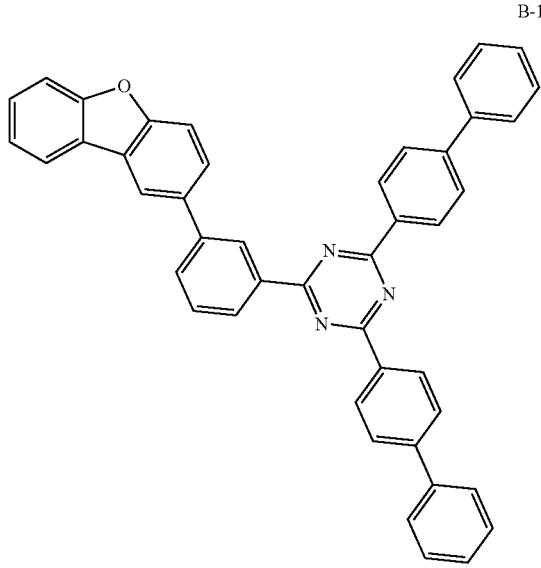
B-179
B-180
B-181
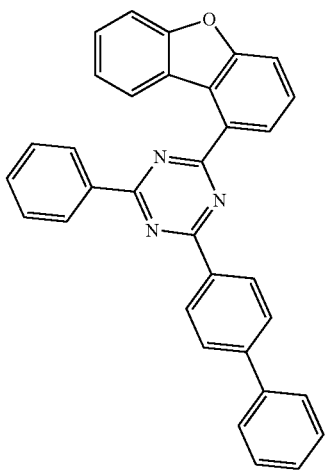
B-182
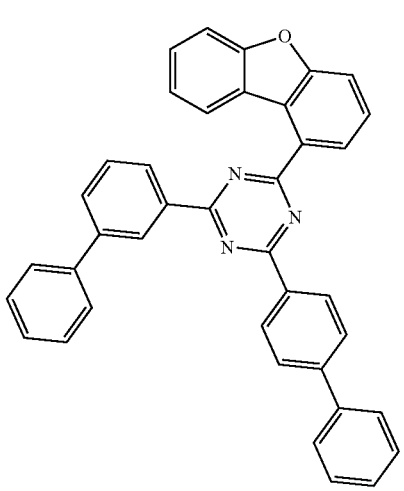
B-183
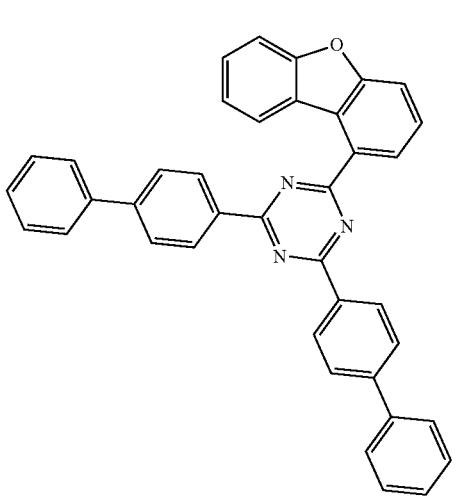

B-184
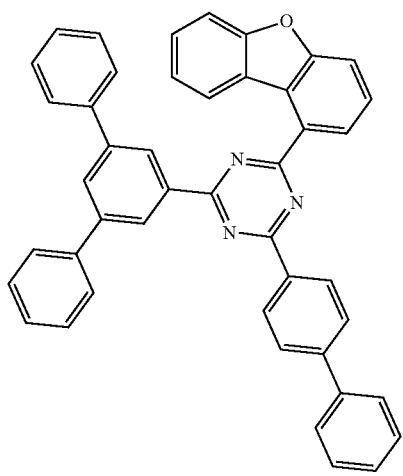
B-185
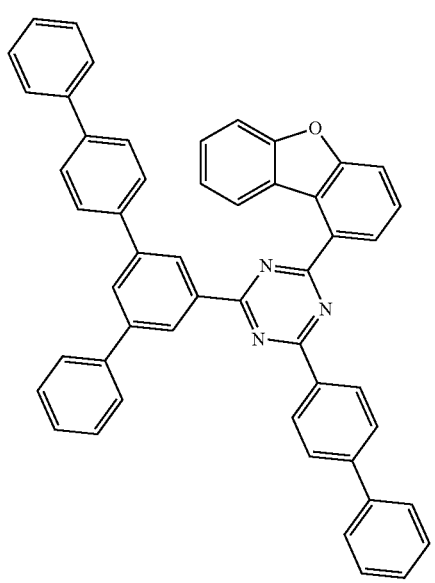
B-186
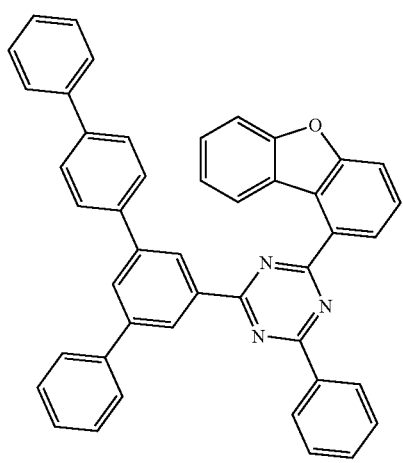
B-187
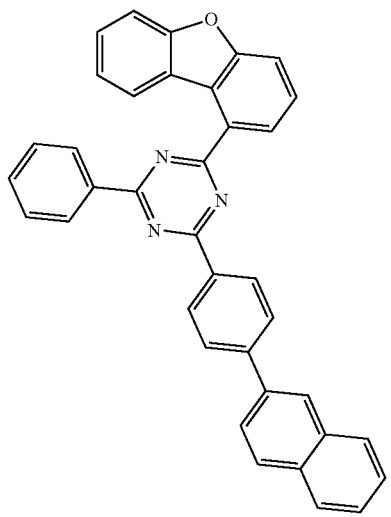
B-188
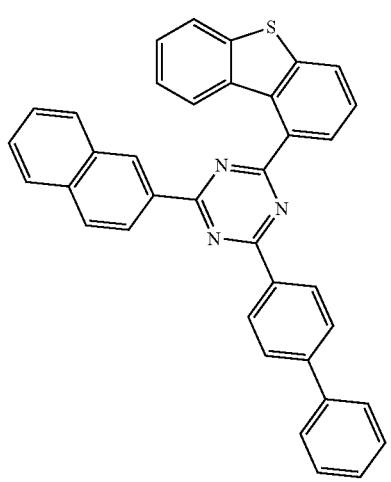
B-189
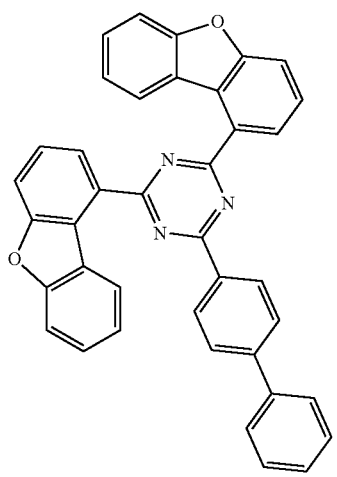

-continued
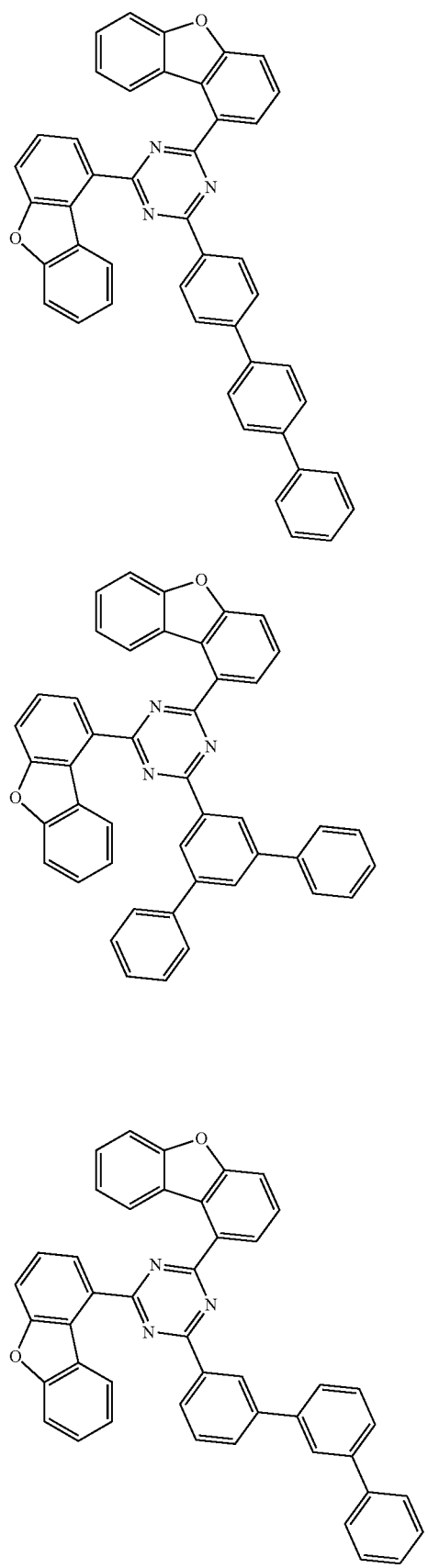
B-190
B-191
B-192
-continued
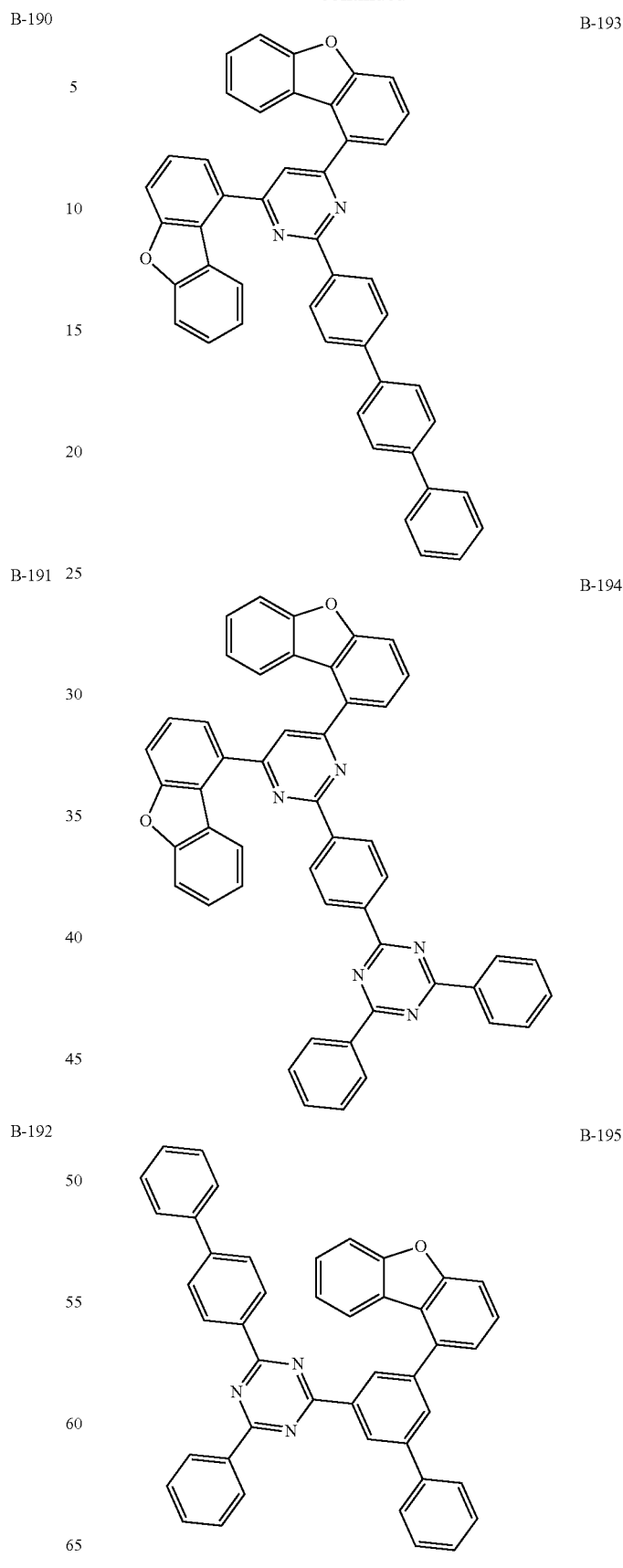
B-193
B-194
B-195

-continued
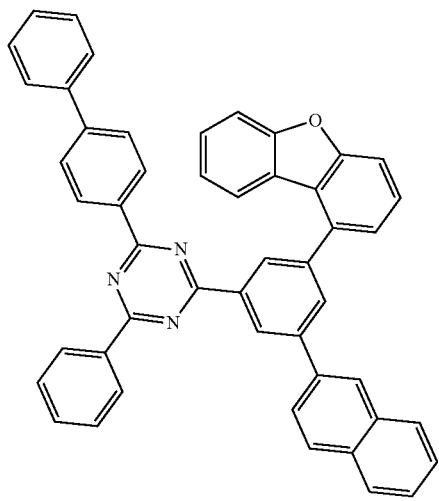
B-196
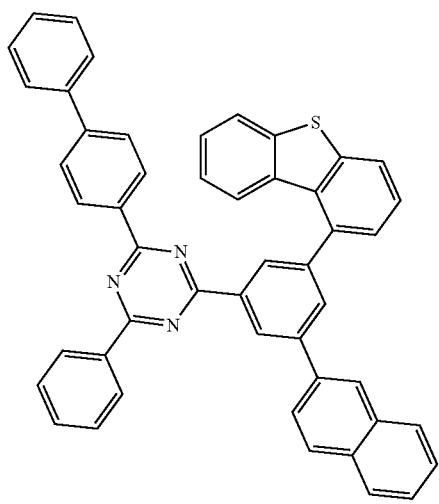
B-197
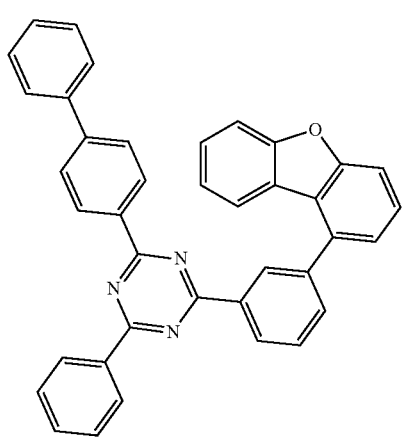
B-198
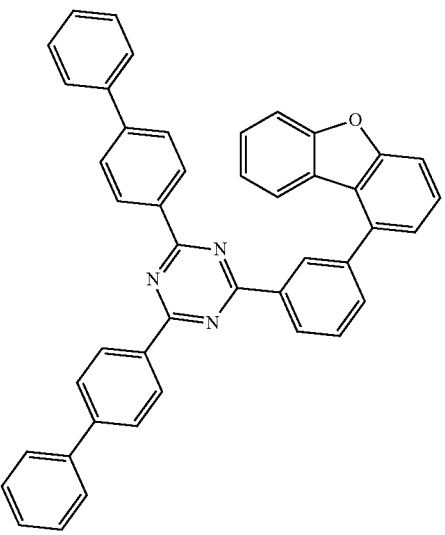
B-199
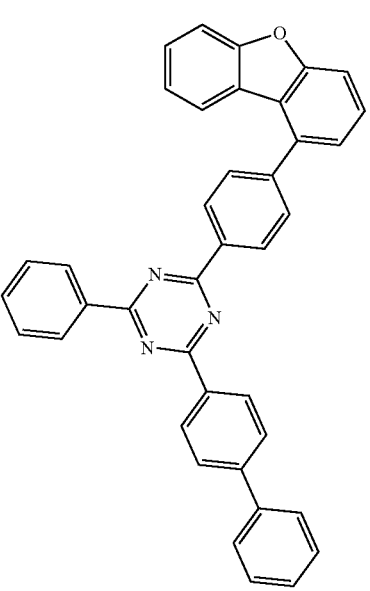
B-200

B-201
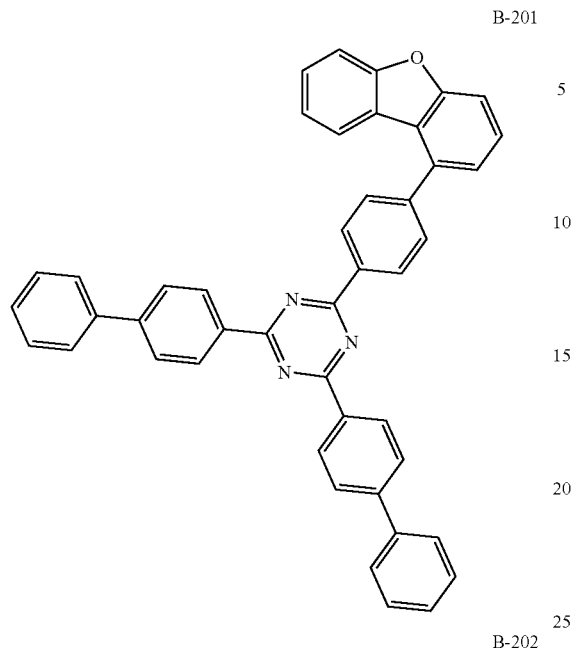
B-204
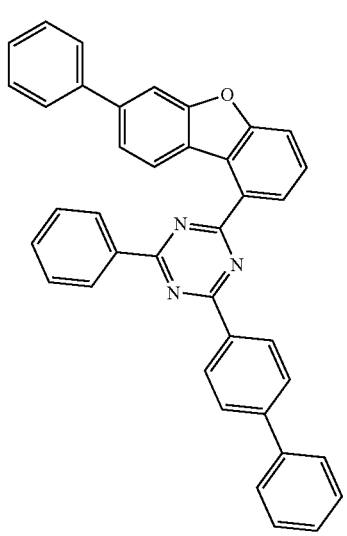
B-202
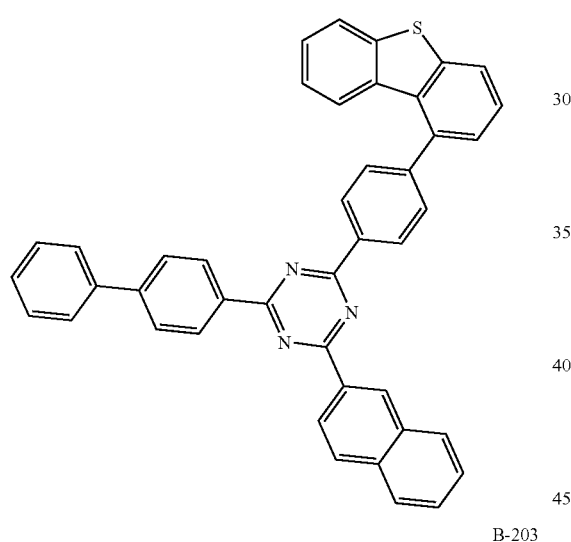
B-205
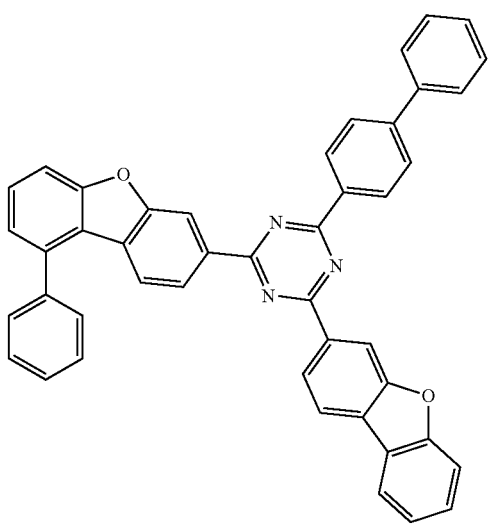
B-203
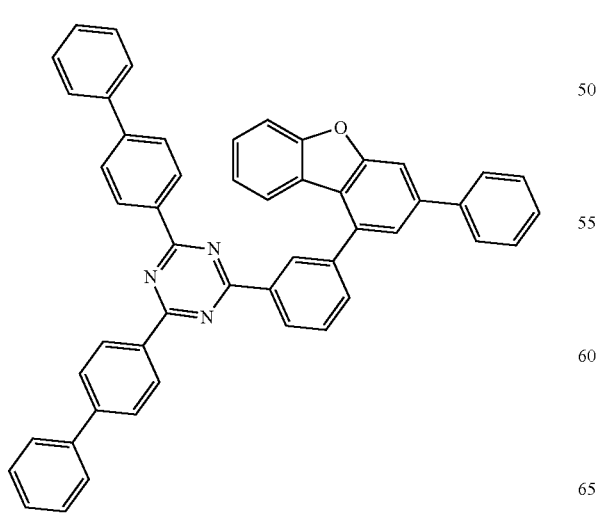
B-206
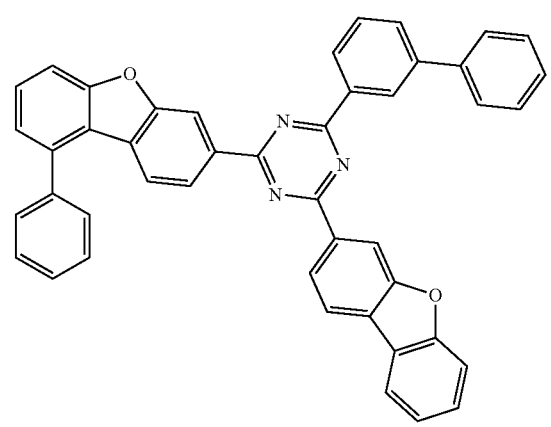

B-207
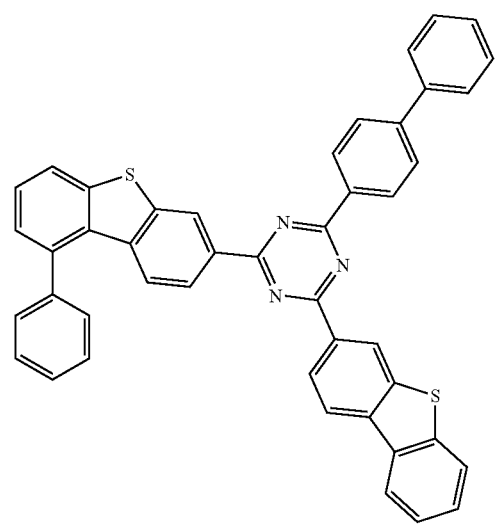
B-208
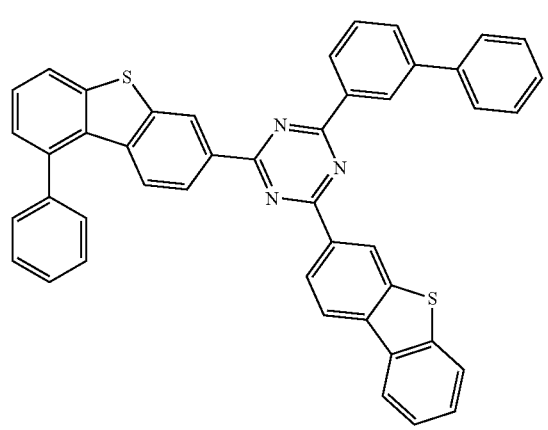
B-209
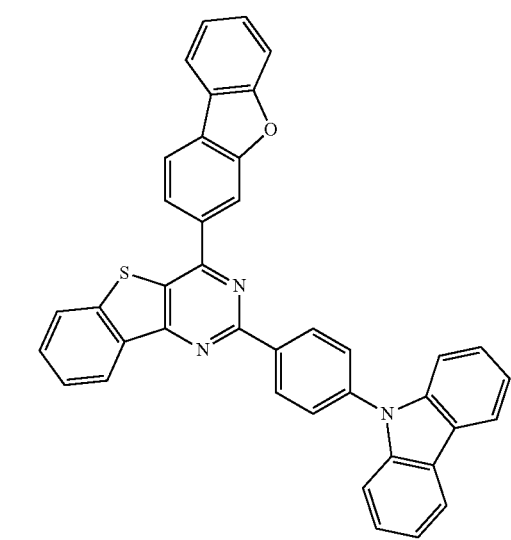
C-1
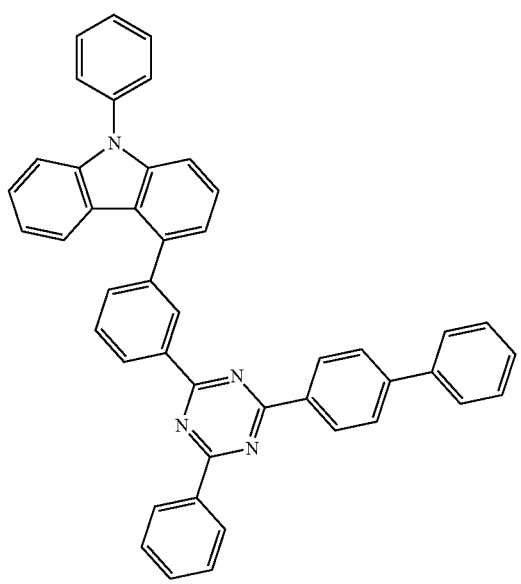
C-2
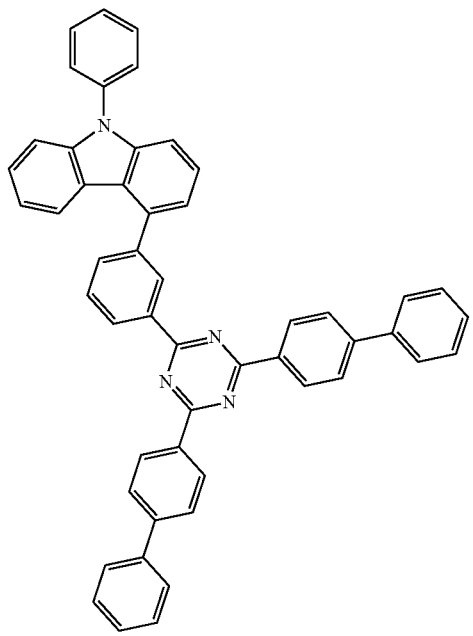

C-3
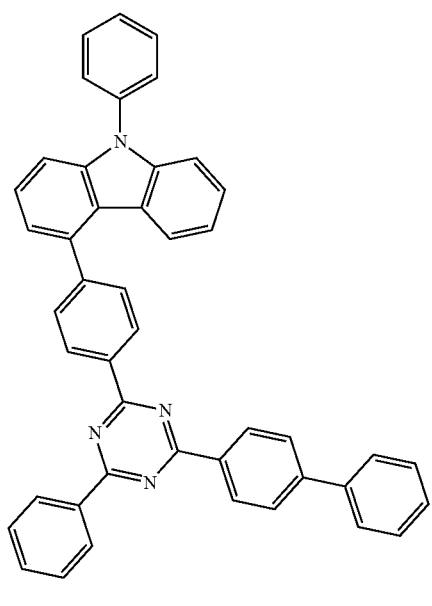
C-5
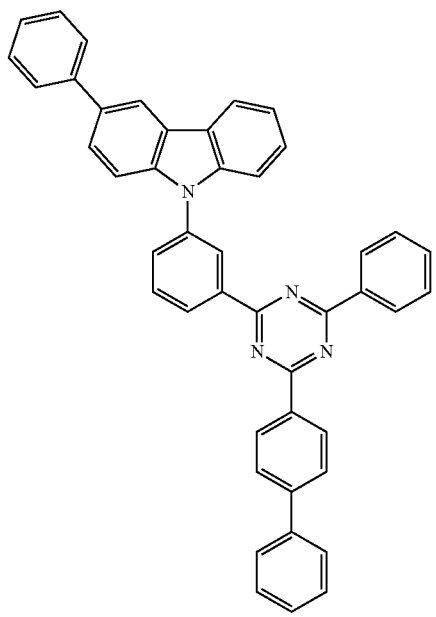
C-4
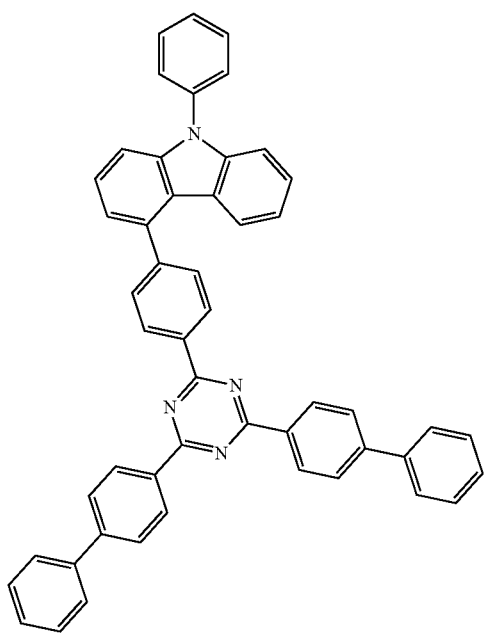
C-6
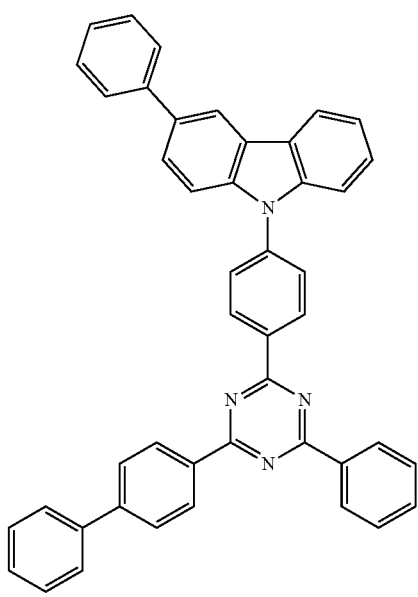

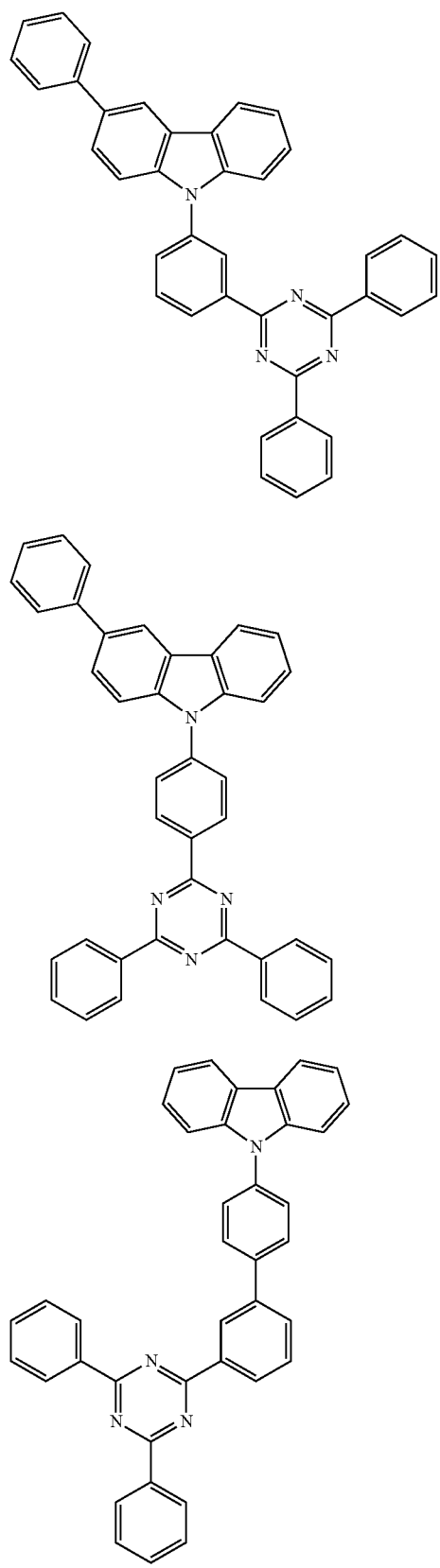
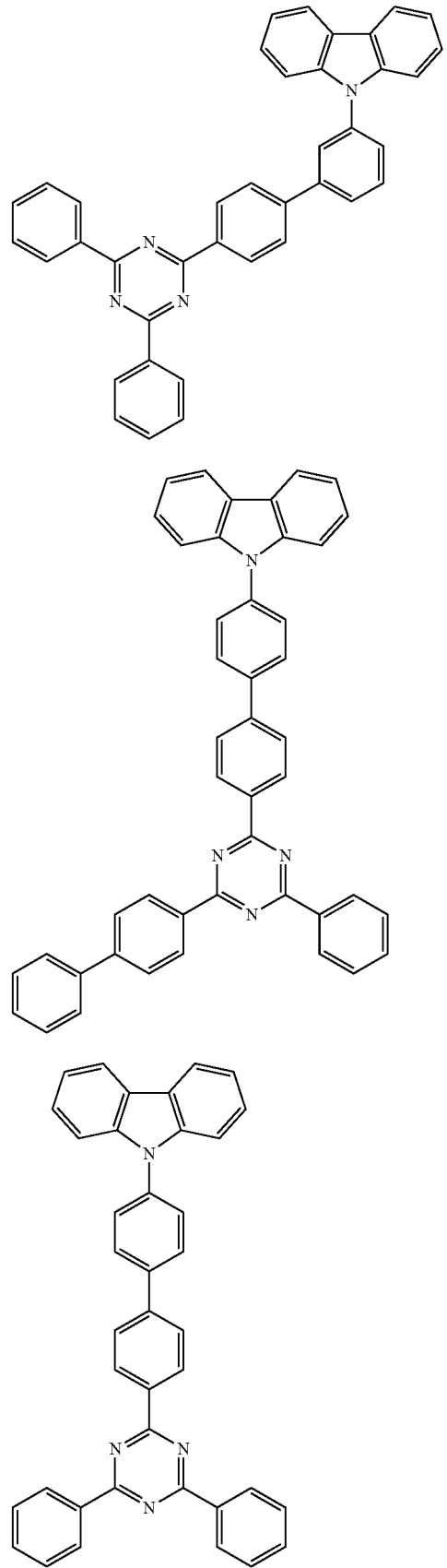

C-13
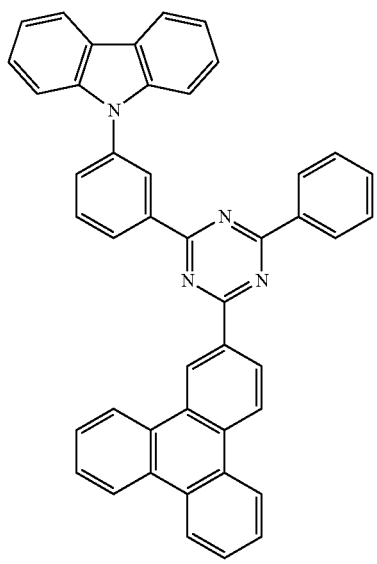
C-14
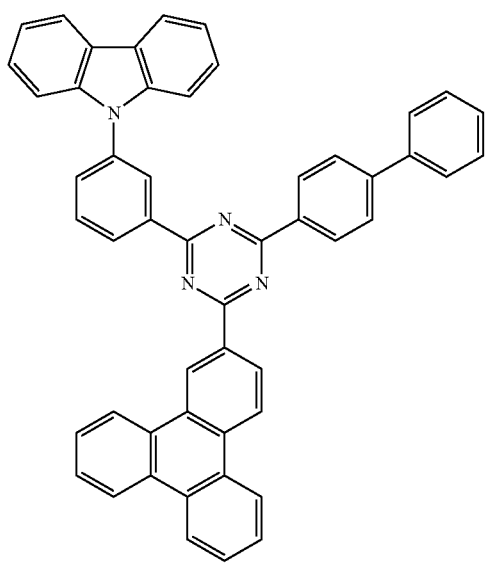
C-15
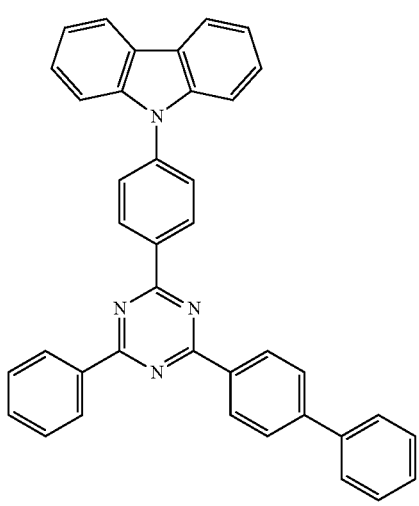
C-16
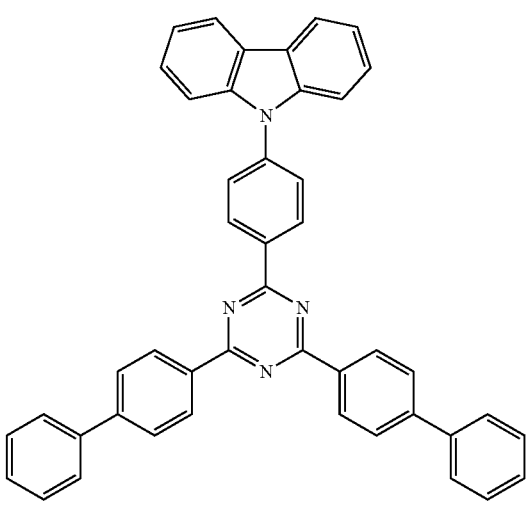
C-17
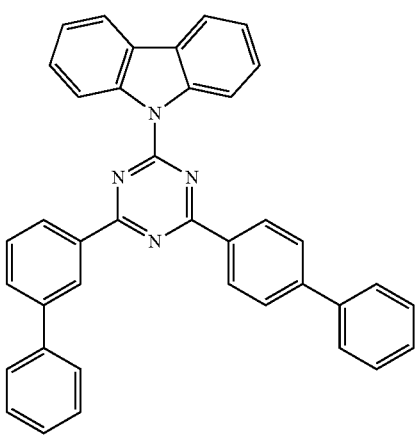
C-18
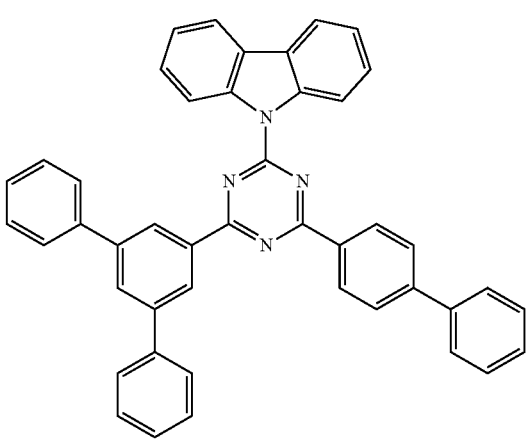

C-19
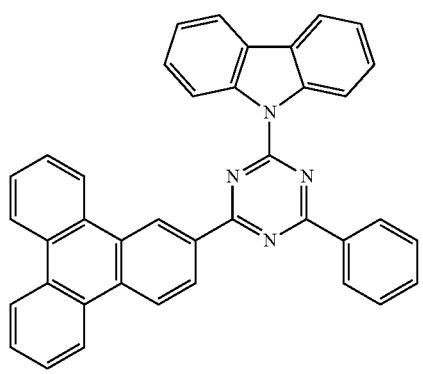
C-22
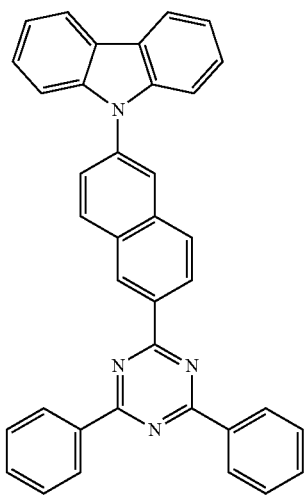
C-20
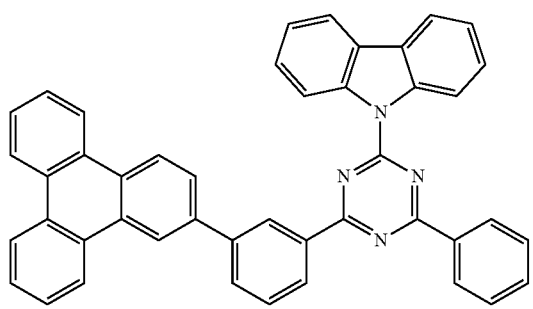
C-23
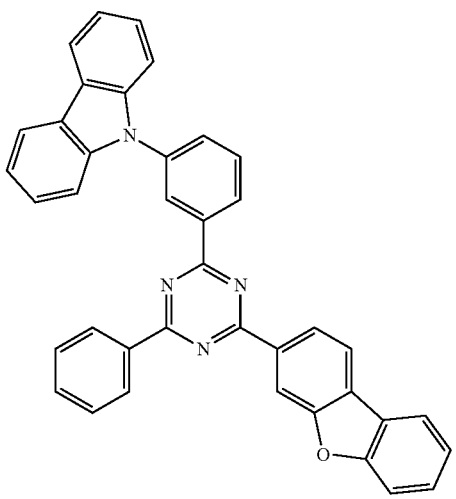
C-21
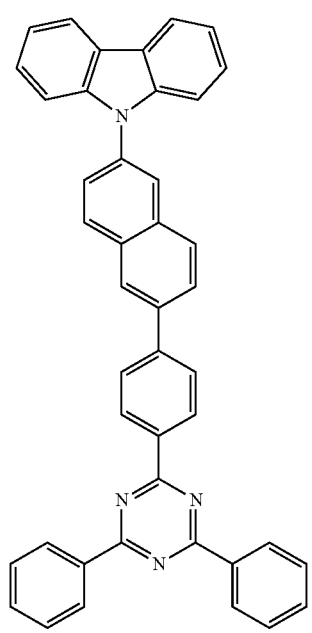
C-24
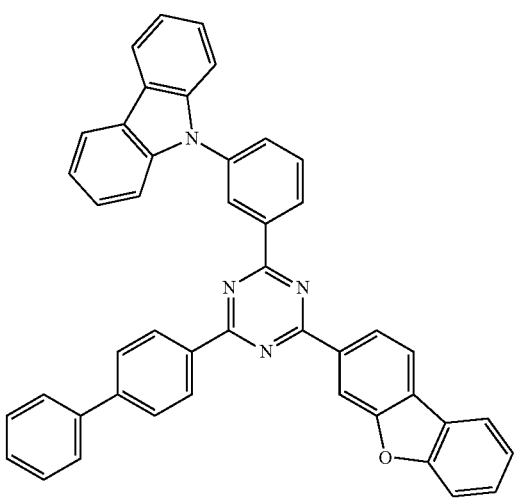

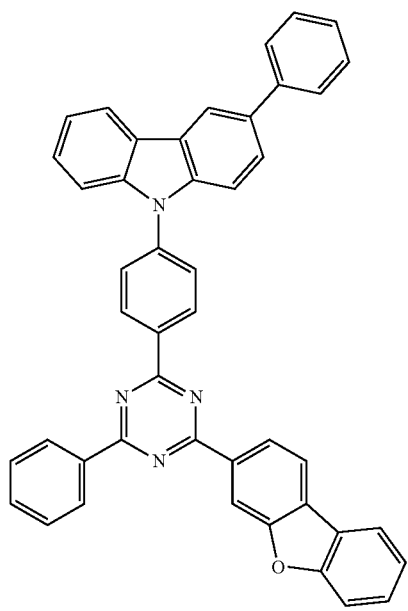
C-25
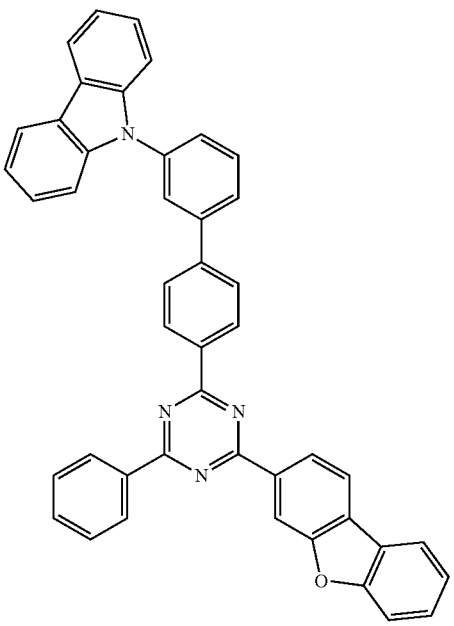
C-27
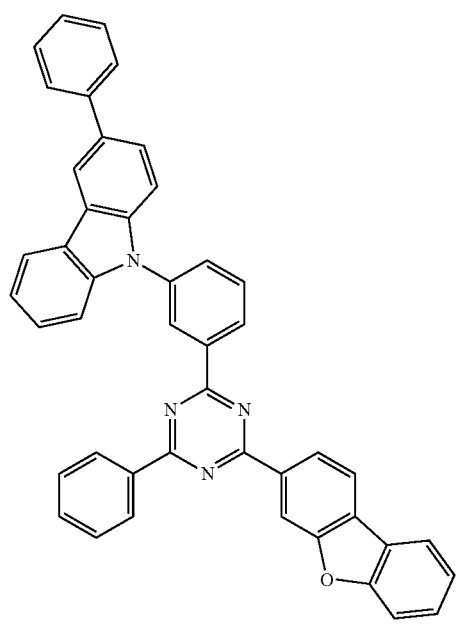
C-26
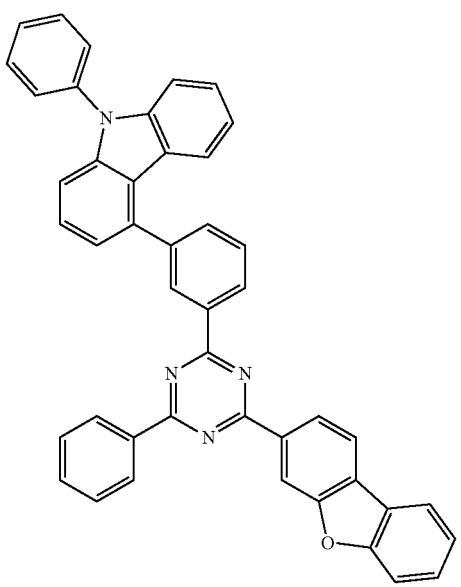
C-28

C-29
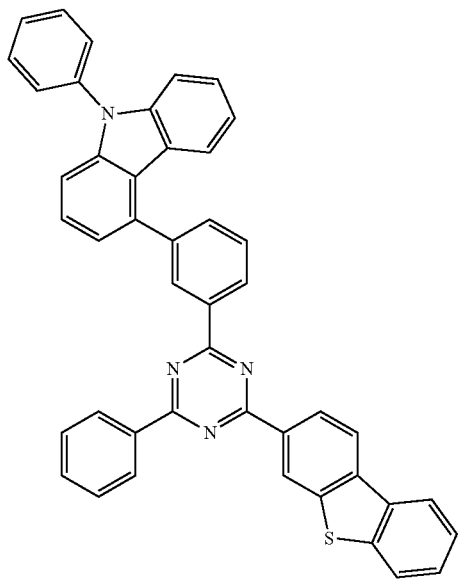
C-30
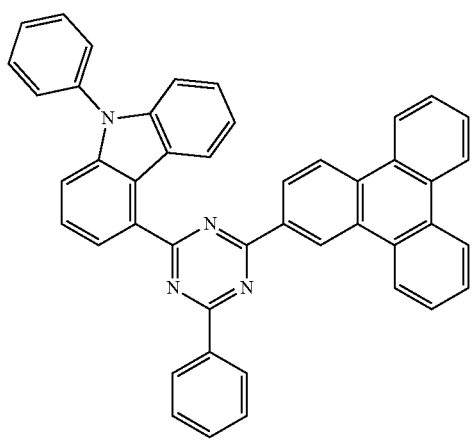
C-31
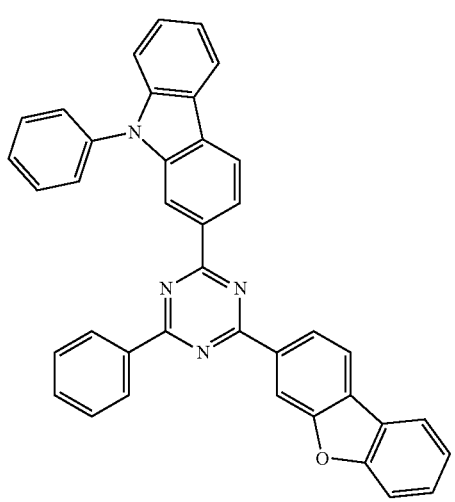
C-32
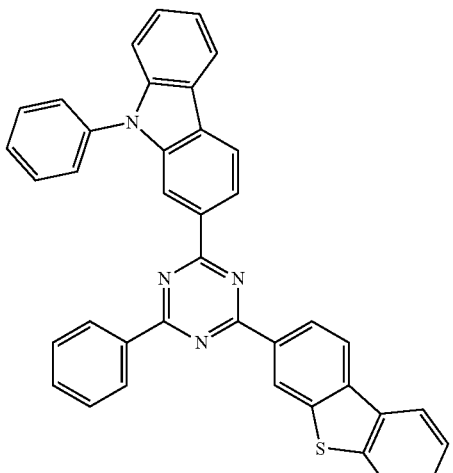
C-33
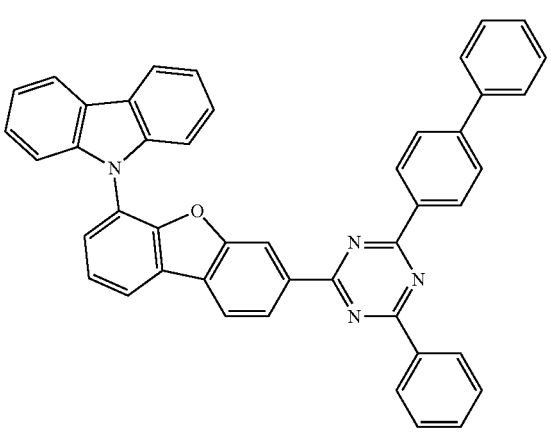
C-34
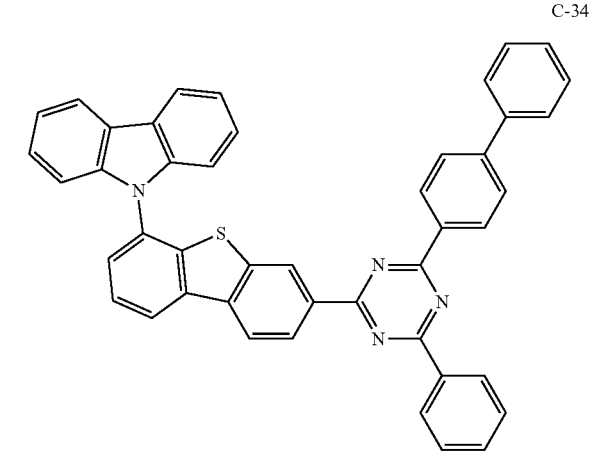

C-35
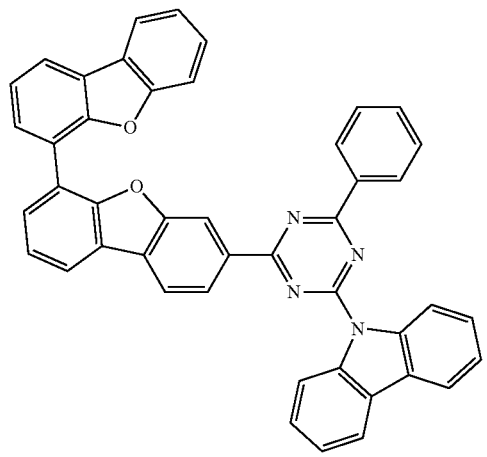
C-36
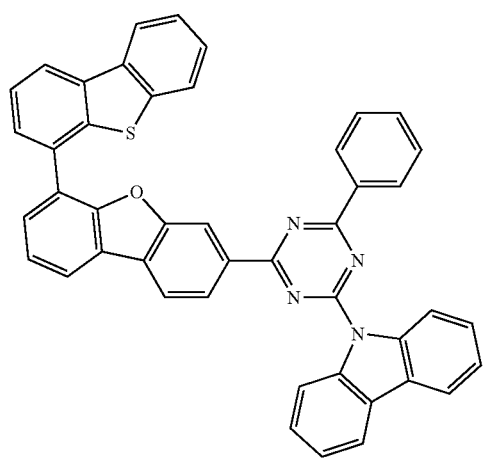
C-37
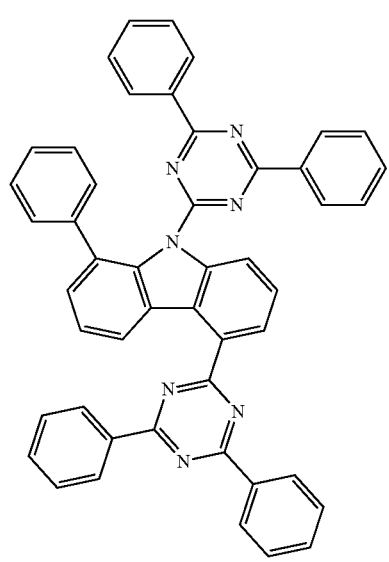
C-38
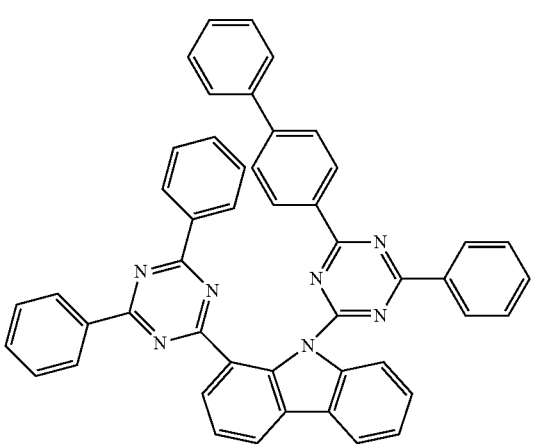
C-39
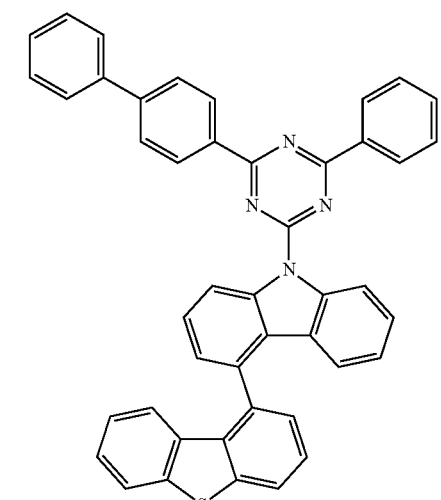
C-40
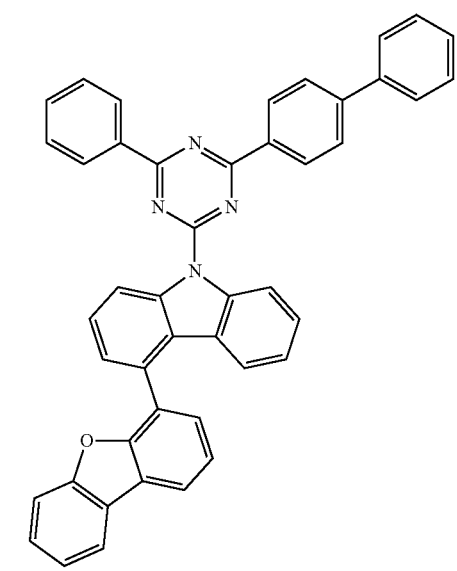

C-41
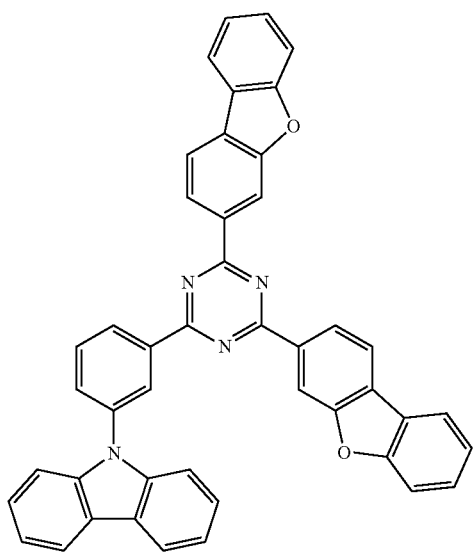
C-42
C-43
C-44
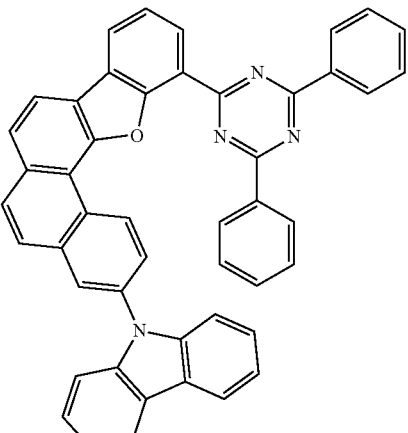
C-45
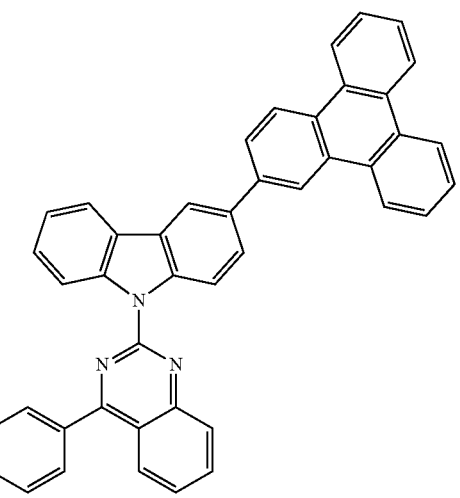
C-46
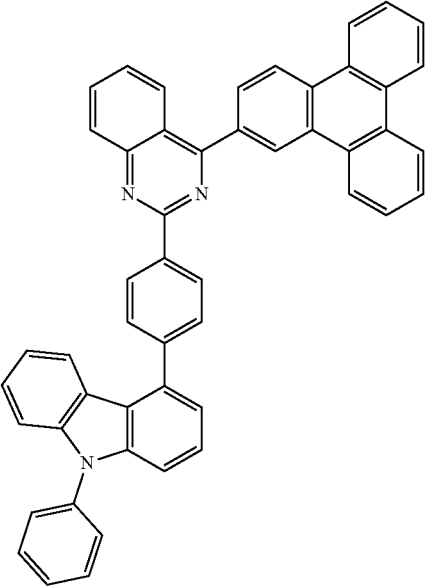

C-47
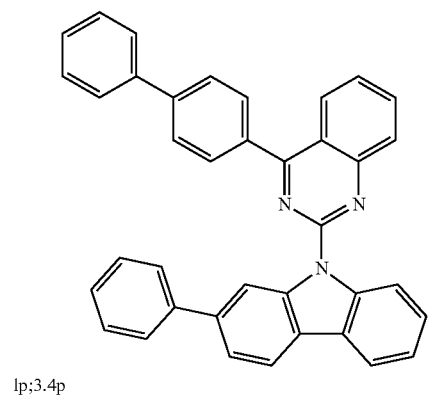
C-48
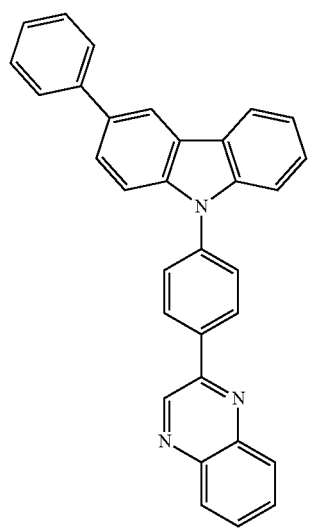
C-49
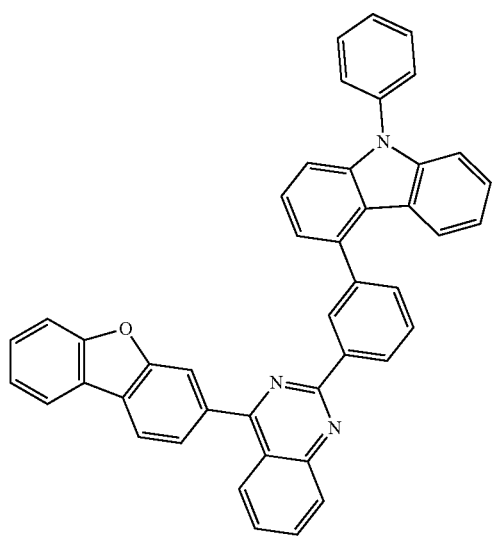
C-50
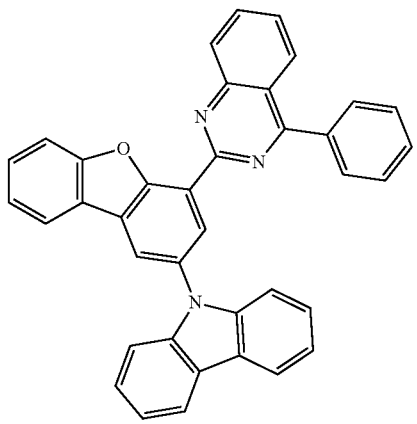
C-51
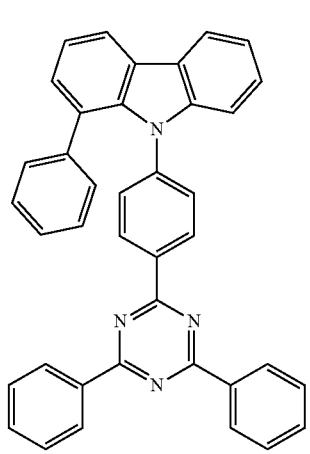
C-52
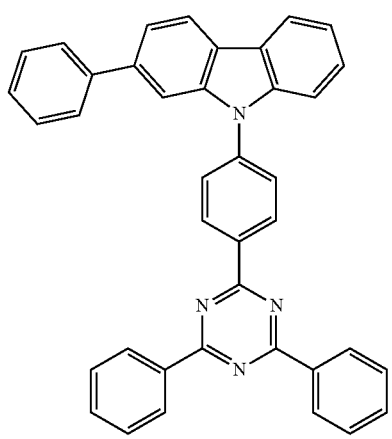

C-53
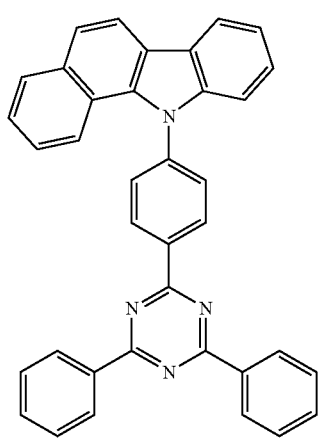
C-54
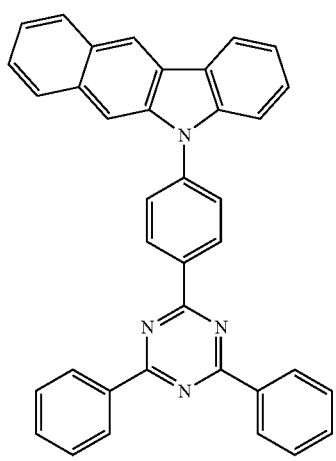
C-55
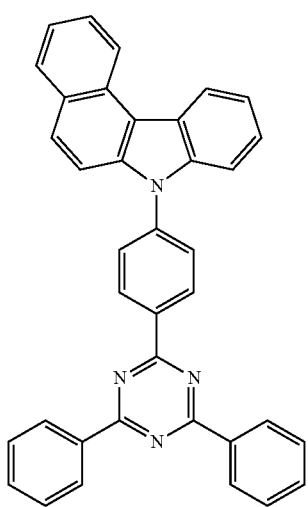
C-56
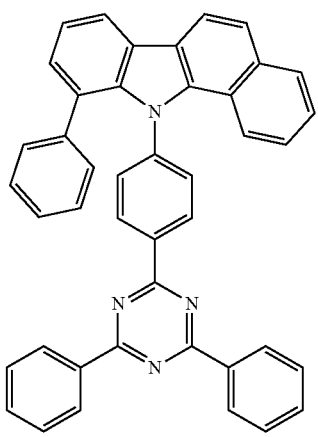
C-57
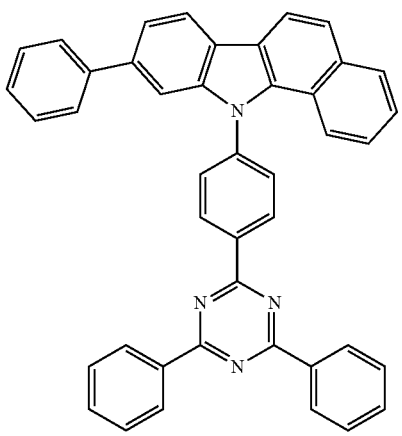
C-58
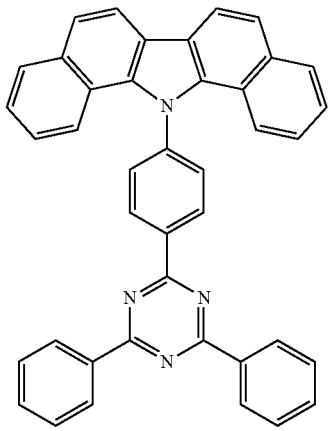

-continued
C-59
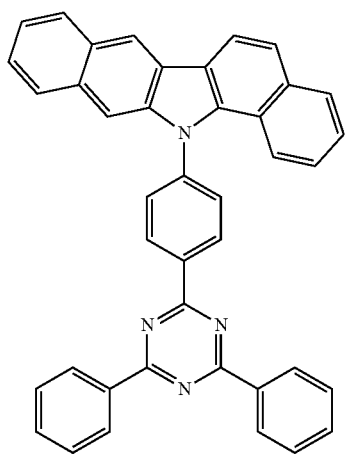
C-62
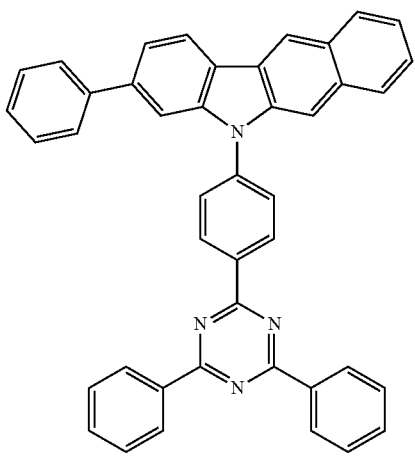
C-60
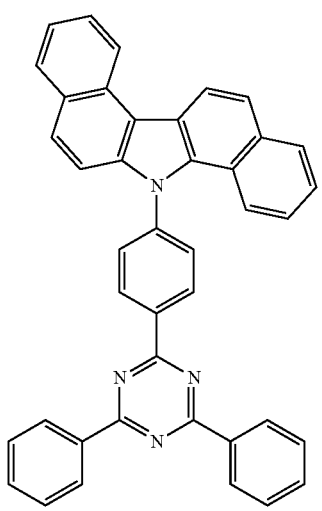
C-63
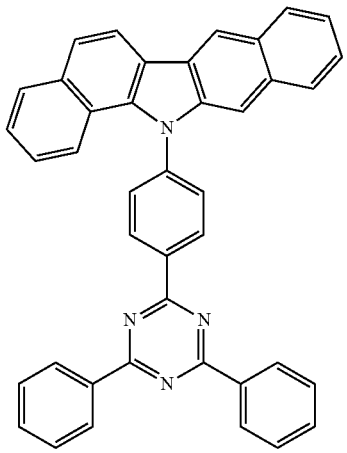
C-61
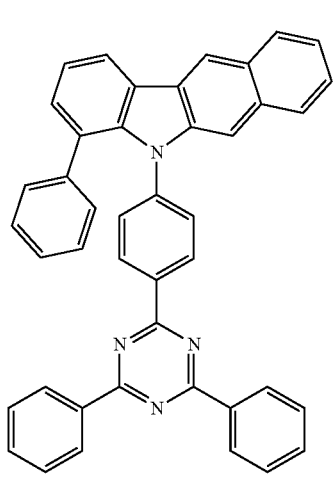
C-64
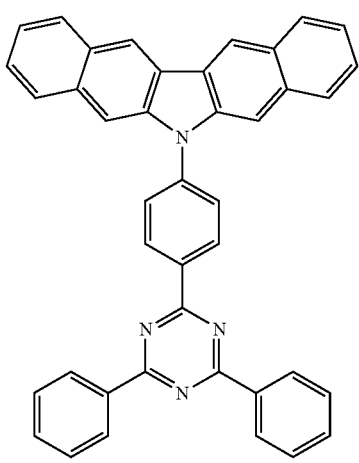

C-65
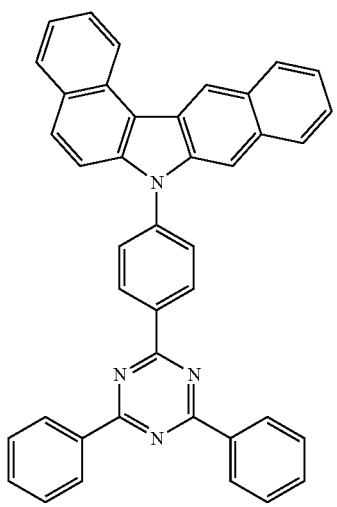
C-66
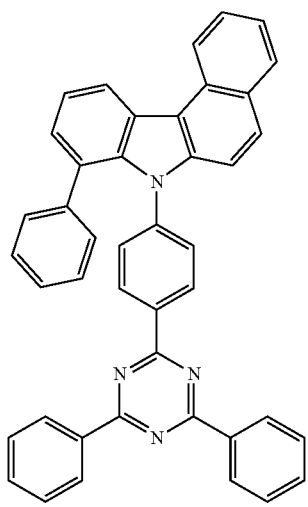
C-67
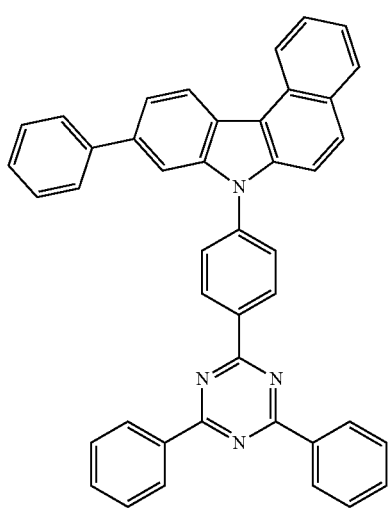
C-68
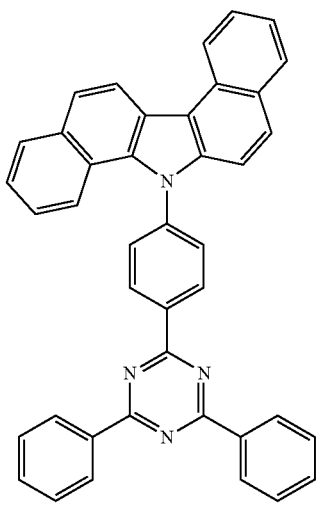
C-69
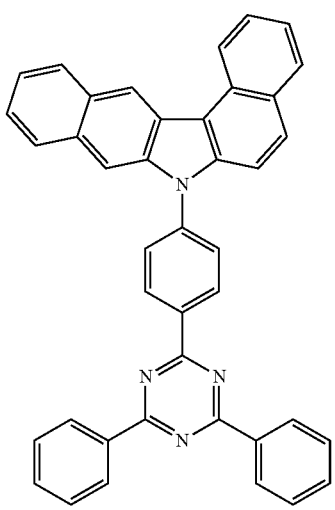
C-70
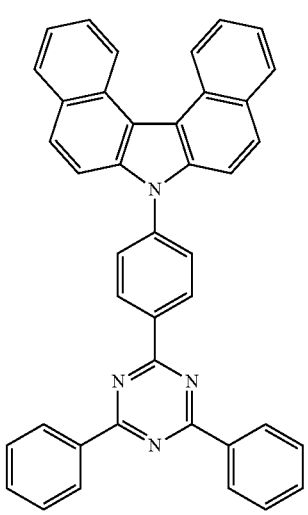

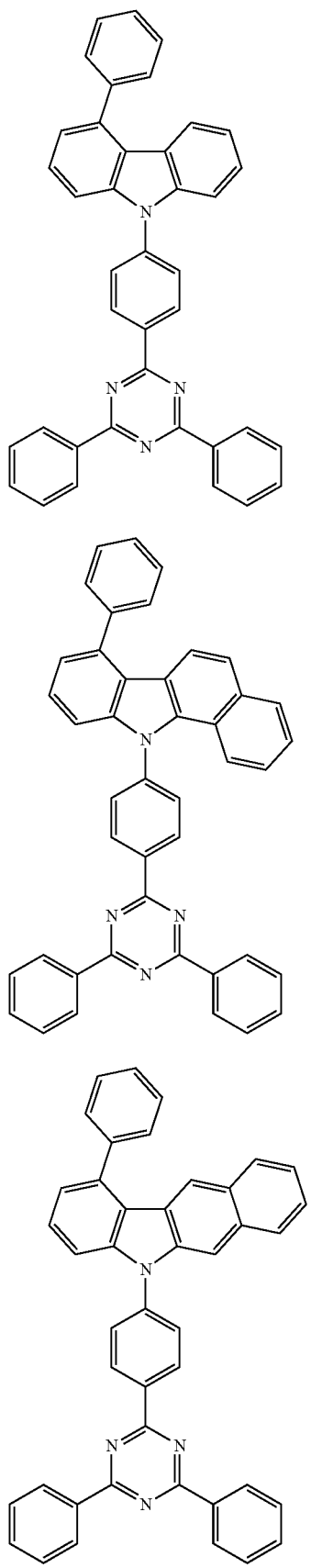
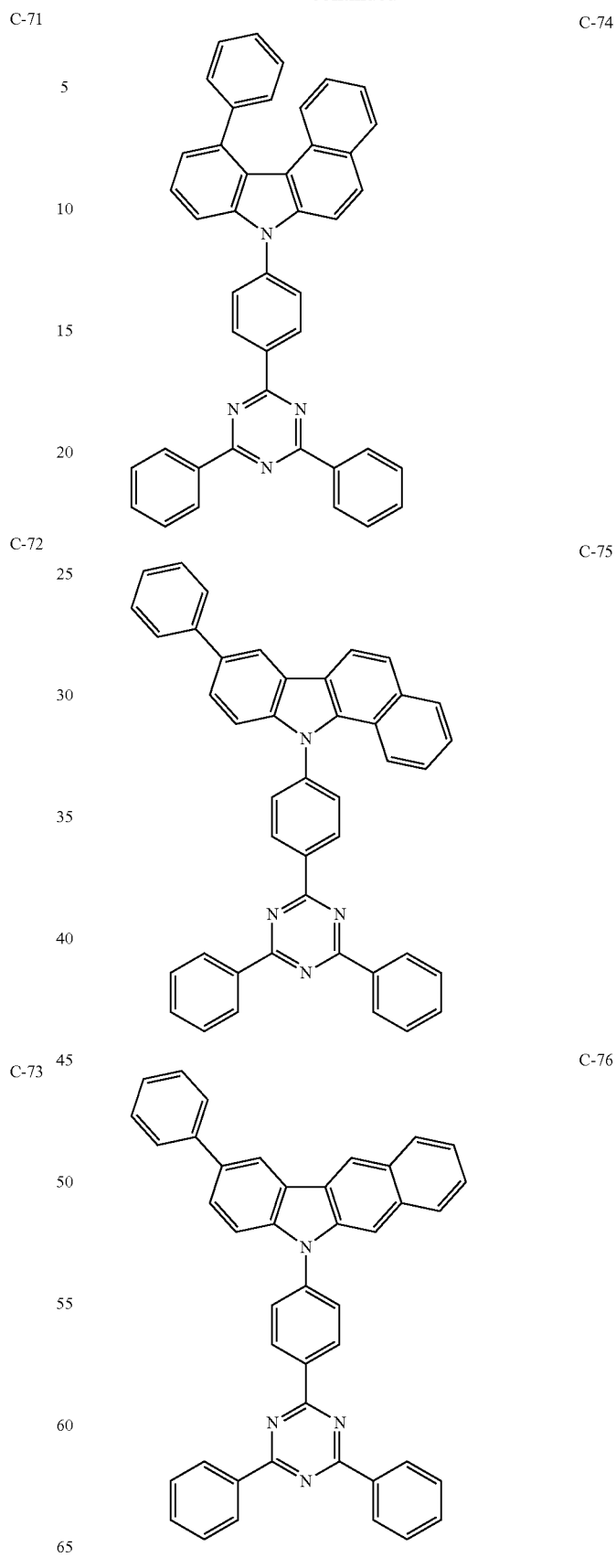

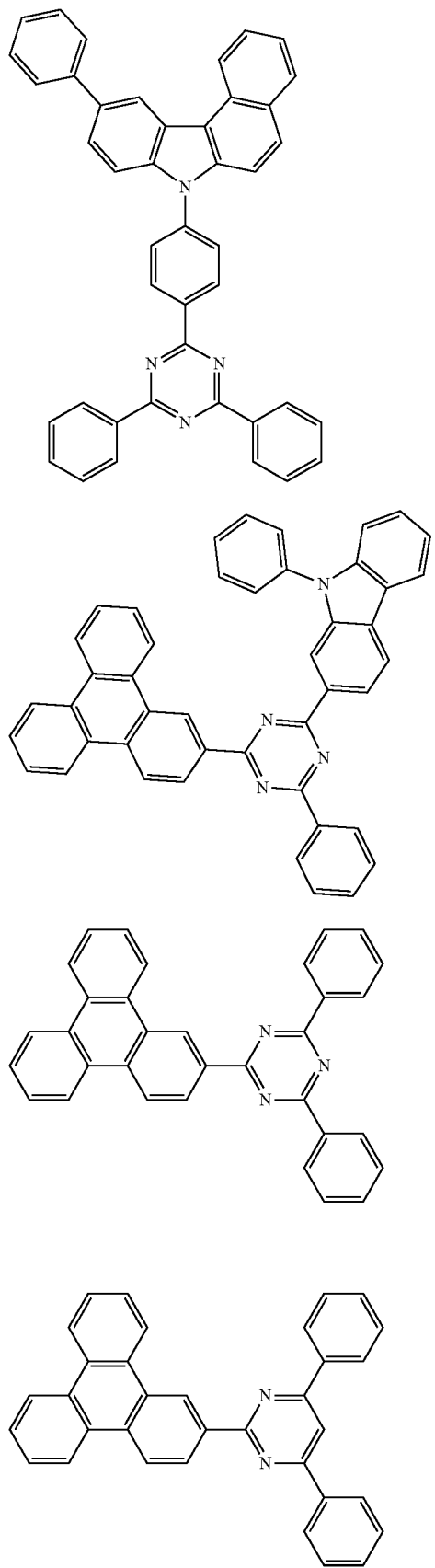
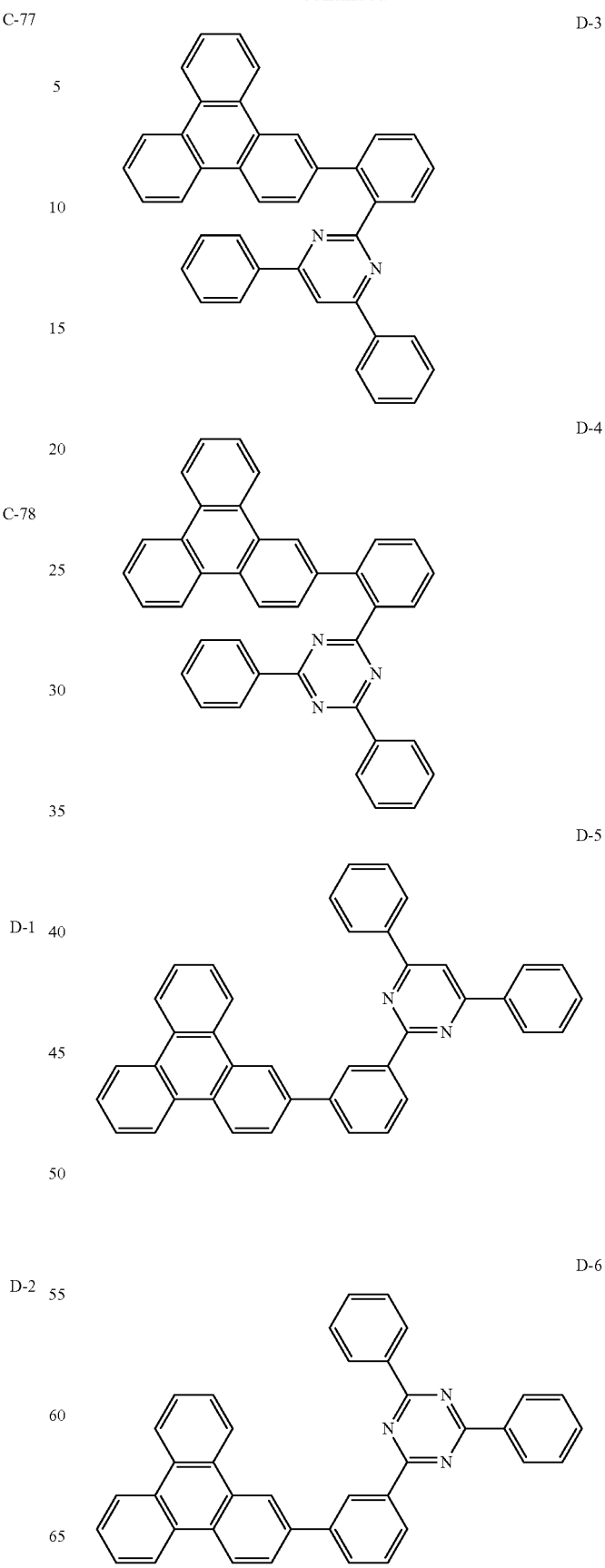

-continued
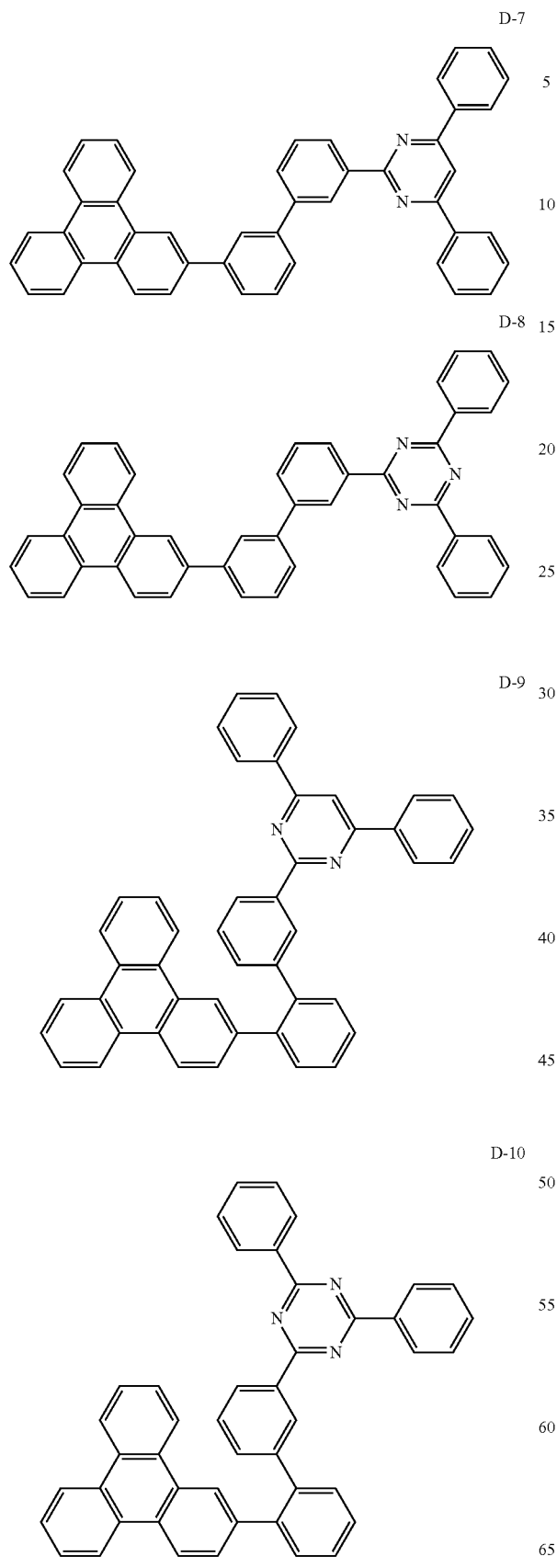
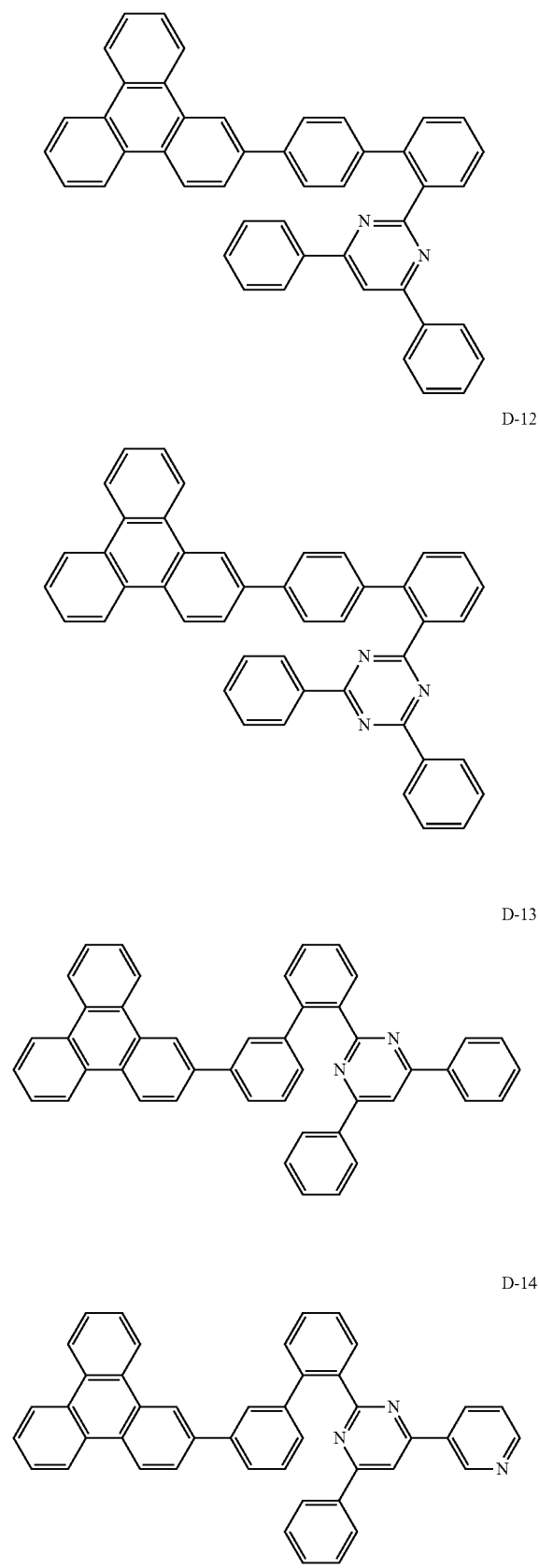

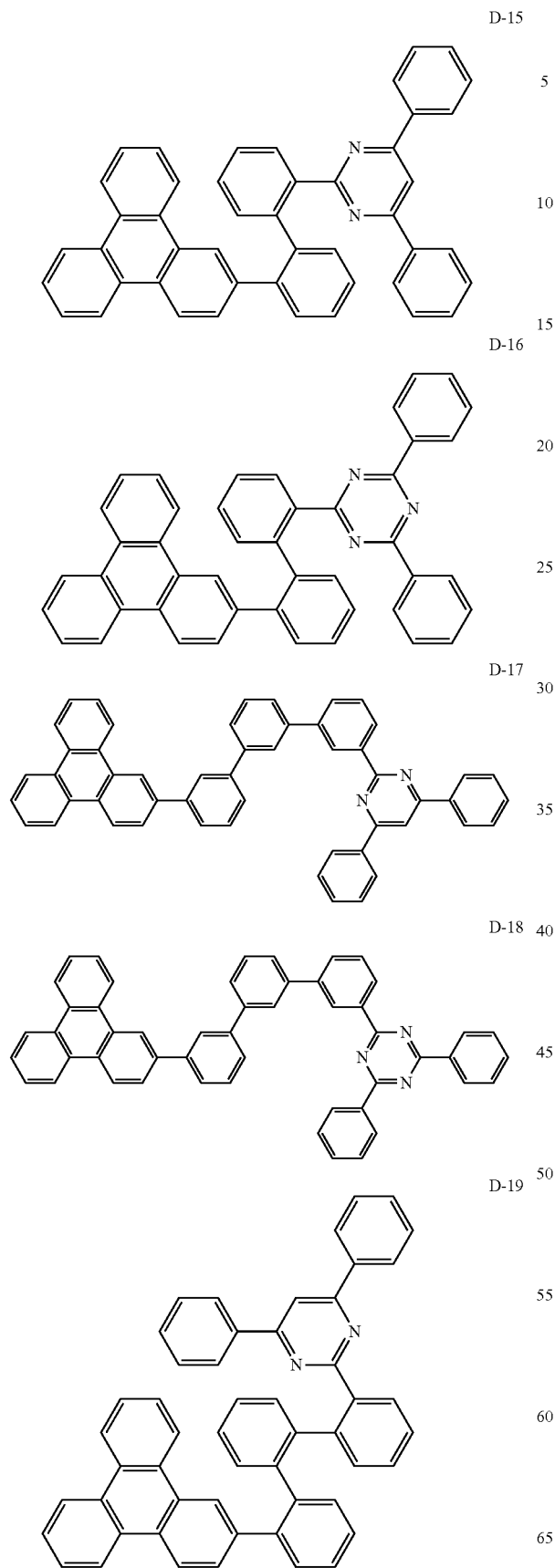
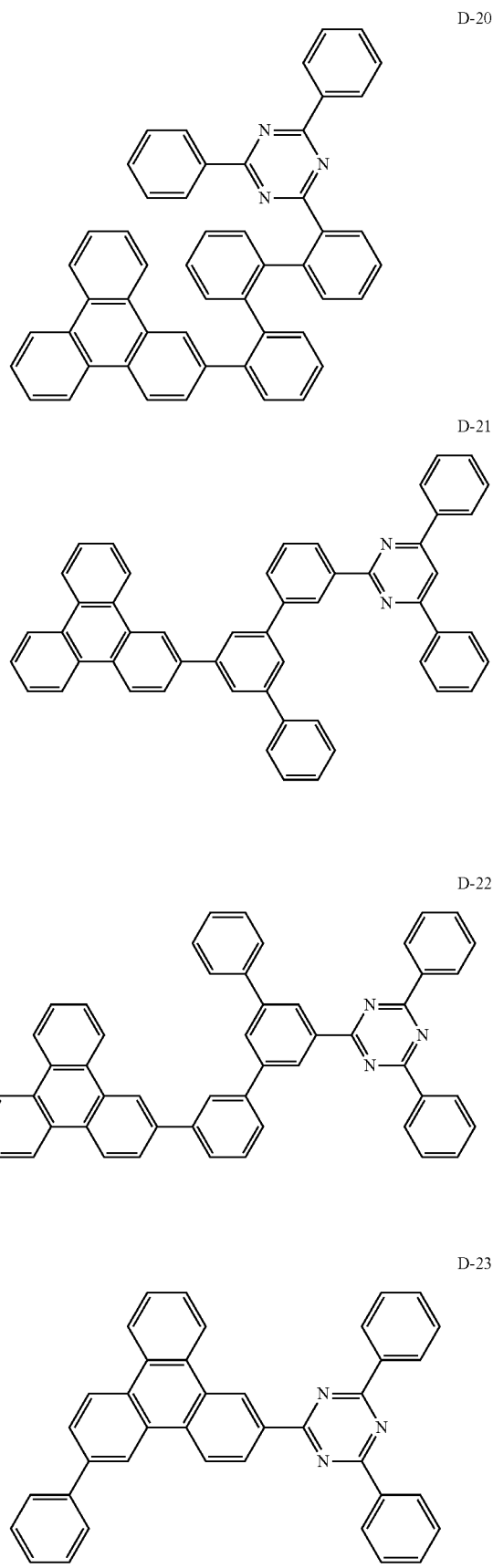

D-24
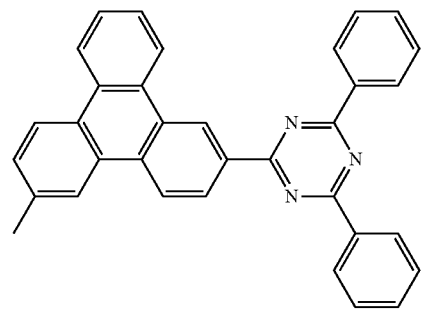
D-25
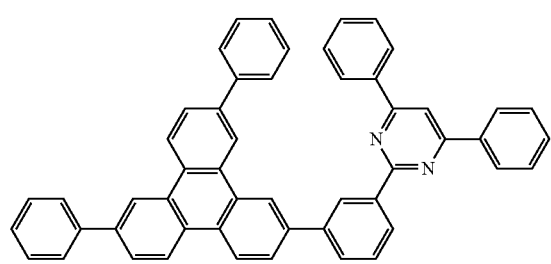
D-26
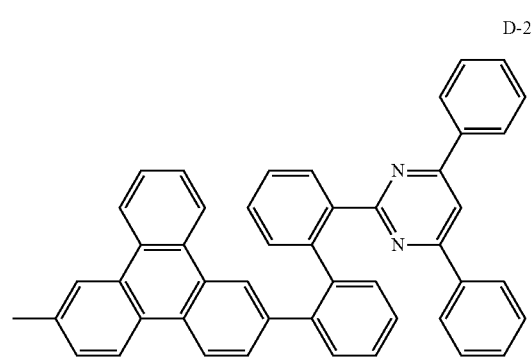
D-27
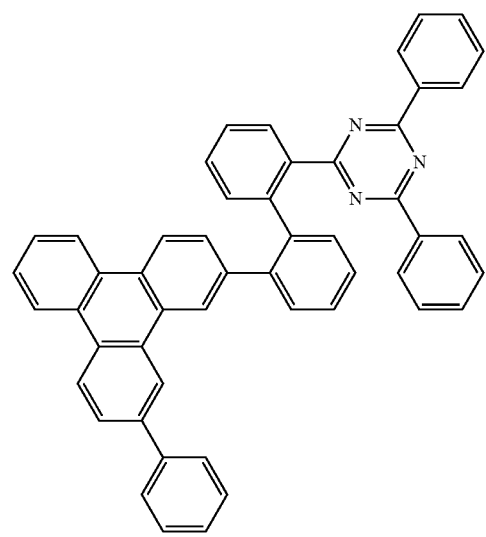
D-28
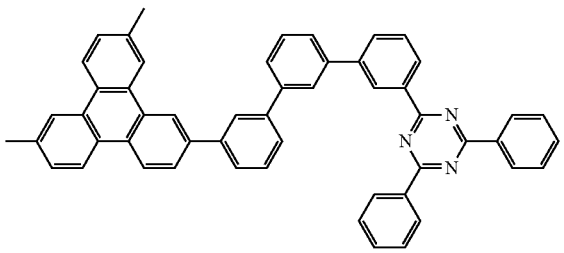
D-29
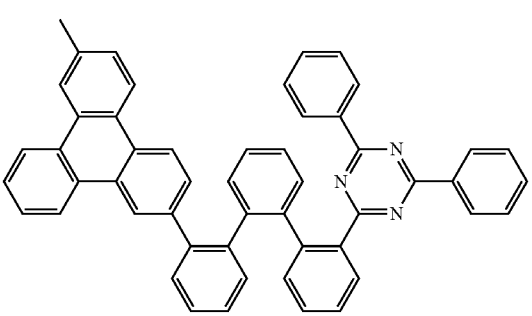
D-30
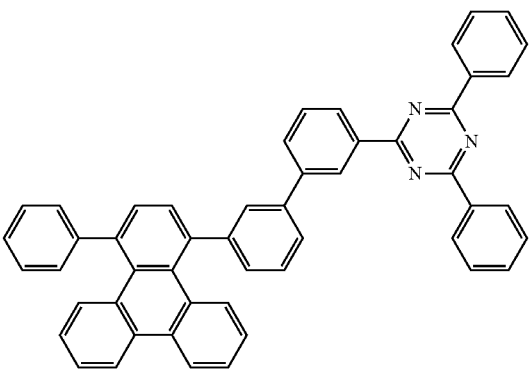
D-31
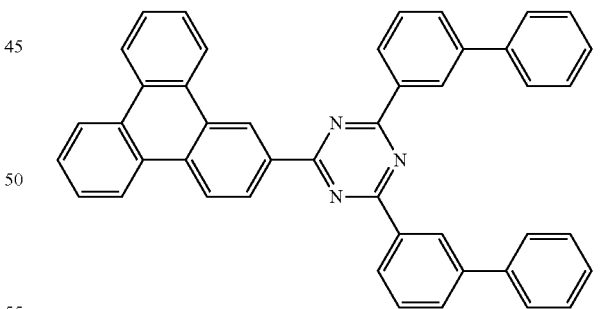
D-32
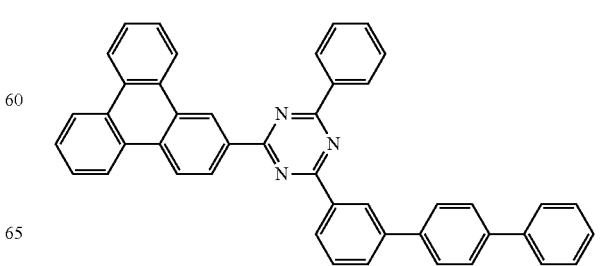

D-33
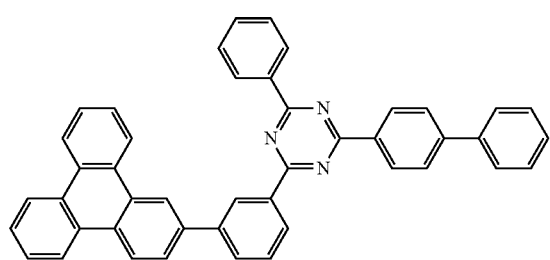
D-34
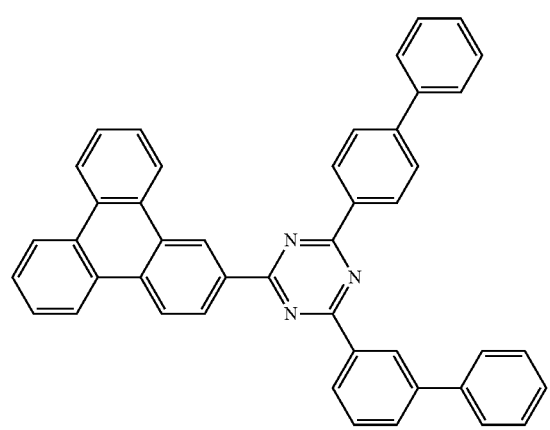
D-35
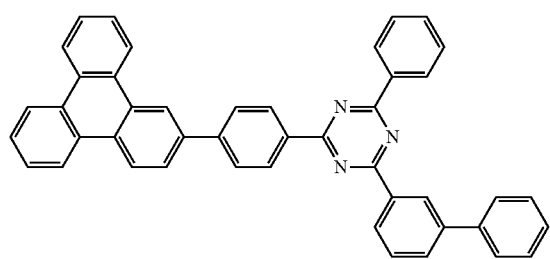
D-36
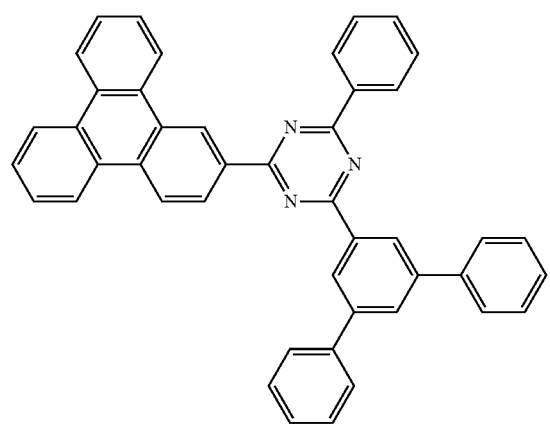
D-37
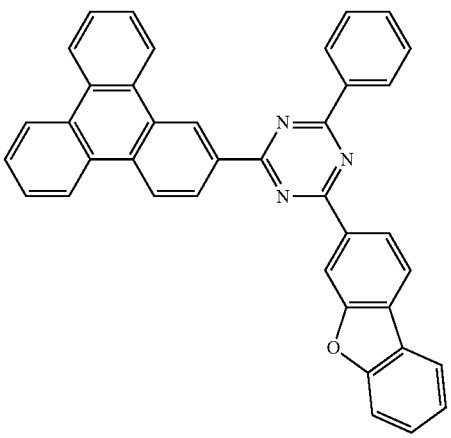
D-38
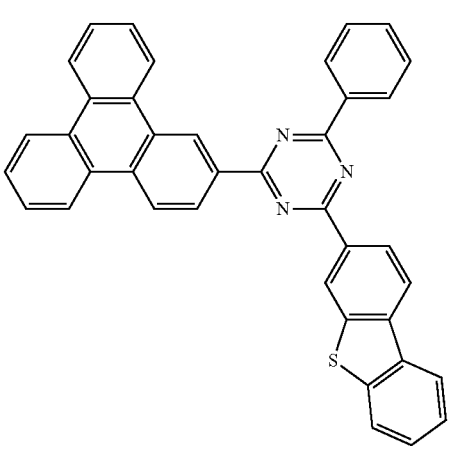
D-39
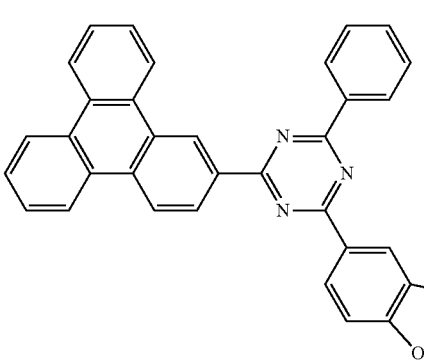
D-40
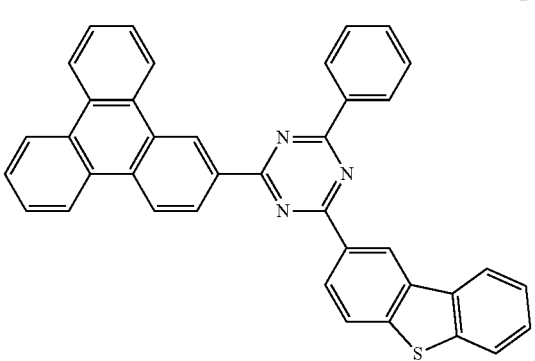

D-41
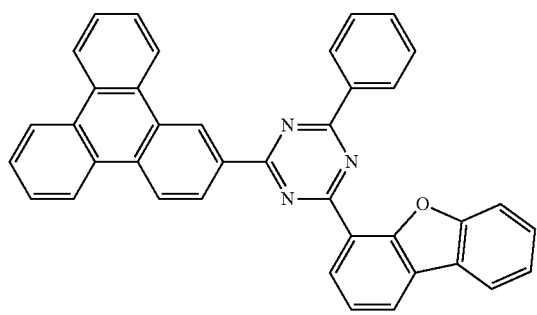
D-42
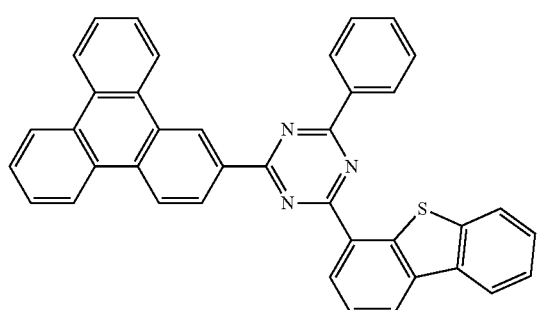
D-43
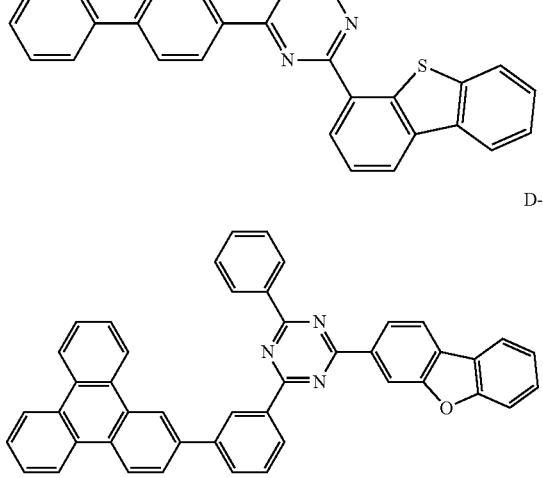
D-44
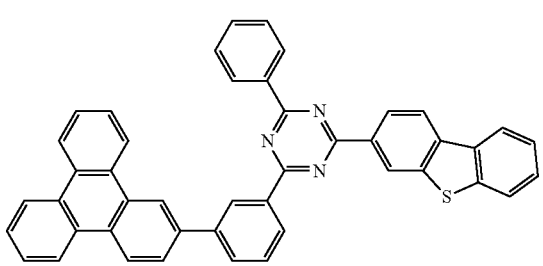
D-45
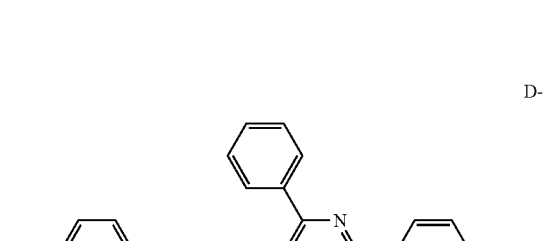
D-46
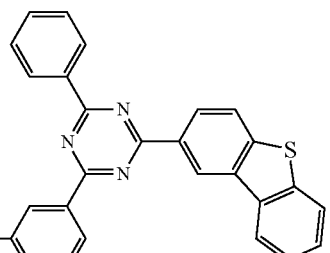
D-47
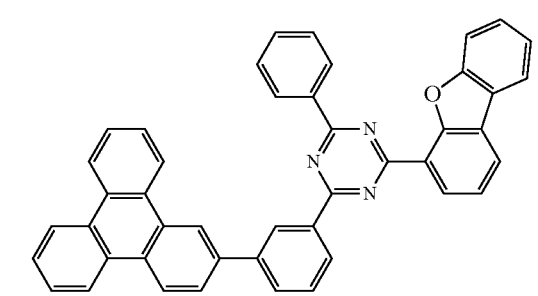
D-48
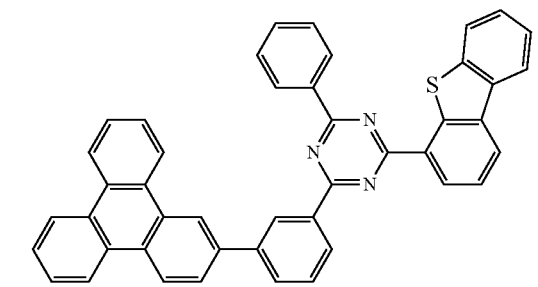
D-49
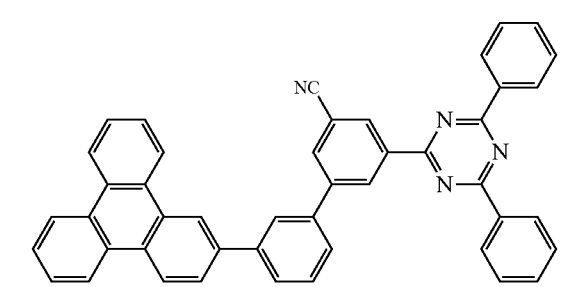
D-50
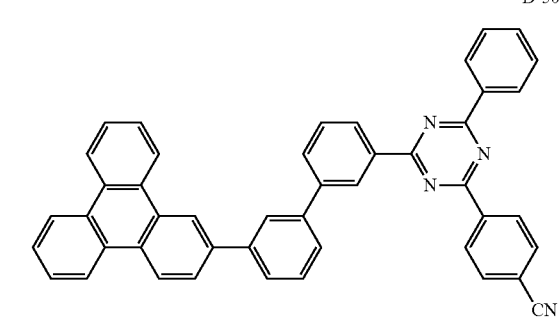

-continued

D-51
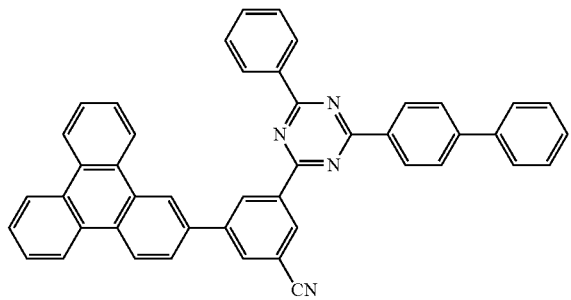

D-52
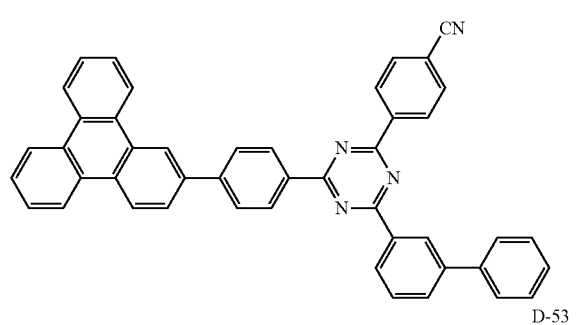

D-53
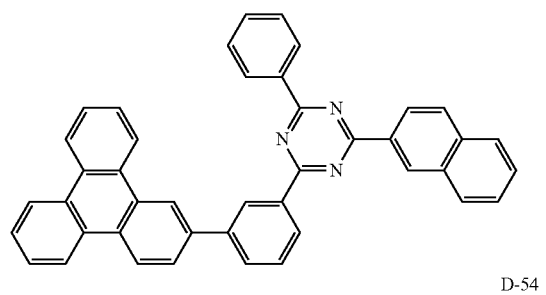

D-54
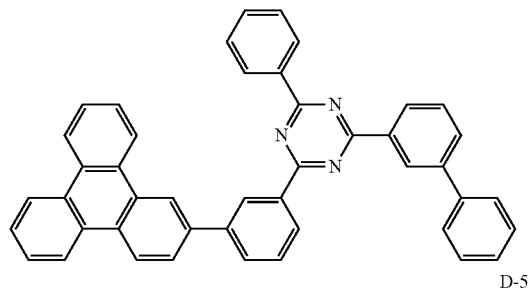

D-55
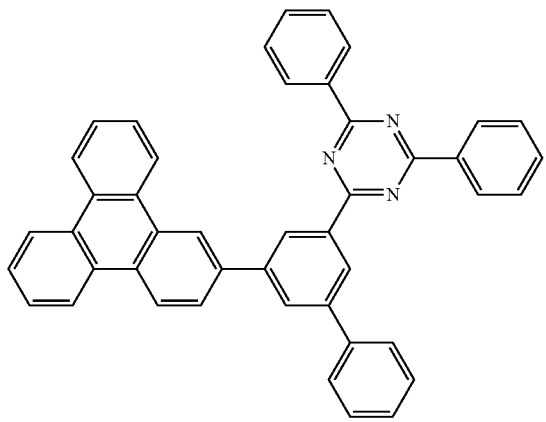

-continued

D-56
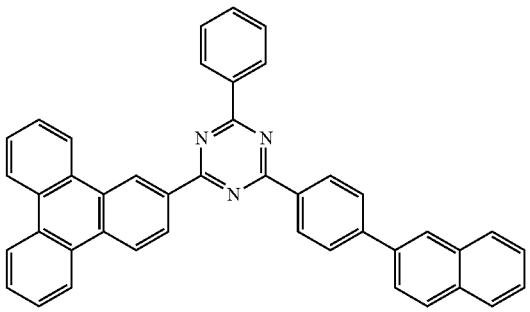

D-57
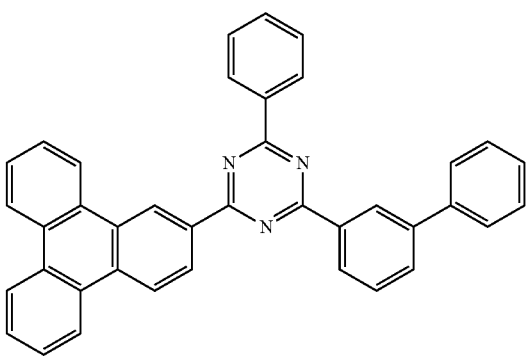

In an implementation, the first compound may be represented by Chemical Formula 1A-1-b, Chemical Formula 1A-1-c, or Chemical Formula 1A-2-a and the second compound may be represented by Chemical Formula 3-1a or Chemical Formula 3-3a.

In an implementation, Ar of Chemical Formula 1A-1-b, Chemical Formula 1A-1-c and Chemical Formula 1A-2-a may be, e.g., a substituted or unsubstituted phenyl group, or a substituted or unsubstituted biphenyl group, $L^a$ and $L^1$ to $L^4$ may each independently be, e.g., a single bond or a substituted or unsubstituted phenylene group, $R^a$ and $R^1$ to $R^4$ may each independently be, e.g., hydrogen or the group represented by Chemical Formula a, $L^b$ and $L^c$ may each independently be, e.g., a single bond or a substituted or unsubstituted C6 to C12 arylene group, and $R^b$ and $R^c$ may each independently be, e.g., a substituted or unsubstituted, phenyl group, a substituted or unsubstituted biphenyl group, substituted or naphthyl group, a substituted or unsubstituted fluorenyl group, a substituted or unsubstituted dibenzofuranyl group, or a substituted or unsubstituted dibenzothiophenyl group. In an implementation, when the group is substituted, the substituent may be, e.g., a phenyl group, a naphthyl group, an anthracenyl group, a phenanthrenyl group, a triphenylene group, a carbazolyl group, a dibenzofuranyl group, or a dibenzothiophenyl group.

In an implementation, $L^6$, $L^8$, and $L^{10}$ of Chemical Formula 3-1a may each independently be, e.g., a single bond or a substituted or unsubstituted phenylene group, $R^6$, $R^8$ and $R^{10}$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, and at least one of $R^6$, $R^8$ and $R^{10}$ may be, e.g., a substituted or unsubstituted triphenylene group, a substituted or unsubstituted carbazolyl group, a substituted or unsubstituted dibenzofuranyl group, or a substituted or unsubstituted dibenzothiophenyl group.

In an implementation, $X^2$ of Chemical Formula 3-3a may be, e.g., O or S, $L^5$ and $L^9$ may each independently be a single bond or a substituted or unsubstituted phenylene group, $R^5$ and $R^9$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, and at least one of $R^5$ and $R^9$ may be, e.g., a substituted or unsubstituted carbazolyl group, a substituted or unsubstituted dibenzofuranyl group, or a substituted or unsubstituted dibenzothiophenyl group.

The first compound and the second compound may be, e.g., included in a weight ratio of about 1:99 to about 99:1. Within the range, a desirable weight ratio may be adjusted using a hole transport capability of the first compound and an electron transport capability of the second compound to realize bipolar characteristics and thus to improve efficiency and life-span. Within the range, they may be, e.g., included in a weight ratio of about 10:90 to about 90:10, about 20:80 to about 80:20, about 30:70 to about 70:30, about 40:60 to about 60:40, or about 50:50. In an implementation, they may be included in a weight ratio of about 50:50 to about 60:40, e.g., about 60:40.

In an implementation, the first compound and the second compound may be included as a host, e.g., a phosphorescent host of the light emitting layer, respectively.

The light emitting layer may further include at least one compound in addition to the aforementioned host.

The light emitting layer may further include a dopant. The dopant may be, e.g., a phosphorescent dopant. In an implementation, the dopant may be a red, green, or blue phosphorescent dopant, e.g., a red phosphorescent dopant.

The dopant may be mixed with the aforementioned host in a small amount to cause light emission, and may be generally a material such as a metal complex that emits light by multiple excitation into a triplet or more. The dopant may be, e.g., an inorganic, organic, or organic/inorganic compound, and one or more types thereof may be used.

Examples of the dopant may include a phosphorescent dopant and examples of the phosphorescent dopant may include an organometal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^{17}MX^4$ [Chemical Formula Z]

In Chemical Formula Z, M may be, e.g., a metal, and $L^{17}$ and $X^4$ may each independently be, e.g., a ligand to form a complex compound with M.

The M may be, e.g., Ir, Pt, Os, Ti, Zr, Hf, Eu, Tb, Tm, Fe, Co, Ni, Ru, Rh, Pd, or a combination thereof and $L^{17}$ and $X^4$ may each independently be, e.g., a bidendate ligand.

The hole transport auxiliary layer 142 may be between light emitting layer 130 and the hole transport layer 141 that will be described below, e.g., contacting the light emitting layer 130. The hole transport auxiliary layer 142 may contact the light emitting layer 130 and may minutely control mobility of holes on the interface of the light emitting layer 130 and the hole transport layer 141. The hole transport auxiliary layer 142 may include a plurality of layers.

The hole transport auxiliary layer 142 may include, e.g., a third compound represented by Chemical Formula 4.

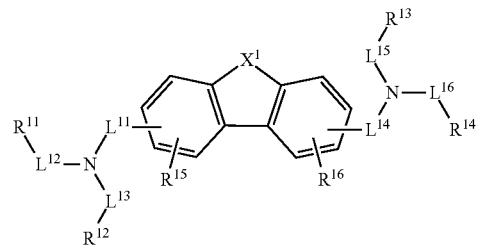

[Chemical Formula 4]

In Chemical Formula 4,
$X^1$ may be, e.g., O or S,
$L^{11}$ to $L^{16}$ may each independently be, e.g., a single bond, a substituted or unsubstituted C6 to C20 arylene group, a substituted or unsubstituted C2 to C20 heterocyclic group, or a combination thereof,
$R^{11}$ to $R^{14}$ may each independently be, e.g., a substituted or unsubstituted C6 to C30 aryl group, a substituted or unsubstituted C2 to C30 heterocyclic group, or a combination thereof, and
$R^{15}$ and $R^{16}$ may each independently be, e.g., hydrogen, deuterium, a cyano group, or a substituted or unsubstituted C1 to C10 alkyl group.

The third compound may be a compound having a high HOMO energy level and may have good hole injection characteristics.

For example, the third compound may be applied to the hole transport auxiliary layer 142 and may effectively improve hole mobility in the interface between the light emitting layer 130 and the hole transport layer 141 to lower a driving voltage of an organic optoelectric device.

In an implementation, the third compound may be represented by one of Chemical Formula 4-1 to Chemical Formula 4-4 according to a specific substitution position of the amine group(s).

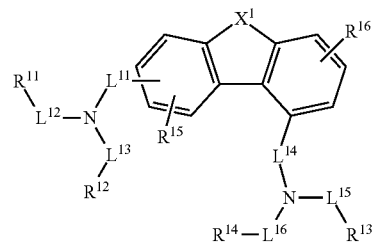

[Chemical Formula 4-1]

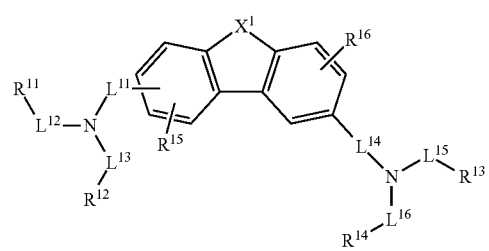

[Chemical Formula 4-2]

[Chemical Formula 4-3]

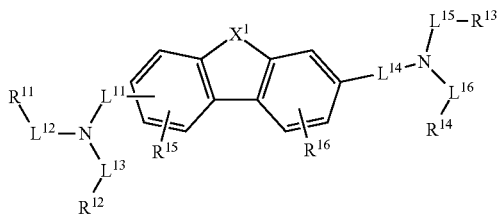

[Chemical Formula 4-4]

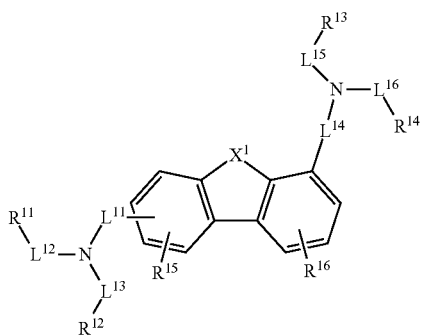

[Chemical Formula 4-1c]

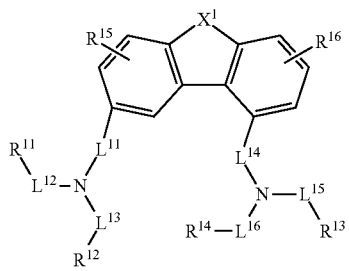

[Chemical Formula 4-1d]

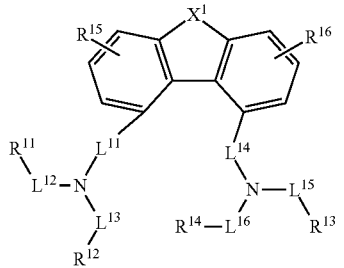

In Chemical Formula 4-1 to Chemical Formula 4-4, $X^1$, $L^{11}$ to $L^{16}$, and $R^{11}$ to $R^{16}$ may be the same as described above.

In an implementation, the third compound may be represented by one of Chemical Formula 4-1 to Chemical Formula 4-3.

In an implementation, Chemical Formula 4-1 may be, e.g., represented by one of Chemical Formula 4-1a, Chemical Formula 4-1b, Chemical Formula 4-1c, and Chemical Formula 4-1d.

In Chemical Formula 4-1a to Chemical Formula 4-1d, $X^1$, $L^{11}$ to $L^{16}$, and $R^{11}$ to $R^{16}$ may be the same as described above.

In an implementation, Chemical Formula 4-2 may be, e.g., represented by one of Chemical Formula 4-2a, Chemical Formula 4-2b, Chemical Formula 4-2c, and Chemical Formula 4-2d.

[Chemical Formula 4-1a]

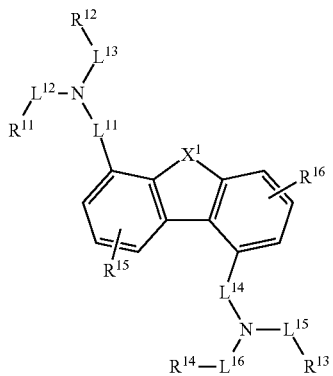

[Chemical Formula 4-1b]

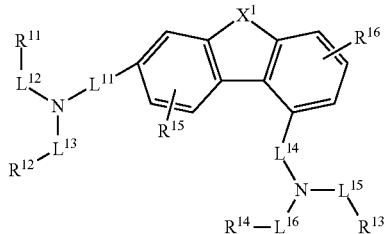

[Chemical Formula 4-2a]

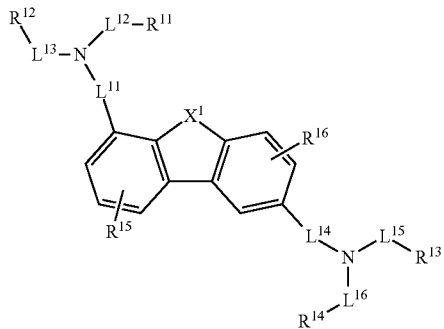

[Chemical Formula 4-2b]

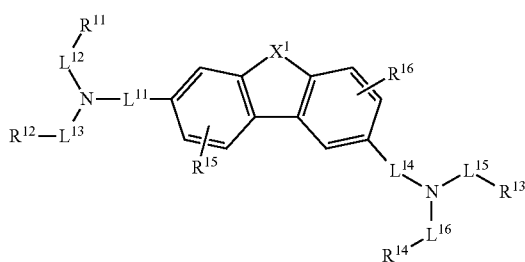

[Chemical Formula 4-2c]

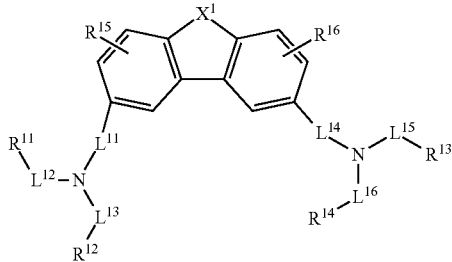

[Chemical Formula 4-2d]

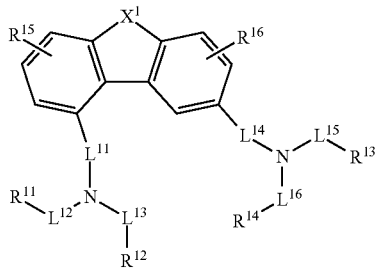

In Chemical Formula 4-2a to Chemical Formula 4-2d, $X^1$, $L^{11}$ to $L^{16}$, and $R^{11}$ to $R^{16}$ may be the same as described above.

In an implementation, Chemical Formula 4-3 may be, e.g., represented by one of Chemical Formula 4-3a, Chemical Formula 4-3b, Chemical Formula 4-3c, and Chemical Formula 4-3d.

[Chemical Formula 4-3a]

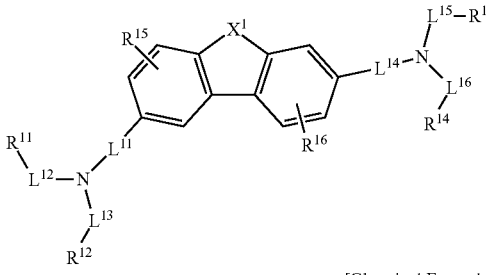

[Chemical Formula 4-3b]

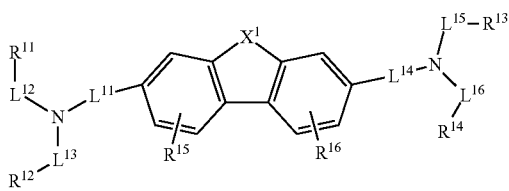

[Chemical Formula 4-3c]

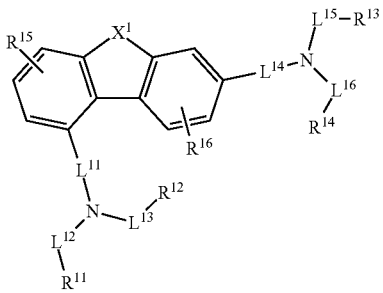

[Chemical Formula 4-3d]

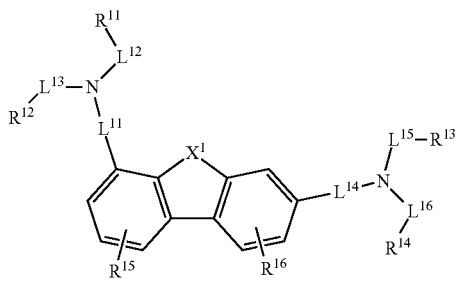

In Chemical Formula 4-3a to Chemical Formula 4-3d, $X^1$, $L^{11}$ to $L^{16}$, and $R^{11}$ to $R^{16}$ may be the same as described above.

In an implementation, the third compound may be represented by one of Chemical Formula 4-1b, Chemical Formula 4-2b, Chemical Formula 4-2c, Chemical Formula 4-3b, Chemical Formula 4-3c, and Chemical Formula 4-3d.

In an implementation, $L^{11}$ and $L^{14}$ may each be, e.g., a single bond, and $L^{12}$, $L^{13}$, $L^{15}$, and $L^{16}$ may each independently be, e.g., a single bond or a substituted or unsubstituted phenylene group.

In an implementation, $R^{11}$ to $R^{14}$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted fused dibenzofuranyl group, or a substituted or unsubstituted fused dibenzothiophenyl group.

In an implementation, $R^{11}$ to $R^{14}$ may each independently be, e.g., a substituted or unsubstituted phenyl group, a substituted or unsubstituted naphthyl group, a substituted or unsubstituted dibenzofuranyl group, or a substituted or unsubstituted dibenzothiophenyl group.

In an implementation, at least one of $R^{11}$ to $R^{14}$ may be, e.g., a substituted or unsubstituted dibenzofuranyl group, or a substituted or unsubstituted dibenzothiophenyl group.

In an implementation, $R^{15}$ and $R^{16}$ may each independently be hydrogen or a C1 to C5 alkyl group.

In an implementation, $R^{15}$ and $R^{16}$ may each be, e.g., hydrogen.

In an implementation, the first compound may be represented by Chemical Formula 1-2b, the second compound may be represented by Chemical Formula 2-1a or Chemical Formula 2-3a, and the third compound may be represented by one of Chemical Formula 3-1b, Chemical Formula 3-2b, Chemical Formula 3-2c, Chemical Formula 3-3b, Chemical Formula 3-3c, and Chemical Formula 3-3d.

In an implementation, the first compound may be represented by Chemical Formula 1A-1-b, Chemical Formula 1A-1-c, or Chemical Formula 1A-2-a, the second compound may be represented by Chemical Formula 3-1a, or Chemical Formula 3-3a, and the third compound may be represented by one of Chemical Formula 4-1b, Chemical Formula 4-2b, Chemical Formula 4-2c, Chemical Formula 4-3b, Chemical Formula 4-3c, and Chemical Formula 4-3d.

In an implementation, the third compound may be, e.g., a compound of the following Group 3.

[Group 3]

E-1

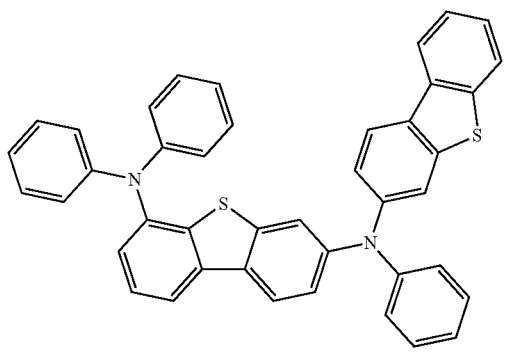

E-2

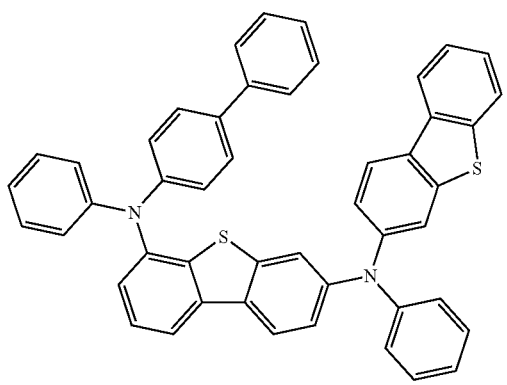

E-3

E-4

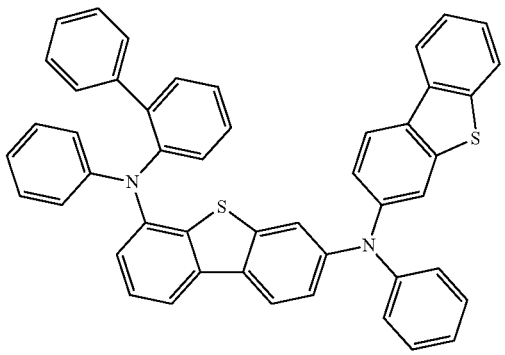

E-5

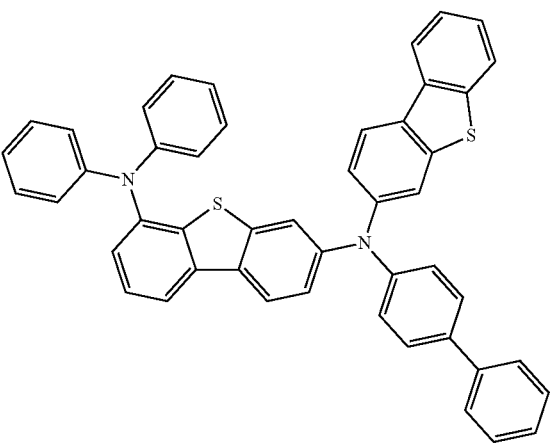

E-6

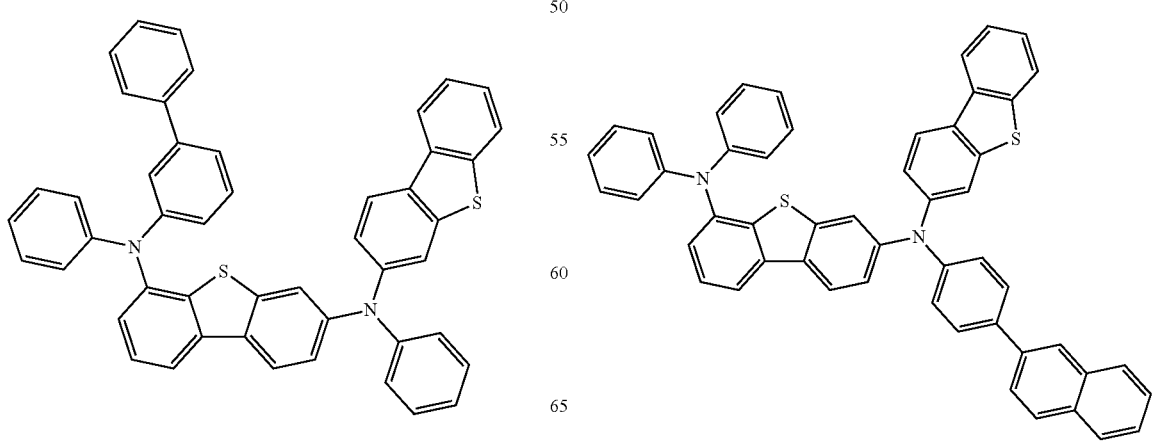

E-7
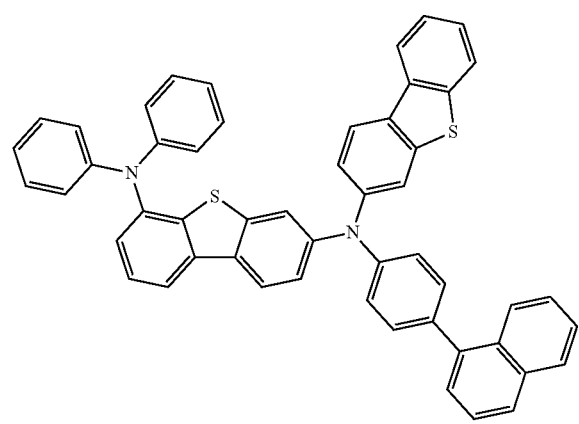
E-8
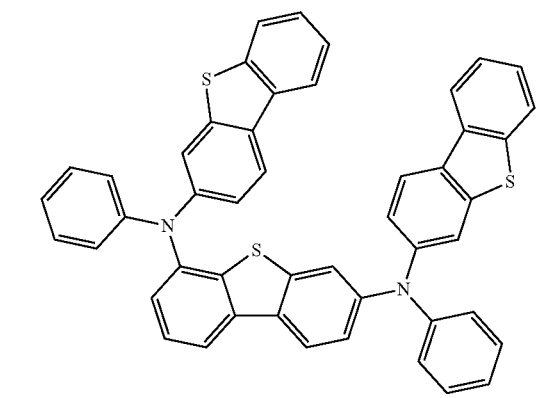
E-9
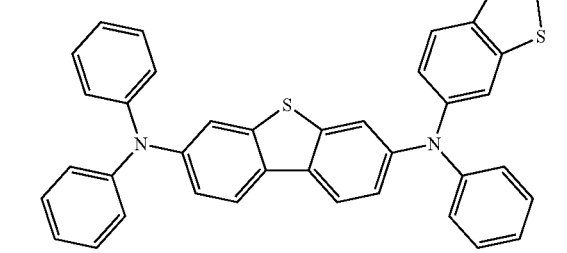
E-10
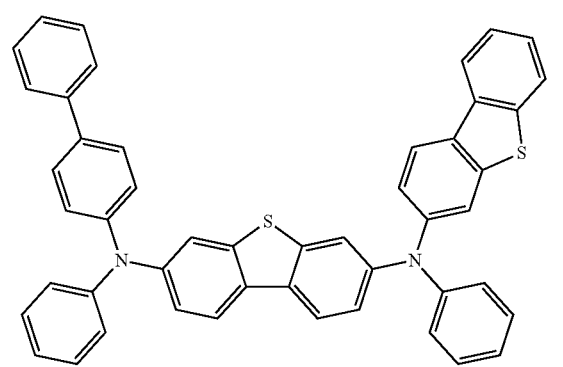
E-11
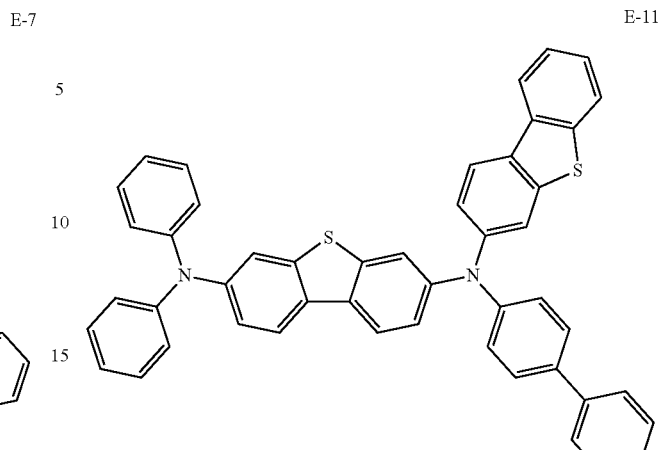
E-12
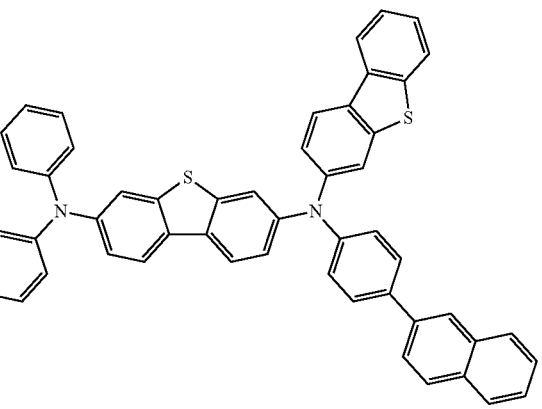
E-13
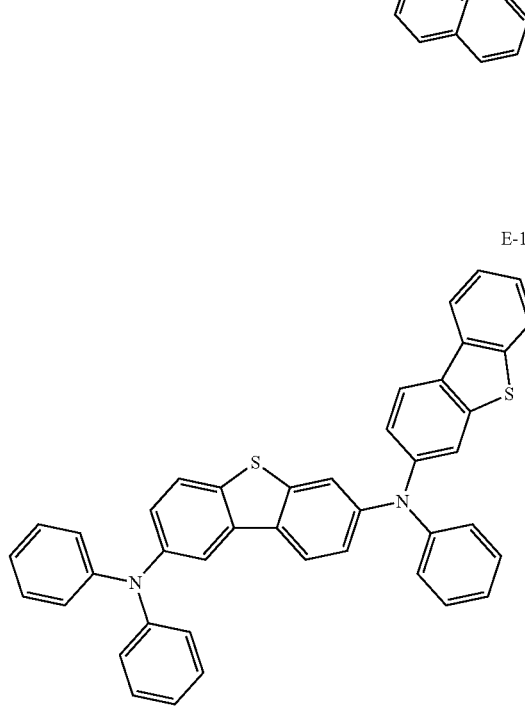

E-14
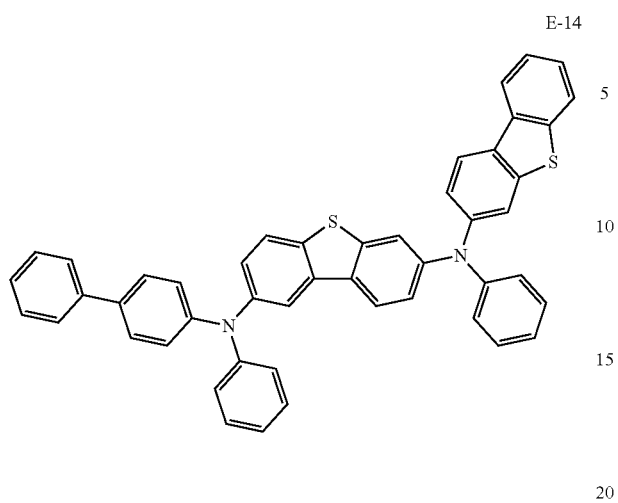
E-15
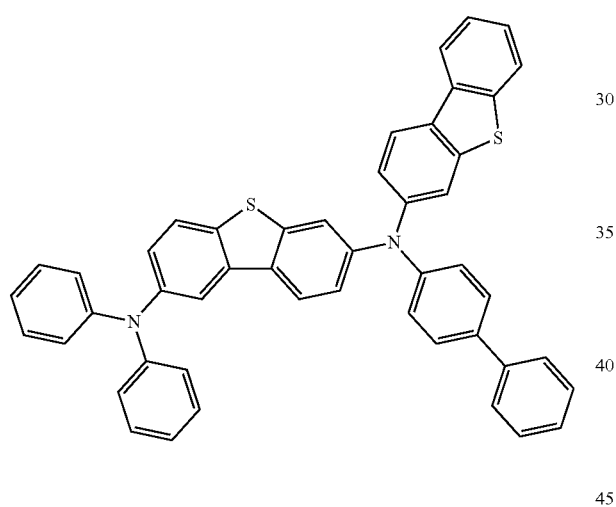
E-16
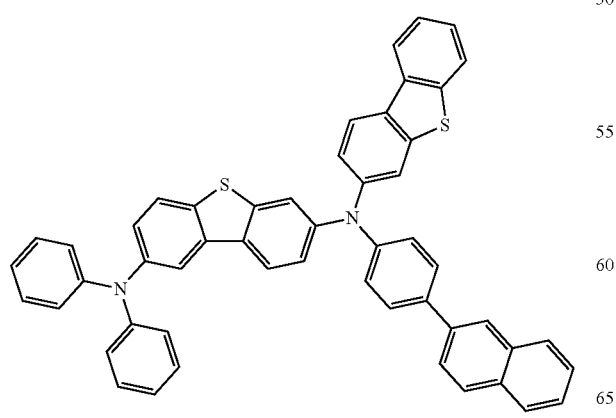
E-17
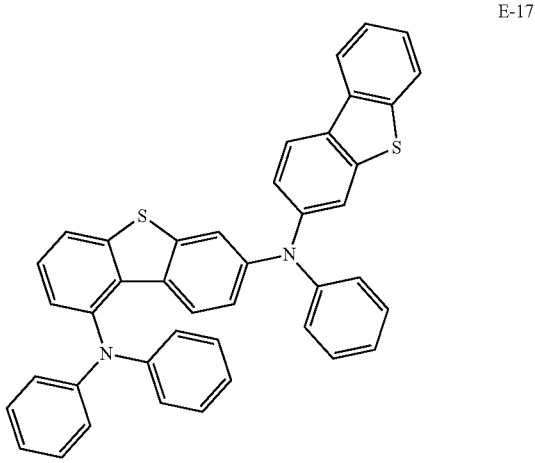
E-18
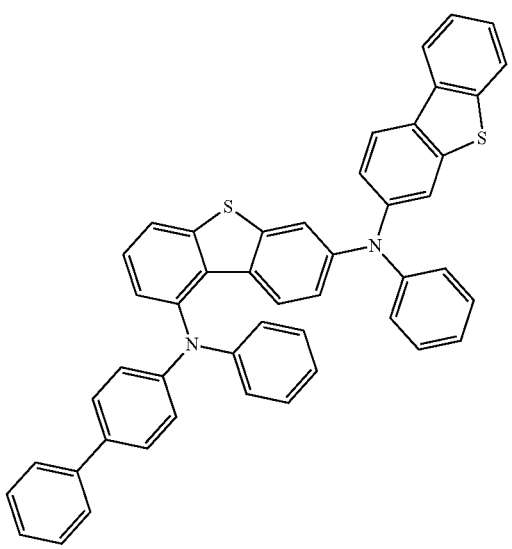
E-19
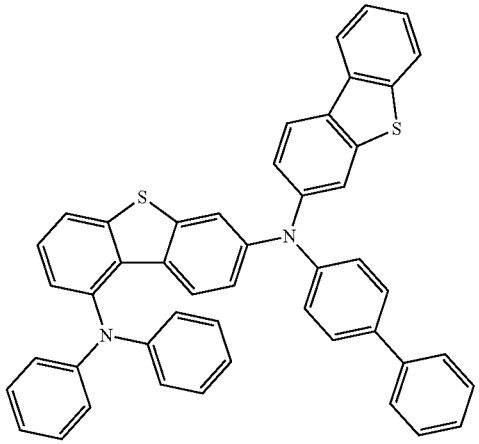

E-20
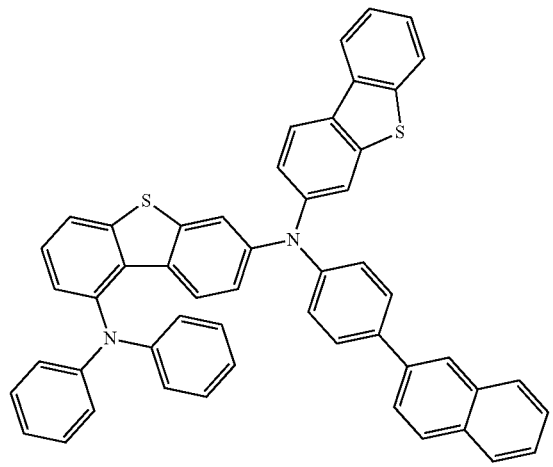
E-23
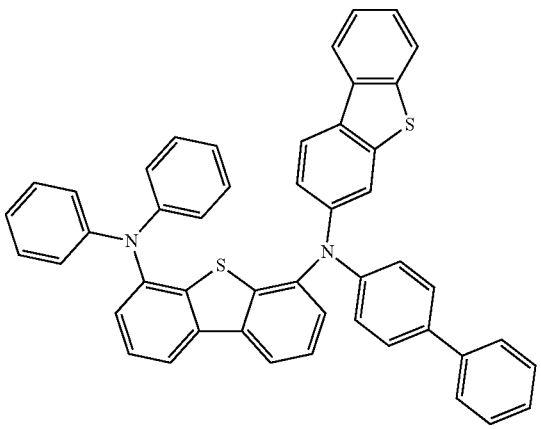
E-21
E-24
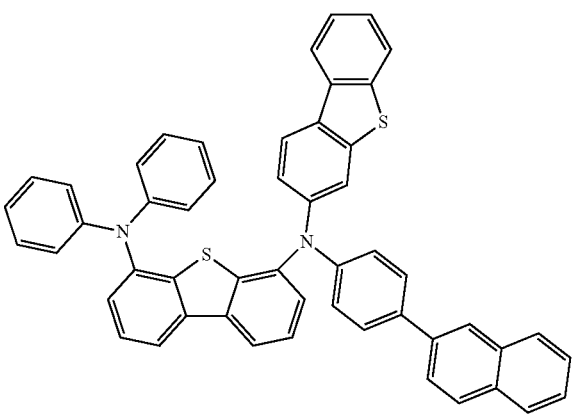
E-25
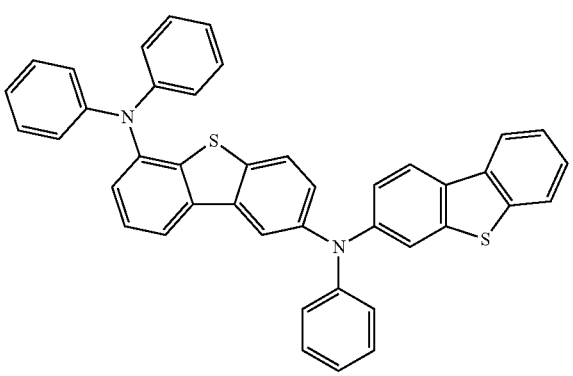
E-22
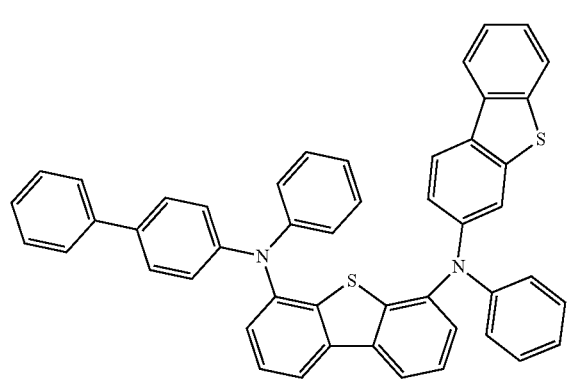
E-26

E-27
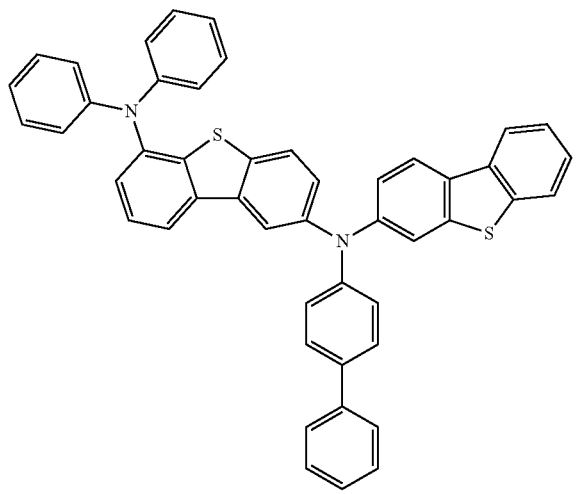
E-28
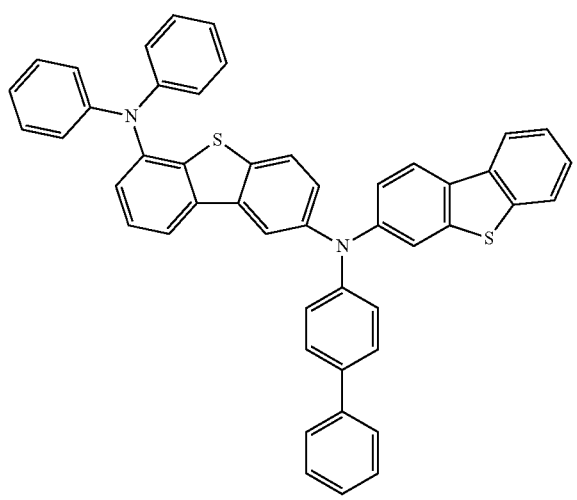
E-29
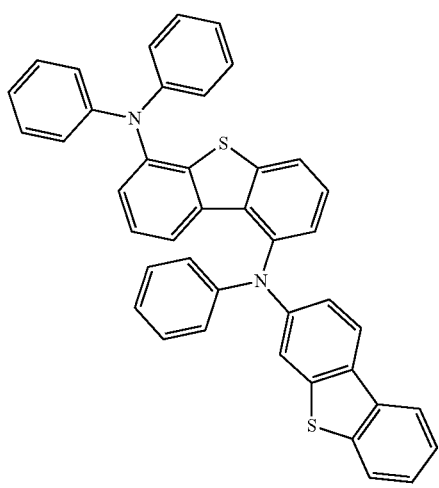
E-30
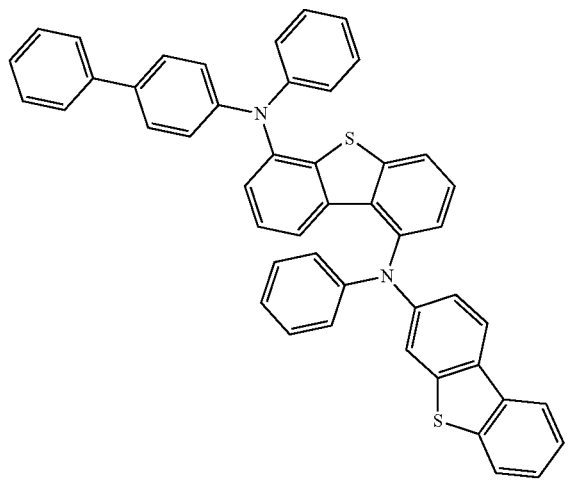
E-31
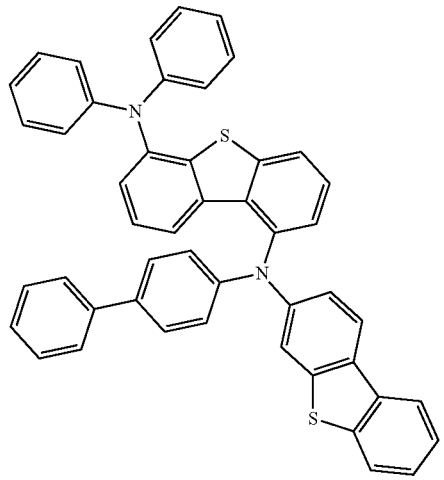
E-32
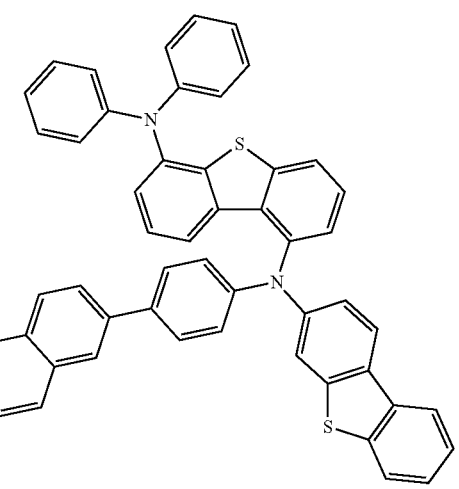

E-33
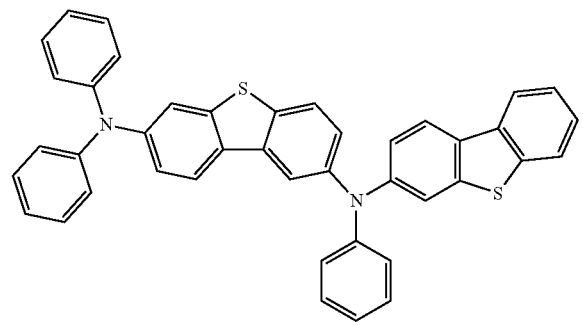
E-34
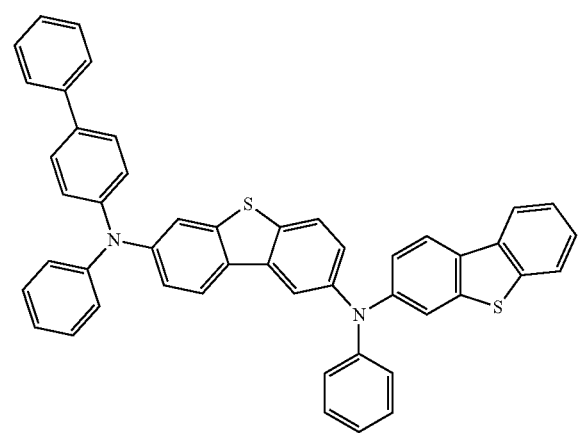
E-35
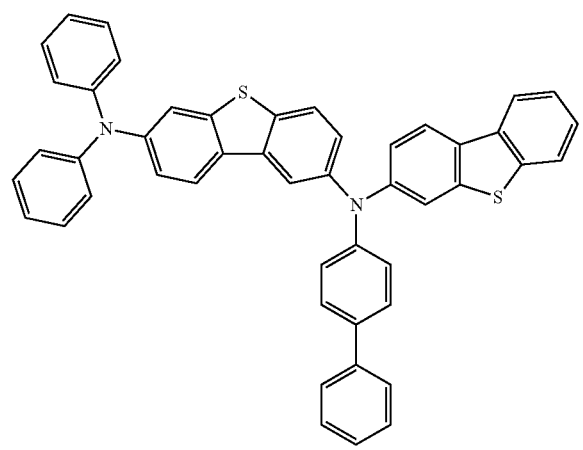
E-36
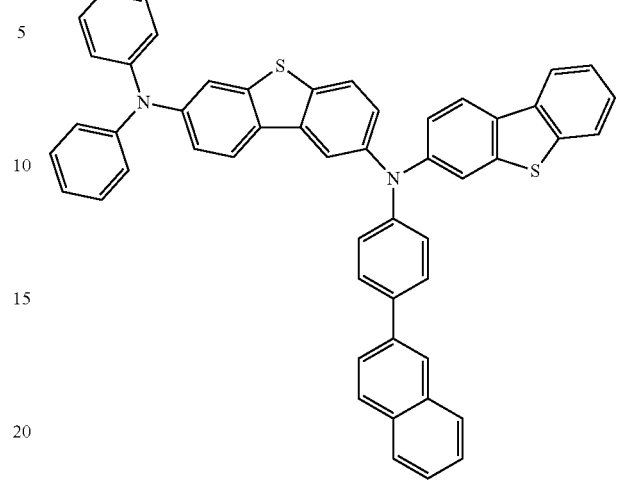
E-37
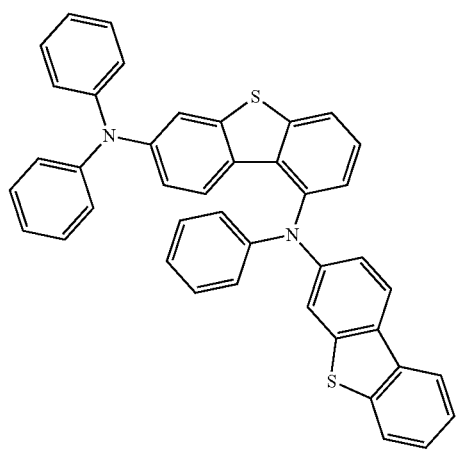
E-38
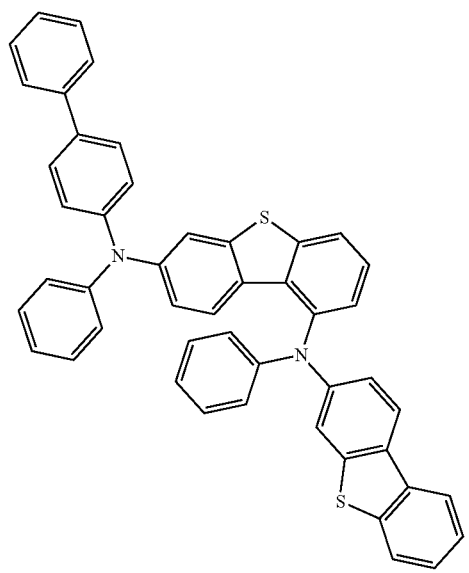

E-39
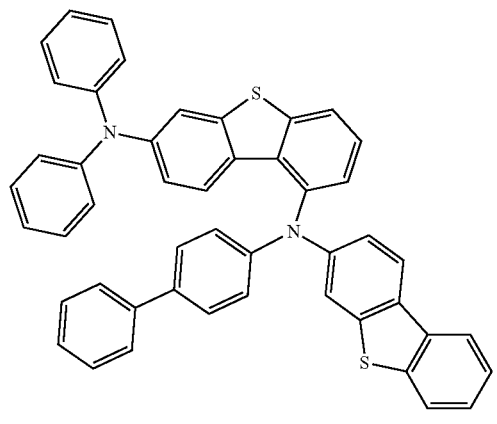
E-40
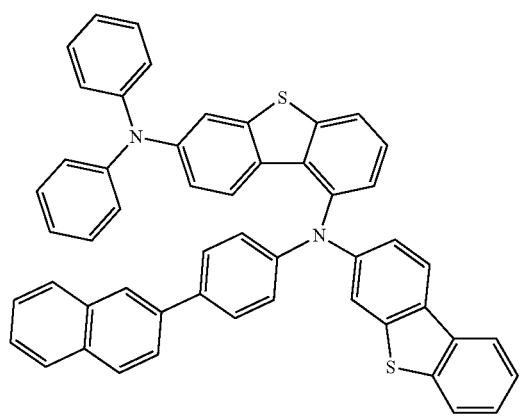
E-41
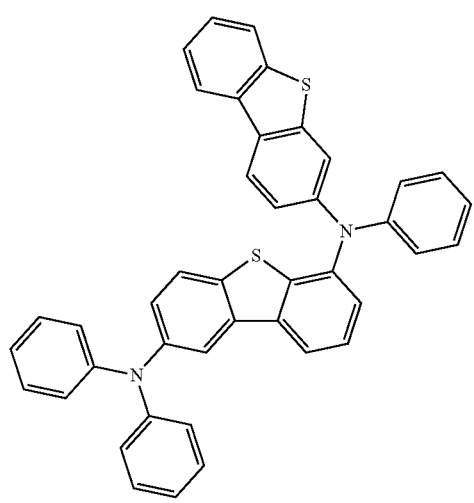
E-42
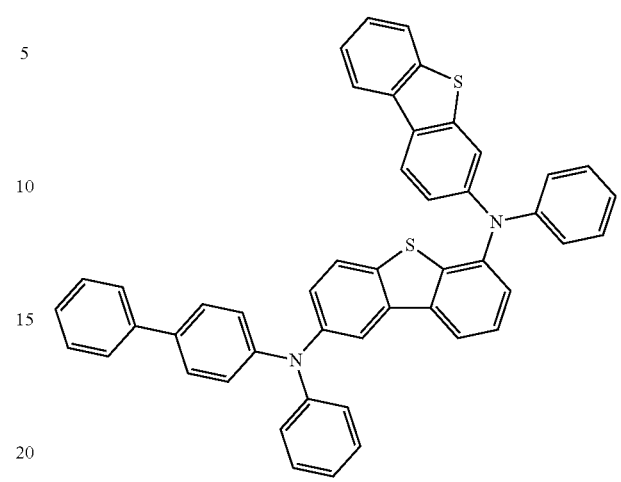
E-43
E-44
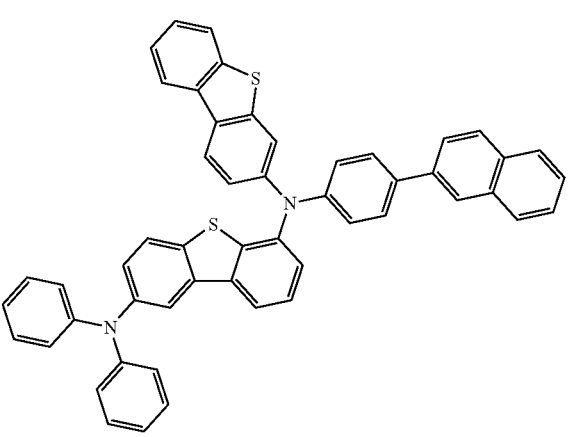

E-45
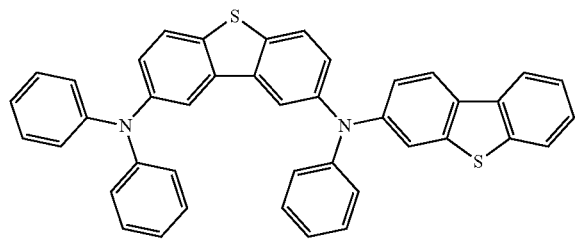
E-46
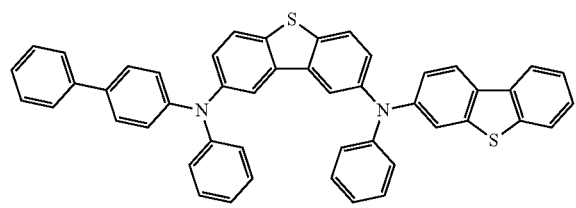
E-47
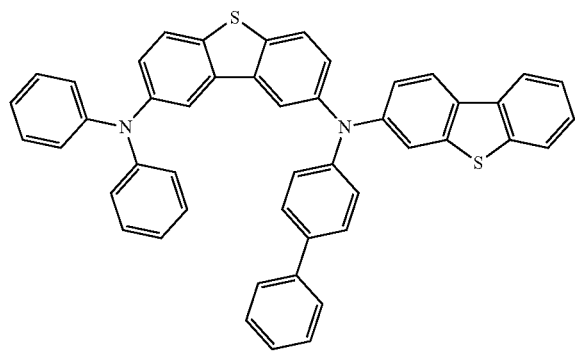
E-48
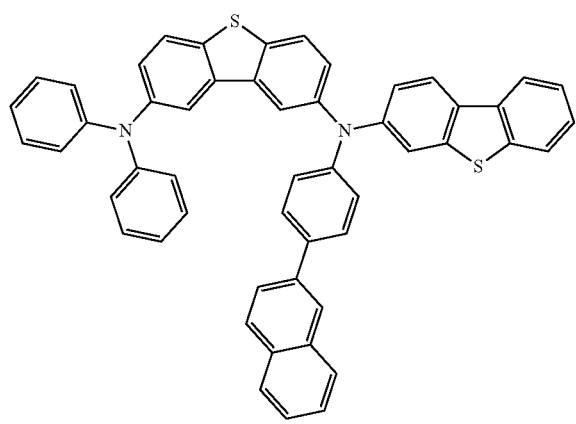
E-49
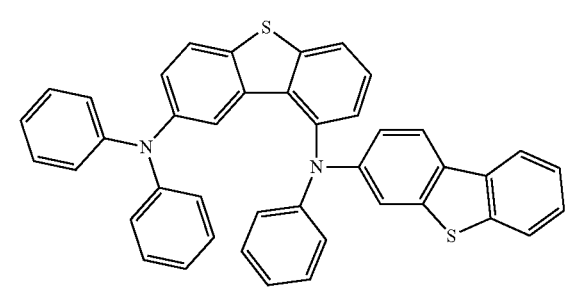
E-50
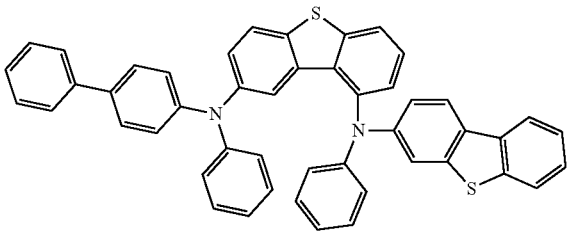
E-51
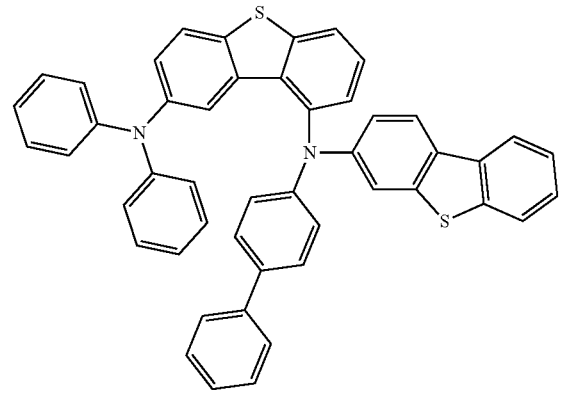
E-52
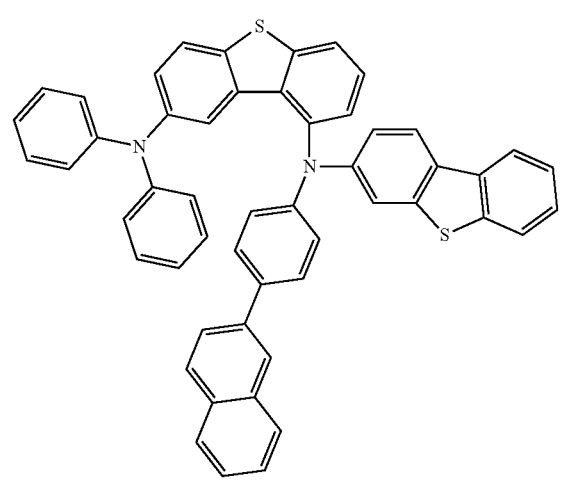
E-53
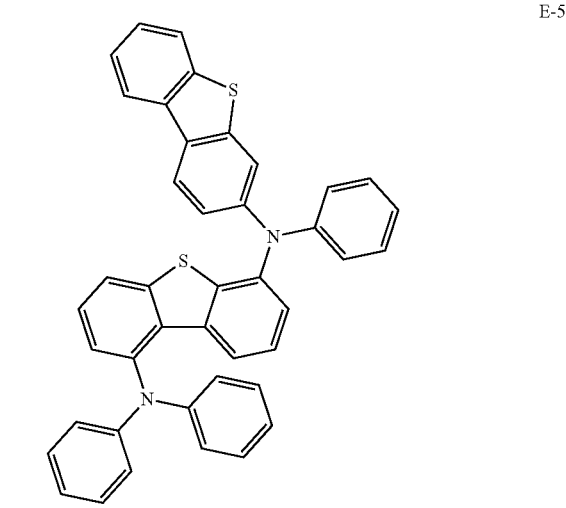

E-54
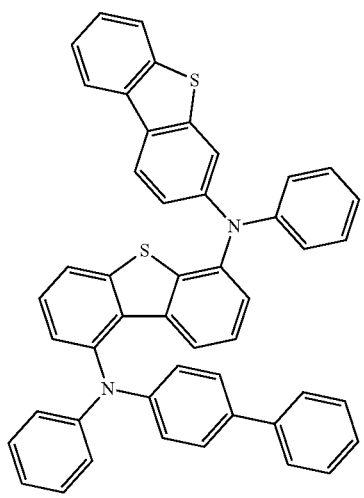
E-55
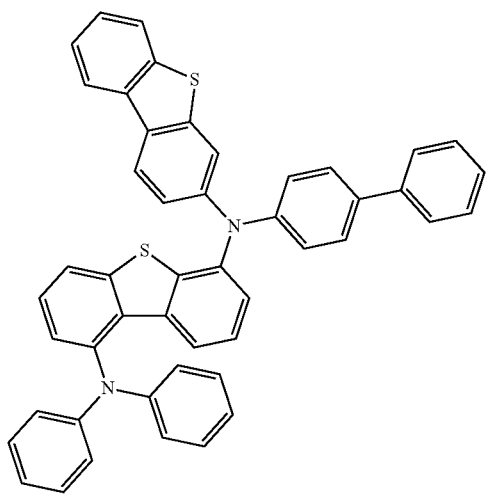
E-56
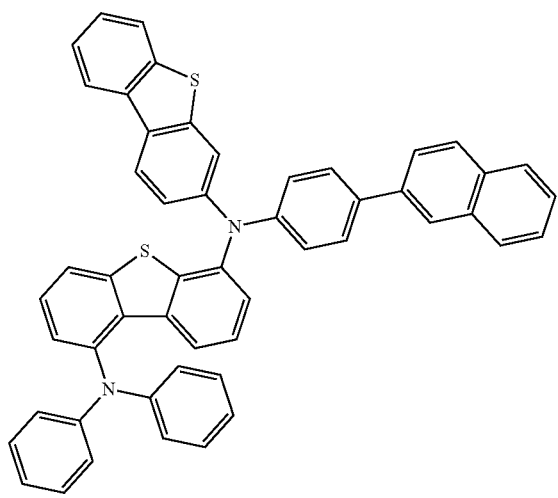
E-57
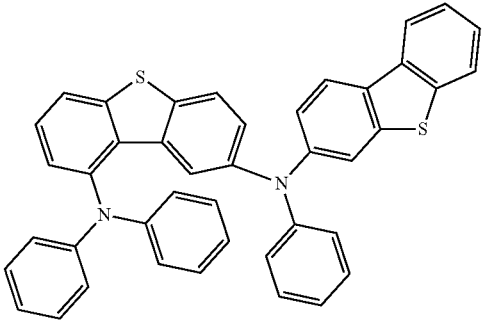
E-58
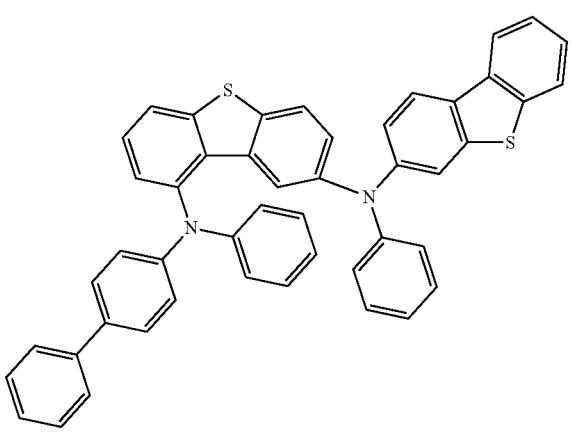
E-59
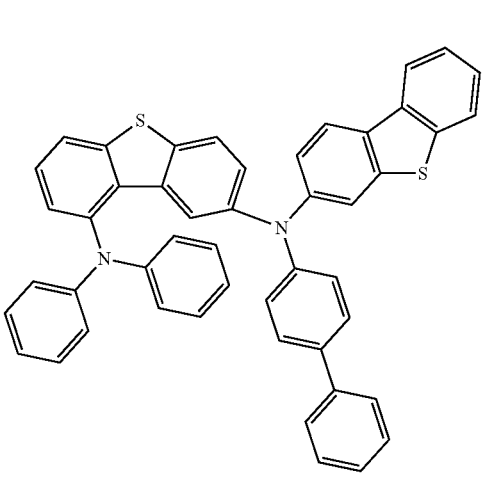

E-60
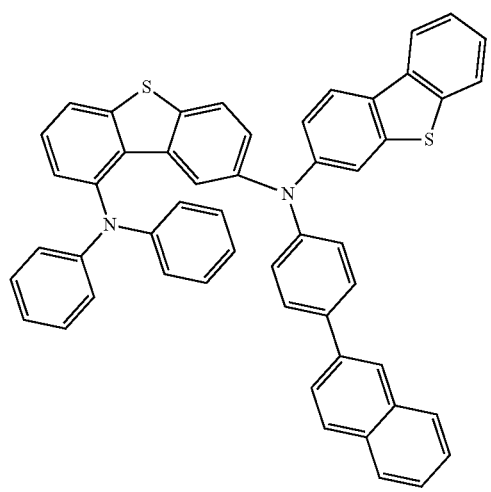
E-61
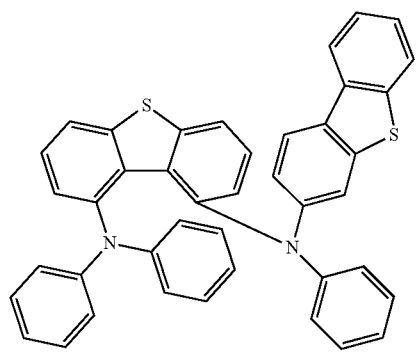
E-62
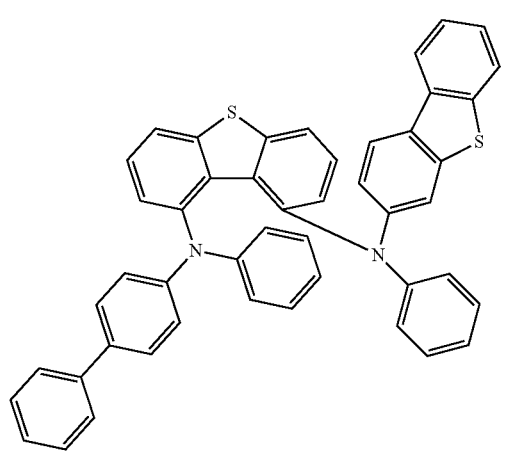
E-63
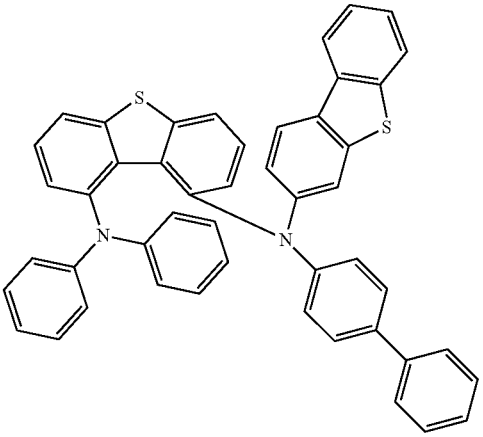
E-64
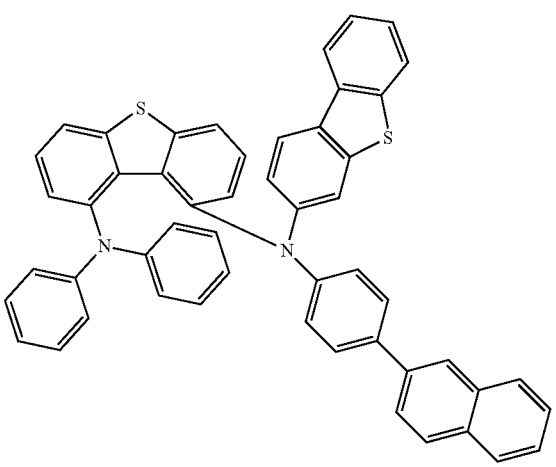
E-65
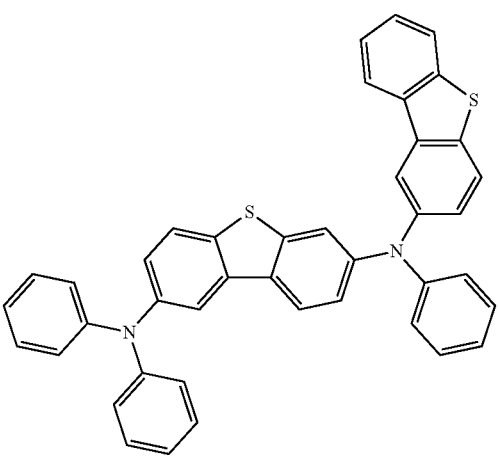

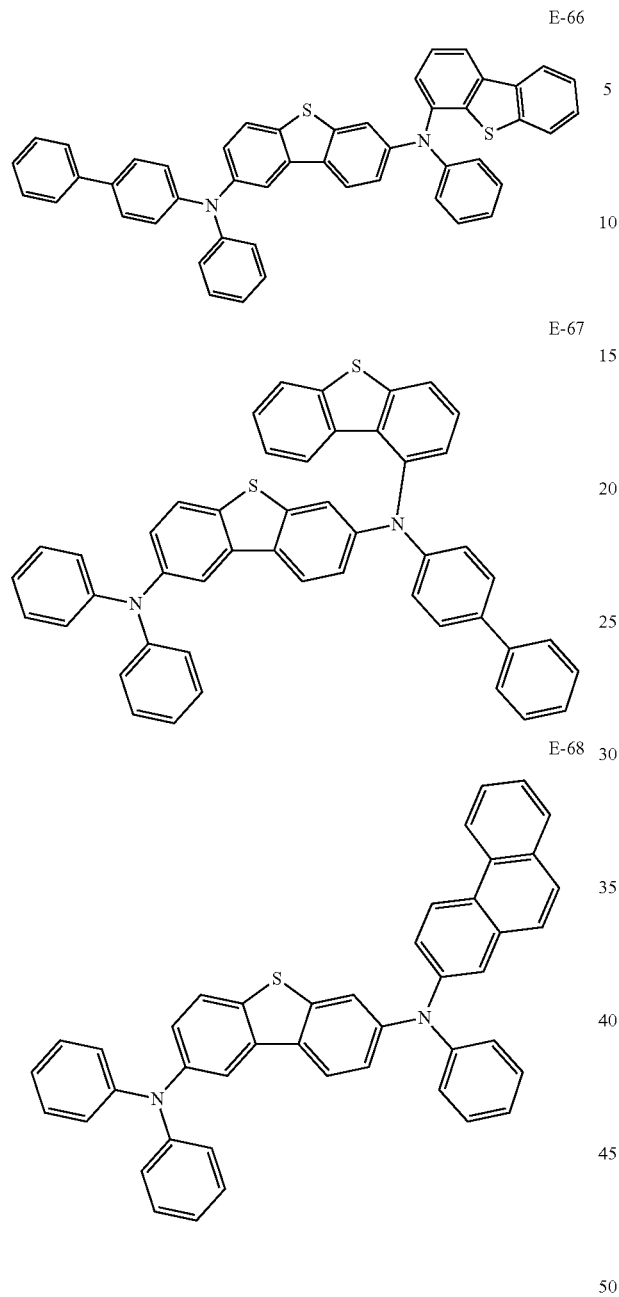
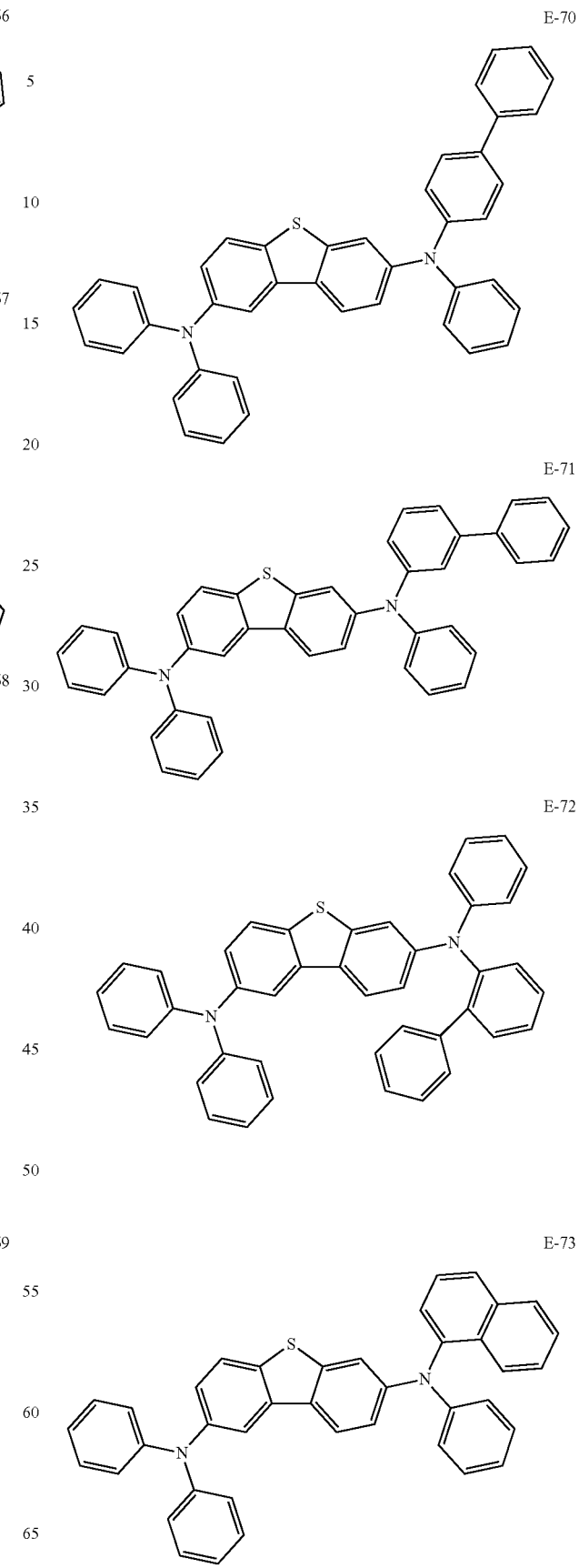

E-74
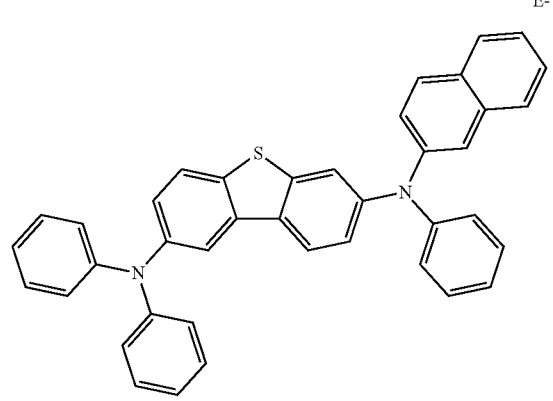
E-75
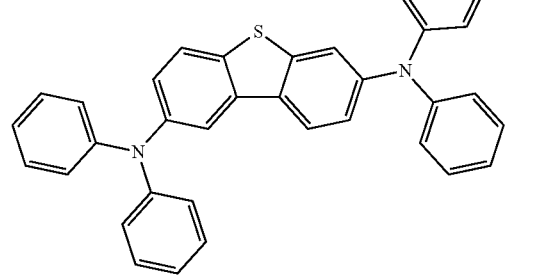
E-76
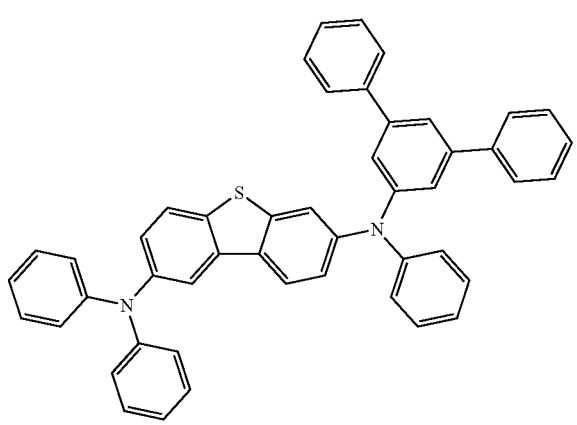
E-77
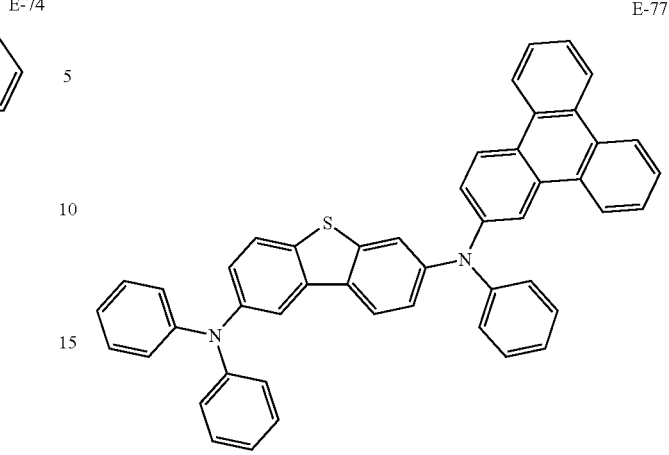
E-78
E-79
E-80
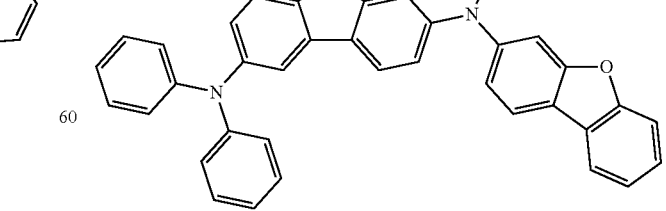

E-81
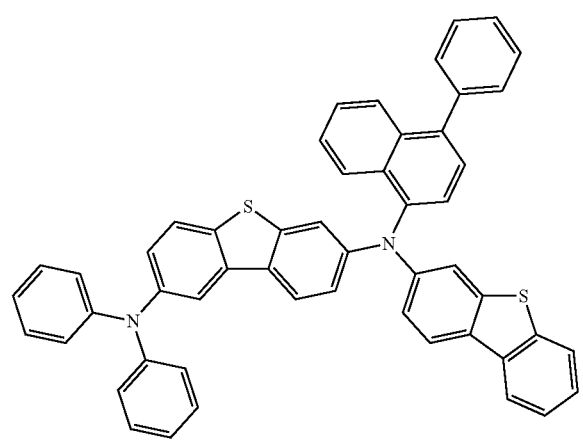
E-82
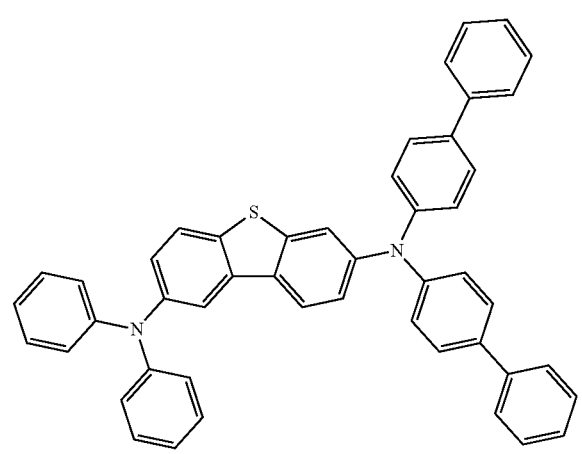
E-83
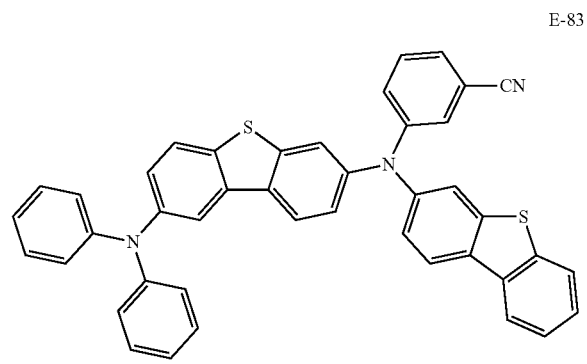
E-84
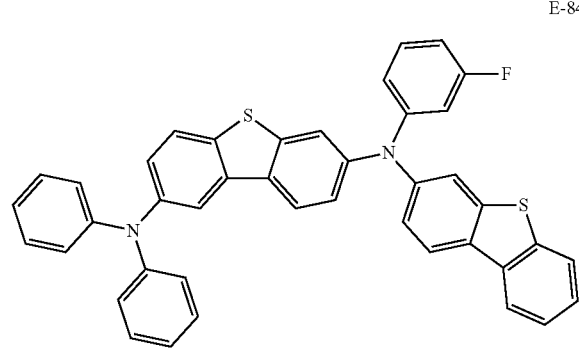
E-85
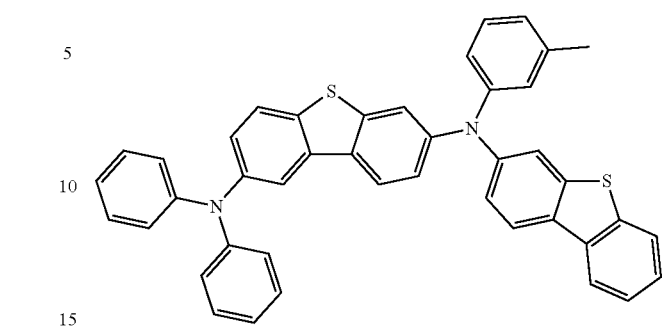
E-86
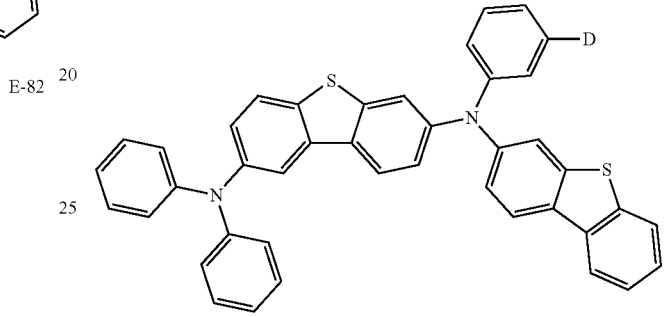
E-87
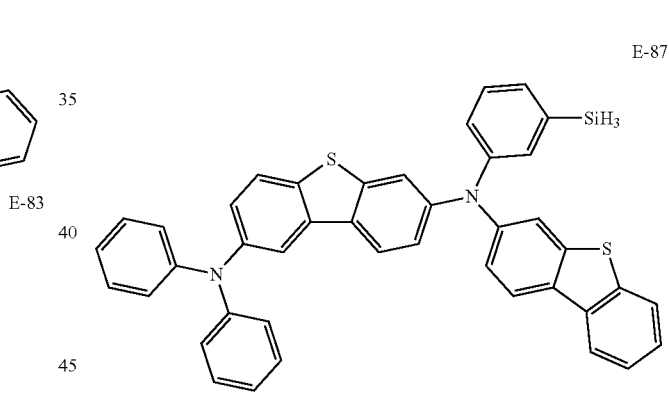
E-88
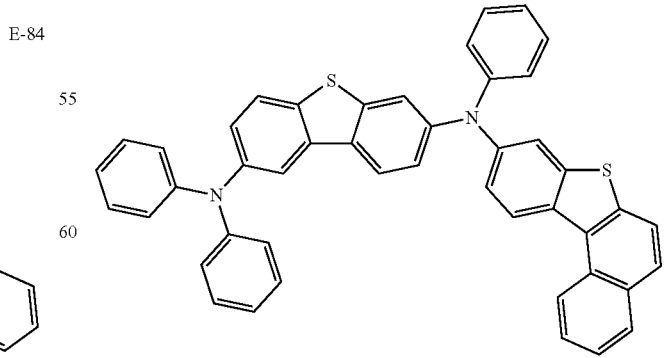

E-89
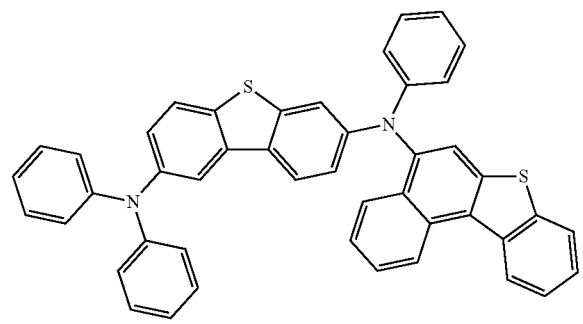
E-90
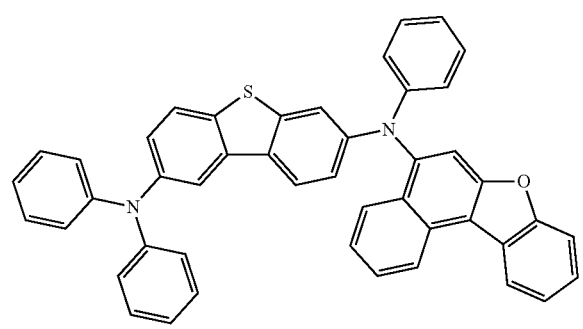
E-91
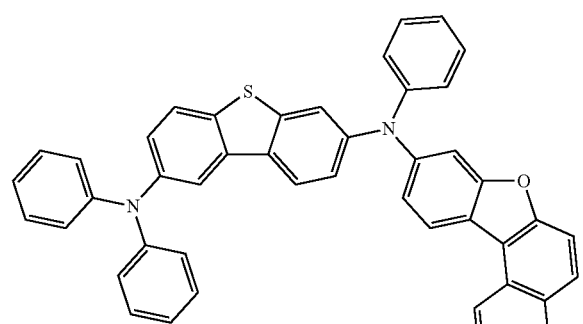
E-92
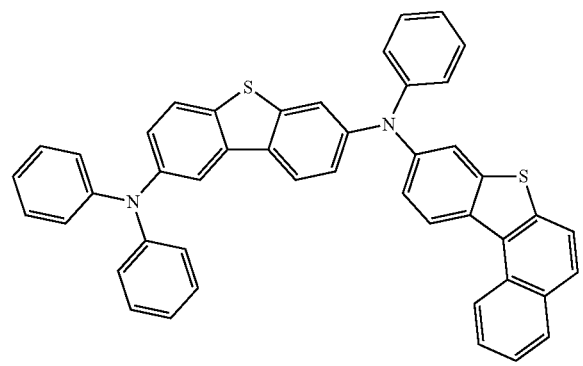
E-93
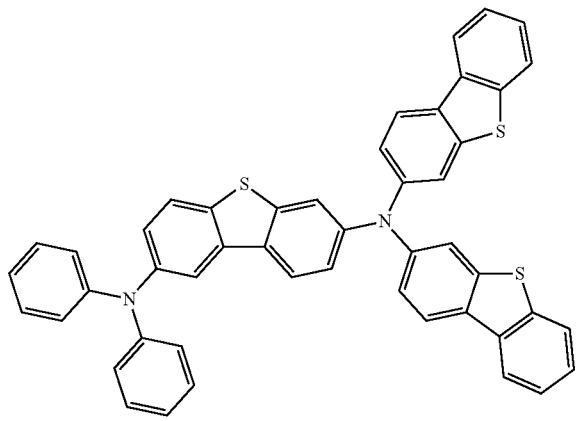
E-94
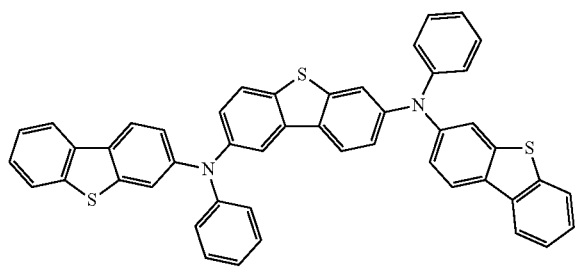
E-95
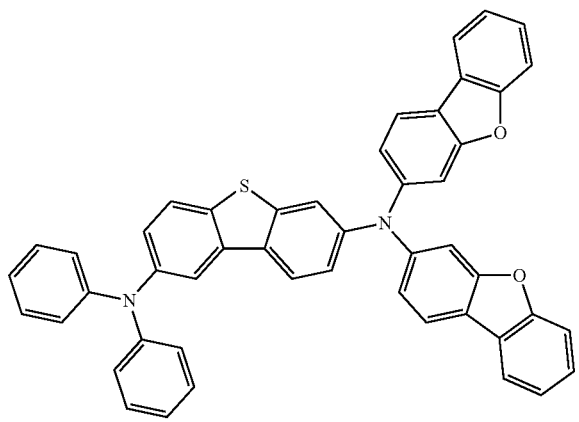
E-96
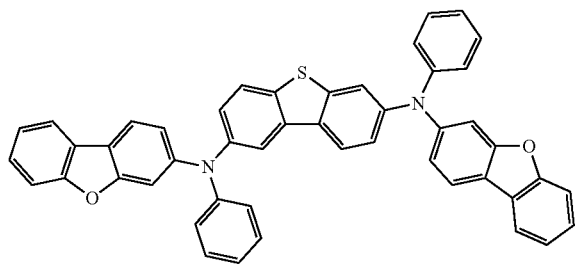

F-1
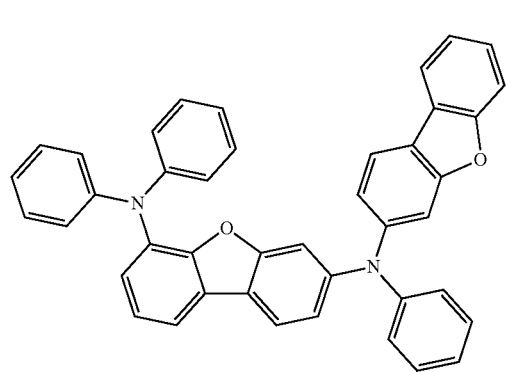
F-2
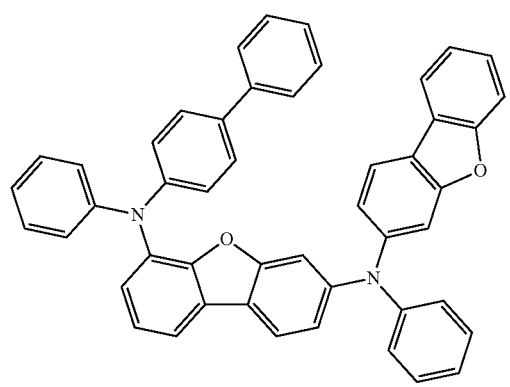
F-3
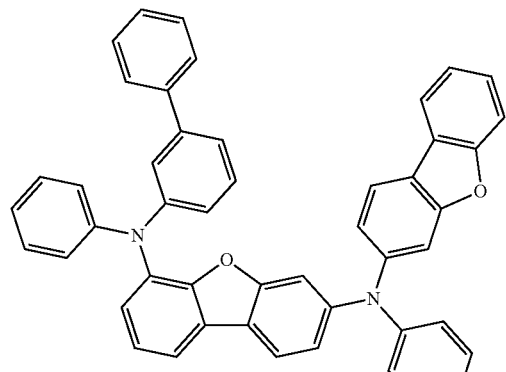
F-4
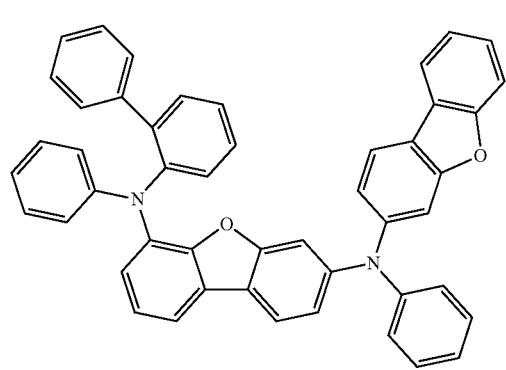
F-5
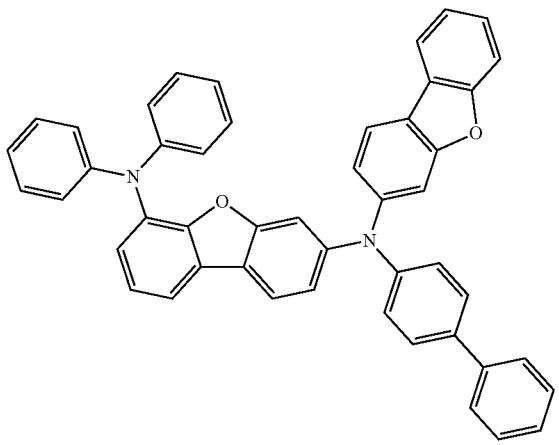
F-6
F-7
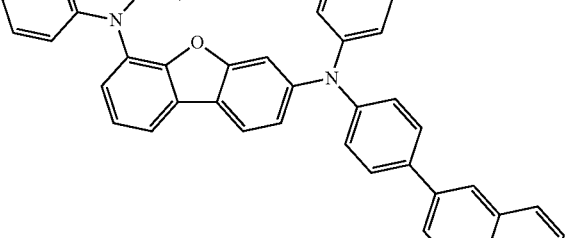

F-8
F-9
F-10
F-11
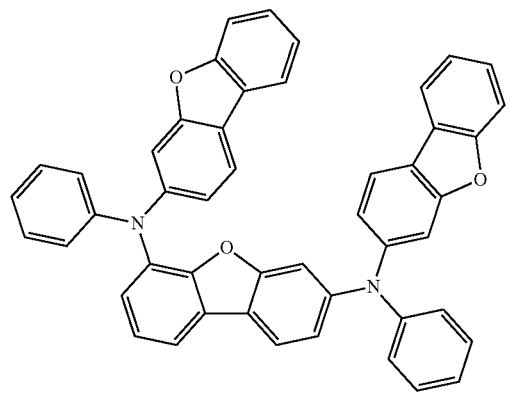
F-12
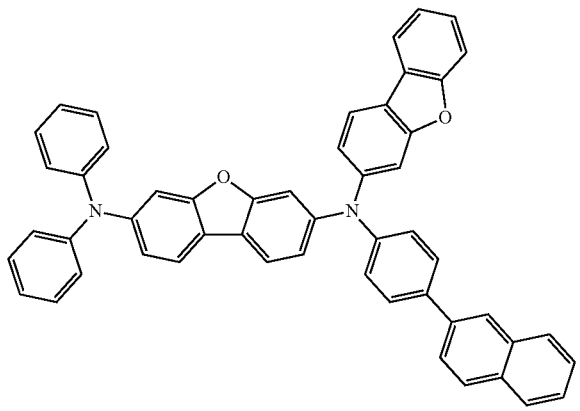
F-13
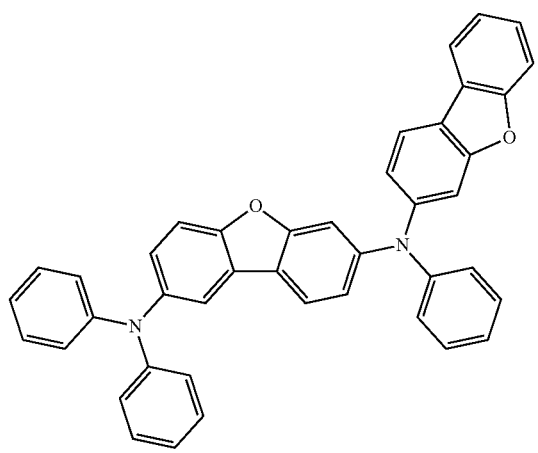
F-14
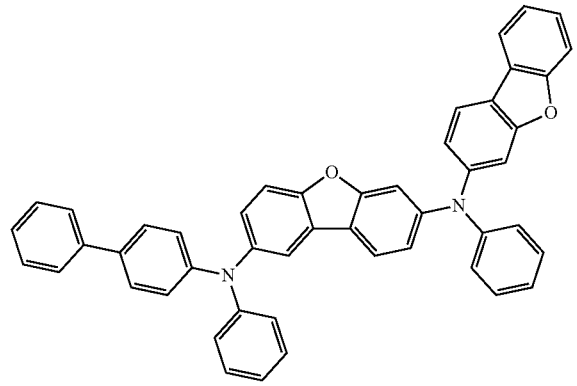

F-15
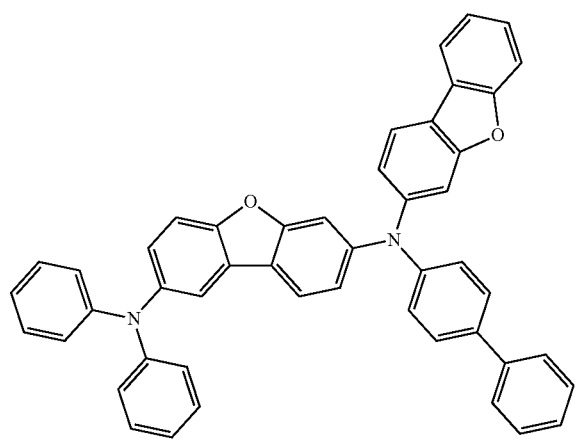
F-16
F-17
F-18
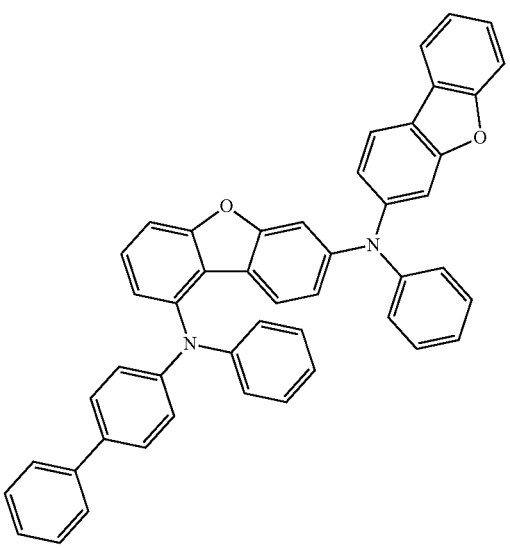
F-19
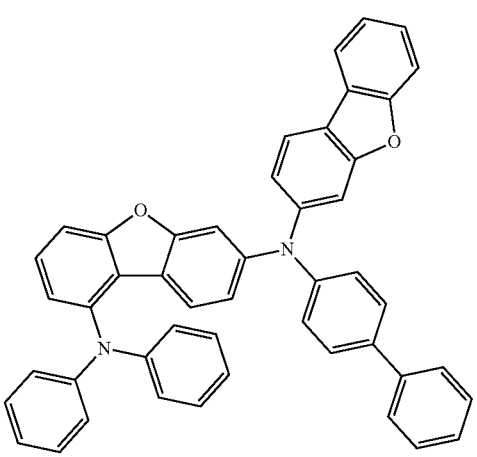
F-20
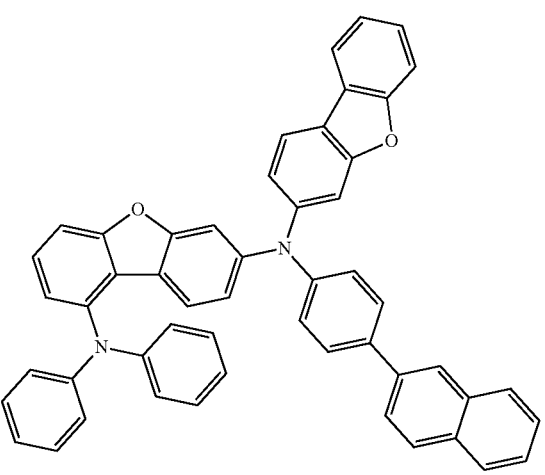

-continued
F-21
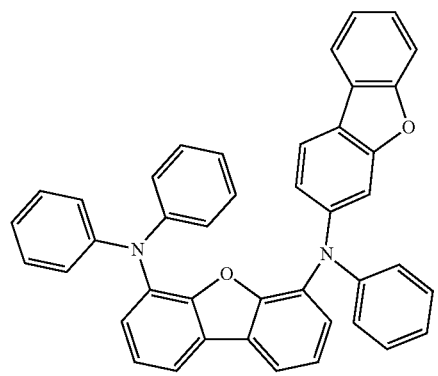
F-22
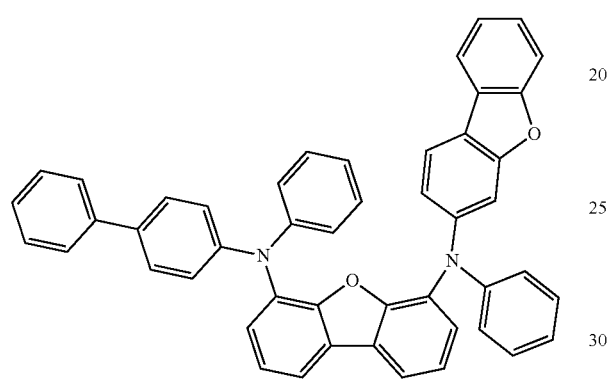
F-23
F-24
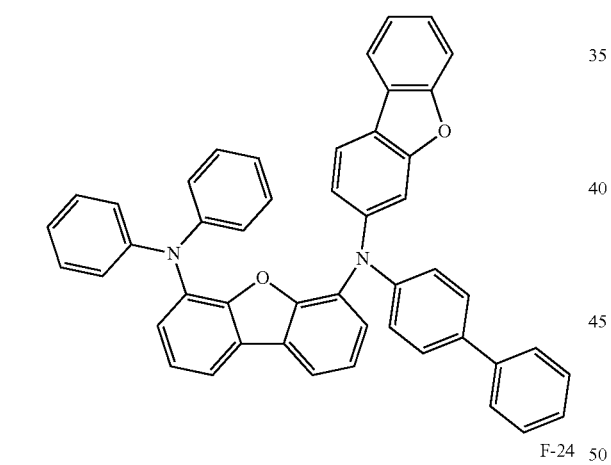
-continued
F-25
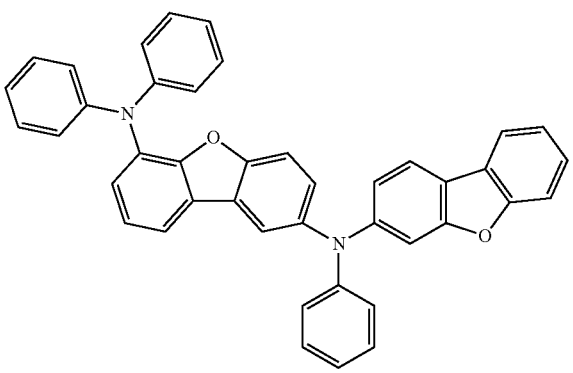
F-26
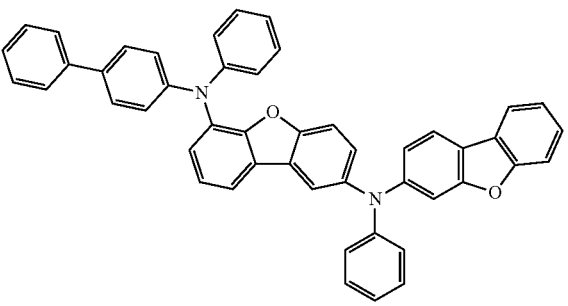
F-27
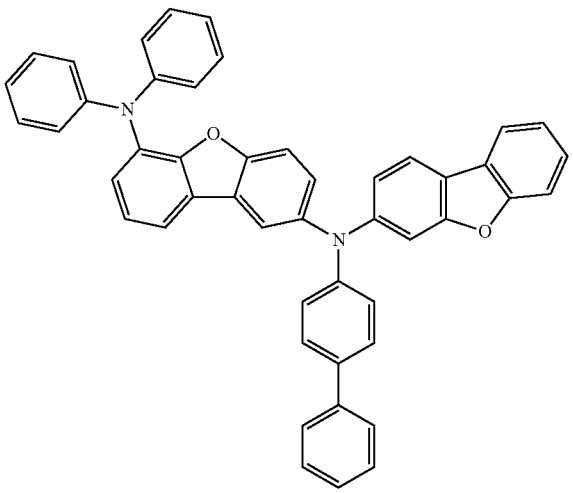

F-28
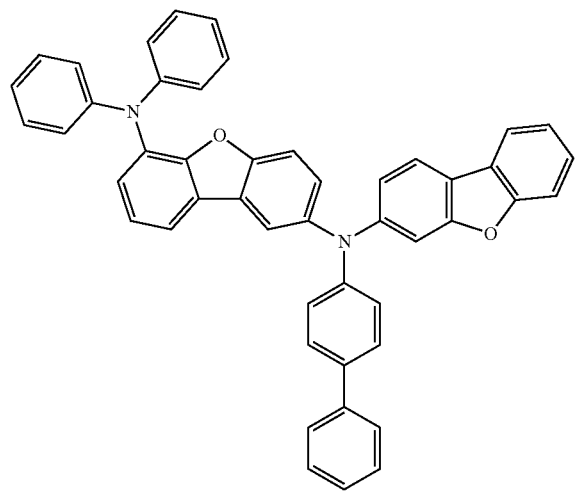
F-29
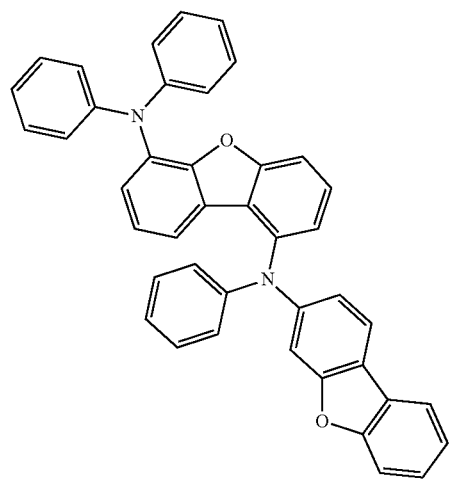
F-30
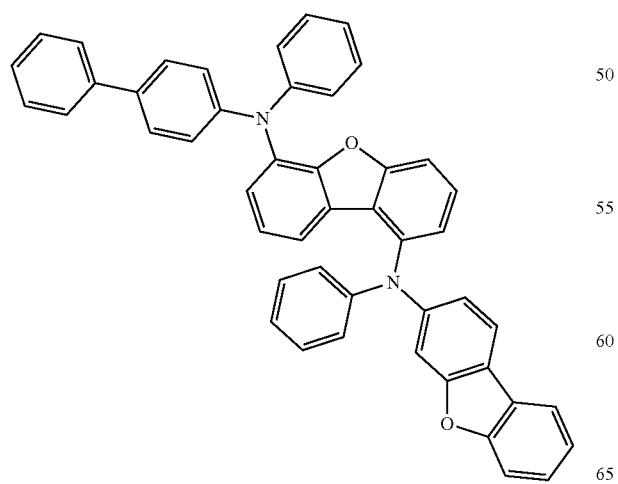
F-31
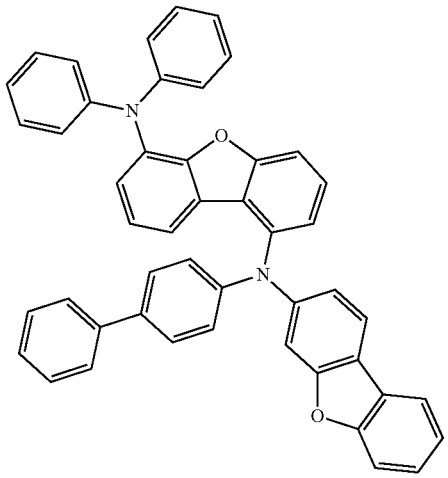
F-32
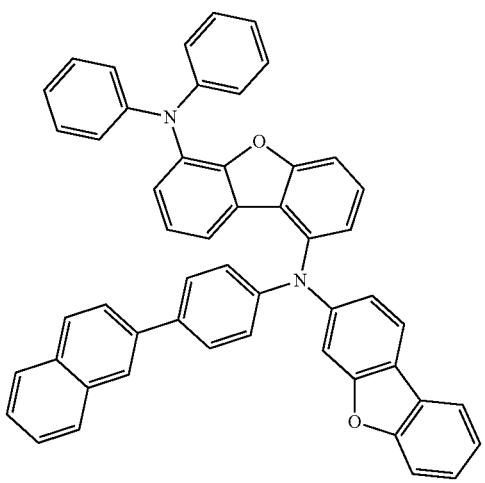
F-33
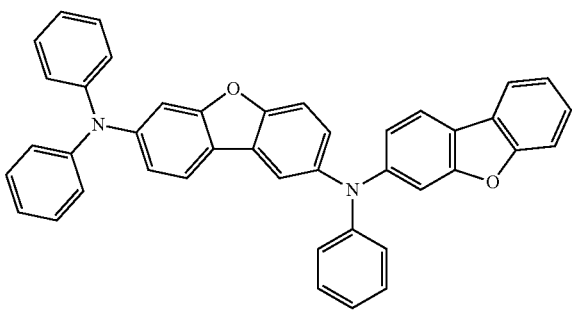

F-34
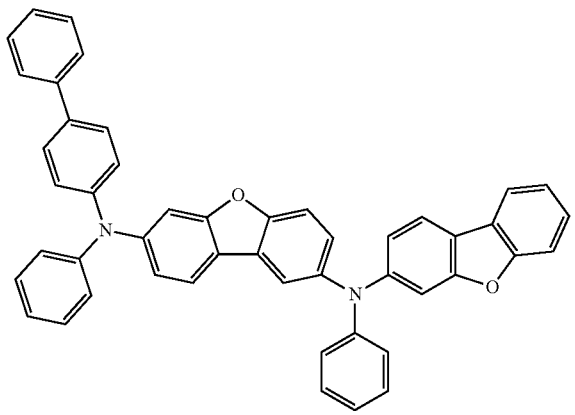
F-35
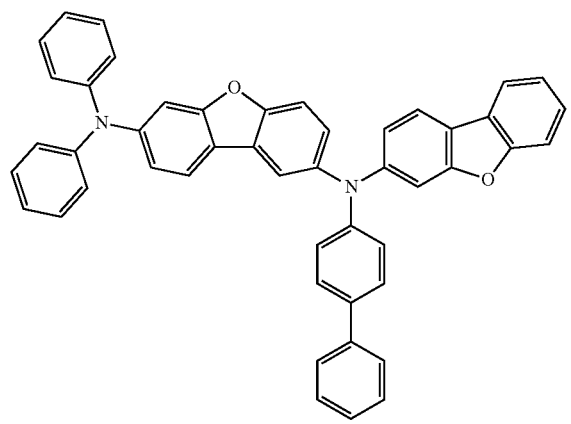
F-36
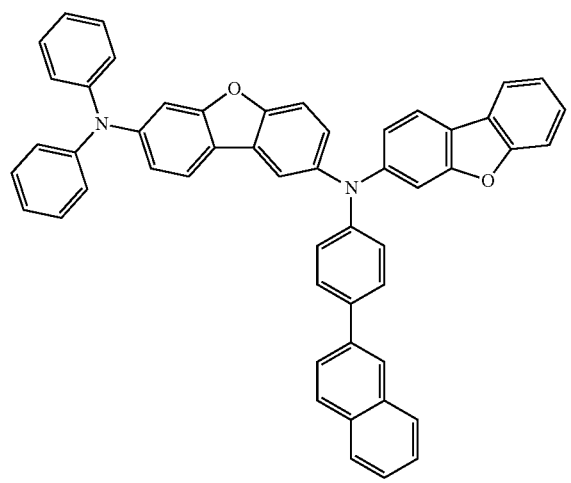
F-37
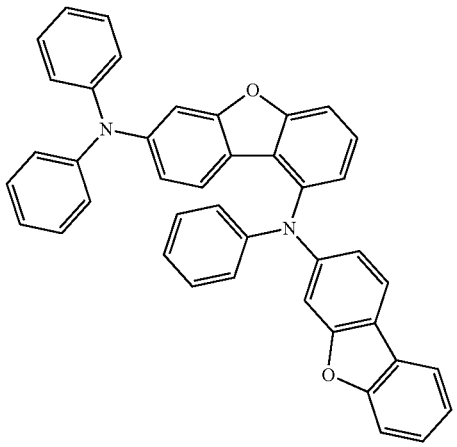
F-38
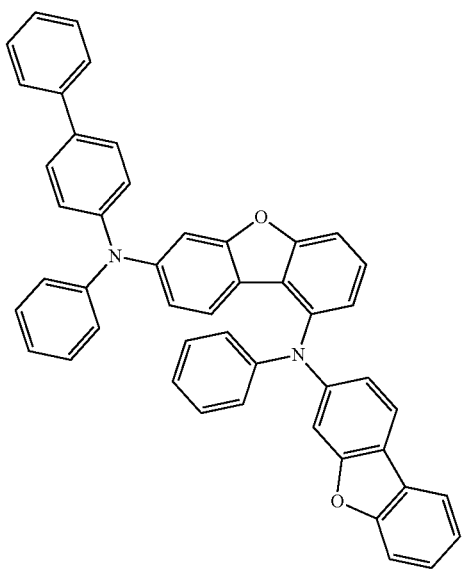
F-39
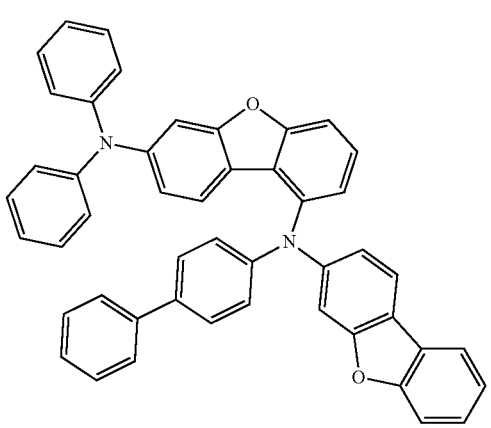

F-40
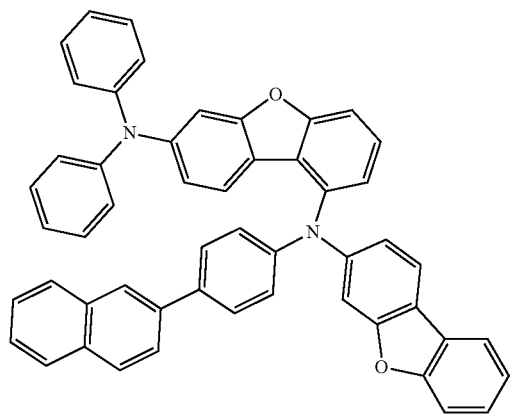
F-41
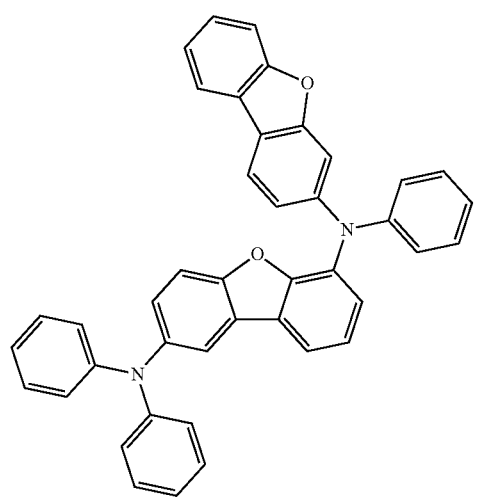
F-42
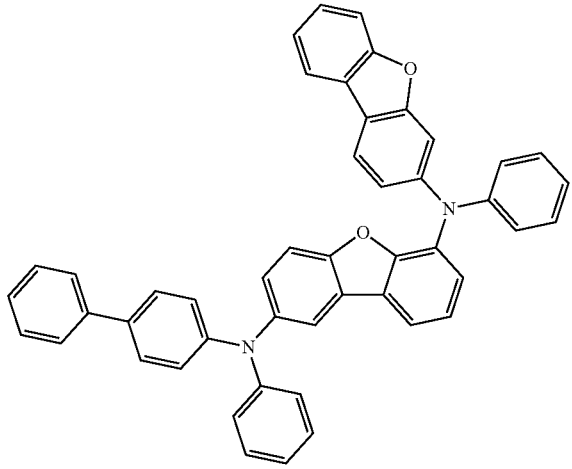
F-43
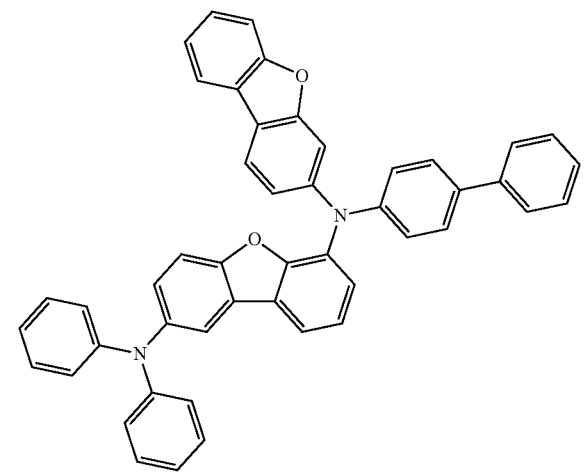
F-44
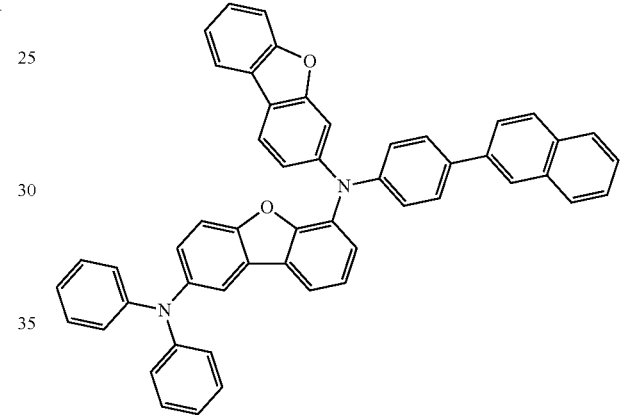
F-45
F-46
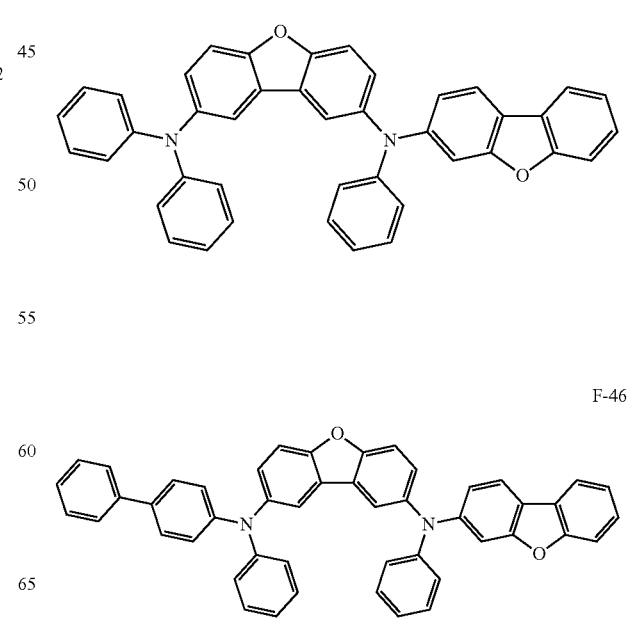

F-47
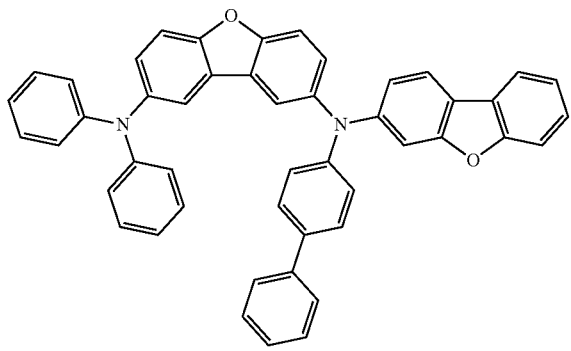
F-48
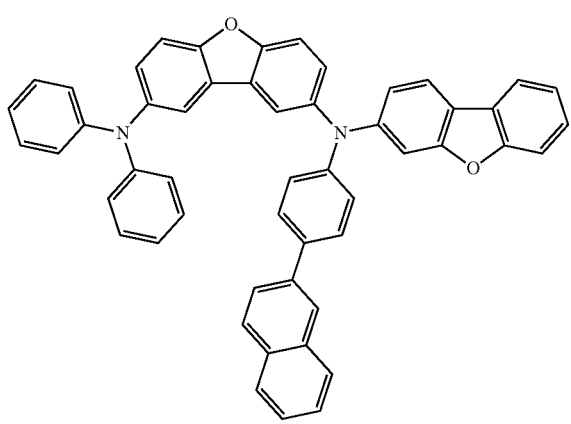
F-49
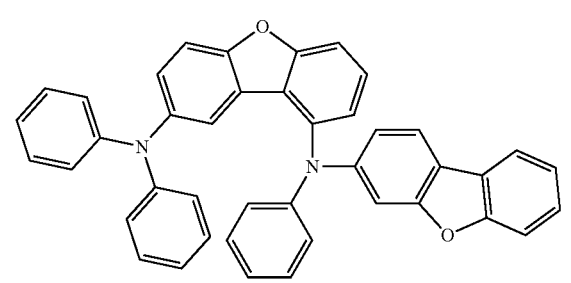
F-50
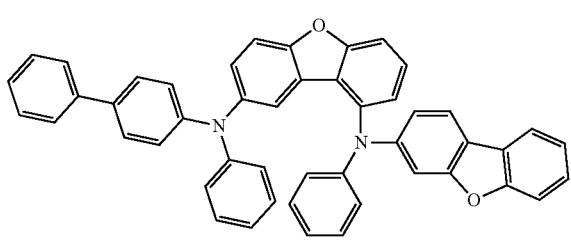
F-51
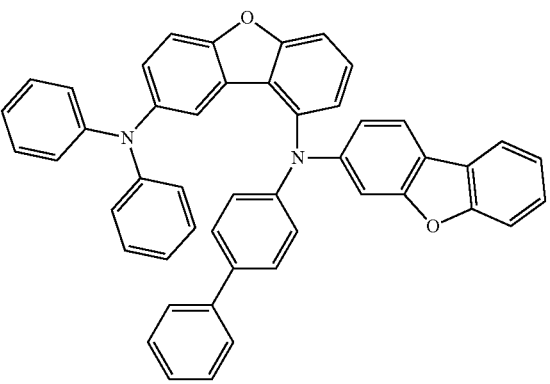
F-52
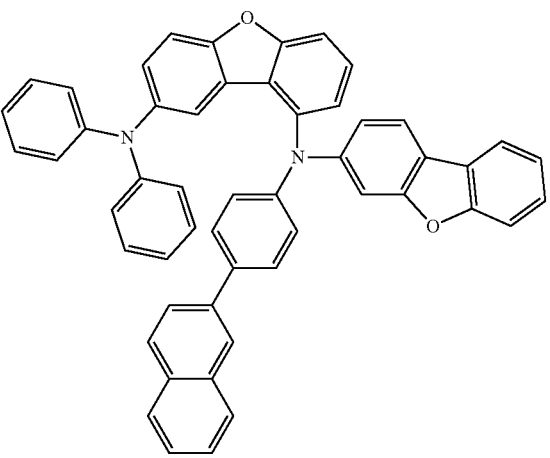
F-53
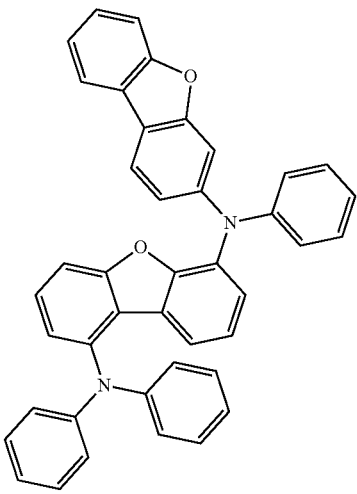

F-54
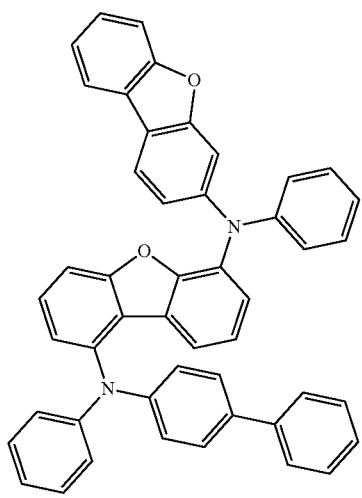
F-55
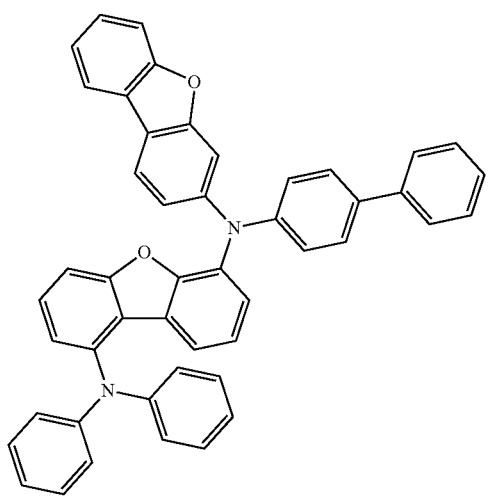
F-56
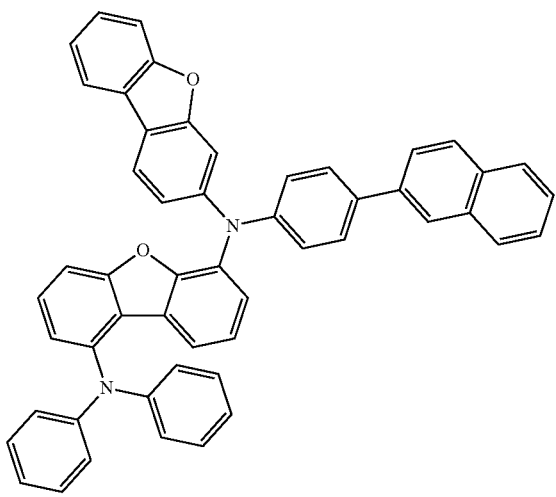
F-57
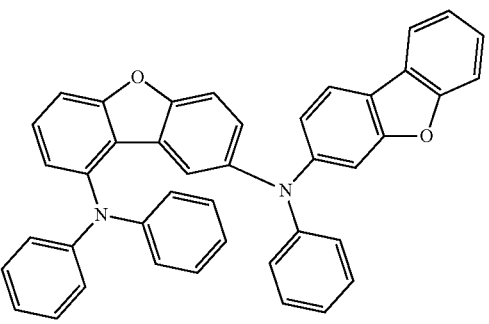
F-58
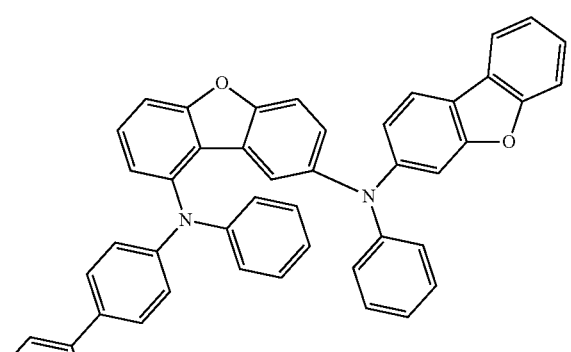
F-59
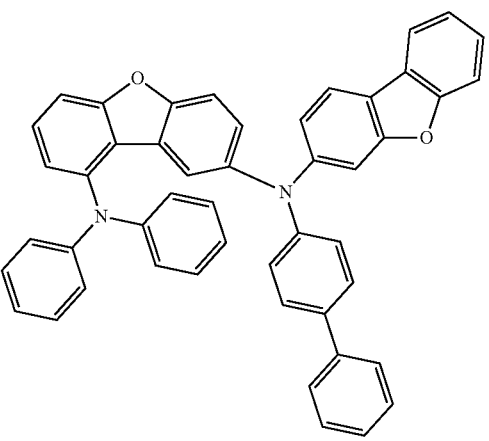

F-60
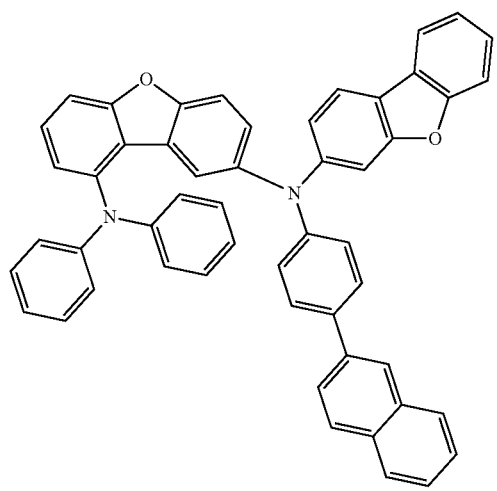
F-61
F-63
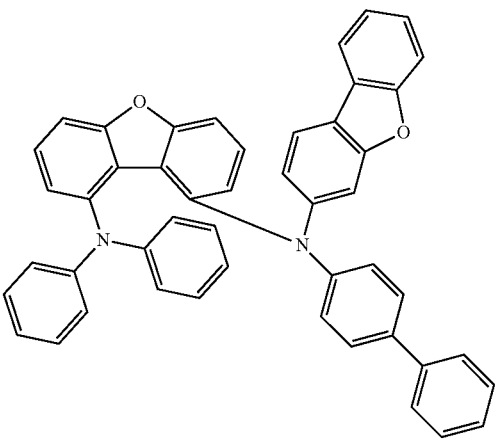
F-64
F-62
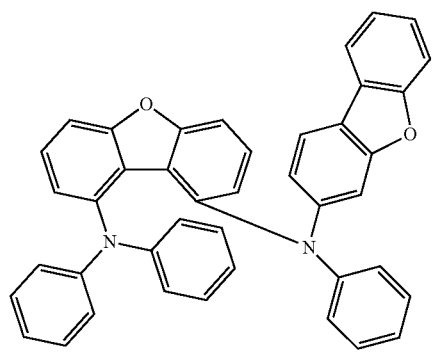
F-65
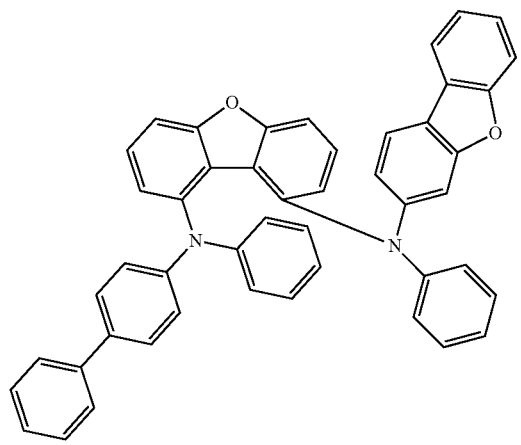
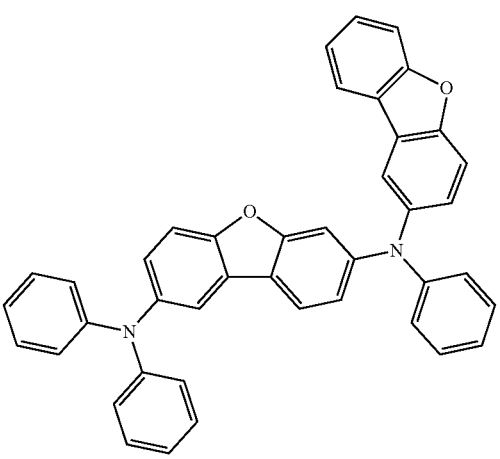

F-66
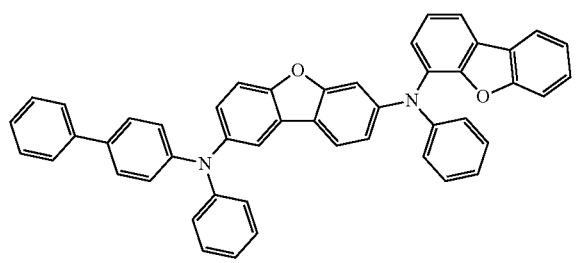
F-67
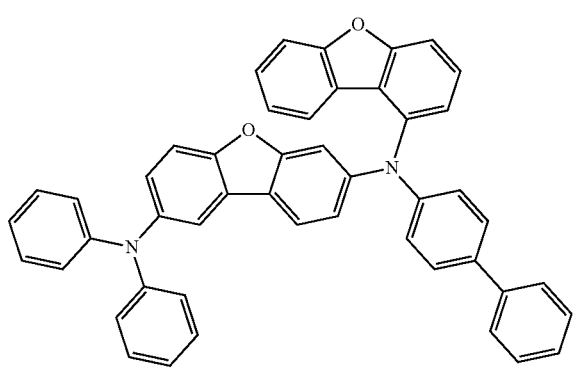
F-68
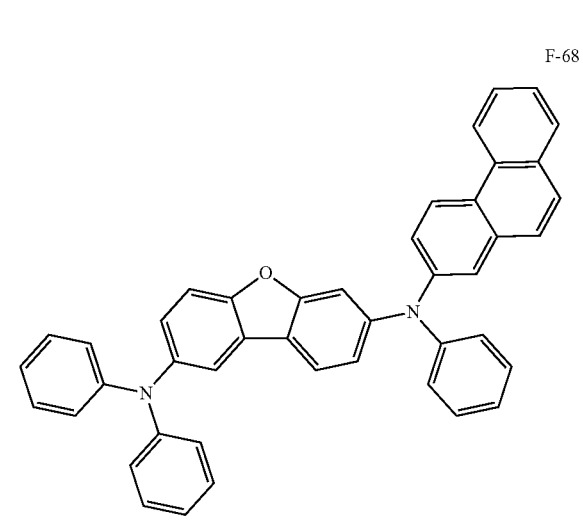
F-69
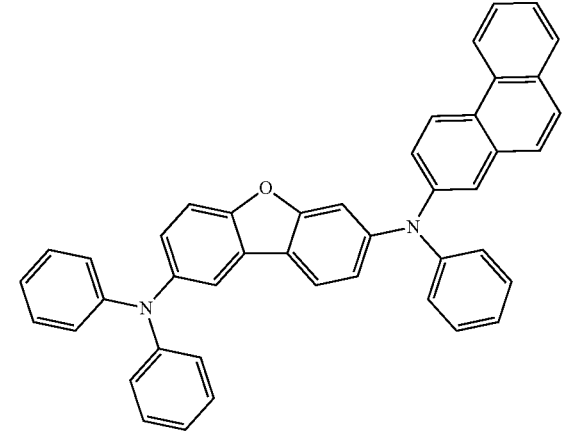
F-70
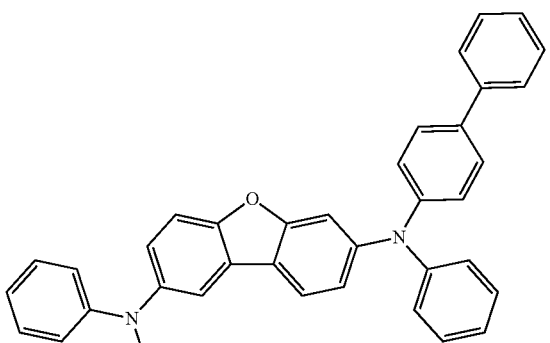
F-71
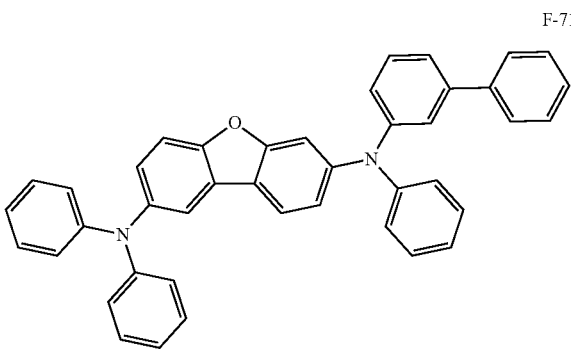
F-72
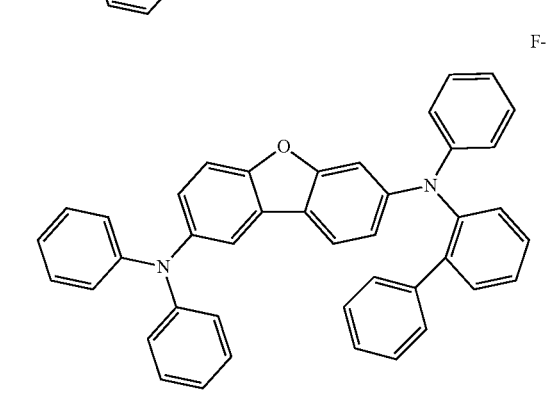
F-73
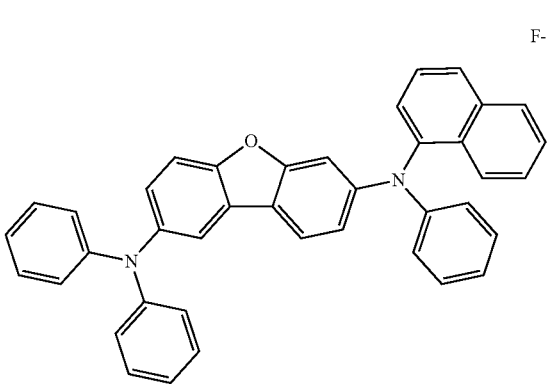

F-74
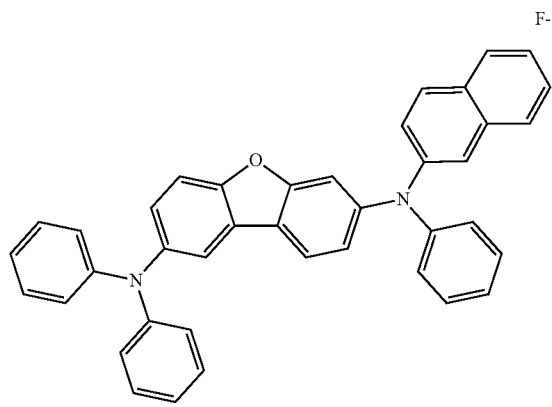
F-75
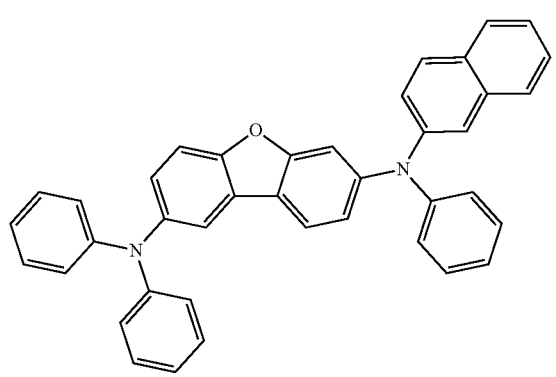
F-76
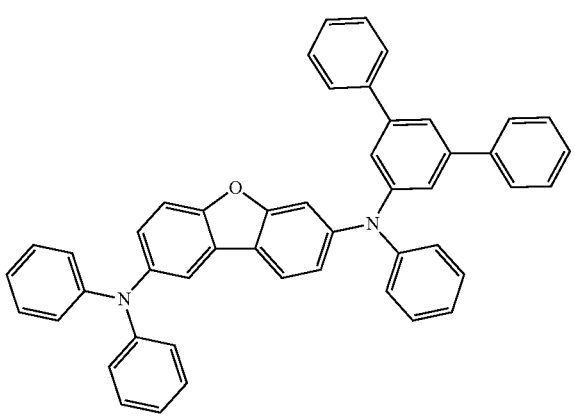
F-77
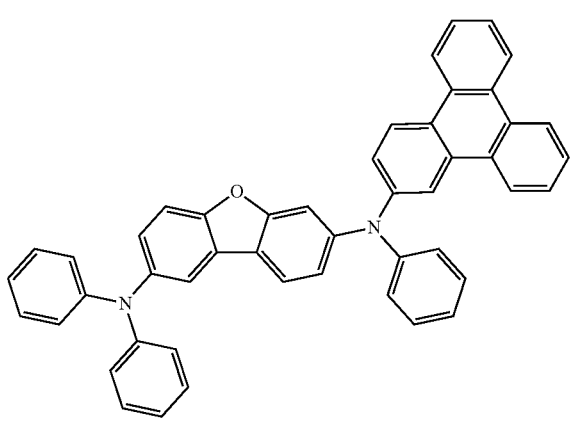
F-78
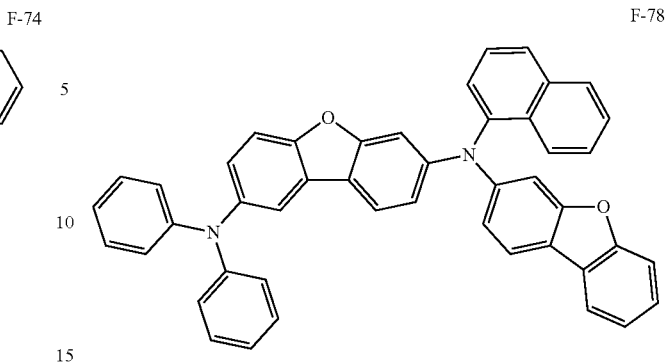
F-79
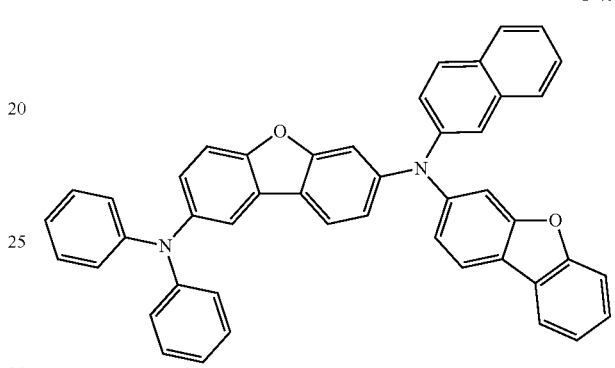
F-80
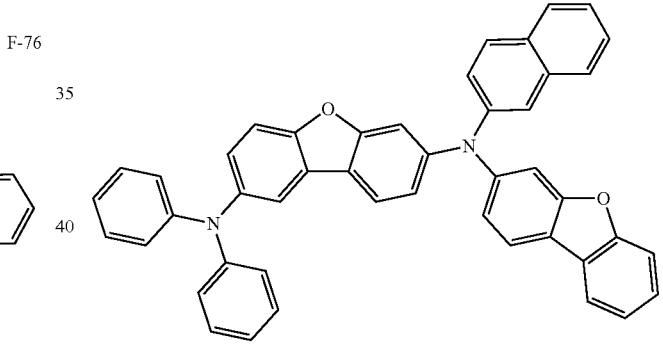
F-81
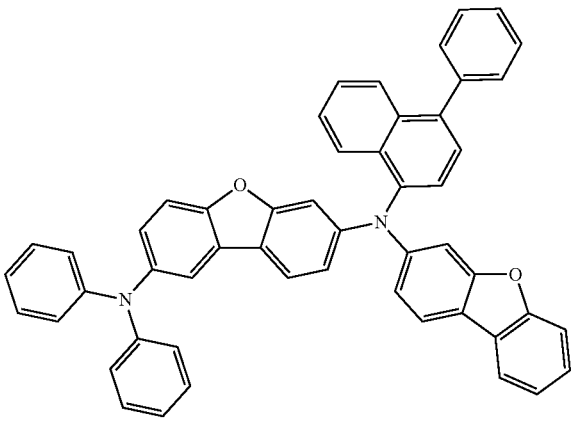

F-82
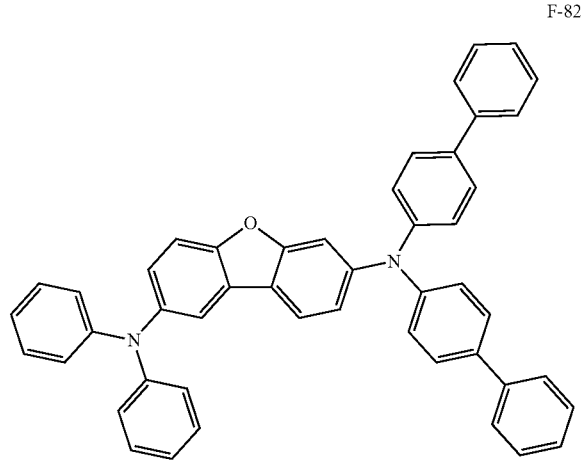
F-83
F-84
F-85
F-86
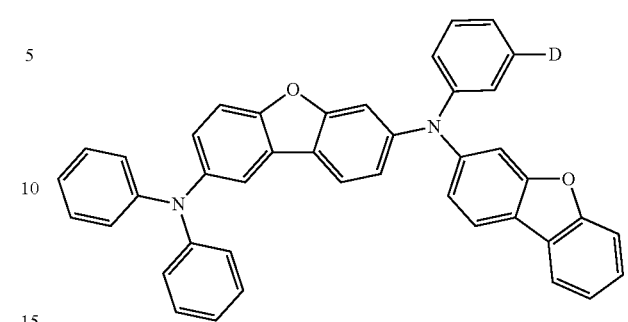
F-87
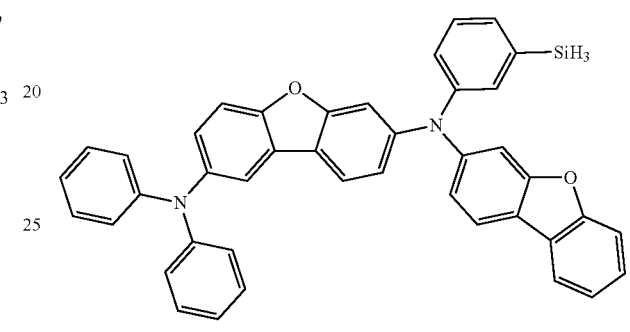
F-88
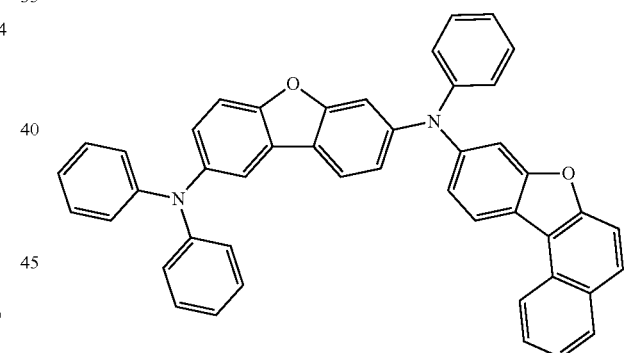
F-89
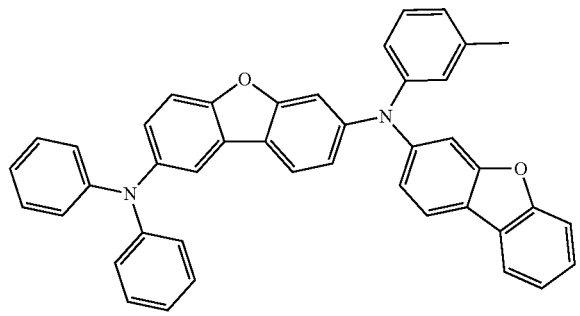

F-90
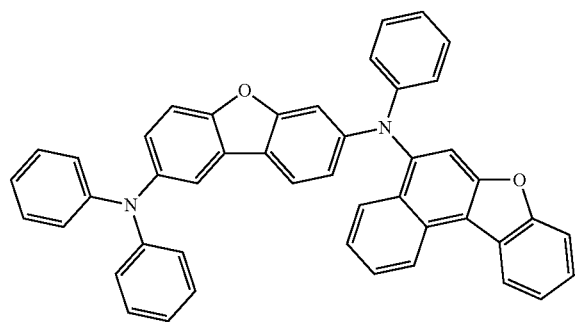
F-91
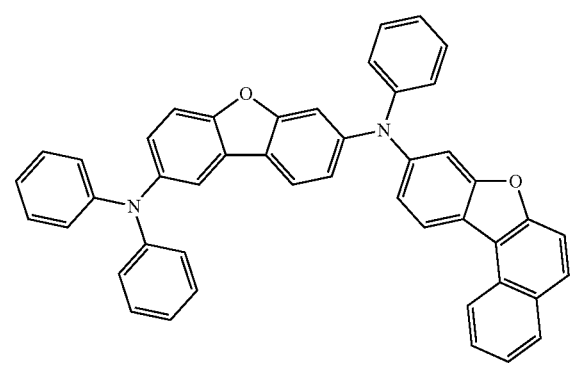
F-92
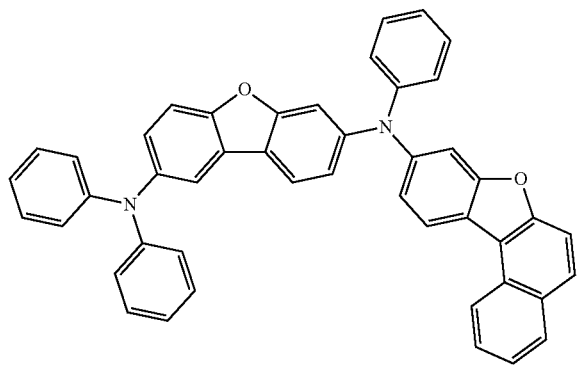
F-93
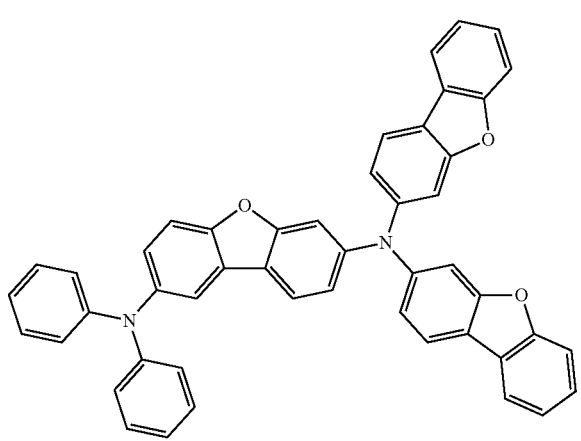
F-94
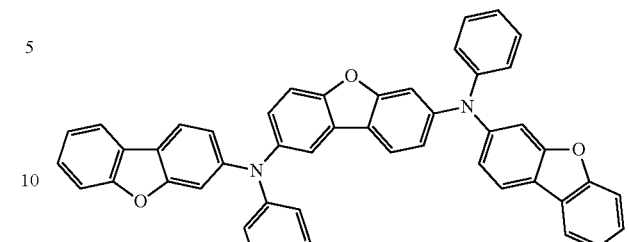
F-95
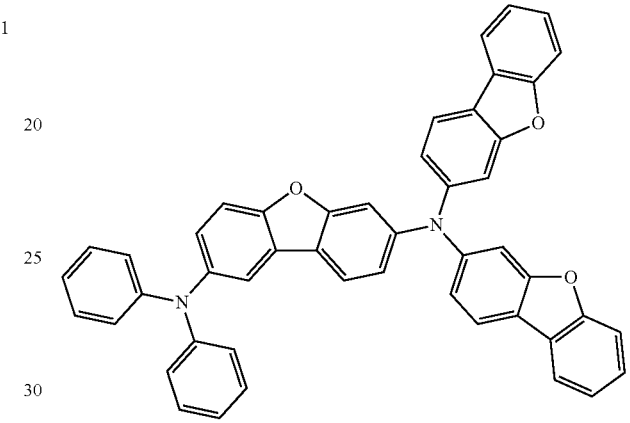
F-96
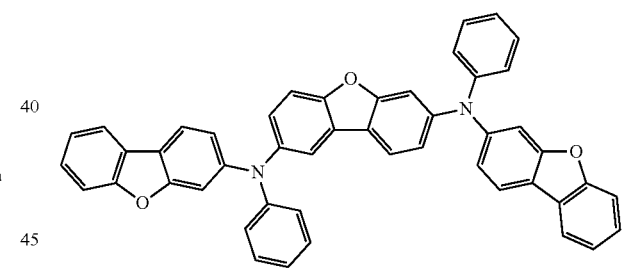
G-1
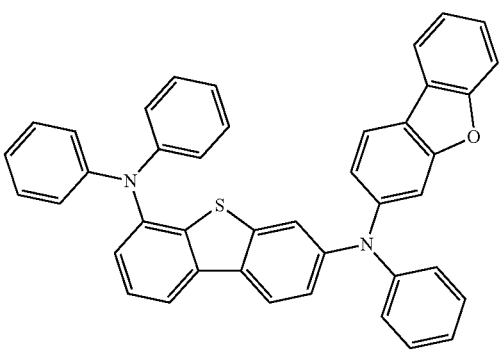

G-2
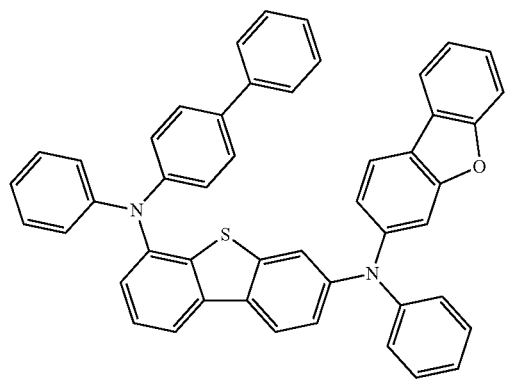
G-3
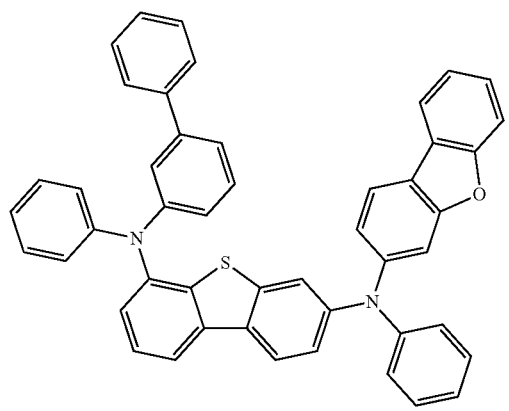
G-4
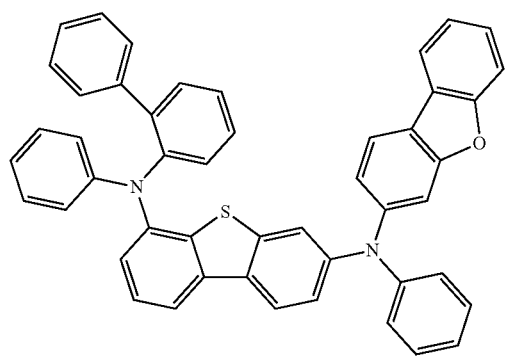
G-5
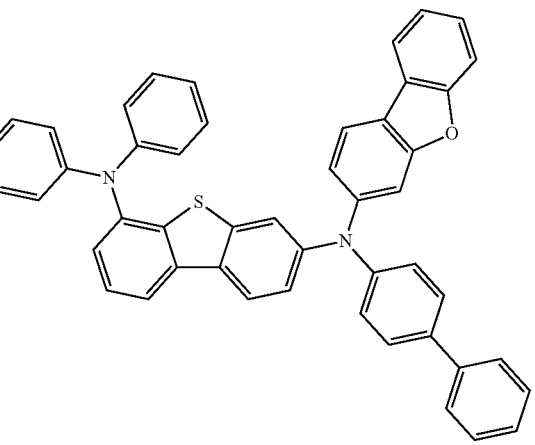
G-6
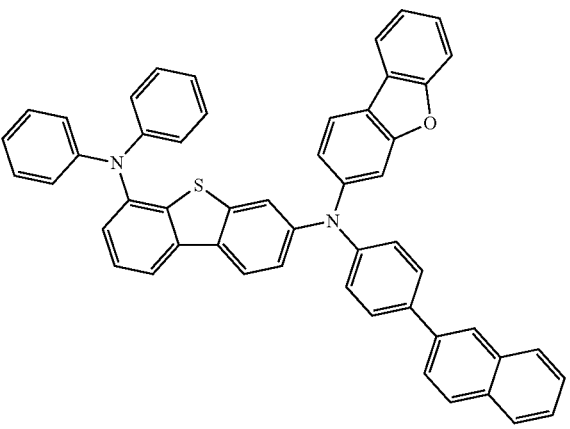
G-7
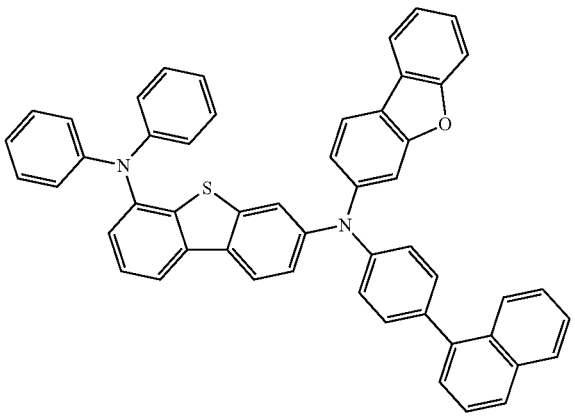

G-8
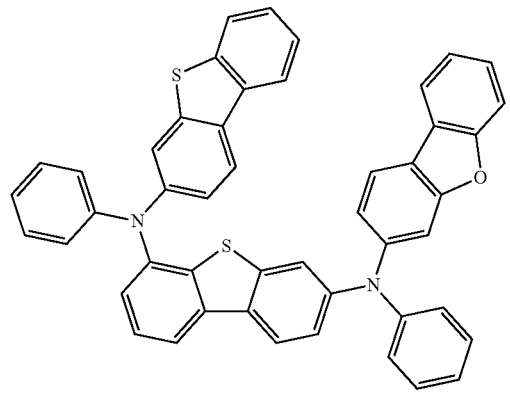
G-9
G-10
G-11
G-12
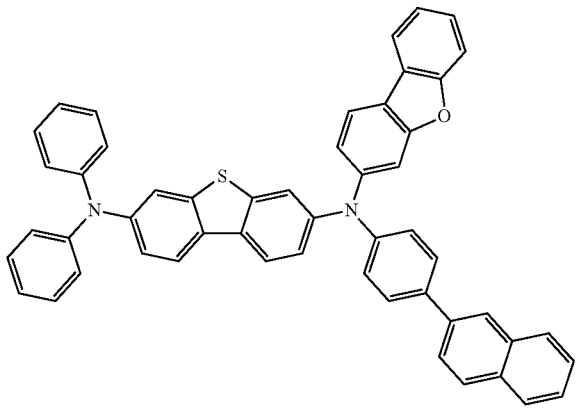
G-13
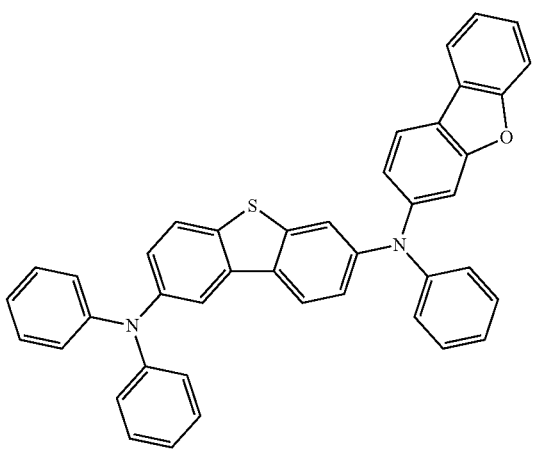
G-14
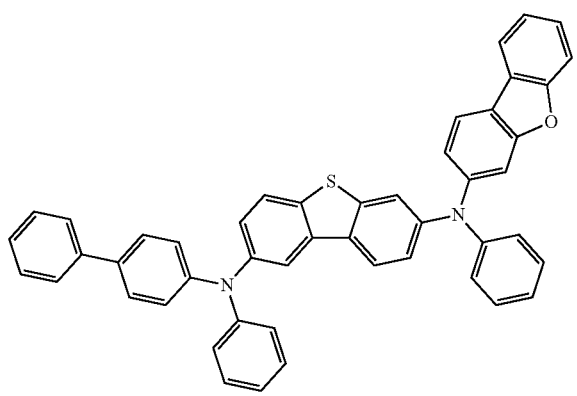

G-15
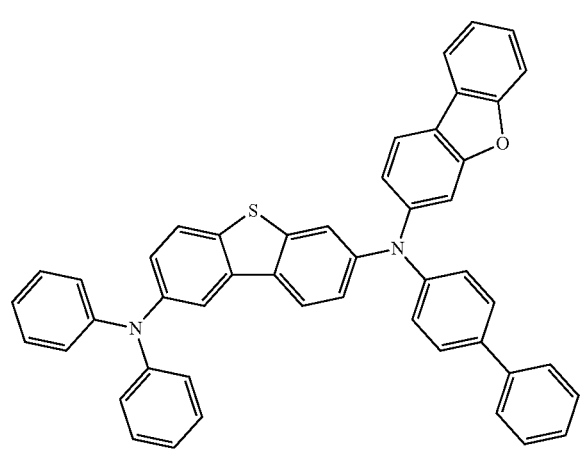
G-16
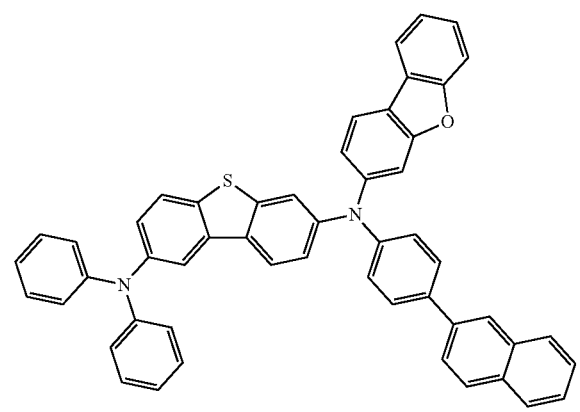
G-17
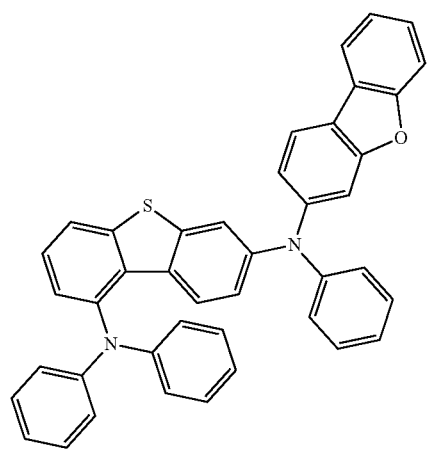
G-18
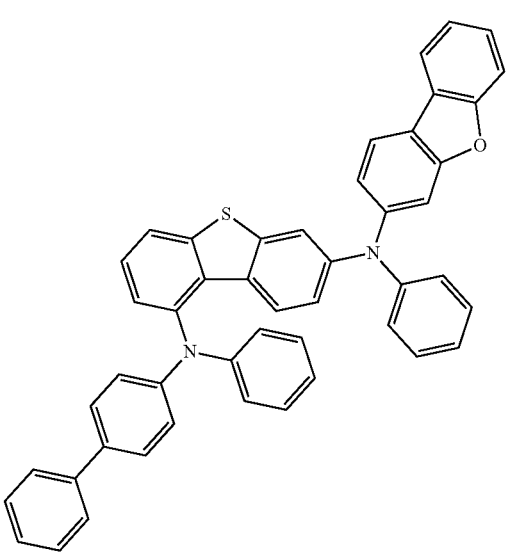
G-19
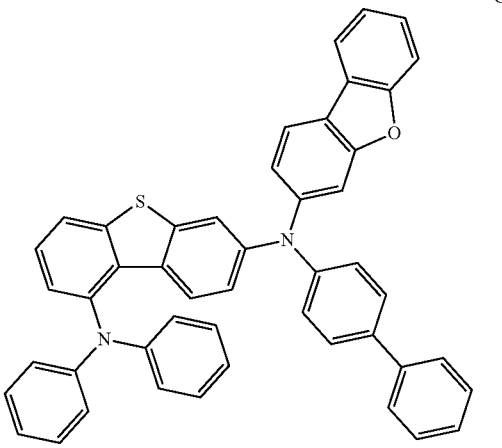
G-20
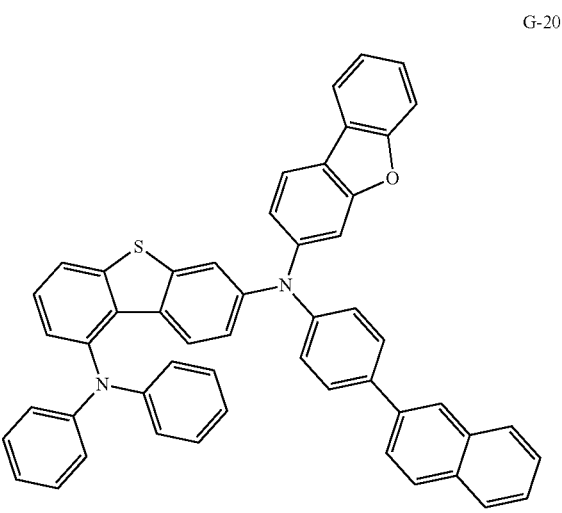

-continued
G-21
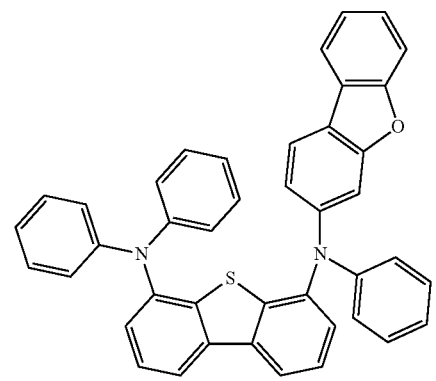
G-22
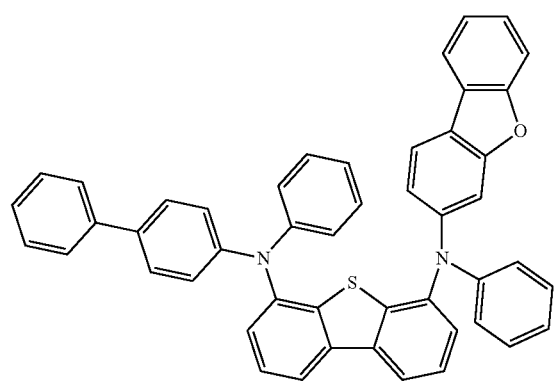
G-23
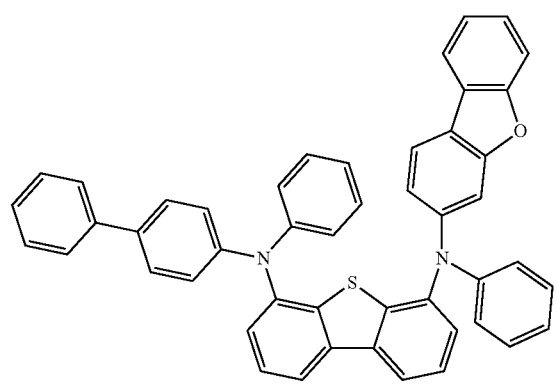
G-24
-continued
G-25
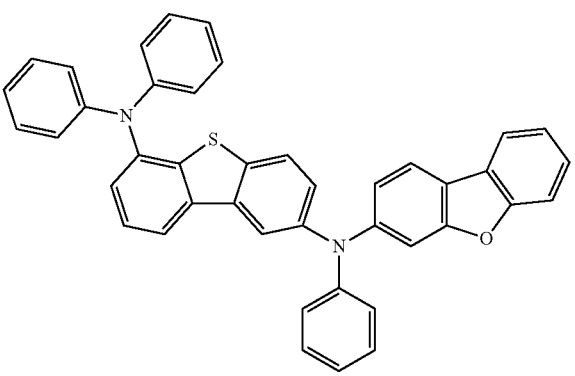
G-26
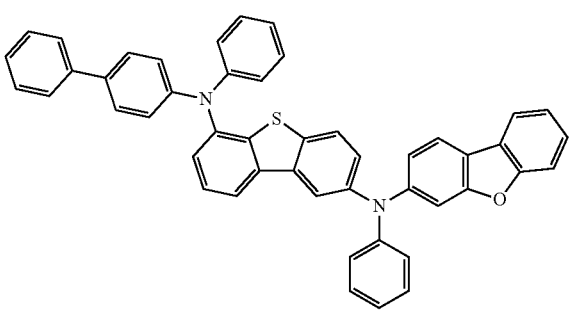
G-27
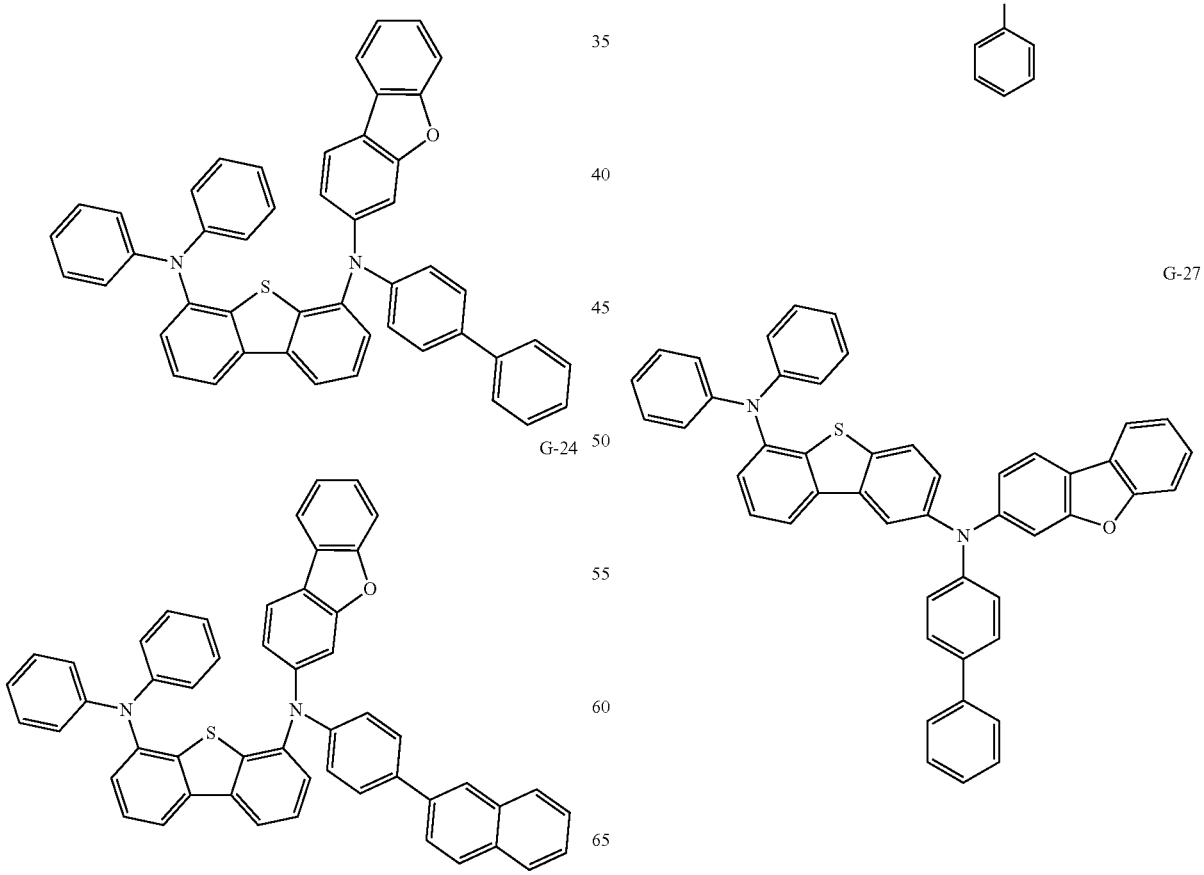

G-28
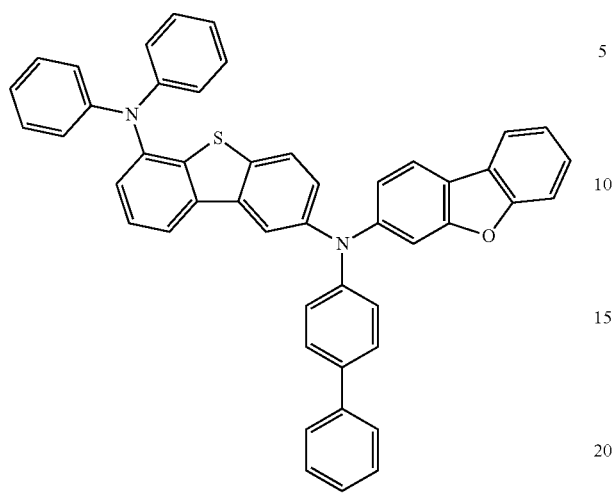
G-29
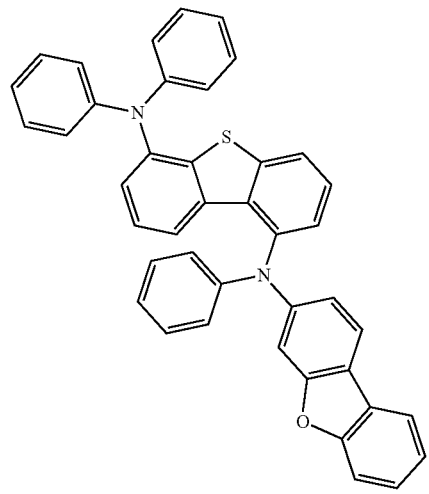
G-30
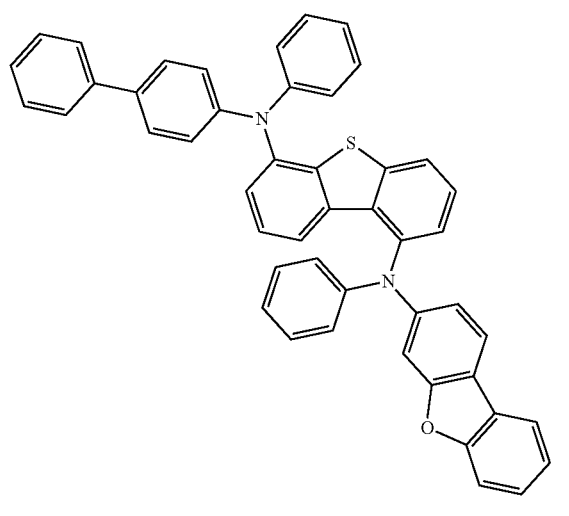
G-31
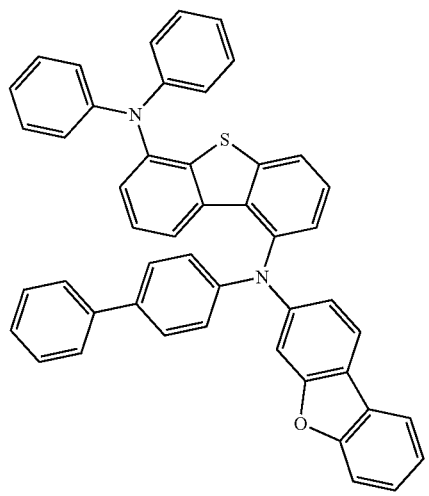
G-32
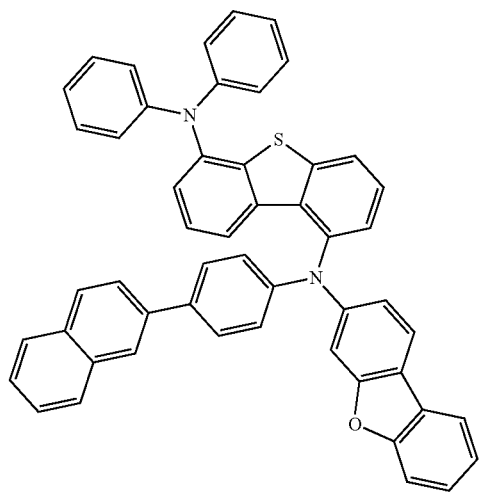
G-33
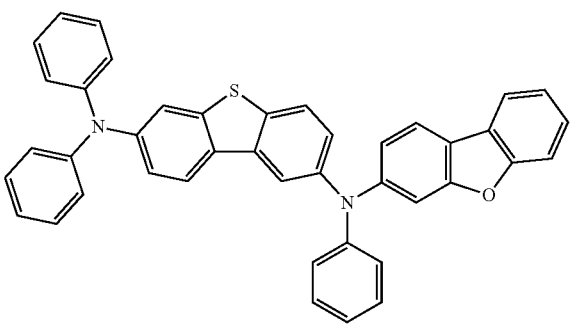

G-34
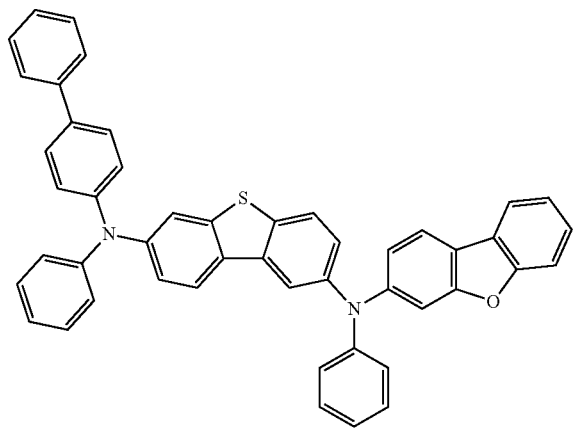
G-37
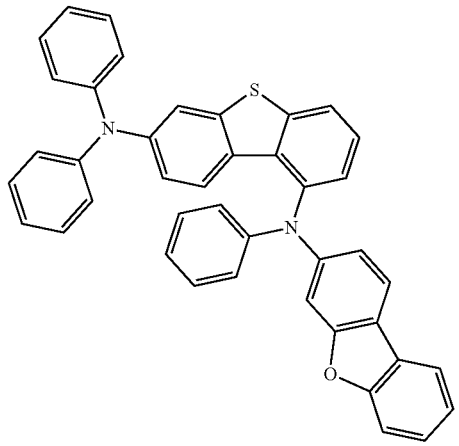
G-35
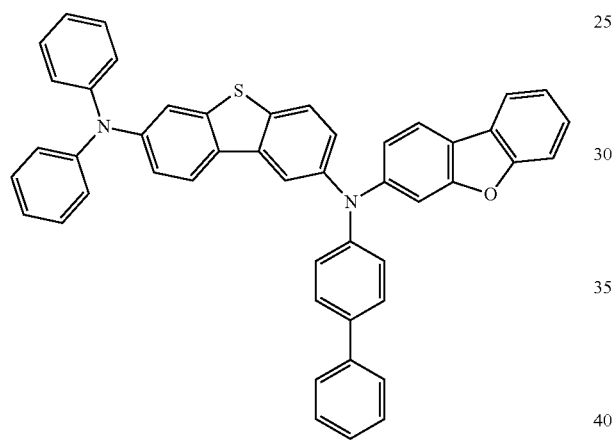
G-38
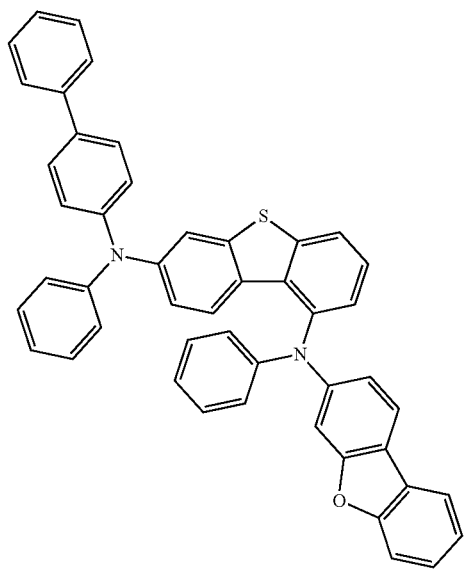
G-36
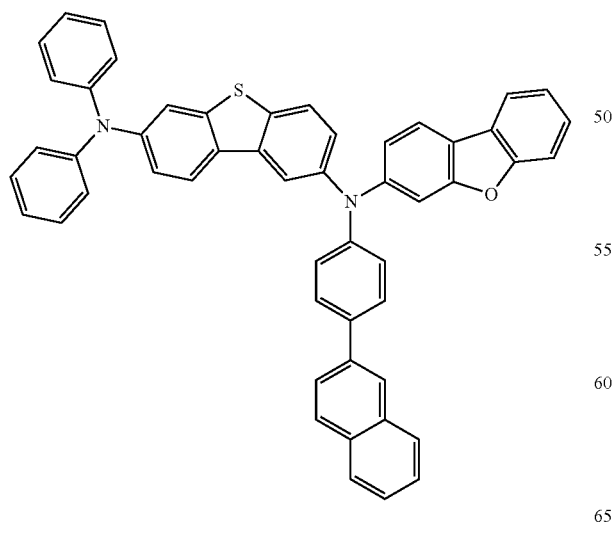
G-39
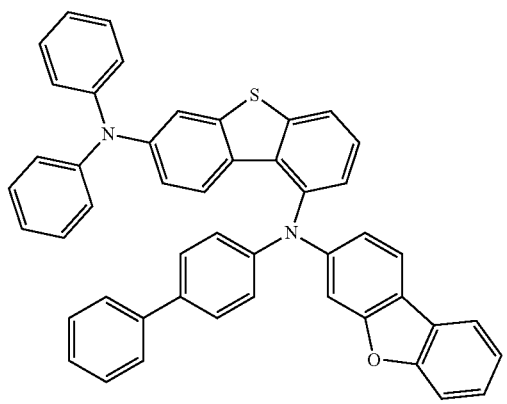

-continued
G-40
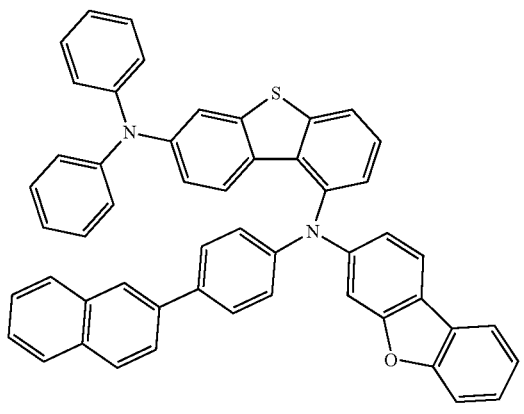
G-41
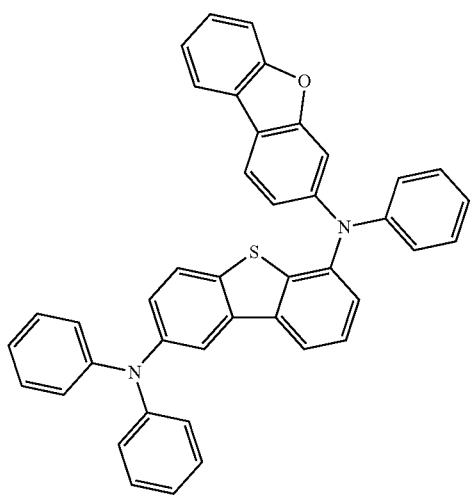
G-42
G-43
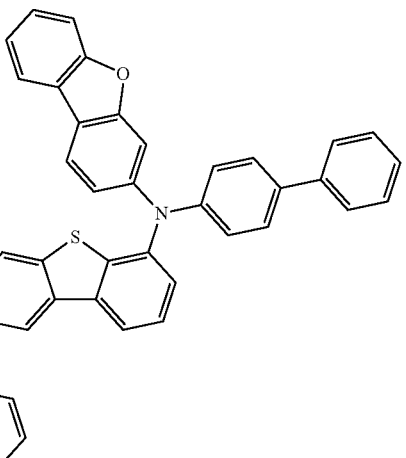
G-44
G-45
G-46
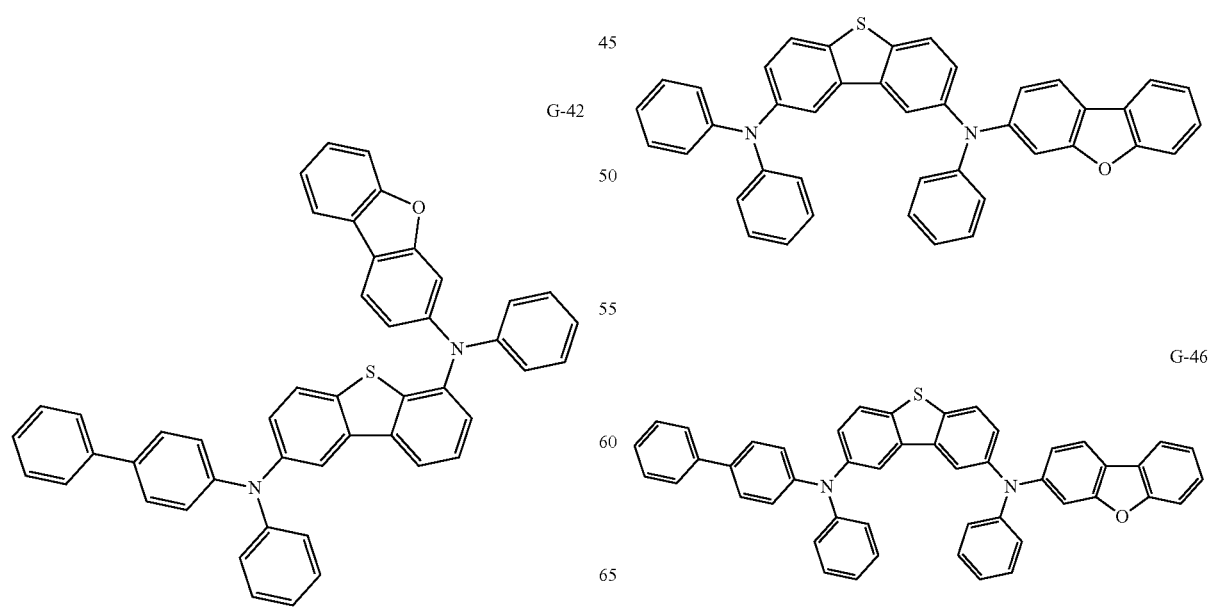

G-47
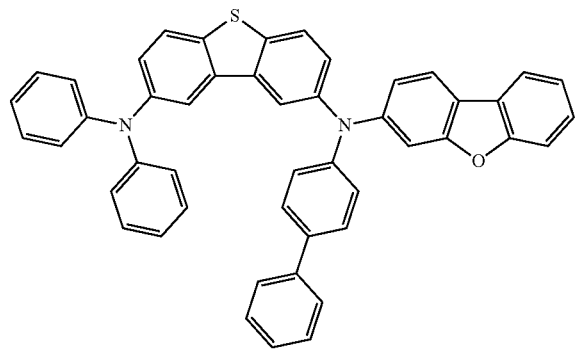
G-48
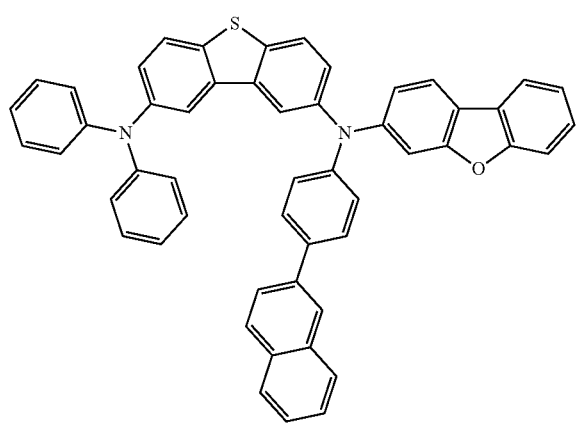
G-49
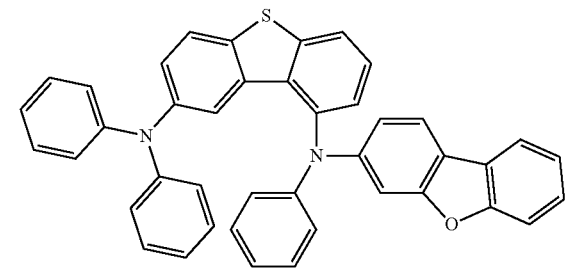
G-50
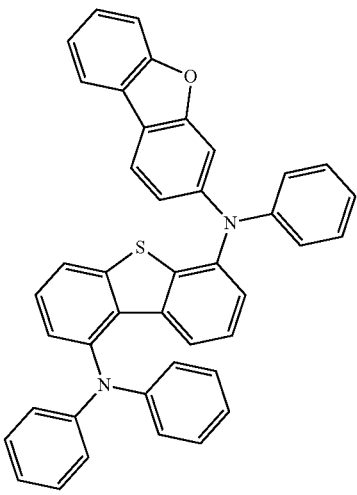
G-51
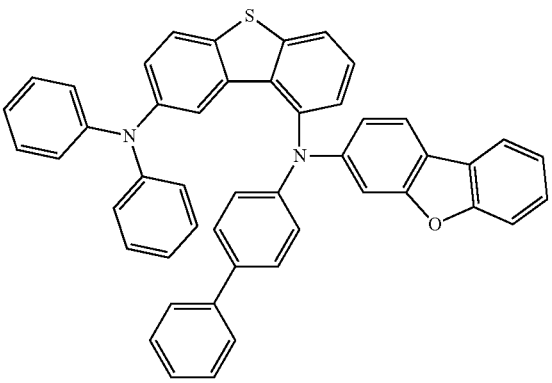
G-52
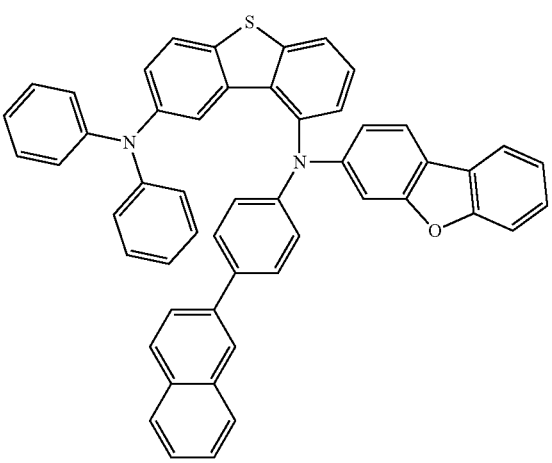
G-53

-continued
G-54
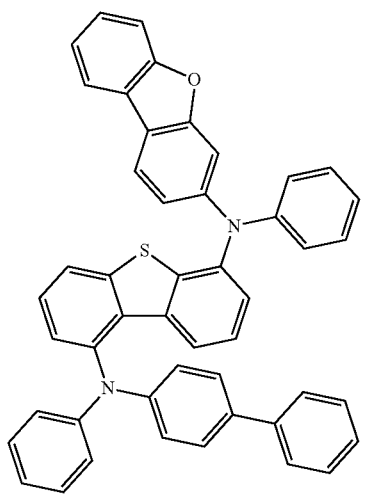
G-55
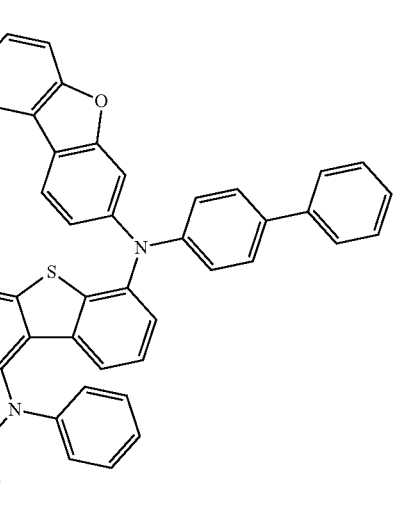
G-56
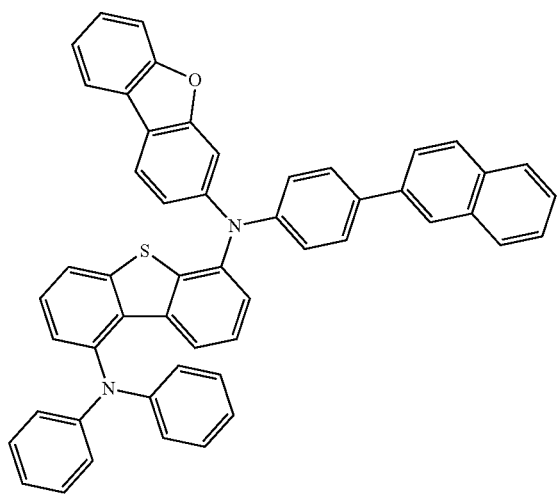
-continued
G-57
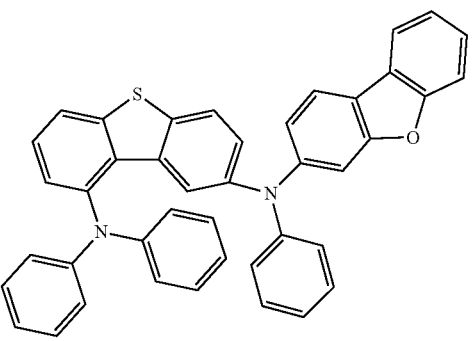
G-58
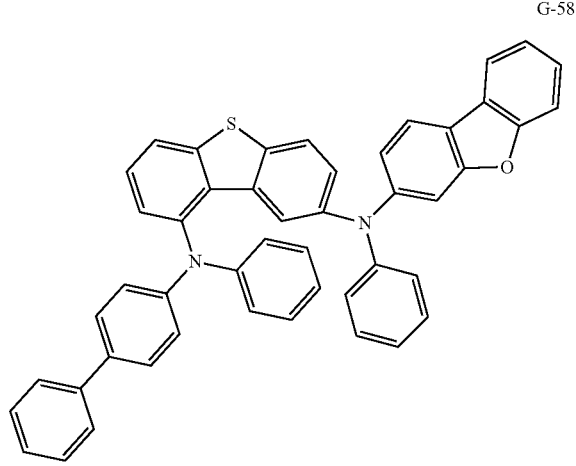
G-59
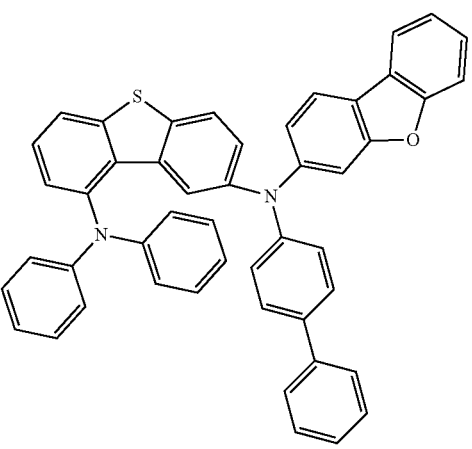

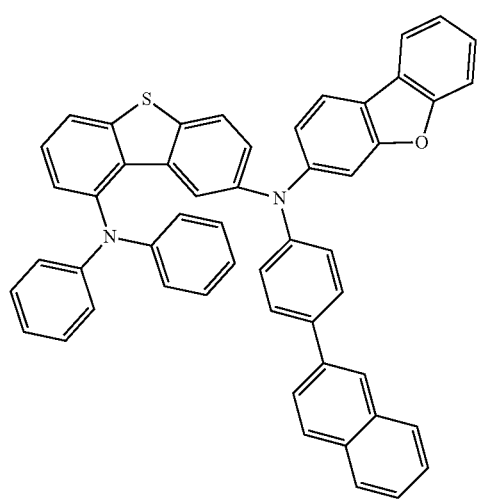
G-60
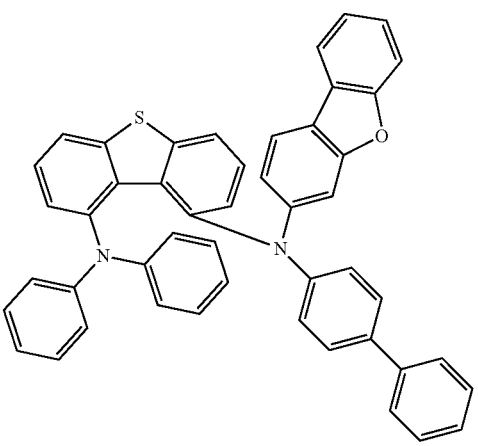
G-63
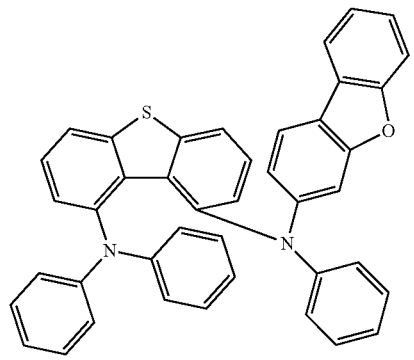
G-61
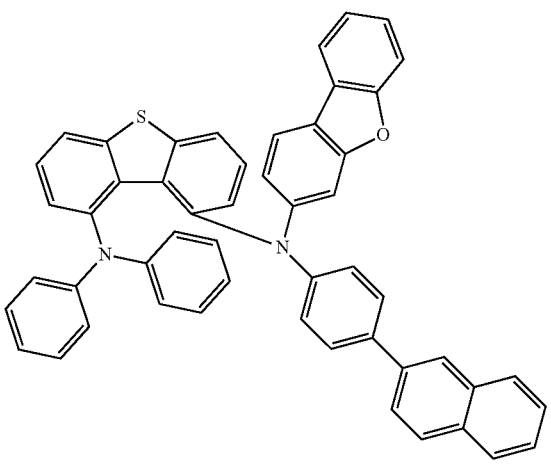
G-64
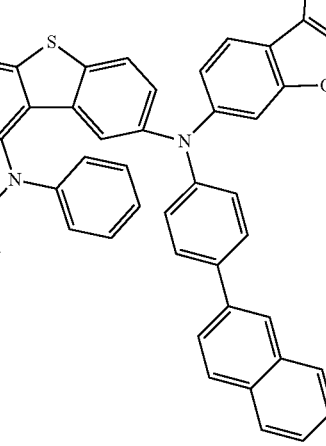
G-62
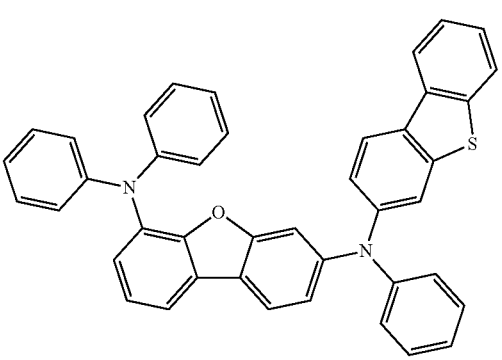
H-1

-continued
H-2
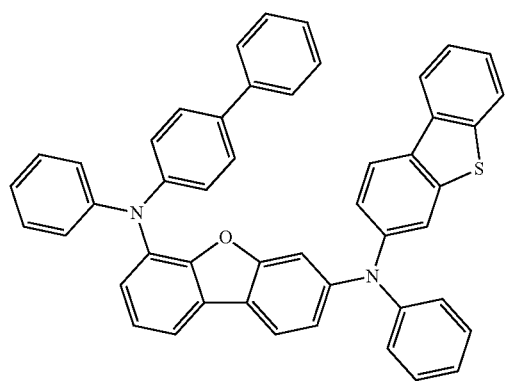
H-3
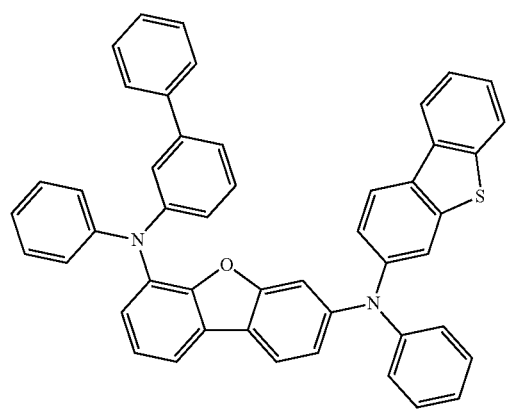
H-4
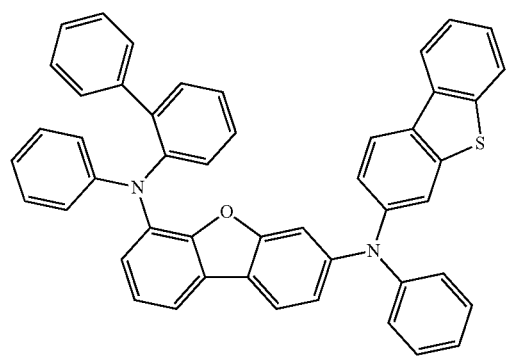
-continued
H-5
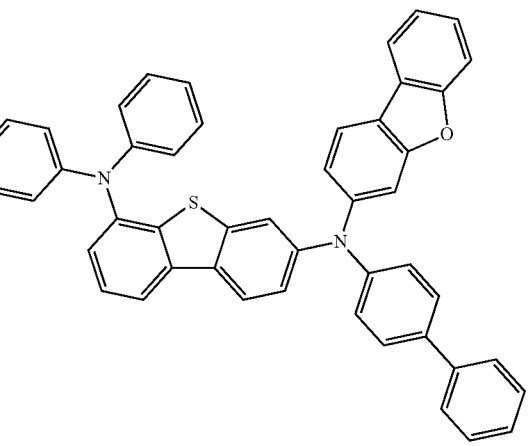
H-6
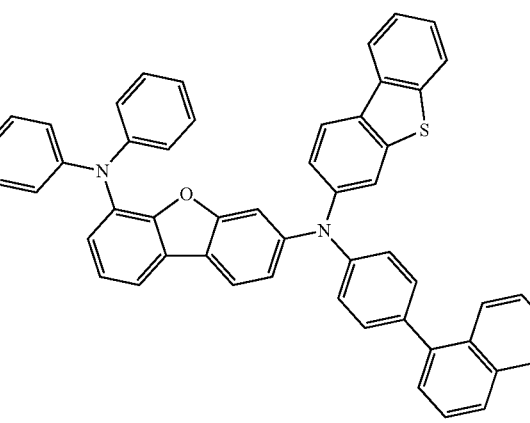
H-7

H-8
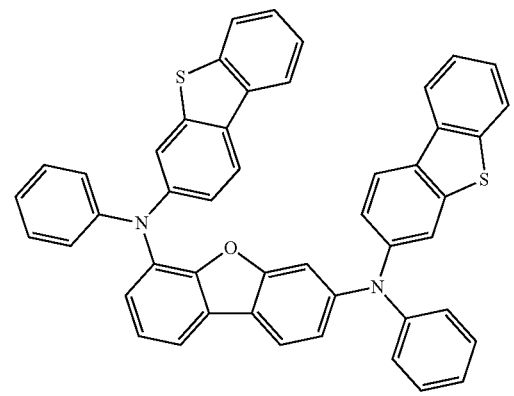
H-9
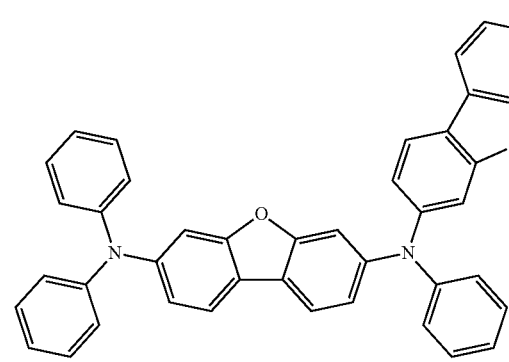
H-10
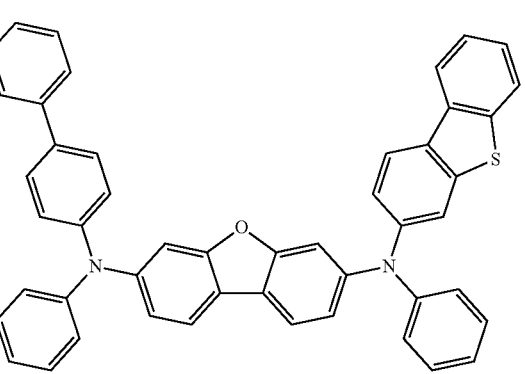
H-11
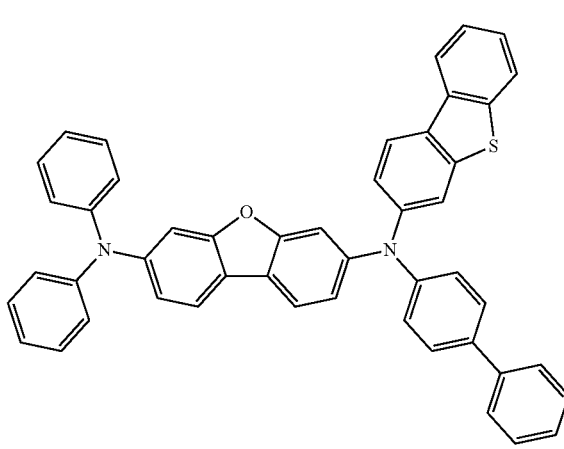
H-12
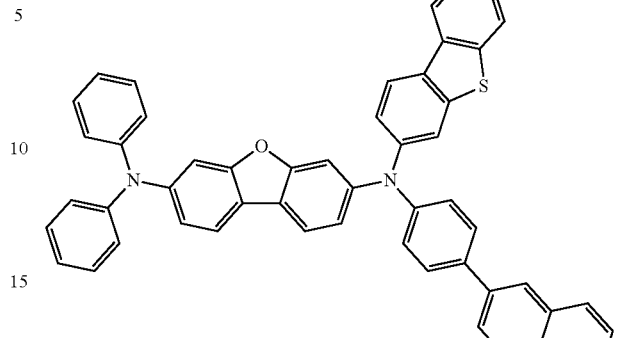
H-13
H-14
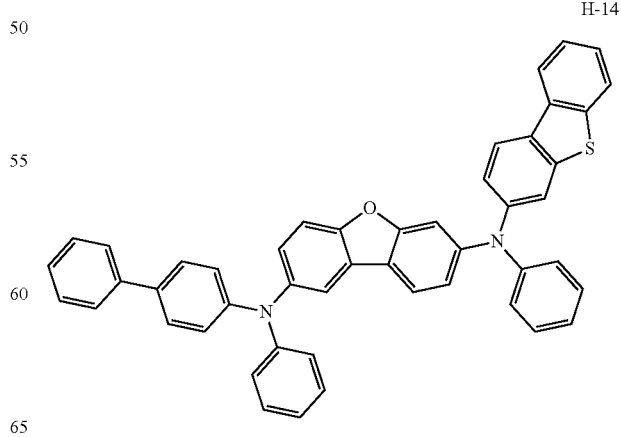

H-15
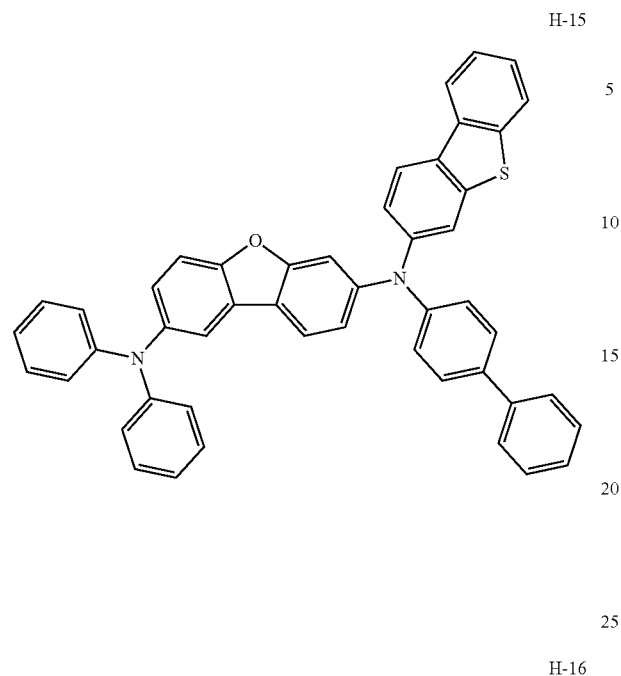
H-16
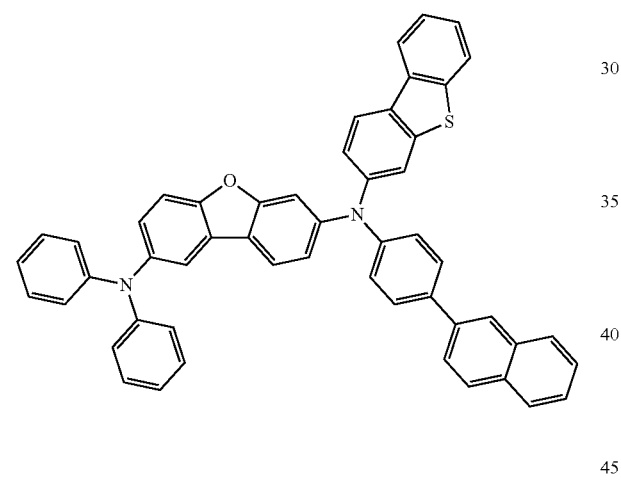
H-17
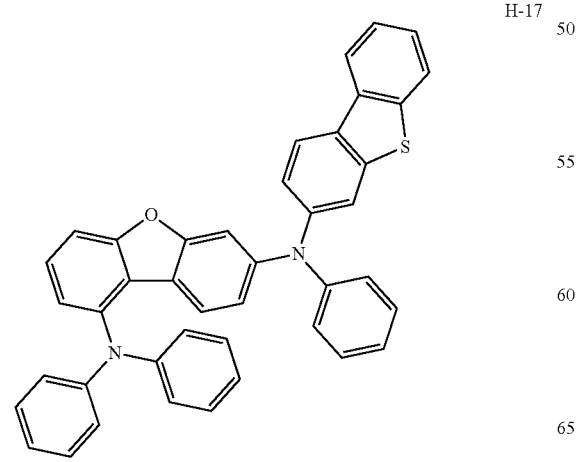
H-18
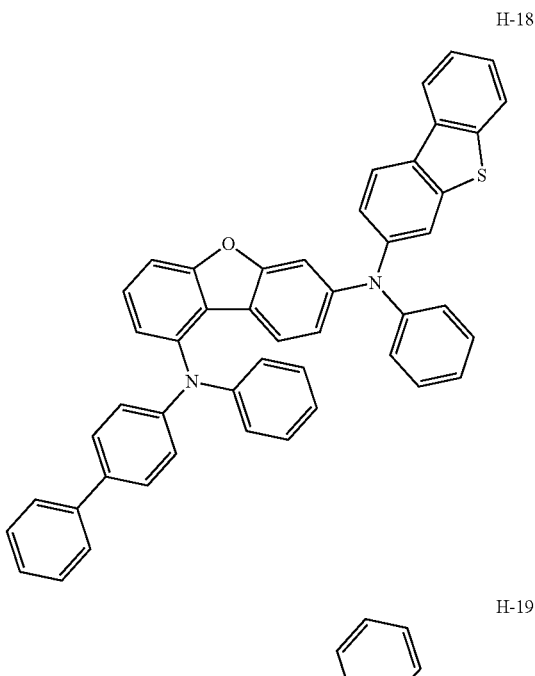
H-19
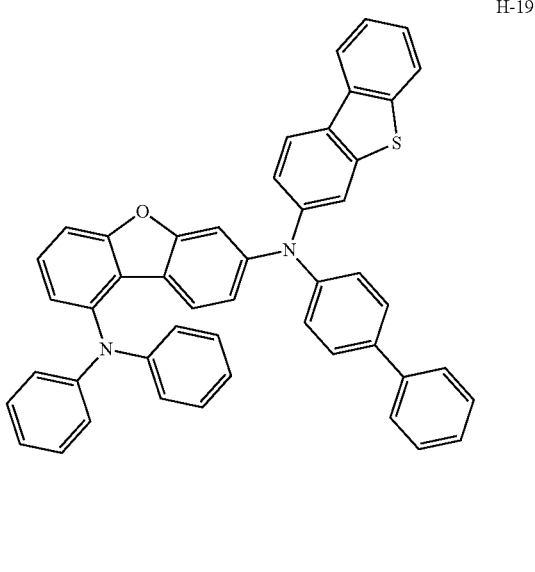
H-20
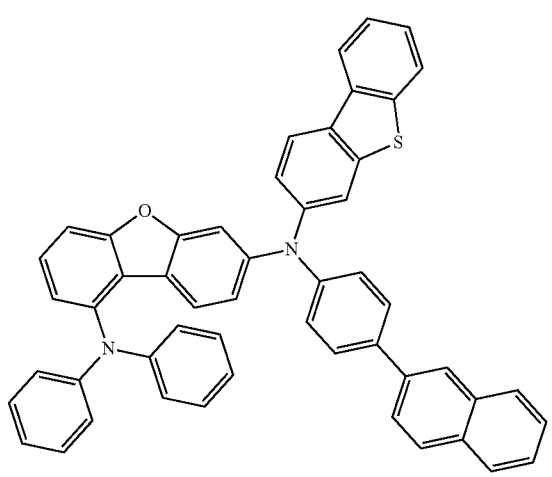

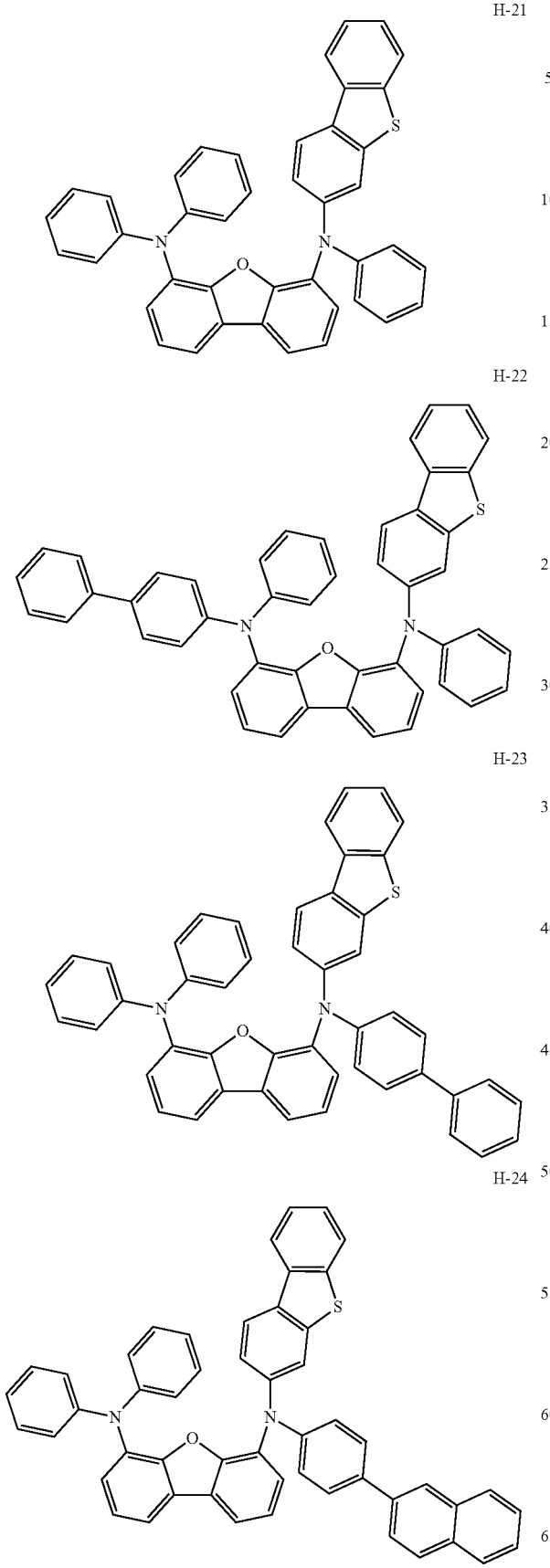
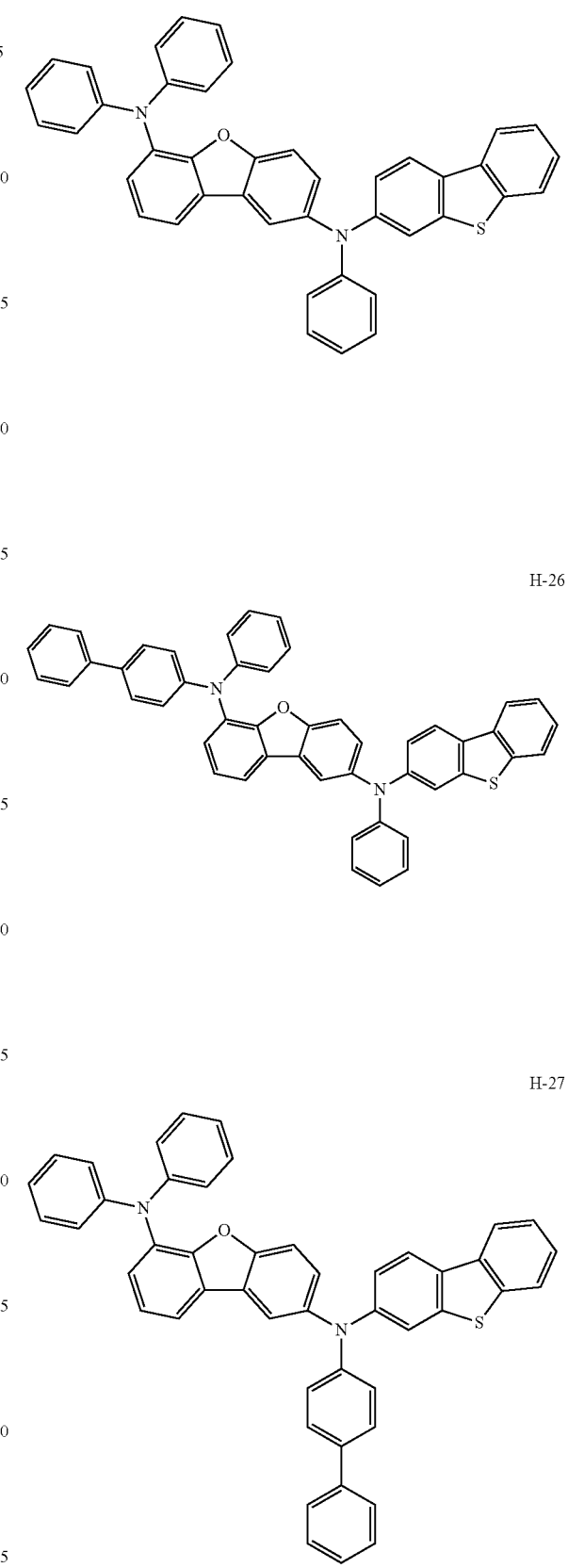

H-28
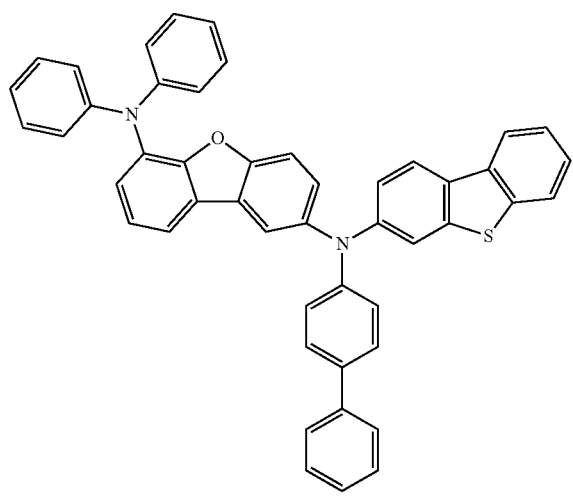
H-29
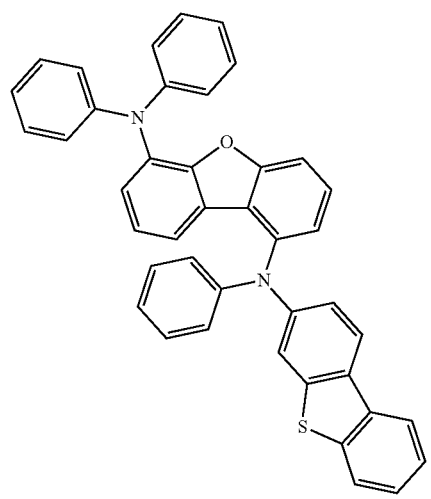
H-30
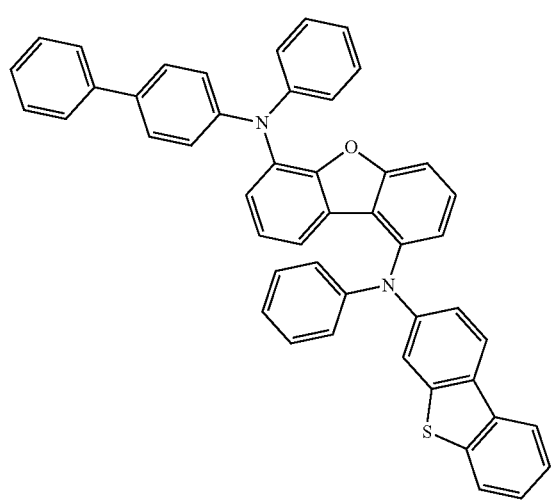
H-31
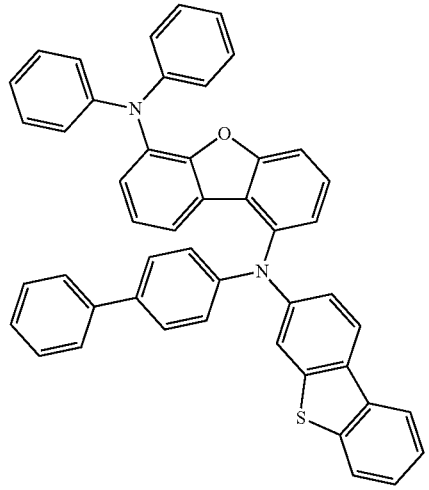
H-32
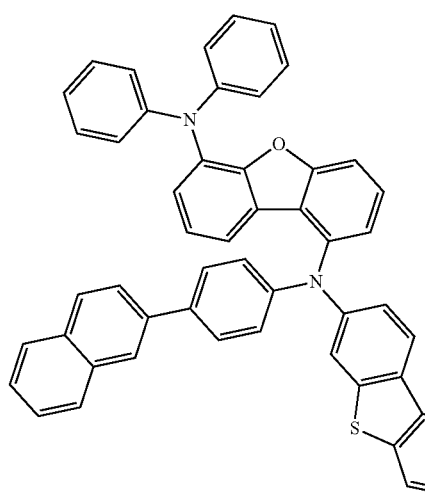
H-33
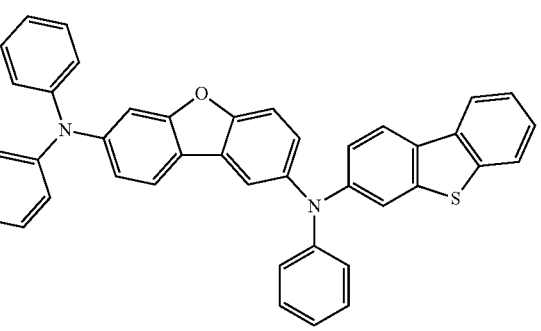

H-34
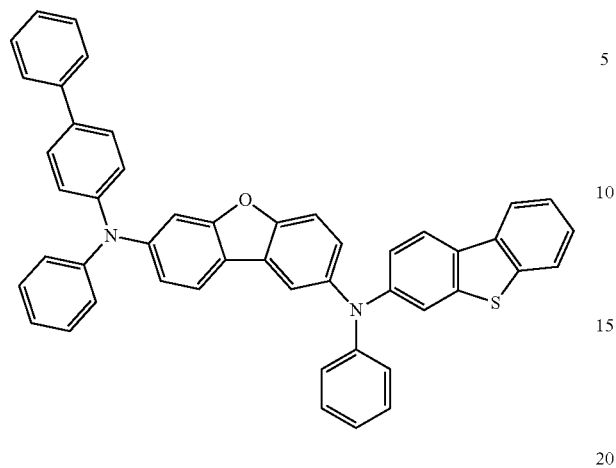
H-35
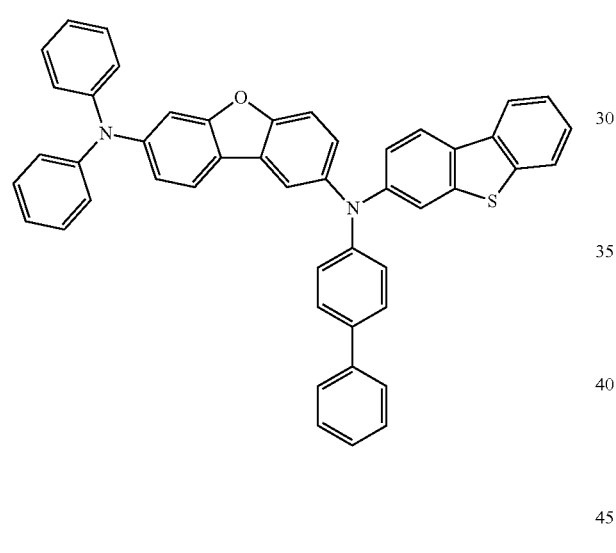
H-36
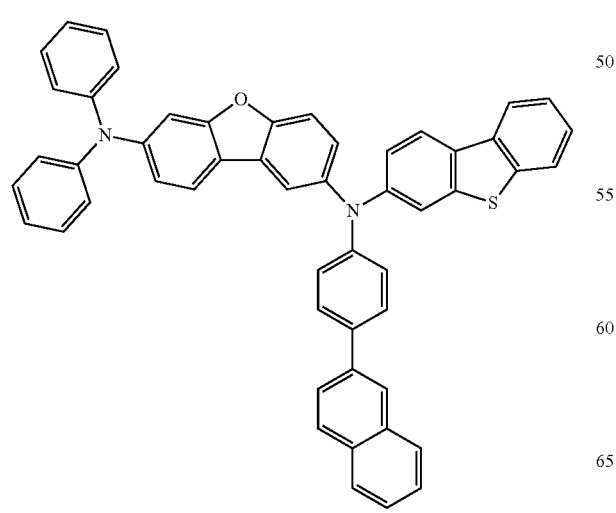
H-37
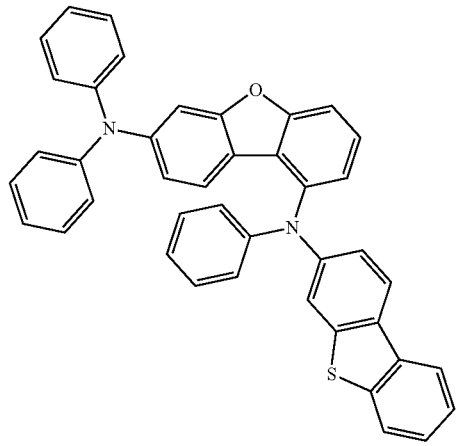
H-38
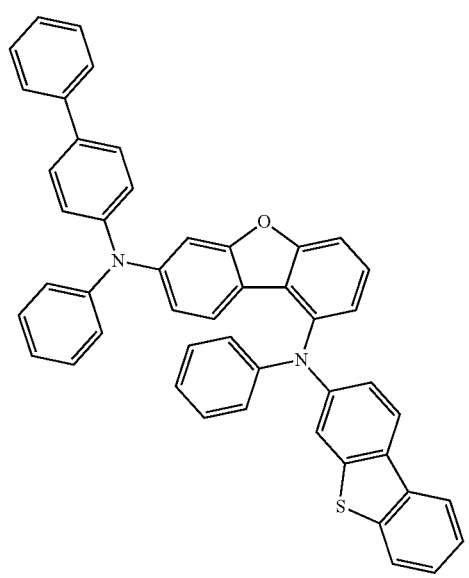
H-39
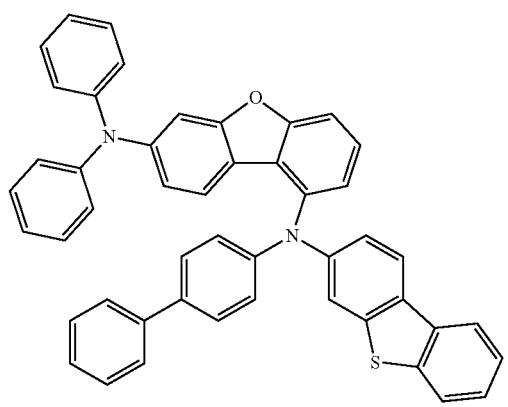

H-40
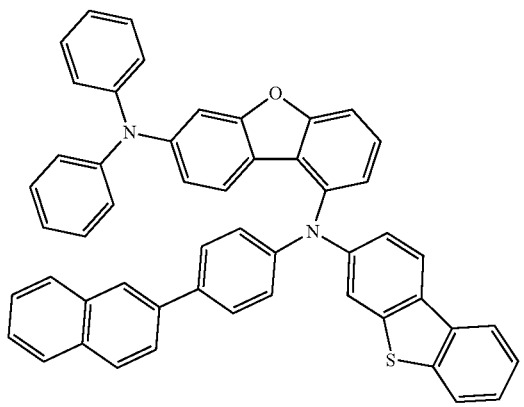
H-41
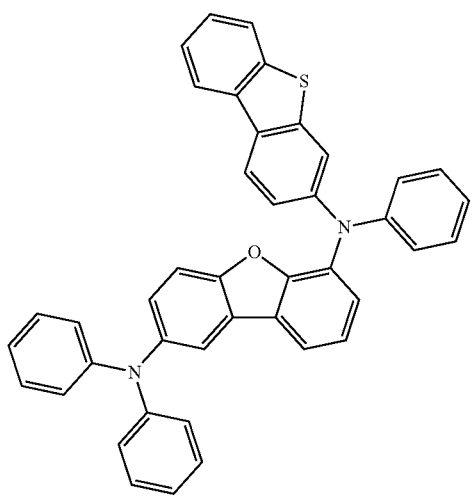
H-42
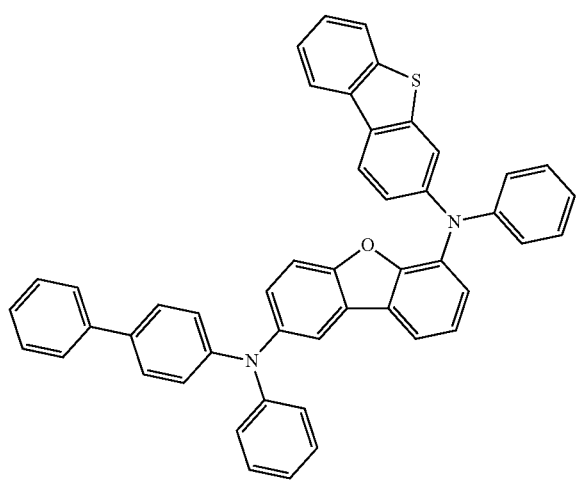
H-43
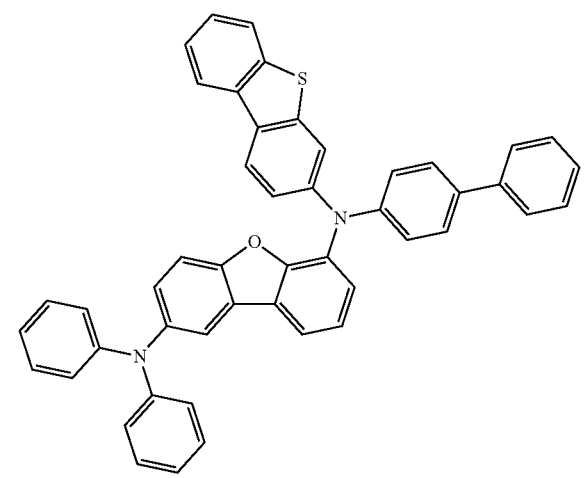
H-44
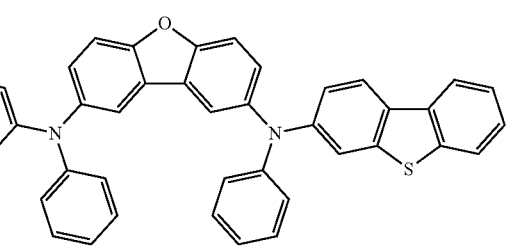
H-45
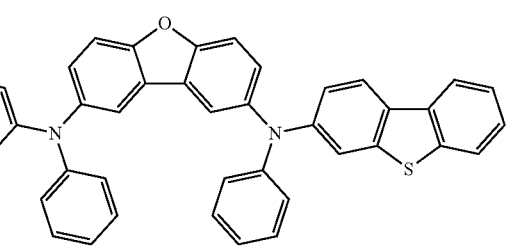
H-46
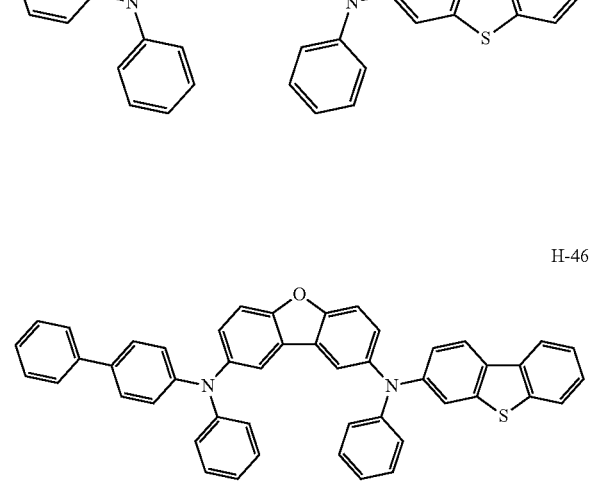

H-47
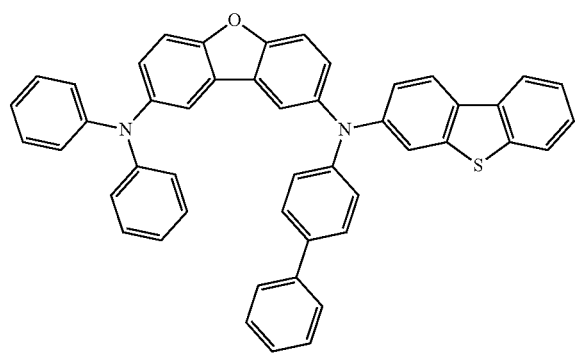
H-48
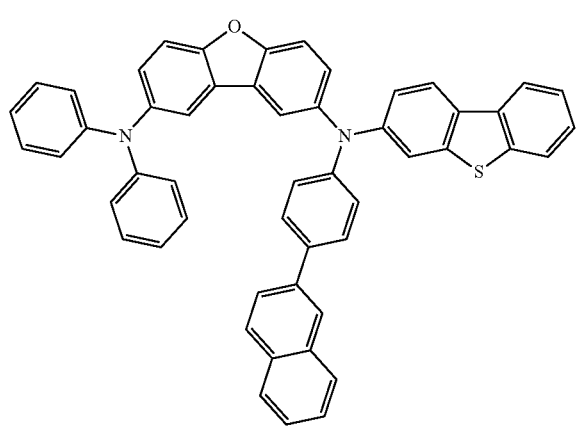
H-49
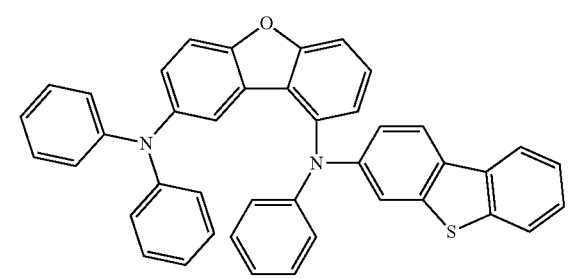
H-50
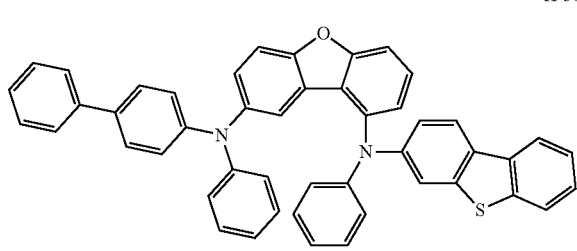
H-51
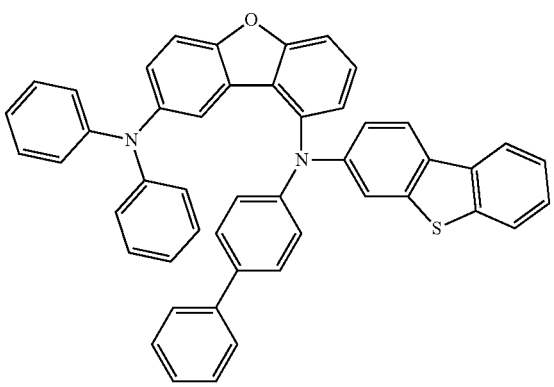
H-52
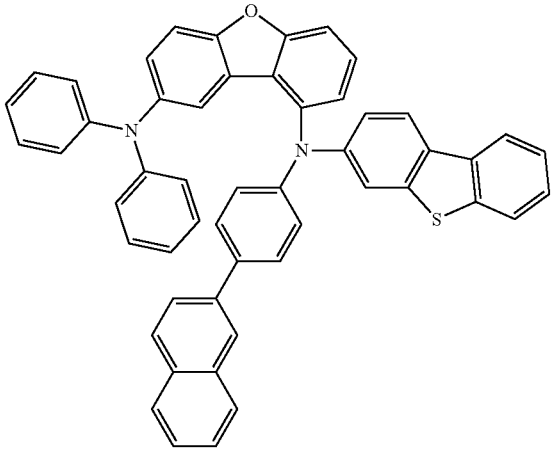
H-53
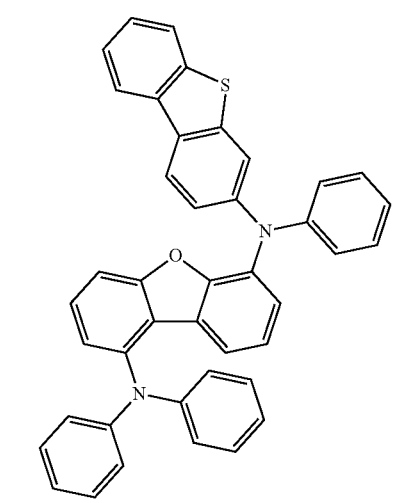

H-54
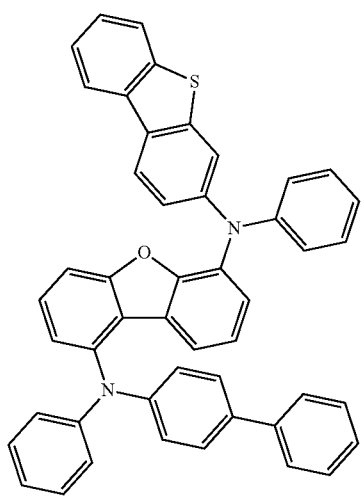
H-55
H-56
H-57
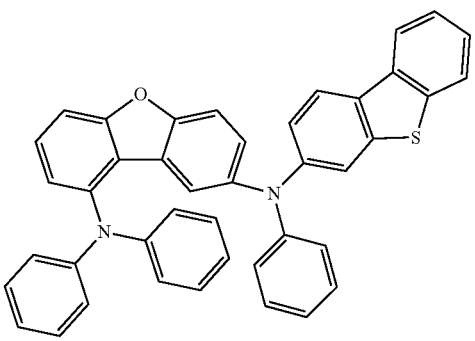
H-58
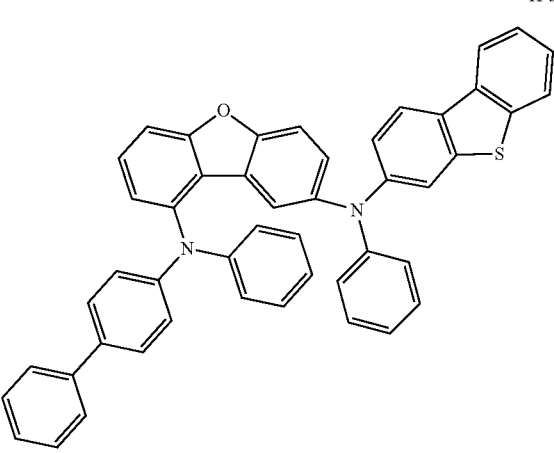
H-59
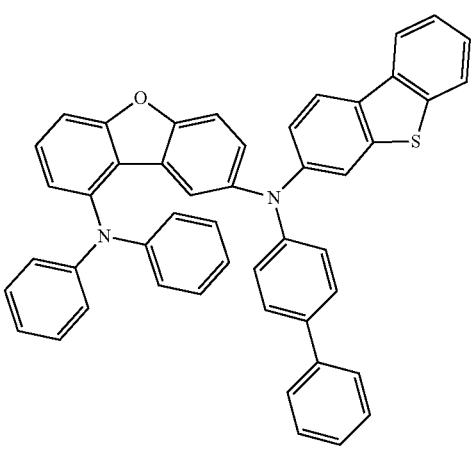

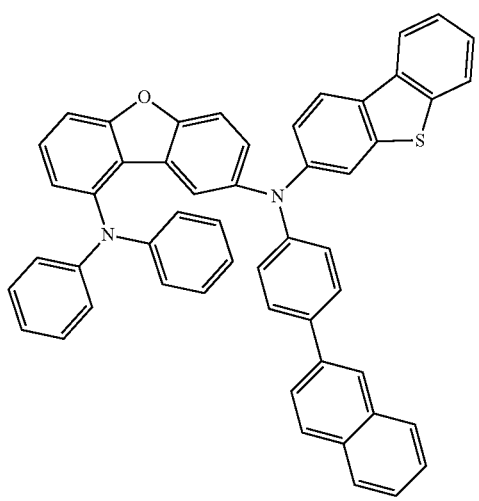

H-60

H-61

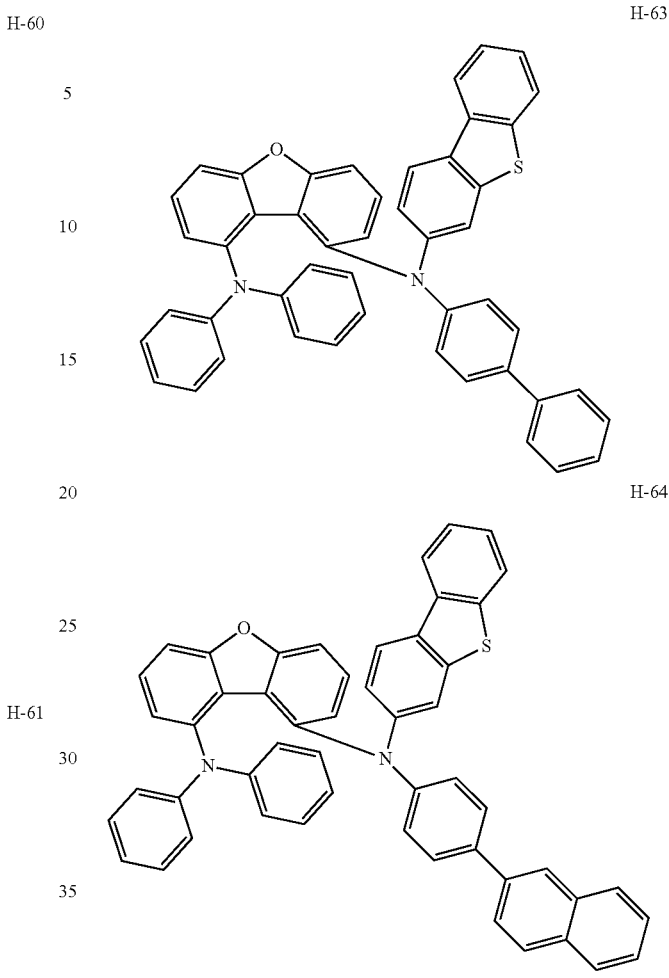

H-63

H-64

The hole transport layer 141 may be between the anode 110 and the light emitting layer 130, and may facilitate hole transport from the anode 110 to the light emitting layer 130. For example, the hole transport layer 141 may include a material having a HOMO energy level between a work function of a conductor of the anode 110 and a HOMO energy level of a material of the light emitting layer 130.

The hole transport layer 141 may include, e.g., an amine derivative (e.g., an amine containing compound).

In an implementation, the hole transport layer 141 may include, e.g., a compound represented by Chemical Formula 5.

[Chemical Formula 5]

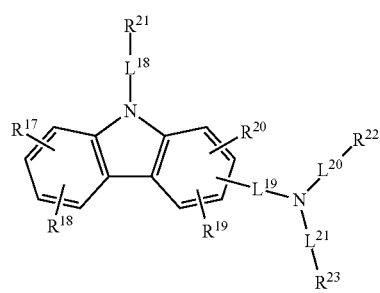

H-62

In Chemical Formula 5, $R^{17}$ to $R^{21}$ may each independently be, e.g., hydrogen, deuterium, a substituted or unsubstituted C1 to C10 alkyl group, a substituted or unsubstituted C6 to C30 aryl group, a substituted or unsubstituted C2 to C30 heterocyclic group, or a combination thereof, $R^{17}$ and $R^{18}$ may be separately present or may be linked with each other to form a ring, $R^{19}$ and $R^{20}$ may be separately present or may be linked with each other to form a ring, $R^{21}$ to $R^{23}$ may each independently be, e.g., a substituted or unsubstituted C6 to C30 aryl group, or a substituted or unsubstituted C2 to C30 heterocyclic group, and $L^{18}$ to $L^{21}$ may each independently be, e.g., a single bond, a substituted or unsubstituted C6 to C30 arylene group, a substituted or unsubstituted C2 to C30 heterocyclic group or a combination thereof.

In an implementation, $R^{21}$ may be, e.g., a substituted or unsubstituted C6 to C30 aryl group, and $R^{19}$ may be, e.g., a substituted or unsubstituted phenyl group or a substituted or unsubstituted biphenyl group.

In an implementation, $R^{22}$ and $R^{23}$ may each independently be, e.g., a substituted or unsubstituted phenyl group, a substituted or unsubstituted biphenyl group, a substituted or unsubstituted fluorenyl group, a substituted or unsubstituted bisfluorene group, a substituted or unsubstituted triphenylenyl group, a substituted or unsubstituted anthracenyl group, a substituted or unsubstituted terphenyl group, a substituted or unsubstituted dibenzofuranyl group, a substituted or unsubstituted dibenzothiophenyl group, or a combination thereof.

In an implementation, the compound represented by Chemical Formula 5 may be, e.g., a compound of the following Group 4.

[Group 4]

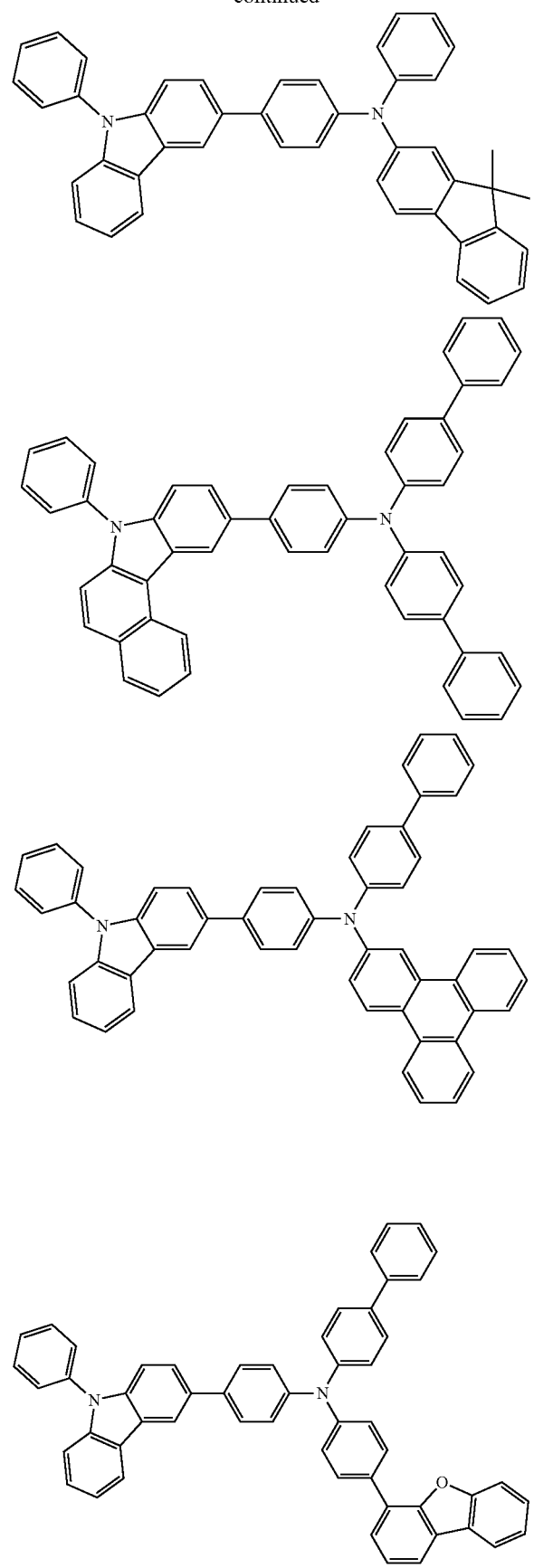

-continued

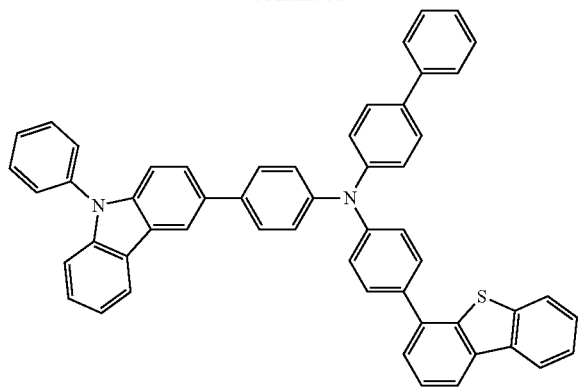

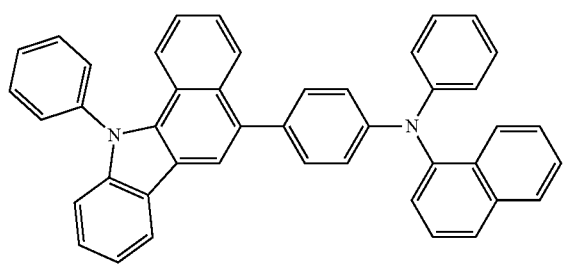

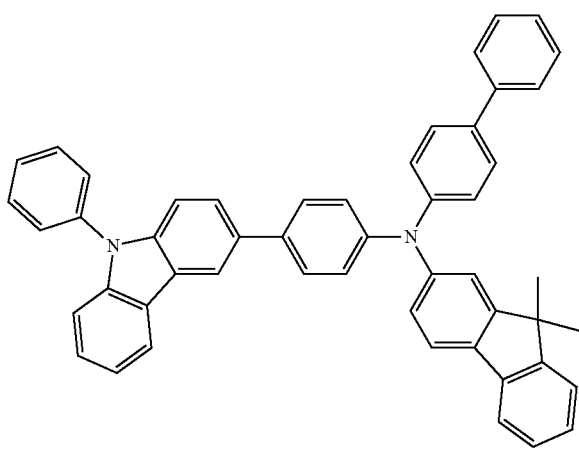

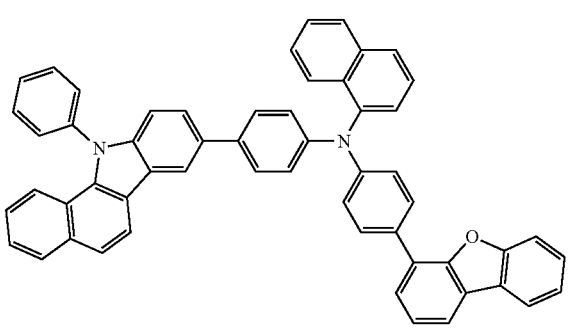

-continued

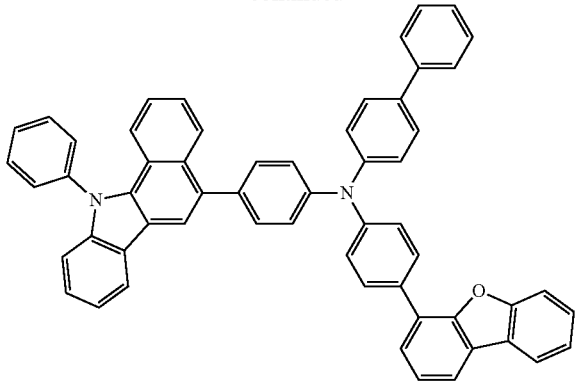

In an implementation, the organic layer 105 may further include a hole injection layer, an electron blocking layer, an electron transport layer, an electron injection layer, and/or a hole blocking layer in addition to the aforementioned light emitting layer 130, hole transport auxiliary layer 142, and hole transport layer 141.

The organic light emitting diode 300 may be manufactured by forming an anode or a cathode on a substrate, forming an organic layer using a dry film formation method such as a vacuum deposition method (evaporation), sputtering, plasma plating, and ion plating, or a solution process, and forming a cathode or an anode thereon.

The aforementioned organic light emitting diode may be applied to a display device. For example, the organic light emitting diode may be applied to an organic light emitting diode (OLED) display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of First Compound

Synthesis Example 1: Synthesis of Compound A-2

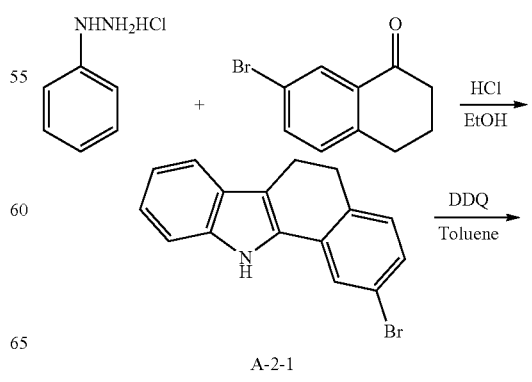

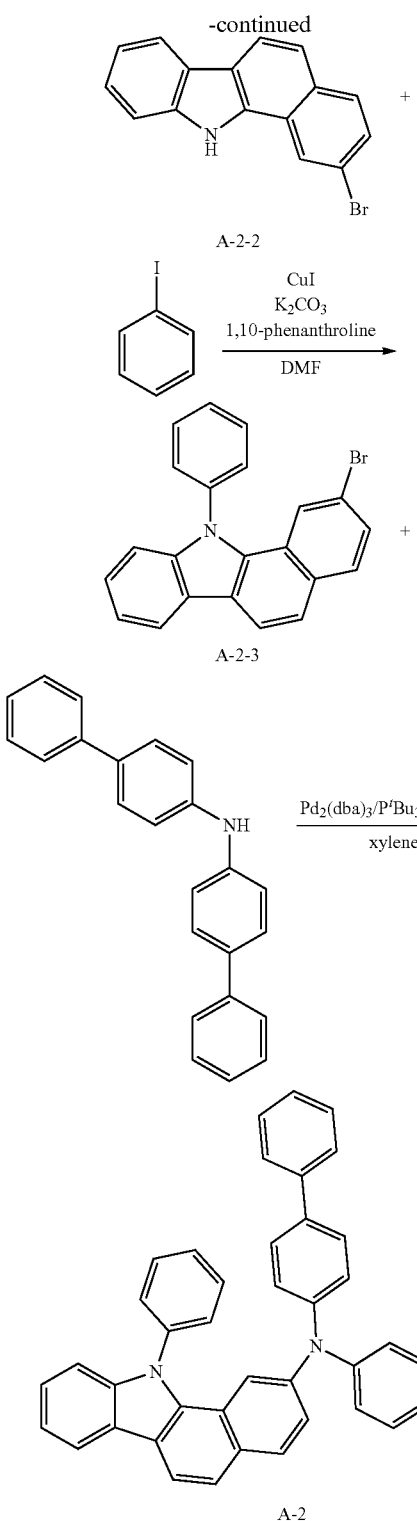

a) Synthesis of Intermediate A-2-1

Phenylhydrazine hydrochloride (70.0 g, 484.1 mmol) and 7-bromo-3,4-dihydro-2H-naphthalen-1-one (108.9 g, 484.1 mmol) were put in a round-bottomed flask and then, dissolved in ethanol (1,200 ml). 60 mL of hydrochloric acid was slowly added in a dropwise fashion thereto at ambient temperature, and the obtained mixture was stirred at 90° C. for 12 hours. When a reaction was complete, the solvent was removed therefrom under a reduced pressure, and an extract was obtained therefrom by using an excess of ethyl acetate (EA). After removing the organic solvent under a reduced pressure, the extract was stirred in a small amount of methanol and then, filtered to obtain 95.2 g (66%) of Intermediate A-2-1.

b) Synthesis of Intermediate A-2-2

Intermediate A-2-1 (95.2 g, 319.3 mmol) and 2,3-dichloro-5,6-dicyano-1,4-benzoquinone (108.7 g, 478.9 mmol) were put in a round-bottomed flask and dissolved in 600 ml of toluene. The solution was stirred at 80° C. for 12 hours. When a reaction was complete, a reaction solvent was removed, and the rest thereof was treated through column chromatography to obtain 41.3 g (44%) of Intermediate A-2-2.

c) Synthesis of Intermediate A-2-3

Intermediate A-2-2 (41.3 g, 139.0 mmol), iodobenzene (199.2 g, 976.0 mmol), CuI (5.31 g, 28.0 mmol), $K_2CO_3$ (28.9 g, 209.0 mmol), and 1,10-phenanthroline (5.03 g, 28.0 mmol) were put in a round-bottomed flask and dissolved in 500 ml of DMF. The solution was stirred at 180° C. for 12 hours. When a reaction was complete, the reaction solvent was removed therefrom under a reduced pressure, and then, a product therefrom was dissolved in dichloromethane and filtered with silica gel. After dichloromethane concentration, the filtered product was recrystallized with hexane to obtain 39.0 g (75%) of Intermediate A-2-3.

d) Synthesis of Compound A-2

Intermediate A-2-3 (23.2 g, 62.5 mmol), bis-biphenyl-4-yl-amine (21.1 g, 65.6 mmol), sodium t-butoxide (NaOtBu) (9.0 g, 93.8 mmol), $Pd_2(dba)_3$ (3.4 g, 3.7 mmol), and tri t-butylphosphine (P(tBu)$_3$) (4.5 g, 50% in toluene) were put in xylene (300 mL) and then, heated and refluxed under a nitrogen flow for 12 hours. After removing the xylene, 200 mL of methanol was added thereto to crystallize a solid, the crystallized solid was filtered, dissolved in toluene, and filtered again with silica gel/Celite, and then, the organic solvent in an appropriate amount was concentrated to obtain 29 g (76%) of Compound A-2.

LC/MS calculated for: C46H32N2 Exact Mass: 612.26 found for 612.32 [M+H]

Synthesis Example 2: Synthesis of Compound A-3

[Reaction Scheme 2]

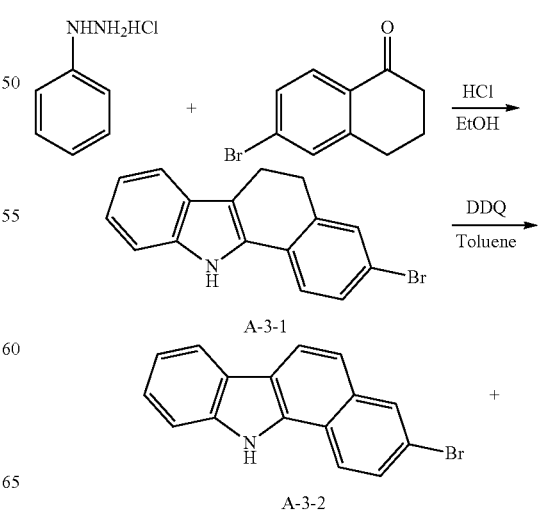

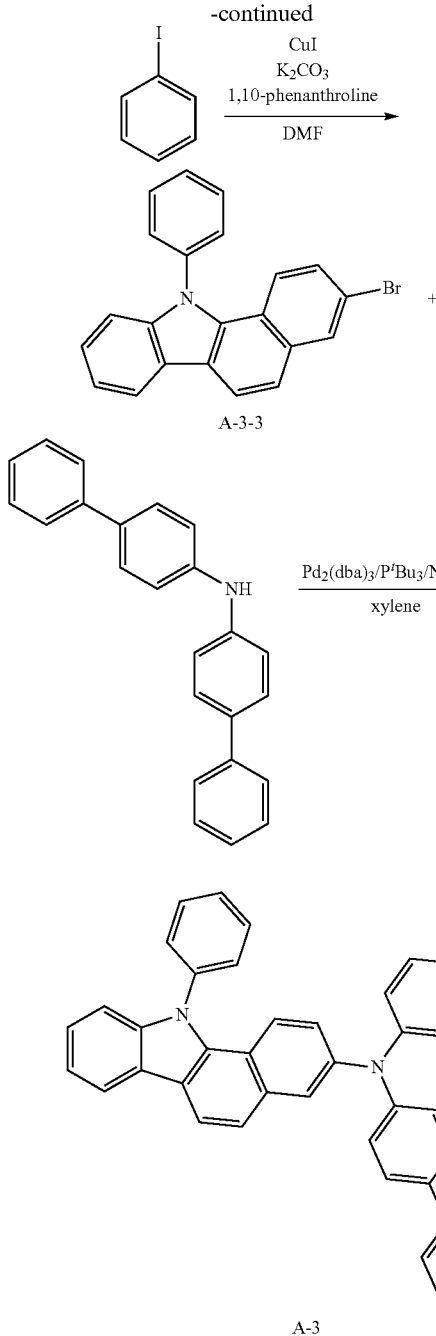

A-3-3

A-3 a) Synthesis of Intermediate A-3-1

Intermediate A-3-1 was synthesized according to the same method as the a) of Synthesis Example 1 by respectively using phenylhydrazinehydrochloride and 6-bromo-3,4-dihydro-2H-naphthalen-1-one in an amount of 1.0 equivalent.

b) Synthesis of Intermediate A-3-2

Intermediate A-3-2 was synthesized according to the same method as the b) of Synthesis Example 1 by using Intermediate A-3-1 and 2,3-dichloro-5,6-dicyano-1,4-benzoquinone in an equivalent ratio of 1:1.5.

c) Synthesis of Intermediate A-3-3

Intermediate A-3-3 was synthesized according to the same method as the c) of Synthesis Example 1 by using Intermediate A-3-2 and iodobenzene in an equivalent ratio of 1:3.

d) Synthesis of Compound A-3

Compound A-3 was synthesized according to the same method as the d) of Synthesis Example 1 by using Intermediate A-3-3 and bis-biphenyl-4-yl-amine in an equivalent ratio of 1:1.

LC/MS calculated for: C46H32N2 Exact Mass: 612.26 found for 612.28 [M+H]

Synthesis Example 3: Synthesis of Compound A-5

[Reaction Scheme 3]

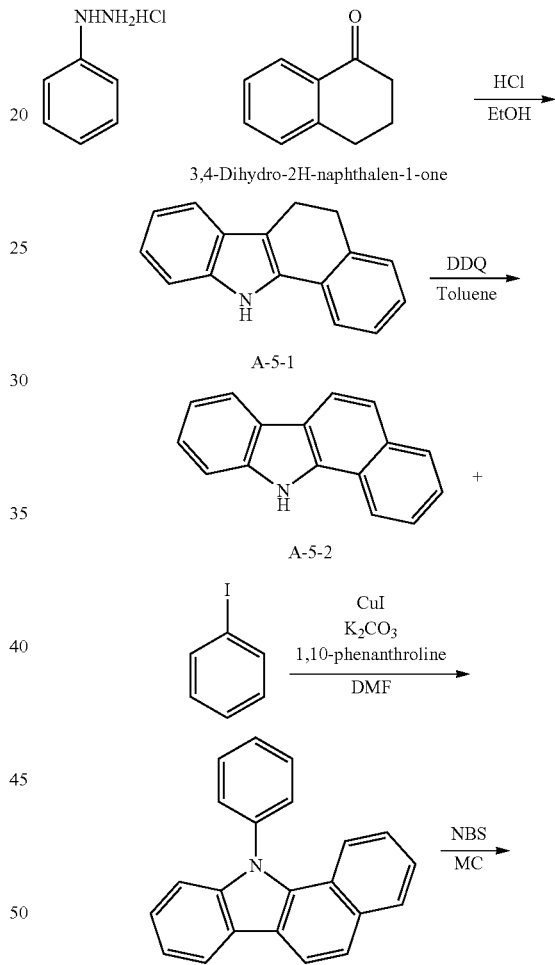

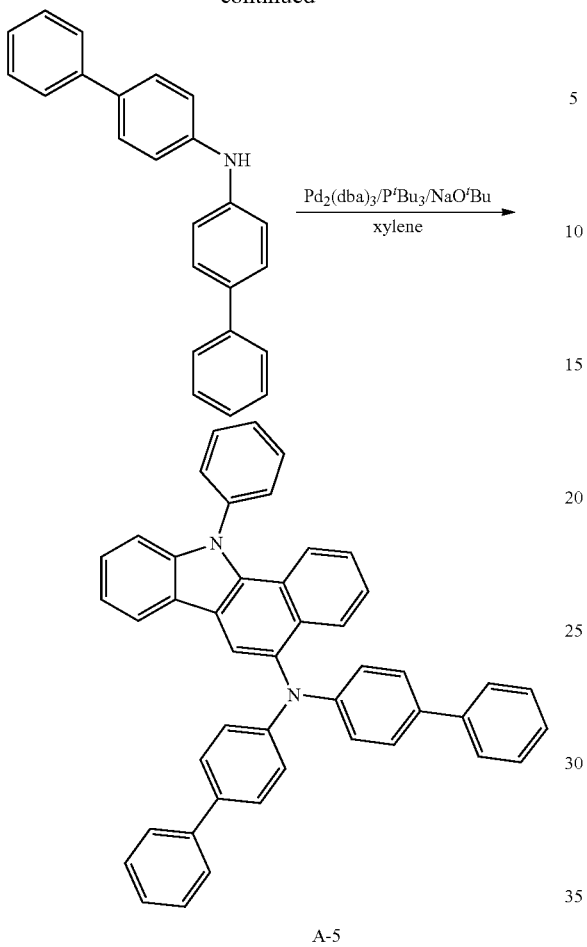

A-5 a) Synthesis of Intermediate A-5-1

Intermediate A-5-1 was synthesized according to the same method as the a) of Synthesis Example 1 by respectively using phenylhydrazinehydrochloride and 3,4-dihydro-2H-naphthalen-1-one in an amount of 1.0 equivalent.

b) Synthesis of Intermediate A-5-2

Intermediate A-5-2 was synthesized according to the same method as the b) of Synthesis Example 1 by respectively using Intermediate A-5-1 and 2,3-dichloro-5,6-dicyano-1,4-benzoquinone in an equivalent ratio of 1:1.5.

c) Synthesis of Intermediate A-5-3

Intermediate A-5-3 was synthesized according to the same method as the c) of Synthesis Example 1 by using Intermediate A-5-2 and iodobenzene in an equivalent ratio of 1:3.

d) Synthesis of Intermediate A-5-4

Intermediate A-5-3 (23.6 g, 80.6 mmol) was put in a round-bottomed flask and then, dissolved in 300 mL of dichloromethane. Subsequently, N-bromosuccinimide (NBS) (14.1 g, 79.0 mmol) was dissolved in 100 mL of DMF, the solution was slowly added thereto in a dropwise fashion, and the mixed solution was stirred at ambient temperature for 2 hours. When a reaction was complete, the reaction solvent was removed, and a product therefrom was treated through column chromatography to obtain 25 g (83%) of Intermediate A-5-4.

e) Synthesis of Compound A-5

Compound A-5 was synthesized according to the same method as the d) of Synthesis Example 1 by using Intermediate A-5-4 and bis-biphenyl-4-yl-amine in an equivalent ratio of 1:1.

LC/MS calculated for: C46H32N2 Exact Mass: 612.26 found for 612.33 [M+H]

Synthesis Example 4: Synthesis of Compound A-7

[Reaction Scheme 4]

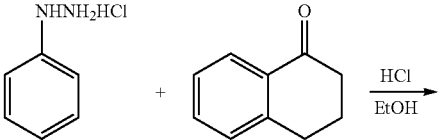

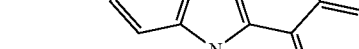

A-7-1

A-7-2

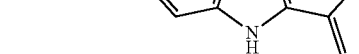

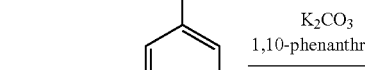

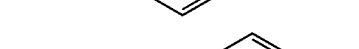

A-7-3

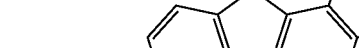

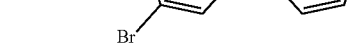

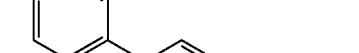

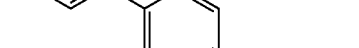

287
-continued

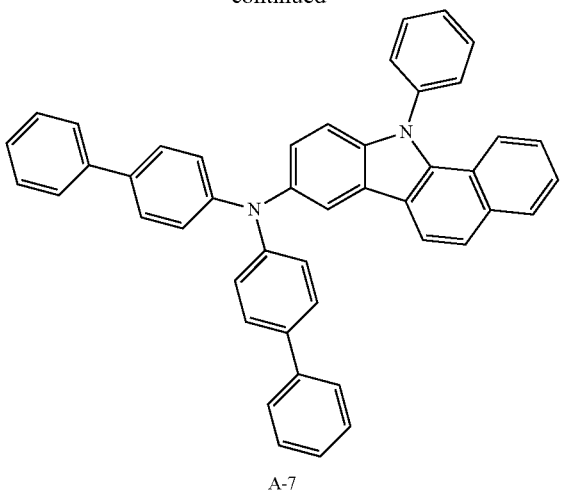

A-7 a) Synthesis of Intermediate A-7-1

Intermediate A-7-1 was synthesized according to the same method as the a) of Synthesis Example 1 by respectively using 4-bromophenylhydrazinehydrochloride and 3,4-dihydro-2H-naphthalen-1-one in an amount of 1.0 equivalent.

b) Synthesis of Intermediate A-7-2

Intermediate A-7-2 was synthesized according to the same method as the b) of Synthesis Example 1 by using Intermediate A-7-1 and 2,3-dichloro-5,6-dicyano-1,4-benzoquinone in an equivalent ratio of 1:1.5.

c) Synthesis of Intermediate A-7-3

Intermediate A-7-3 was synthesized according to the same method as the c) of Synthesis Example 1 by using Intermediate A-7-2 and iodobenzene in an equivalent ratio of 1:3.

d) Synthesis of Compound A-7

Compound A-7 was synthesized according to the same method as the d) of Synthesis Example 1 by using Intermediate A-7-3 and bis-biphenyl-4-yl-amine in an equivalent ratio of 1:1.

LC/MS calculated for: C46H32N2 Exact Mass: 612.26 found for 612.30 [M+H]

Synthesis Example 5: Synthesis of Compound A-8

[Reaction Scheme 5]

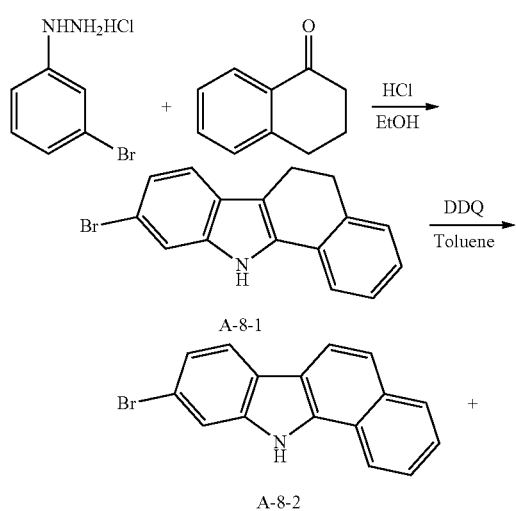

288
-continued

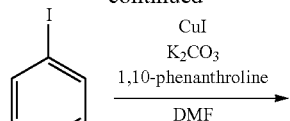

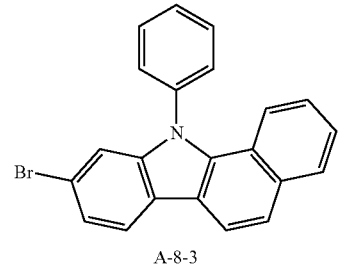

A-8-3

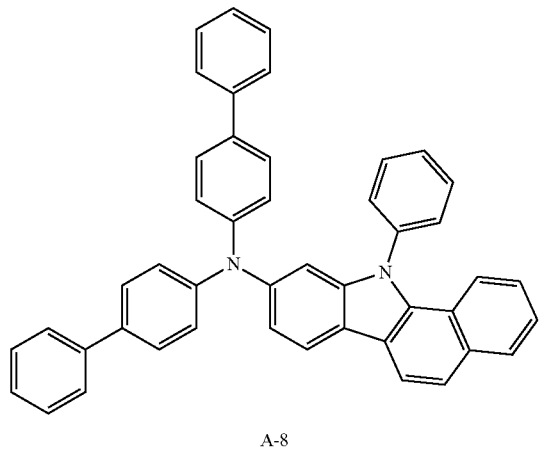 [SMILES: c1ccc(-c2ccc(N(c3ccc(-c4ccccc4)cc3)c3ccc4c5ccc6ccccc6c5n(-c5ccccc5)c4c3)cc2)cc1 ; "A-8"]

A-8 a) Synthesis of Intermediate A-8-1

Intermediate A-8-1 was synthesized according to the same method as the a) of Synthesis Example 1 by respectively using 3-bromophenylhydrazinehydrochloride and 3,4-dihydro-2H-naphthalen-1-one in an amount of 1.0 equivalent.

b) Synthesis of Intermediate A-8-2

Intermediate A-8-2 was synthesized according to the same method as the b) of Synthesis Example 1 by using Intermediate A-8-1 and 2,3-dichloro-5,6-dicyano-1,4-benzoquinone in an equivalent ratio of 1:1.5.

c) Synthesis of Intermediate A-8-3

Intermediate A-8-3 was synthesized according to the same method as the c) of Synthesis Example 1 by using Intermediate A-8-2 and iodobenzene in an equivalent ratio of 1:3.

d) Synthesis of Compound A-8

Compound A-8 was synthesized according to the same method as the d) of Synthesis Example 1 by using Intermediate A-8-3 and bis-biphenyl-4-yl-amine in an equivalent ratio of 1:1.

LC/MS calculated for: C46H32N2 Exact Mass: 612.26 found for 612.33 [M+H]

Synthesis Example 6: Synthesis of Compound A-11

[Reaction Scheme 6]

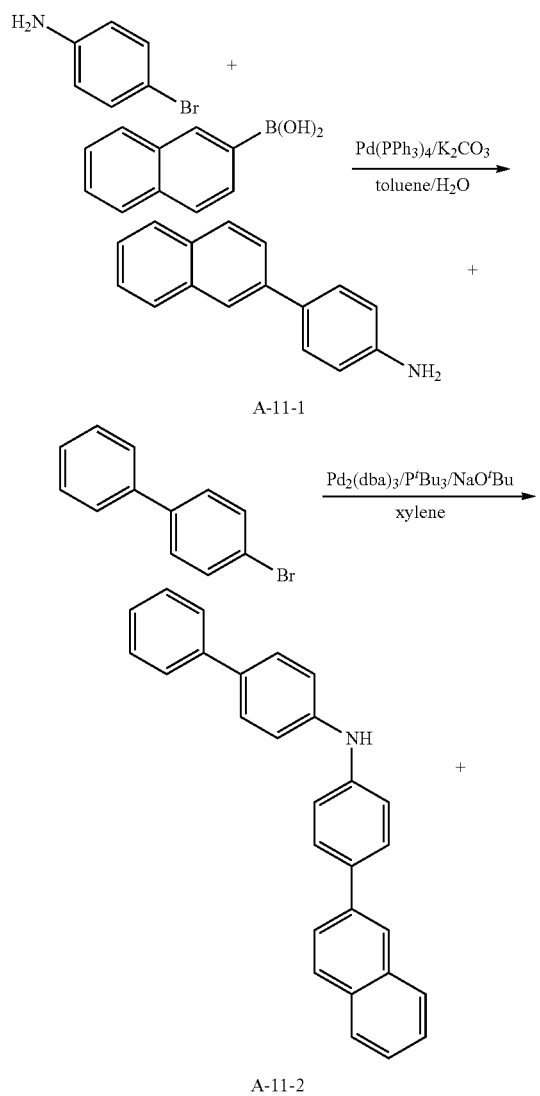

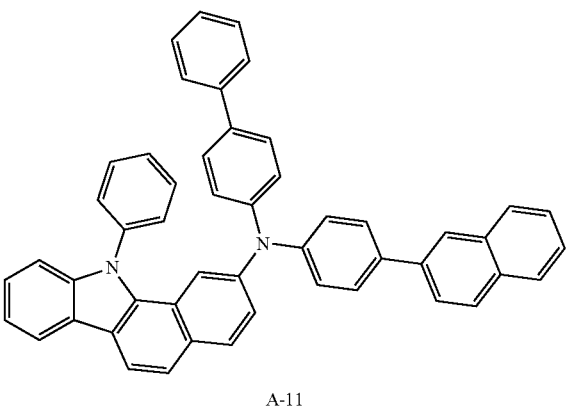 [SMILES: c1ccc(-c2ccc(N(c3ccc(-c4ccc5ccccc5c4)cc3)c3ccc4ccc5c6ccccc6n(-c6ccccc6)c5c4c3)cc2)cc1 ; "A-11"]

A-11 a) Synthesis of Intermediate A-11-1

4-bromo-phenylamine (50.0 g, 290.7 mmol), 2-naphthalene boronic Acid (59.9 g, 171.9 mmol), K₂CO₃ (80.4 g, 581.3 mmol), and Pd(PPh₃)₄ (10.1 g, 8.7 mmol) were put in a round-bottomed flask and dissolved in 800 ml of toluene and 400 ml of distilled water, and the solution was stirred at 80° C. for 12 hours. When a reaction was complete, an aqueous layer was removed therefrom, and the rest thereof was treated through column chromatography to obtain 40.0 g (63%) of Intermediate A-11-1.

b) Synthesis of Intermediate A-11-2

Intermediate A-11-1 (17.7 g, 80.8 mmol), 4-bromo-biphenyl (18.8 g, 80.8 mmol), sodium t-butoxide (NaOtBu) (11.6 g, 121.1 mmol), Pd₂(dba)₃ (4.4 g, 4.8 mmol), and tri t-butylphosphine (P(tBu)₃) (5.9 g, 50% in toluene) were added to xylene (400 mL) and then, heated and refluxed together under a nitrogen flow for 12 hours. After removing the xylene, the rest thereof was treated through column chromatography to obtain 20.0 g (67%) of Intermediate A-11-2.

c) Synthesis of Compound A-11

Compound A-11 was synthesized according to the same method as the d) of Synthesis Example 1 by using Intermediate A-11-2 and Intermediate A-2-3 in an equivalent ratio of 1:1.

LC/MS calculated for: C50H34N2 Exact Mass: 662.27 found for 662.31 [M+H]

Synthesis Example 7: Synthesis of Compound A-12

[Reaction Scheme 7]

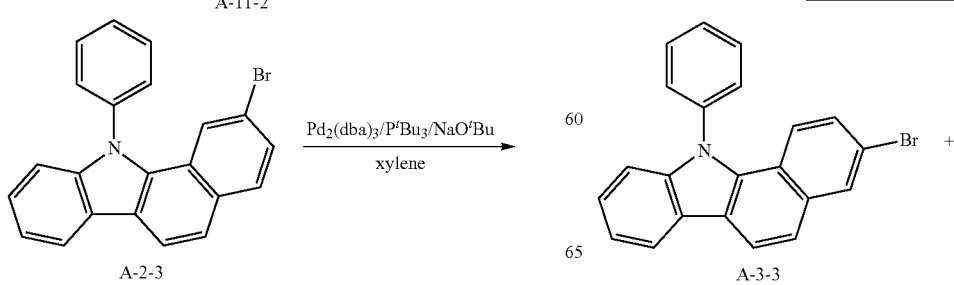

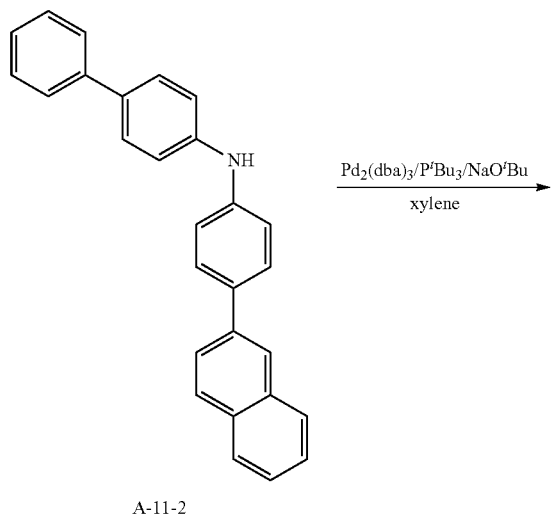

A-11-2

Pd₂(dba)₃/P'Bu₃/NaO'Bu
xylene
→

A-12

Compound A-12 was synthesized according to the same method as the d) of Synthesis Example 1 by using Intermediate A-3-3 and Intermediate A-11-2 in an equivalent ratio of 1:1.

LC/MS calculated for: C50H34N2 Exact Mass: 662.27 found for 662.30 [M+H]

Synthesis Example 8: Synthesis of Compound A-29

[Reaction Scheme 8]

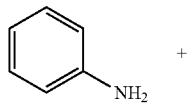

+

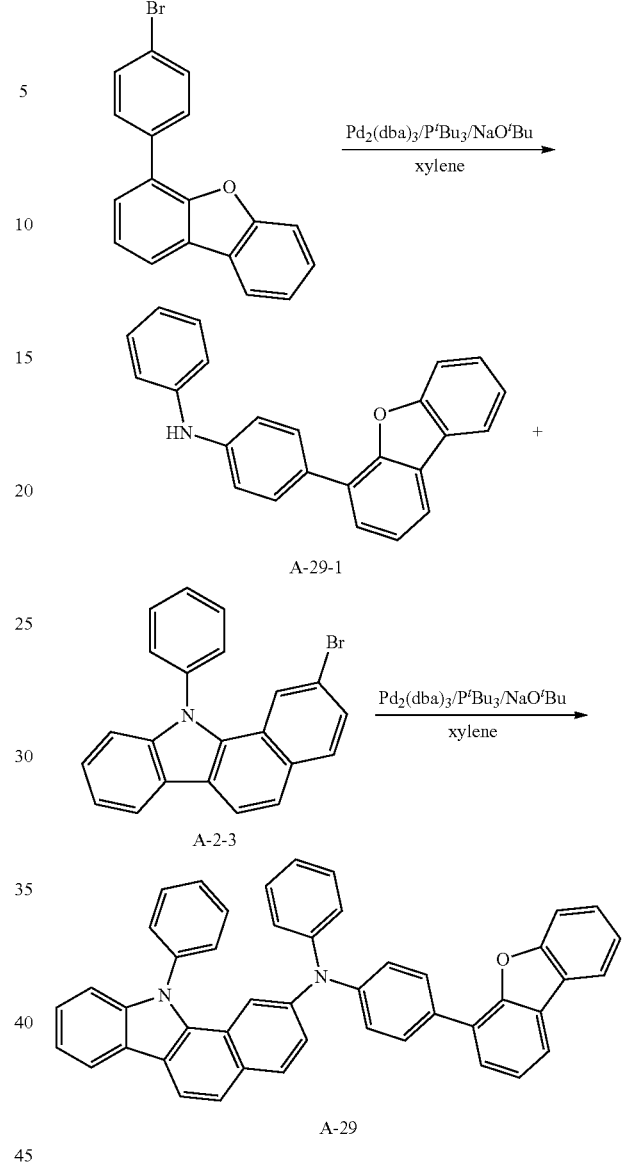

a) Synthesis of Intermediate A-29-1

Aniline (8.3 g, 89.5 mmol), 4-(4-bromo-phenyl)-dibenzofuran (23.1 g, 71.5 mmol), sodium t-butoxide (NaOtBu) (12.9 g, 134.2 mmol), Pd₂(dba)₃ (4.9 g, 5.4 mmol), and tri t-butylphosphine (P(tBu)₃) (6.5 g, 50% in toluene) were added to xylene (400 mL) and then, heated and refluxed together under a nitrogen flow for 12 hours. After removing the xylene, the rest thereof was treated through column chromatography to obtain 20.0 g (67%) of Intermediate A-29-1.

b) Synthesis of Compound A-29

Compound A-29 was synthesized according to the same method as the d) of Synthesis Example 1 by using Intermediate A-29-1 and Intermediate A-2-3 in an equivalent ratio of 1:1.

LC/MS calculated for: C46H30N2O Exact Mass: 626.24 found for 626.28 [M+H]

Synthesis Example 9: Synthesis of Compound A-38

[Reaction Scheme 9]

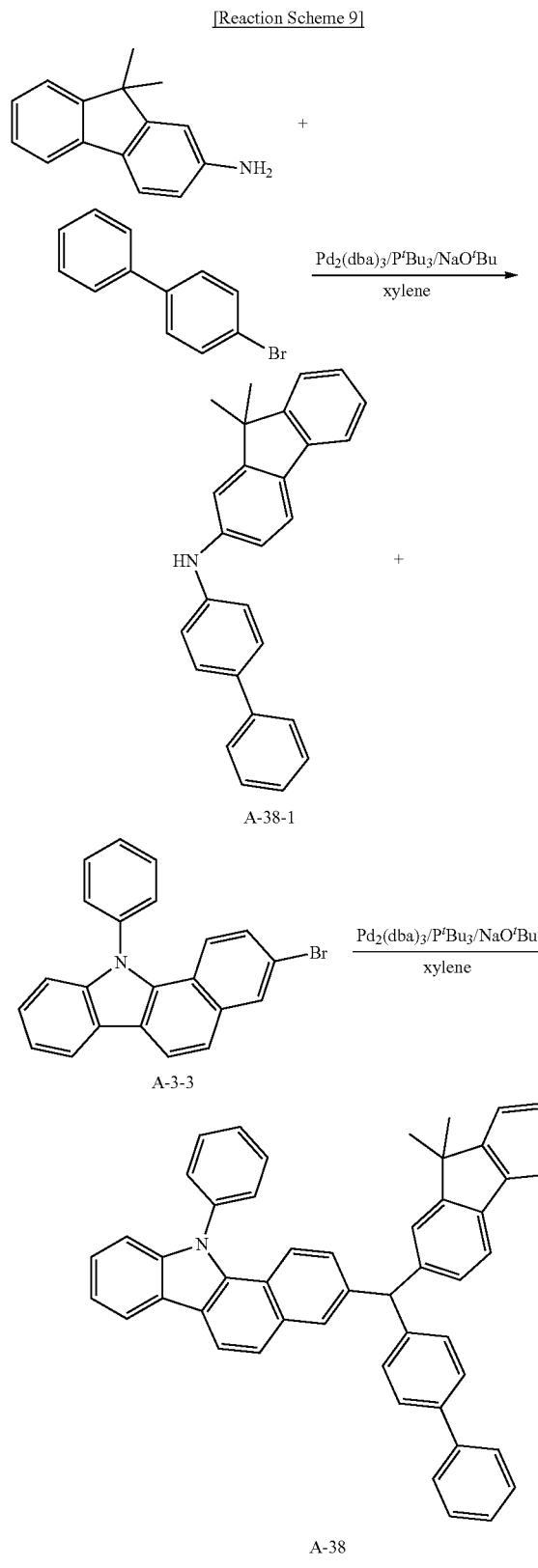

a) Synthesis of Intermediate A-38-1

9,9-Dimethyl-9H-fluoren-2-ylamine (17.4 g, 83.0 mmol), 4-bromo-biphenyl (15.5 g, 66.4 mmol), sodium t-butoxide (NaOtBu) (12.0 g, 124.5 mmol), $Pd_2(dba)_3$ (4.6 g, 5.0 mmol), and tri t-butylphosphine ($P(tBu)_3$) (6.0 g, 50% in toluene) were put in xylene (400 mL) and then, heated and refluxed under a nitrogen flow for 12 hours. After removing the xylene, the rest thereof was treated through column chromatography to obtain 18.0 g (60%) of Intermediate A-38-1.

b) Synthesis of Compound A-38

Compound A-38 was synthesized according to the same method as the d) of Synthesis Example 1 by using Intermediate A-38-1 and Intermediate A-3-3 in an equivalent ratio of 1:1.

LC/MS calculated for: C49H36N2 Exact Mass: 652.29 found for 652.33 [M+H]

Synthesis Example 10: Synthesis of Compound A-51

[Reaction Scheme 10]

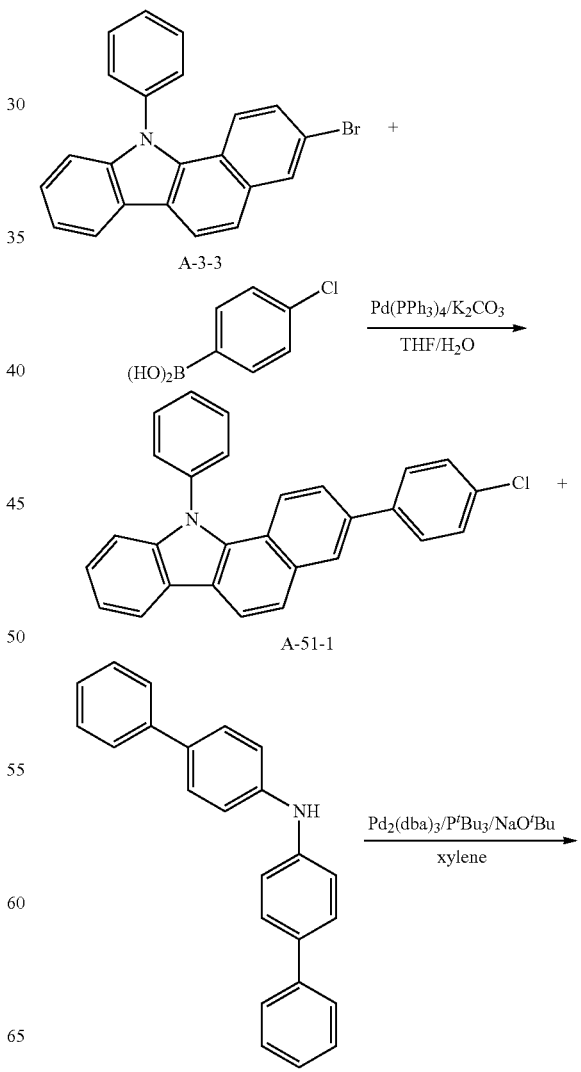

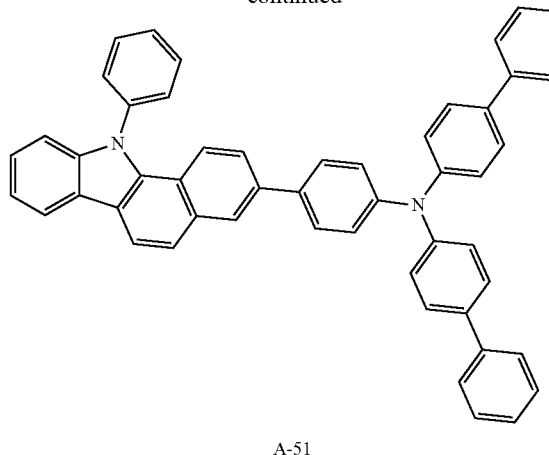

A-51 a) Synthesis of Intermediate A-51-1

Intermediate A-3-3 (30.0 g, 80.6 mmol), 4-chlorophenyl boronic acid (15.1 g, 96.7 mmol), K₂CO₃ (22.3 g, 161.2 mmol), and Pd(PPh₃)₄ (2.8 g, 2.4 mmol) were put in a round-bottomed flask and then, dissolved in 200 ml of tetrahydrofuran and 100 ml of distilled water, and the solution was stirred at 80° C. for 12 hours. When a reaction was complete, an aqueous layer was removed, and the rest thereof was treated through column chromatography to obtain 27.0 g (83%) of Intermediate A-51-1.

b) Synthesis of Compound A-51

Compound A-51 was synthesized according to the same method as the d of Synthesis Example 1 by using Intermediate A-51-1 and bis-biphenyl-4-yl-amine in an equivalent ratio of 1:1.

LC/MS calculated for: C52H36N2 Exact Mass: 688.29 found for 688.34 [M+H]

Synthesis Example 11: Synthesis of Compound A-65

[Reaction Scheme 11]

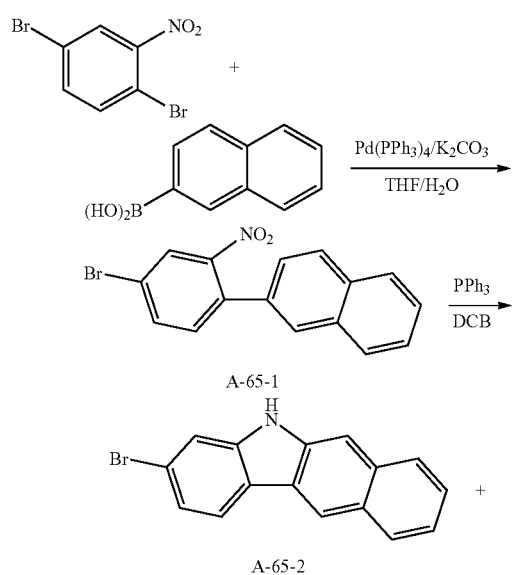

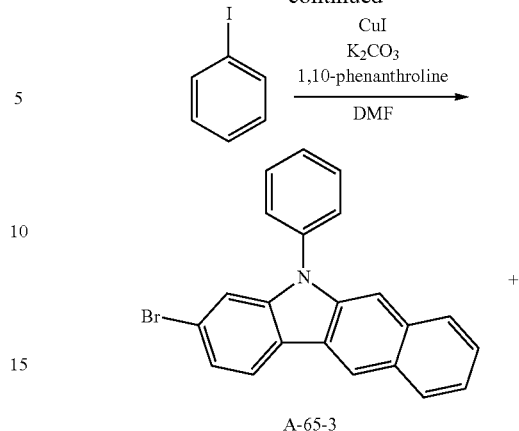

A-65 a) Synthesis of Intermediate A-65-1

1,4-dibromo-2-nitro-benzene (30.0 g, 106.8 mmol), 2-naphthalene boronic acid (18.4 g, 106.8 mmol), K₂CO₃ (29.5 g, 213.6 mmol), and Pd(PPh₃)₄ (3.7 g, 3.2 mmol) were put in a round-bottomed flask and then, dissolved in 300 mL of tetrahydrofuran and 150 mL of distilled water, and the solution was stirred at 80° C. for 12 hours. When a reaction was complete, an aqueous layer was removed, and the rest thereof was treated through column chromatography to obtain 27.0 g (77%) of Intermediate A-65-1.

b) Synthesis of Intermediate A-65-2

Intermediate A-65-1 (27.0 g, 82.3 mmol) and triphenylphosphine (86.3 g, 329.1 mmol) were put in a round-bottomed flask and then, dissolved in 300 mL of 1,2-dichlorobenzene, and the solution was stirred at 180° C. for 12 hours. When a reaction was complete, a solvent was removed therefrom, and the rest thereof was treated through column chromatography to obtain 18.0 g (74%) of Intermediate A-65-2.

c) Synthesis of Intermediate A-65-3

Intermediate A-65-3 was synthesized according to the same method as the c) of Synthesis Example 1 by using Intermediate A-65-2 and iodobenzene in an equivalent ratio of 1:3.

d) Synthesis of Compound A-65

Intermediate A-65 was synthesized according to the same method as the d) of Synthesis Example 1 by using Intermediate A-65-3 and bis-biphenyl-4-yl-amine in an equivalent ratio of 1:1.

LC/MS calculated for: C46H32N2 Exact Mass: 612.26 found for 612.30 [M+H]

Synthesis Example 12: Synthesis of Compound A-72

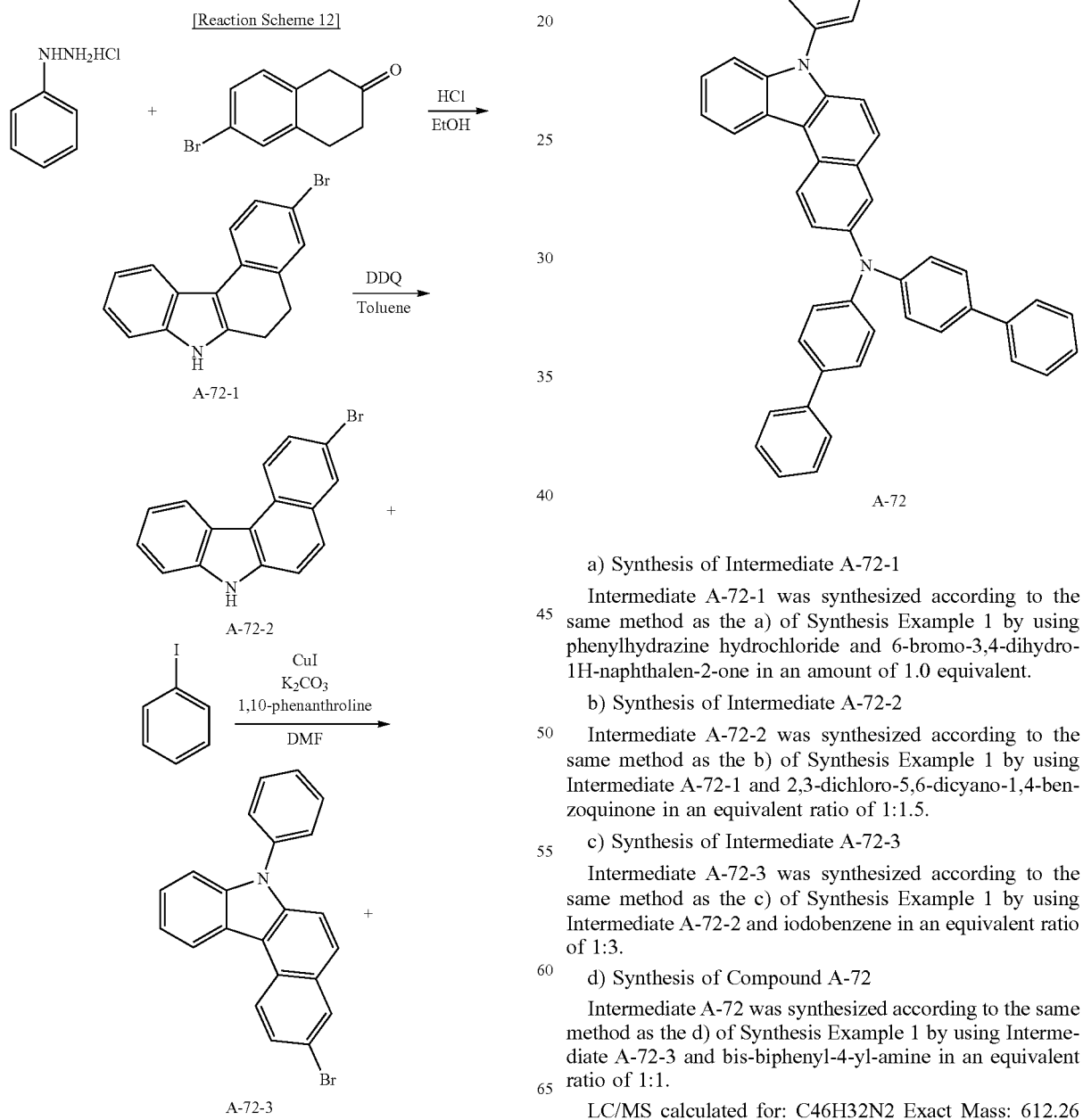

a) Synthesis of Intermediate A-72-1

Intermediate A-72-1 was synthesized according to the same method as the a) of Synthesis Example 1 by using phenylhydrazine hydrochloride and 6-bromo-3,4-dihydro-1H-naphthalen-2-one in an amount of 1.0 equivalent.

b) Synthesis of Intermediate A-72-2

Intermediate A-72-2 was synthesized according to the same method as the b) of Synthesis Example 1 by using Intermediate A-72-1 and 2,3-dichloro-5,6-dicyano-1,4-benzoquinone in an equivalent ratio of 1:1.5.

c) Synthesis of Intermediate A-72-3

Intermediate A-72-3 was synthesized according to the same method as the c) of Synthesis Example 1 by using Intermediate A-72-2 and iodobenzene in an equivalent ratio of 1:3.

d) Synthesis of Compound A-72

Intermediate A-72 was synthesized according to the same method as the d) of Synthesis Example 1 by using Intermediate A-72-3 and bis-biphenyl-4-yl-amine in an equivalent ratio of 1:1.

LC/MS calculated for: C46H32N2 Exact Mass: 612.26 found for 612.31 [M+H]

Synthesis Example 13: Synthesis of Compound A-77

[Reaction Scheme 13]

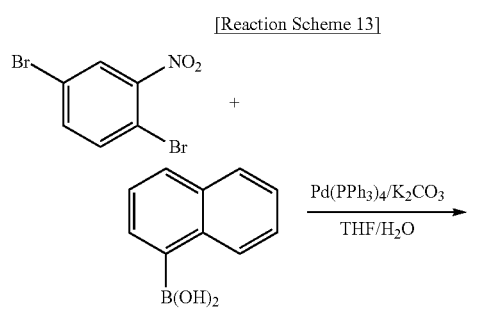

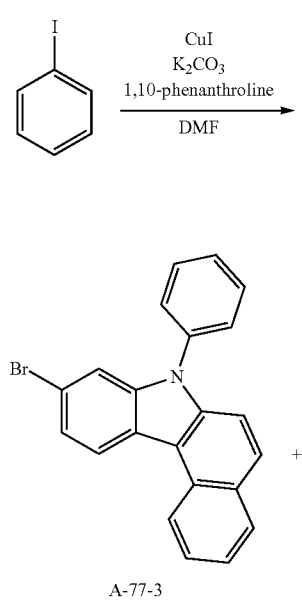

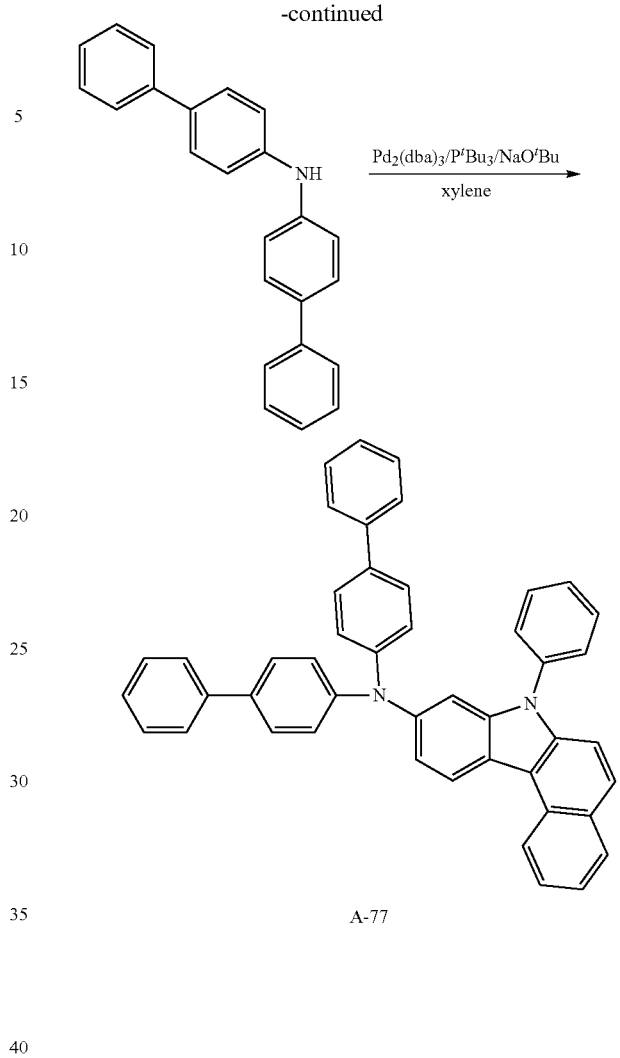

a) Synthesis of Intermediate A-77-1

Intermediate A-77-1 was synthesized in the same method as the a) of Synthesis Example 11 by using 1,4-dibromo-2-nitro-benzene and 1-naphthalene boronic acid in an amount of 1.0 equivalent.

b) Synthesis of Intermediate A-77-2

Intermediate A-77-2 was synthesized according to the same method as the b) of Synthesis Example 11 by using Intermediate A-77-1 and triphenylphosphine in an equivalent ratio of 1:4.

c) Synthesis of Intermediate A-77-3

Intermediate A-77-3 was synthesized according to the same method as the c) of Synthesis Example 1 by using Intermediate A-77-2 and iodobenzene in an equivalent ratio of 1:3.

d) Synthesis of Compound A-77

Compound A-77 was synthesized according to the same method as the d) of Synthesis Example 1 by using Intermediate A-77-3 and bis-biphenyl-4-yl-amine in an equivalent ratio of 1:1.

LC/MS calculated for: $C_{46}H_{32}N_2$ Exact Mass: 612.26 found for 612.29 [M+H]

Comparative Synthesis Example 1: Synthesis of Compound V-1

[Reaction Scheme 14]

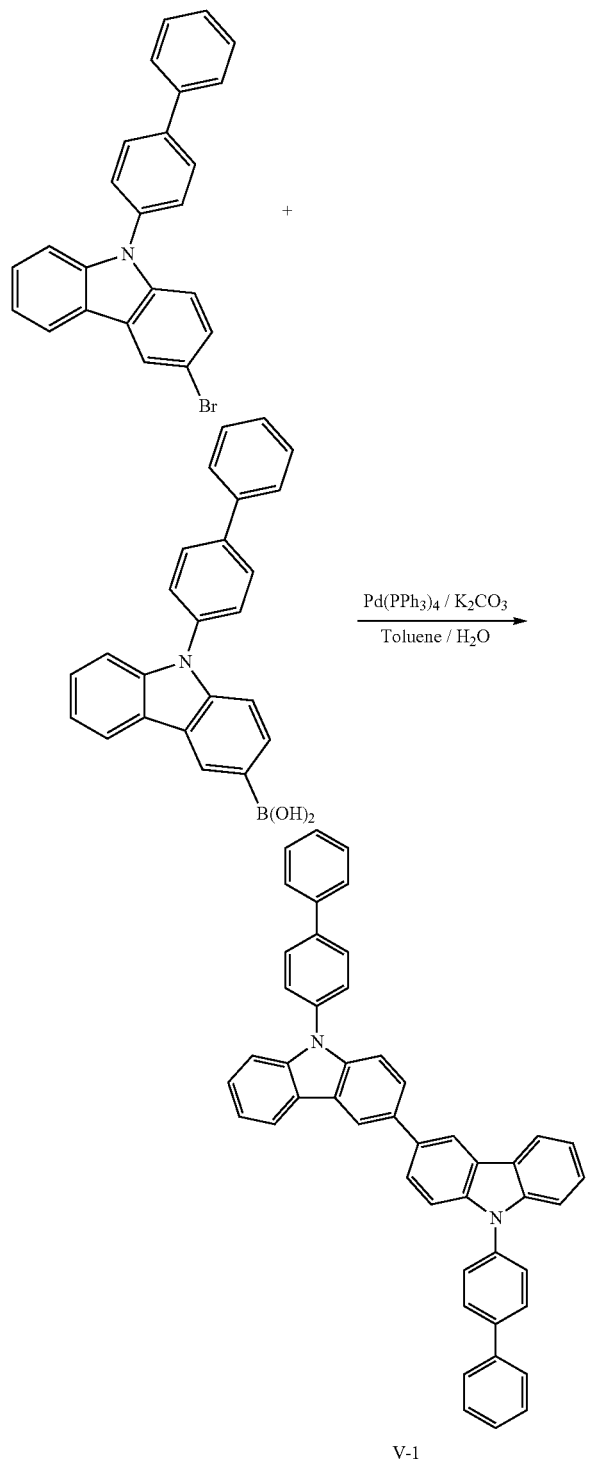

V-1

Biphenylcarbazolyl bromide (12.33 g, 30.95 mmol) was dissolved in 200 mL of toluene under a nitrogen environment, biphenylcarbazolylboronic acid (12.37 g, 34.05 mmol) and tetrakis(triphenylphosphine)palladium (1.07 g, 0.93 mmol) were added thereto, and the obtained mixture was stirred. Potassium carbonate saturated in water (12.83 g, 92.86 mmol) was added thereto, and the obtained mixture was heated and refluxed at 90° C. for 12 hours. When a reaction was complete, water was added to the reaction solution, and the mixture was extracted by using dichloromethane (DCM), filtered after removing moisture therefrom by using anhydrous $MgSO_4$, and concentrated under a reduced pressure. A residue obtained therefrom was separated and purified through flash column chromatography to obtain Compound V-1 (18.7 g, 92%).

LC/MS calculated for: C48H32N2 Exact Mass: 636.26 found for 636.30 [M+H]

Comparative Synthesis Example 2: Synthesis of Compound V-2

[Reaction Scheme 15]

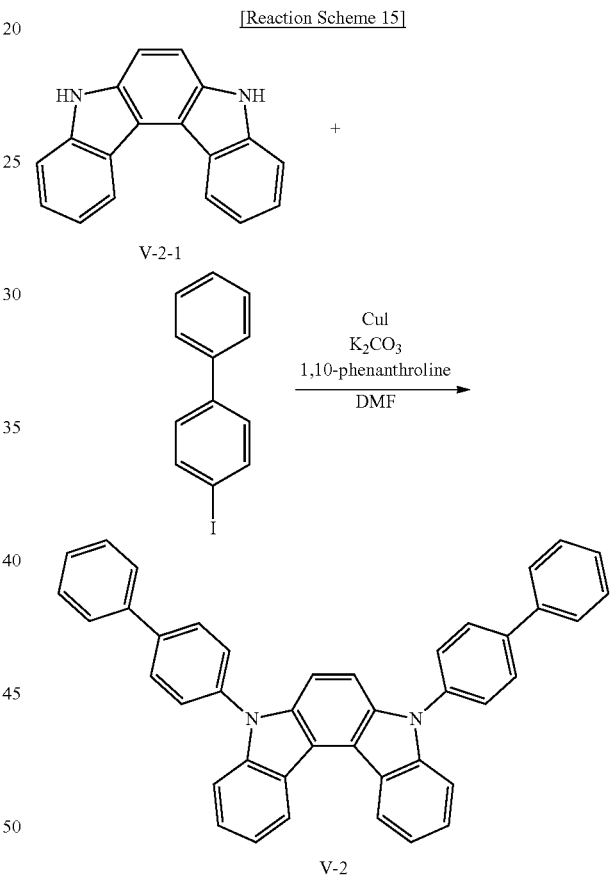

V-2

8 g (31.2 mmol) of Intermediate V-2-1 (5,8-dihydroindolo[2,3-C]carbazole), 20.5 g (73.32 mmol) of 4-iodobiphenyl, 1.19 g (6.24 mmol) of CuI, 1.12 g (6.24 mmol) of 1,10-phenanthoroline, and 12.9 g (93.6 mmol) of $K_2CO_3$ were put in a round-bottomed flask, 50 ml of DMF was added thereto to dissolve them, and the solution was refluxed and stirred under a nitrogen atmosphere for 24 hours. When a reaction was complete, distilled water was added thereto, and a precipitate therefrom was filtered. The solid was dissolved in 250 ml of xylene, filtered with silica gel, and precipitated into a white solid to obtain 16.2 g (yield: 93%) of Compound V-2.

LC/MS calculated for: C42H28N2 Exact Mass: 560.23 found for 560.27 [M+H]

Synthesis of Second Compound

Synthesis Example 14: Synthesis of Compound B-17

[Reaction Scheme 16]

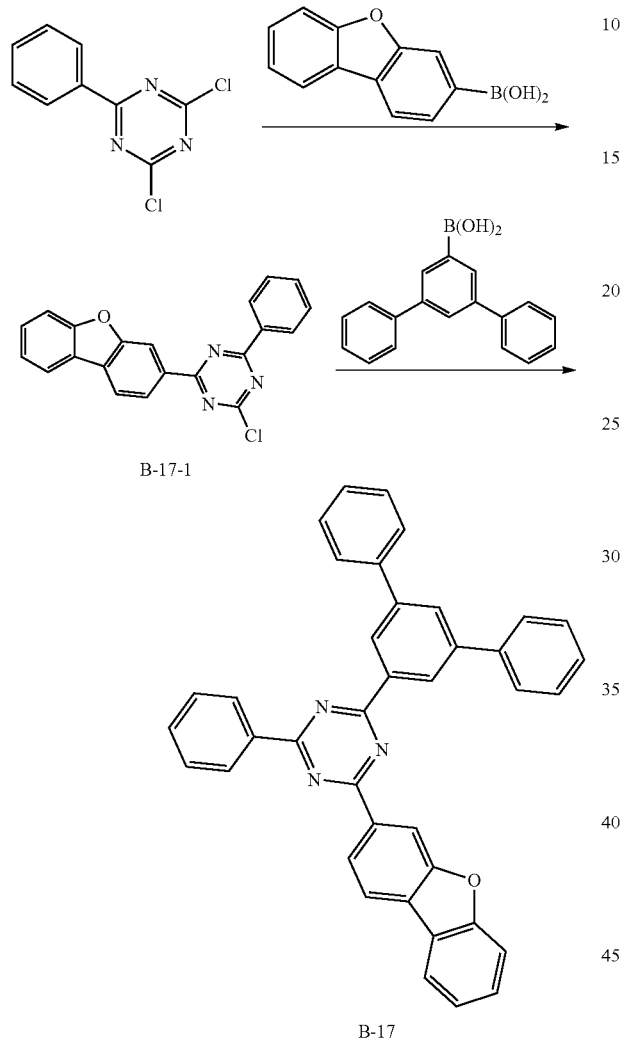

B-17

1st Step: Synthesis of Intermediate B-17-1

22.6 g (100 mmol) of 2,4-dichloro-6-phenyltriazine was added to 100 mL of tetrahydrofuran, 100 mL of toluene, 100 mL of distilled water in a 500 mL round-bottomed flask, 0.9 equivalents of dibenzofuran-3-boronic acid (CAS No.: 395087-89-5), 0.03 equivalents of tetrakis(triphenylphosphine) palladium, and 2 equivalents of potassium carbonate were added thereto and then, heated and refluxed under a nitrogen atmosphere. After 6 hours, the reaction solution was cooled down and then, after removing an aqueous layer therefrom, an organic layer therein was dried under a reduced pressure. The obtained solid was washed with water and hexane and then, recrystallized with 200 mL of toluene to obtain 21.4 g (yield: 60%) of Intermediate B-17-1.

2nd step: Synthesis of Compound B-17

Intermediate B-17-1 (56.9 mmol) was added to 200 mL of tetrahydrofuran and 100 mL of distilled water in a 500 mL round-bottomed flask, 1.1 equivalents of 3,5-diphenylbenzeneboronic acid (CAS No.: 128388-54-5), 0.03 equivalents of tetrakis(triphenylphosphine) palladium, and 2 equivalents of potassium carbonate were added thereto under a nitrogen atmosphere and then, heated and refluxed. After 18 hours, the reaction solution was cooled down, and a solid precipitated therein was filtered and washed with 500 mL of water. The solid was recrystallized with 500 mL of monochlorobenzene to obtain Compound B-17.

LC/MS measurement (C39H25N3O, theoretical value: 555.1998 g/mol, measured value: 556.21 g/mol)

Synthesis Example 15: Synthesis of Compound B-135

[Reaction Scheme 17]

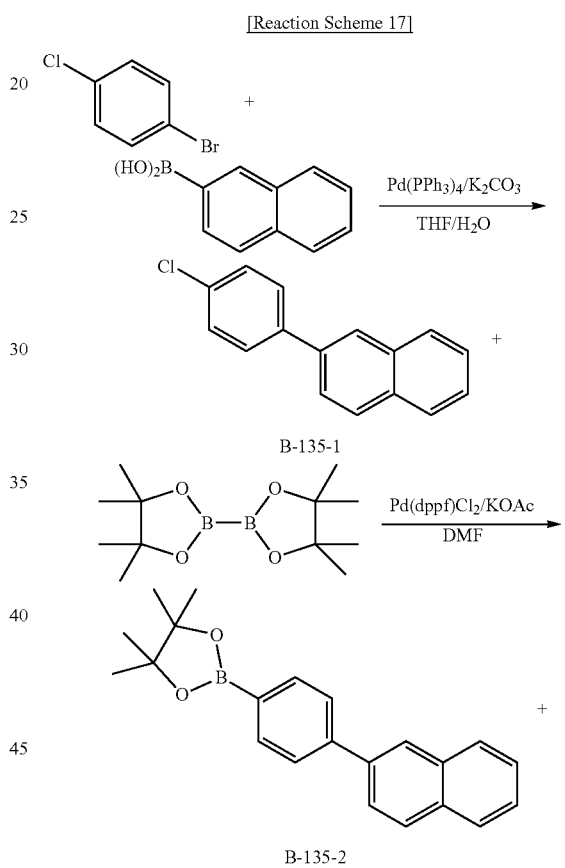

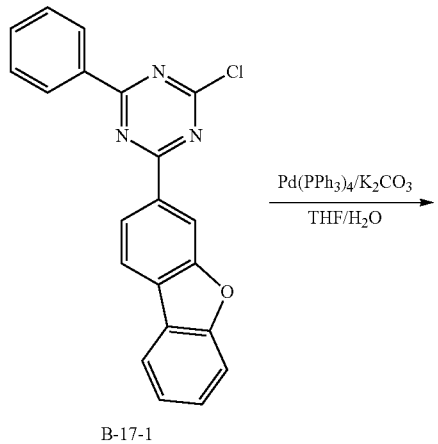

B-17-1

-continued

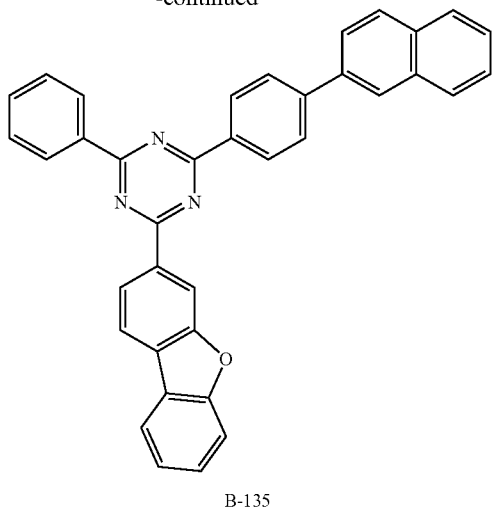
B-135

1st step: Synthesis of Intermediate B-135-1
Intermediate B-135-1 was synthesized according to the same method as the 1st step of the Synthesis Example 14 except that 1-bromo-4-chloro-benzene and 2-naphthalene boronic acid were used in each amount of 1.0 equivalent.

2nd step: Synthesis of Intermediate B-135-2
1 equivalent of Intermediate B-135-1 was added to 250 mL of DMF in a 500 mL round-bottomed flask, and 0.05 equivalents of dichlorodiphenyl phosphinoferrocene palladium, 1.2 equivalents of bis(pinacolato) diboron, and 2 equivalents of potassium acetate were added thereto and then, heated and refluxed under a nitrogen atmosphere for 18 hours. The reaction solution was cooled down and then, added in a dropwise fashion to 1 L of water to obtain a solid. The obtained solid was dissolved in boiling toluene to treat activated carbon and then, filtered with silica gel, and the filtrate was concentrated. The concentrated solid was stirred with a small amount of hexane, and a solid was filtered therefrom to synthesize Intermediate B-135-2.

3rd step: Synthesis of Compound B-135
Compound B-135 was synthesized according to the same method as the 2nd step of Synthesis Example 14 except that Intermediate B-135-2 and Intermediate B-17-1 were respectively used in each amount of 1.0 equivalent.

LC/MS measurement (C37H23N3O, theoretical value: 525.18 g/mol, measured value: M=525.22 g/mol)

Synthesis Example 16: Synthesis of Compound B-205

[Reaction Scheme 18]

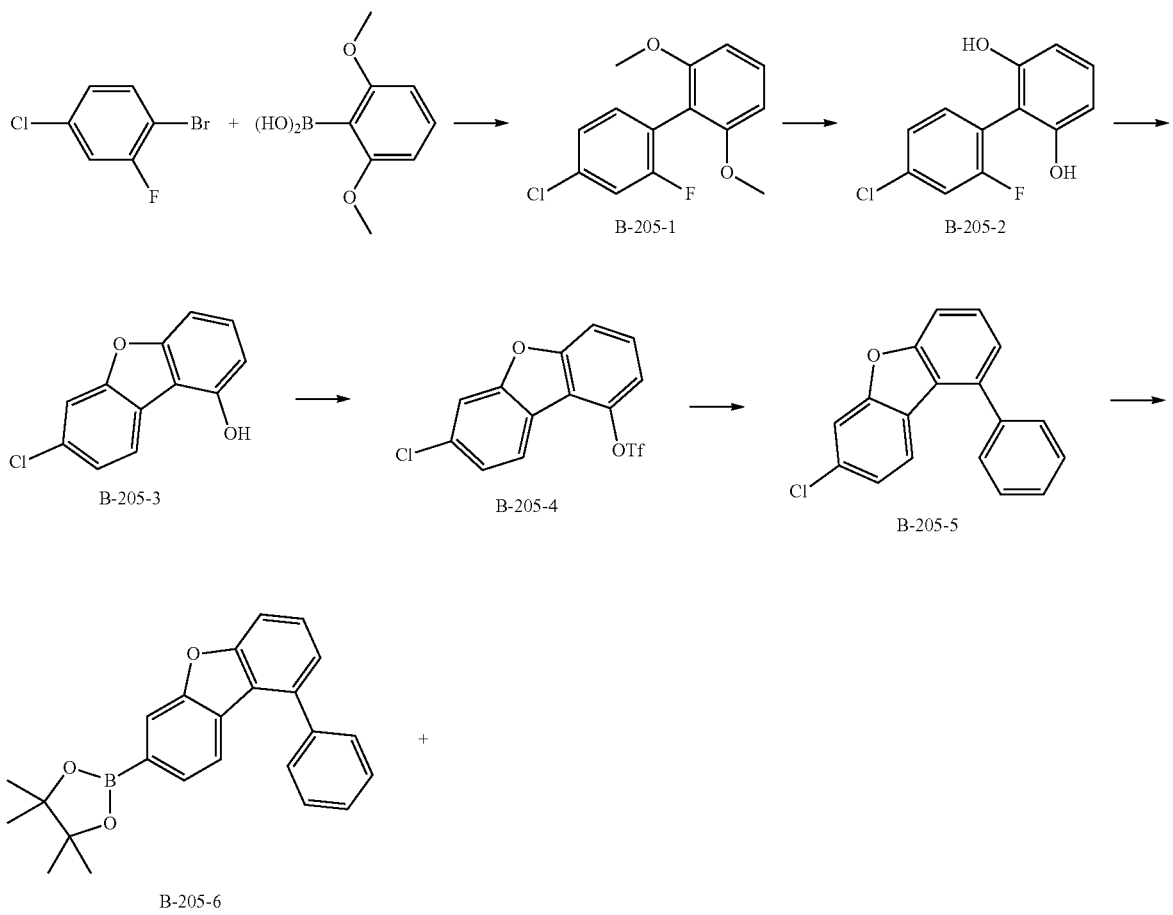

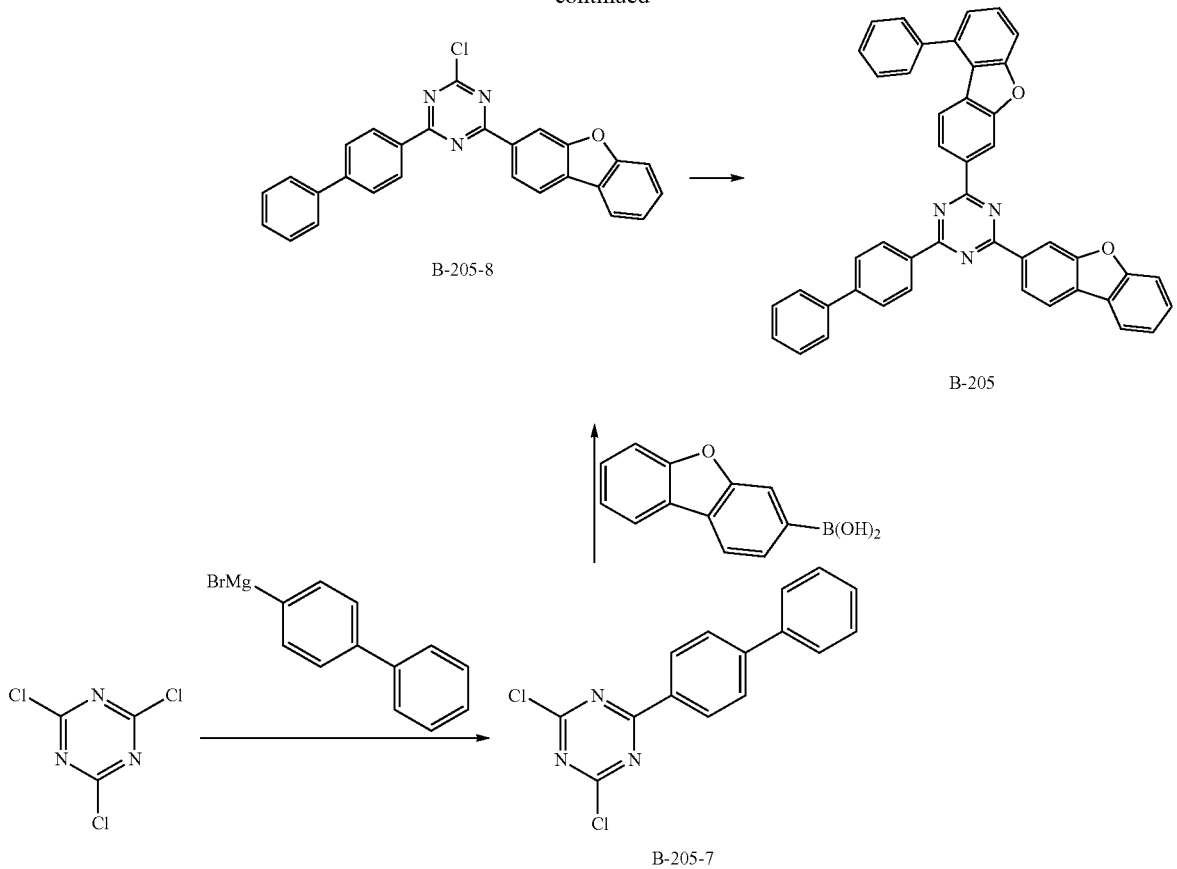

1st step: Synthesis of Intermediate B-205-1

1-bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were put in a round-bottomed flask and dissolved in 500 ml of THF and 200 ml of distilled water and then, refluxed and stirred at 60° C. for 12 hours. When a reaction was complete, after removing an aqueous layer therefrom, column chromatography (hexane:DCM (20%)) was used to obtain 38 g (51%) of Intermediate B-205-1.

2nd step: Synthesis of Intermediate B-205-2

Intermediate B-205-1 (38 g, 142 mmol) and pyridine hydrochloride (165 g, 1425 mmol) were put in a round-bottomed flask and then, refluxed and stirred at 200° C. for 24 hours. When a reaction was complete, the resultant was cooled down to ambient temperature, slowly poured into distilled water, and stirred for 1 hour. A solid therefrom was filtered to obtain 23 g (68%) of Intermediate B-205-2.

3rd step: Synthesis of Intermediate B-205-3

Intermediate B-205-2 (23 g, 96 mmol) and $K_2CO_3$ (20 g, 144 mmol) were put in a round-bottomed flask, dissolved in 100 ml of NMP, and then, refluxed and stirred at 180° C. for 12 hours. When a reaction was complete, the mixture was poured into an excess of distilled water. A solid therefrom was filtered and dissolved in ethyl acetate, and dried with $MgSO_4$, and an organic layer was removed therefrom under a reduced pressure. Column chromatography (hexane:EA 30%) was used to obtain 16 g (76%) of Intermediate B-205-3.

4th step: Synthesis of Intermediate B-205-4

Intermediate B-205-3 (16 g, 73 mmol) and pyridine (12 ml, 146 mmol) were put in a round-bottomed flask and dissolved in 200 ml of DCM. After decreasing the temperature to 0° C., trifluoromethanesulfonic anhydride (14.7 ml, 88 mmol) was slowly added thereto in a dropwise fashion. After stirring the mixture for 6 hours, an excess of distilled water was added thereto and then, stirred for 30 minutes and extracted with DCM. An organic solvent was removed under a reduced pressure and vacuum-dried to obtain 22.5 g (88%) of Intermediate B-205-4.

5th Step: Synthesis of Intermediate B-205-5

14.4 g (81%) of Intermediate B-205-5 was obtained according to the same method as Synthesis Example 11 except that Intermediate B-205-4 (22.5 g, 64 mmol), phenylboronic acid (7.8 g, 64 mmol), $K_2CO_3$ (13.3 g, 96 mmol), and $Pd(PPh_3)_4$ (3.7 g, 3.2 mmol) were used.

6th Step: Synthesis of Intermediate B-205-6

Intermediate B-205-5 (22.5 g, 80 mmol), bis(pinacolato)diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were put in a round-bottomed flask and dissolved in 320 ml of DMF. The mixture was refluxed and stirred at 120° C. for 10 hours. When a reaction was complete, the mixture was poured into an excess of distilled water and then stirred for 1 hour. A solid therefrom was filtered and dissolved in DCM. After removing moisture with $MgSO_4$, an organic solvent was filtered by using a silica gel pad and removed under a reduced pressure. A solid therefrom was recrystallized with EA and hexane to obtain 26.9 g (90%) of Intermediate B-205-6.

7th Step: Synthesis of Intermediate B-205-7

15 g (81.34 mmol) of cyanuric chloride was dissolved in 200 mL of anhydrous tetrahydrofuran in a 500 mL round-bottomed flask, and 1 equivalent of a 4-biphenyl magnesium bromide solution (0.5 M tetrahydrofuran) was added thereto in a dropwise fashion at 0° C. under a nitrogen atmosphere and then, slowly heated up to ambient temperature. The reaction solution was stirred for 1 hour at ambient temperature and put in 500 mL of ice water to separate layers. An organic layer was separated therefrom and treated with magnesium sulfate anhydrous, and the residue was concentrated. The concentrated residue was recrystallized with tetrahydrofuran and methanol to obtain 17.2 g of Intermediate B-205-7.

8th Step: Synthesis of Intermediate B-205-8

Intermediate B-205-8 was synthesized according to the same method as the 1st step of Synthesis Example 14 except that Intermediate B-205-7 was used.

9th Step: Synthesis of Compound B-205

15.5 g (70%) of Compound B-205 was synthesized according to the same method as the 2nd step of Synthesis Example 14 except that Intermediate B-205-6 (12.8 g, 35 mmol), Intermediate B-205-8 (15 g, 35 mmol), $K_2CO_3$ (7.2 g, 52 mmol), and $Pd(PPh_3)_4$ (2 g, 1.7 mmol) were used under a nitrogen condition in a round-bottomed flask.

LC/MS measurement (C45H27N3O2, theoretical value: 641.21 g/mol, measured value: M=641.25 g/mol)

Synthesis Example 17: Synthesis of Compound B-183

[Reaction Scheme 19]

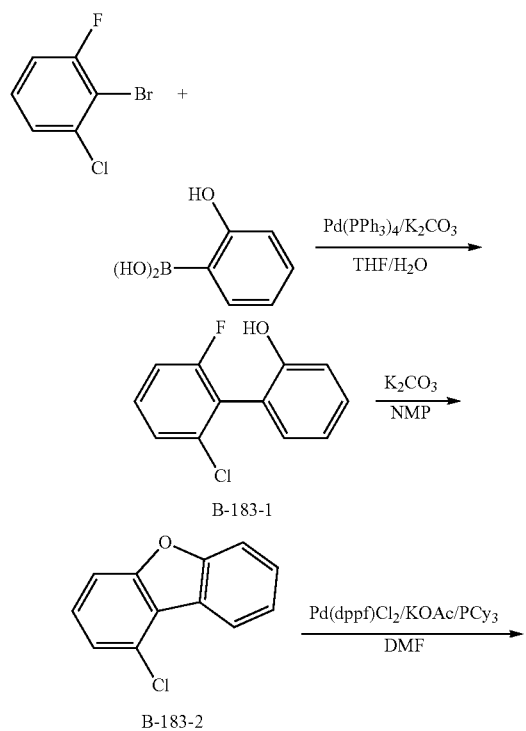

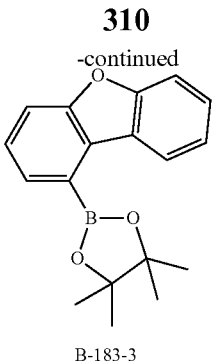

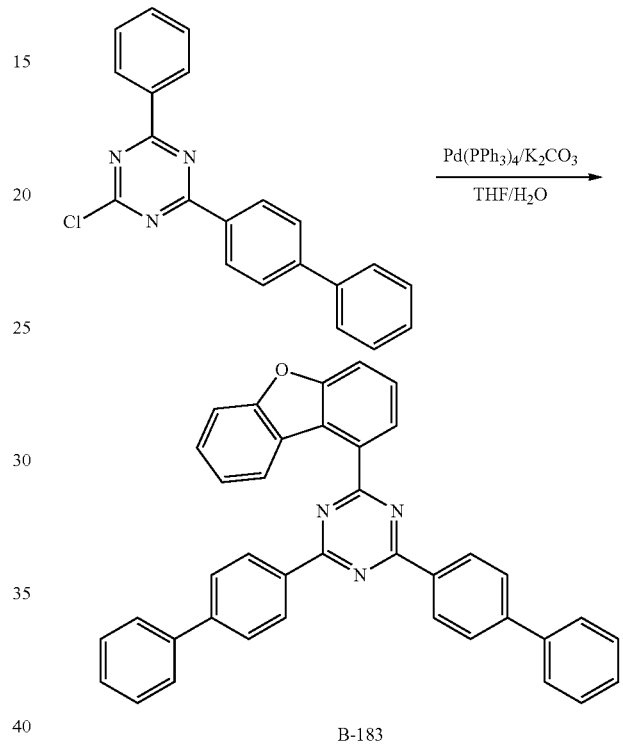

1st Step: Synthesis of Intermediate B-183-1

Intermediate B-183-1 was synthesized according to the same method as the 1st step of Synthesis Example 16 except that 2-bromo-1-chloro-3-fluoro-benzene and 2-hydroxyphenylboronic acid were used in an amount of 1.0 equivalent.

2nd Step: Synthesis of Intermediate B-183-2

Intermediate B-183-2 was synthesized according to the same method as the 3rd step of Synthesis Example 16 except that Intermediate B-183-1 and $K_2CO_3$ were used in an equivalent ratio of 1:1.5.

3rd Step: Synthesis of Intermediate B-183-3

Intermediate B-183-3 was synthesized according to the same method as the 6th step of Synthesis Example 16 except that Intermediate D-3-2 and bis(pinacolato)diboron were used in an equivalent ratio of 1:1.2.

4th Step: Synthesis of Compound B-183

Compound B-183 was synthesized according to the same method as the 2nd step of Synthesis Example 14 except that Intermediate B-183-3 and 2,4-bis([1,1'-biphenyl]-4-yl)-6-chloro-1,3,5-triazine were used in each amount of 1.0 equivalent.

LC/MS measurement (C39H25N3O theoretical value: 551.20 g/mol, measured value: M=551.24 g/mol)

Synthesis Example 18: Synthesis of Compound B-209

[Reaction Scheme 20]

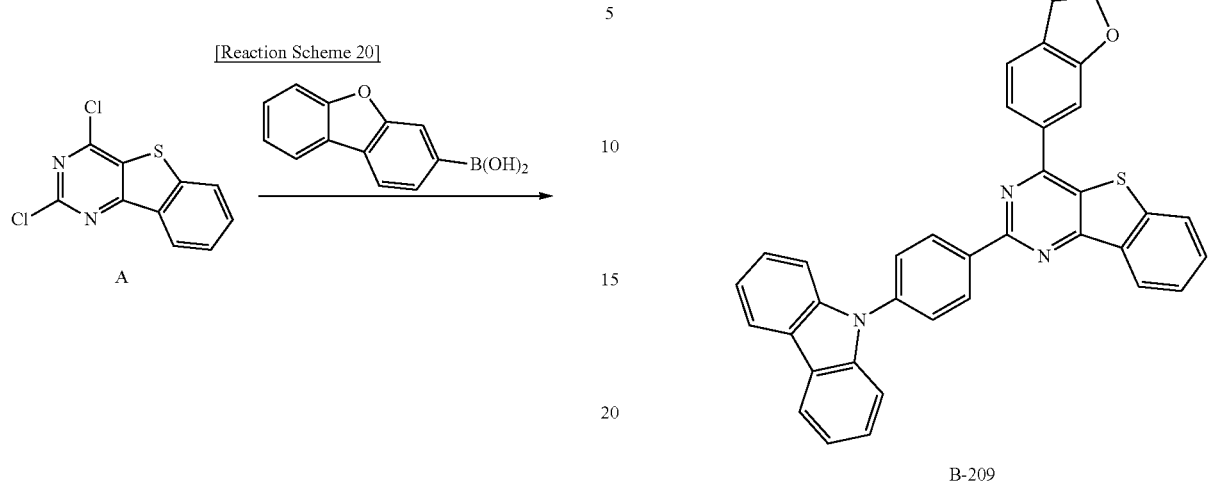

B-209

1st Step: Synthesis of Intermediate B-209-1

10.5 g of Intermediate A, 8.8 g of 3-dibenzofuran boronic acid, 11.4 g of potassium carbonate, and 2.4 g of tetrakis (triphenylphosphine) palladium (0) were added to 140 mL of 1,4-dioxane and 70 mL of water in a 500 mL flask and then, heated at 60° C. under a nitrogen flow for 12 hours. The obtained mixture was added to 500 mL of methanol, and a solid crystallized therein was filtered, dissolved in monochlorobenzene, filtered with silica gel/Celite, and after removing an organic solvent in an appropriate amount, recrystallized with methanol to obtain Intermediate B-209-1 (10.7 g, yield: 67%).

2nd Step: Synthesis of Compound B-209

10.4 g of Intermediate B-209-1, 7.8 g of 4-(9-carbazolyl) phenylboronic acid, 7.5 g of potassium carbonate, and 1.6 g of tetrakis(triphenylphosphine) palladium (0) were added to 90 mL of 1,4-dioxane and 45 mL of water in a 250 mL flask and then, heated at 70° C. under a nitrogen flow for 12 hours. The obtained mixture was added to 250 mL of methanol, and a solid crystallized therein was filtered, dissolved in 1,2-dichlorobenzene, filtered with silica gel/Celite, and after removing an organic solvent in an appropriate amount, recrystallized with methanol to obtain Compound B-209 (13.0 g, yield: 74%).

LC/MS measurement (C40H23N3OS), theoretical value: 593.16 g/mol, measured value: M=593.23 g/mol)

Synthesis Example 19: Synthesis of Compound C-25

[Reaction Scheme 21]

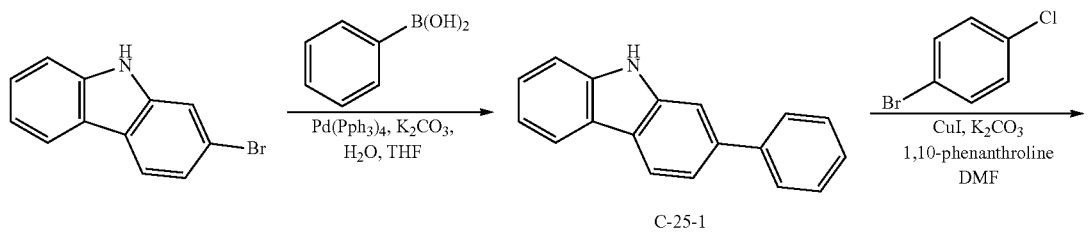

C-25-1

-continued
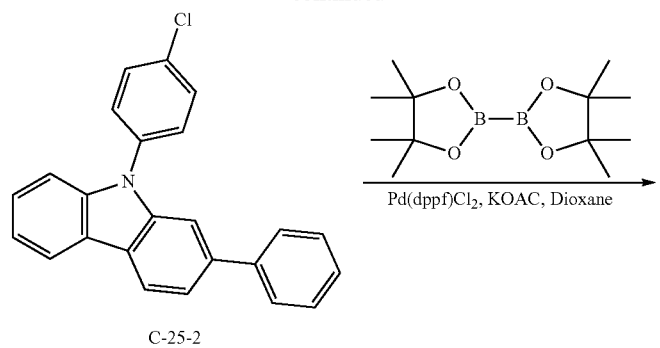
C-25-2
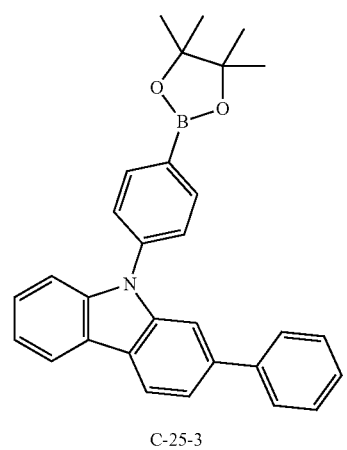
C-25-3
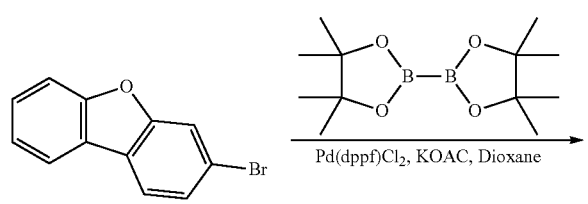
C-25-4
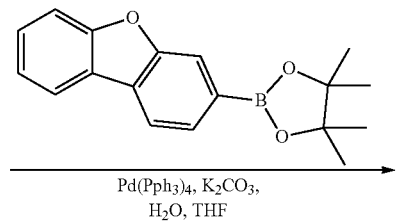
C-25-5 + C-25-3

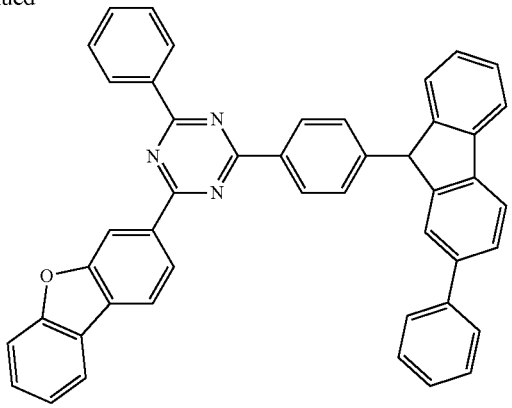

C-25

1st Step: Synthesis of Intermediate C-25-1

2-bromocarbazole (35 g, 142 mmol) was dissolved in 0.5 L of tetrahydrofuran (THF), and phenyl boronic acid (17.3 g, 142 mmol) and tetrakis(triphenylphosphine)palladium (8.2 g, 7.1 mmol) were added thereto and then, stirred. Subsequently, potassium carbonate saturated in water (49.1 g, 356 mmol) was added thereto and then, heated and refluxed at 80° C. for 12 hours. When a reaction was complete, water was added to the reaction solution, dichloromethane (DCM) was used for an extraction, magnesium sulfate anhydrous was used to remove moisture therefrom, and the residue was filtered and concentrated under a reduced pressure. The obtained residue was separated and purified through flash column chromatography to obtain 22 g (63.6%) of Intermediate C-25-1.

2nd Step: Synthesis of Intermediate C-25-2

Intermediate C-25-1 (22 g, 90.4 mmol), 1-bromo-4-chloro-benzene (25.96 g, 135.61 mmol), CuI (1.71 g, 9 mmol), $K_2CO_3$ (18.74 g, 135.61 mmol), and 1,10-phenanthroline (1.62 g, 9 mmol) were put in a round-bottomed flask and then, dissolved in 700 ml of DMF. The solution was stirred at 180° C. for 18 hours. When a reaction was complete, a reaction solvent was removed therefrom under a reduced pressure, dissolved in dichloromethane, and then, filtered with silica gel. After concentrating the dichloromethane, hexane was used for recrystallization to obtain 18 g (56.3%) of Intermediate C-25-2.

3rd Step: Synthesis of Intermediate C-25-3

Intermediate C-25-2 (18 g, 51 mmol), bis(pinacolato)diboron (19.43 g, 76.5 mmol), Pd(dppf)Cl$_2$ (2.24 g, 8.64 mmol), tricyclohexylphosphine (2.86 g, 10.2 mmol), and potassium acetate (15.02 g, 153.01 mmol) were put in a round-bottomed flask and then, dissolved in 720 ml of DMF. The mixture was refluxed and stirred at 120° C. for 12 hours. When a reaction was complete, the mixture was poured into an excess of distilled water and then, stirred for 1 hour. A solid therein was filtered and then, dissolved in DCM. After removing moisture with MgSO$_4$, an organic solvent was filtered by using a silica gel pad and then, removed under a reduced pressure. A solid therefrom was recrystallized with EA and hexane to obtain 14.8 g (65.3%) of Intermediate C-25-3.

4th Step: Synthesis of Intermediate C-25-4

31 g (65.1%) of Intermediate C-25-4 was synthesized according to the same method as the 2nd step of Synthesis Example 15 except that 3-bromo-dibenzofuran (40 g, 162 mmol) was used instead of Intermediate C-25-2.

5th Step: Synthesis of Intermediate C-25-5

Intermediate C-25-4 was dissolved in 0.3 L of tetrahydrofuran (THF), and 2,4-chloro-6-phenyl-1,3,5-triazine (21 g, 93 mmol) and tetrakis(triphenylphosphine)palladium (5.38 g, 4.65 mmol) were added thereto and then, stirred. Potassium carbonate saturated in water (32.14 g, 232 mmol) was added thereto and then, heated and refluxed at 80° C. for 12 hours. When a reaction was complete, water was added to the reaction solution and then, stirred for 30 minutes and filtered, a solid therefrom was dissolved in monochlorobenzene at 133° C., treated with magnesium sulfate anhydrous to remove moisture, and filtered with silica gel, and the filtrate was cooled down to ambient temperature and filtered. The obtained solid was repetitively purified by using monochlorobenzene to obtain 15 g (64.8%) of Intermediate C-25-5.

6th Step: Synthesis of Compound C-25

12.7 g (67.5%) of Compound C-25 were obtained according to the same method as the 2nd step of Synthesis Example 14 by using Intermediate C-25-5 (10.5 g, 29.3 mmol) and Intermediate C-25-3 (14.38 g, 32.28 mmol).

LC/MS measurement (C45H28NO), theoretical value: 640.23 g/mol, measured value: M=641.38 g/mol)

Synthesis Example 20: Synthesis of Compound C-23

[Reaction Scheme 22]

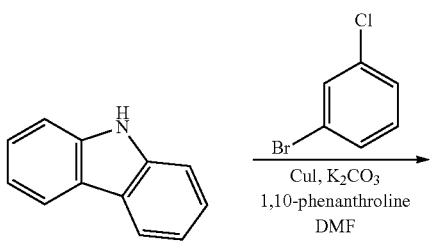

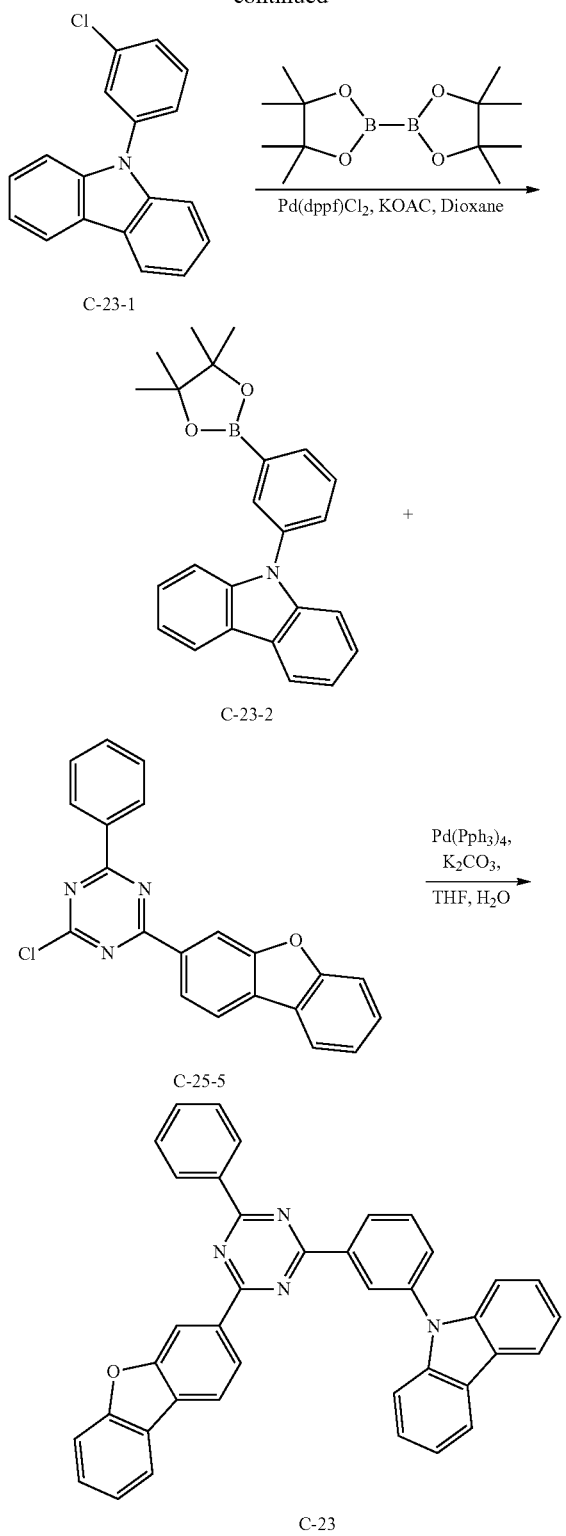

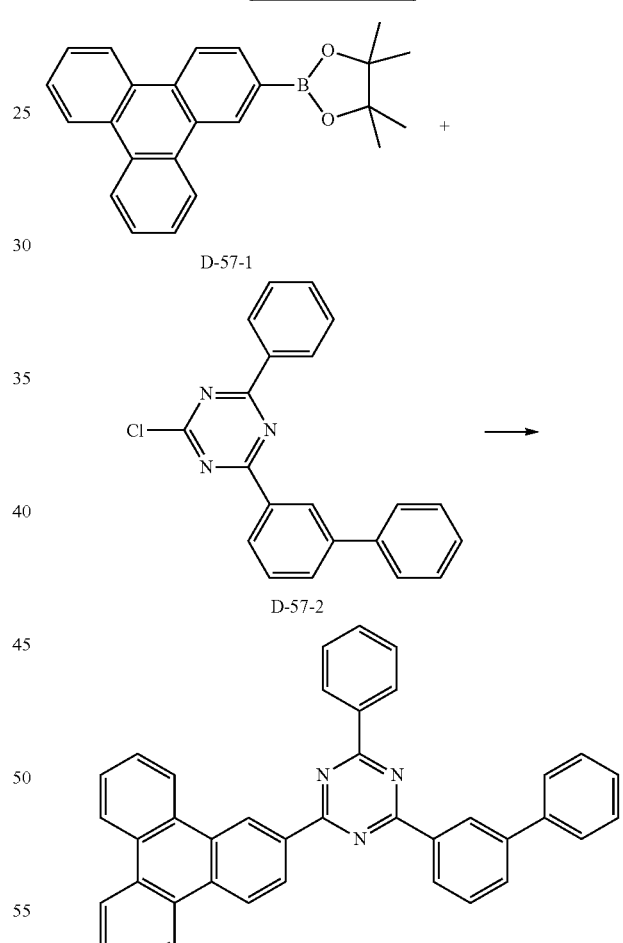

2nd Step: Synthesis of Intermediate C-23-2

16.8 g (70%) of Intermediate C-23-2 were obtained according to the same method as the 3rd step of Synthesis Example 19 except that Intermediate C-23-1 (18 g, 65 mmol) was used.

3rd Step: Synthesis of Compound C-23

16.4 g (66%) of Intermediate C-23 were obtained according to the same method as the 6th step of Synthesis Example 19 except that Intermediate C-23-2 (16.3 g, 44.3 mmol) and Intermediate C-25-3 (15.8 g, 44.3 mmol) were used.

LC/MS measurement (C39H24N4O), theoretical value: 564.20 g/mol, measured value: M=565.36 g/mol)

Synthesis Example 21: Synthesis of Compound D-57

[Reaction Scheme 23]

Compound D-57 was synthesized by using Intermediate D-57-1 and Intermediate D-57-2 (yield: 88%).

LC/MS measurement (C39H25N3), theoretical value: 535.20 g/mol, measured value: M=535.83 g/mol)

1st Step: Synthesis of Intermediate C-23-1

31.5 g (79%) of Intermediate C-23-1 were obtained according to the same method as the 2nd step of Synthesis Example 19 except that 9H-carbazole (24.1 g, 144 mmol) and 1-bromo-3-chloro-benzene (27.6 g 144 mmol) were used.

Comparative Synthesis Example 3: Synthesis of Compound V-3

[Reaction Scheme 24]

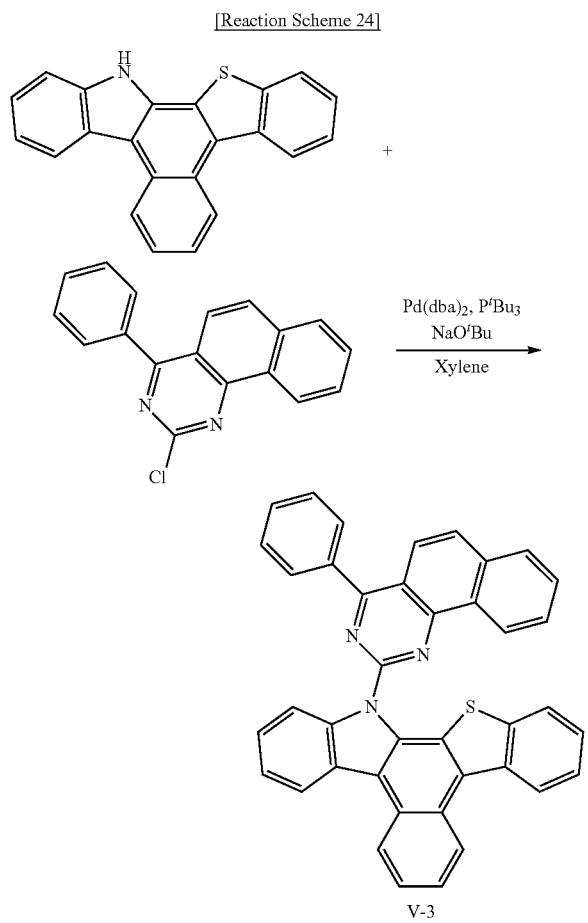

V-3

5.7 g (yield: 57%) of Compound V-3 was obtained according to Reaction Scheme 24.

Comparative Synthesis Example 4: Synthesis of Compound V-4

[Reaction Scheme 25]

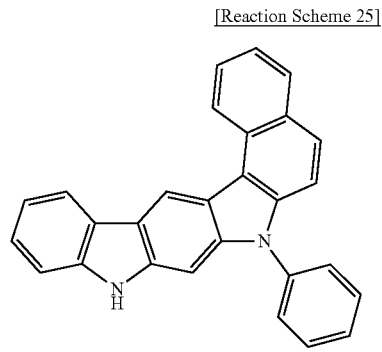

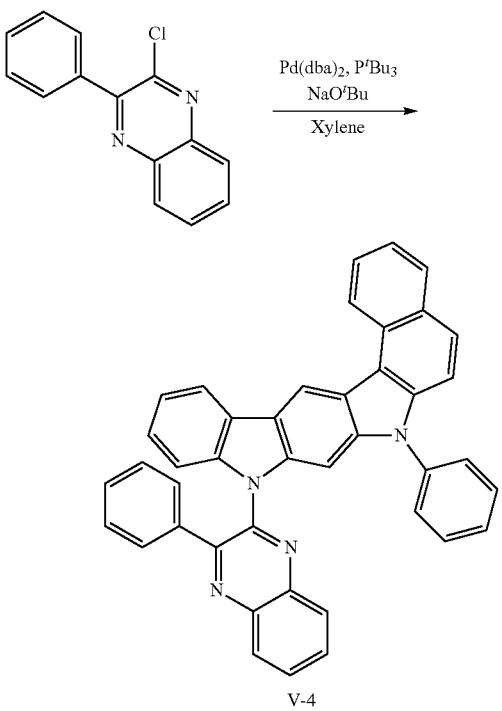

V-4

6.4 g (yield: 47%) of Compound V-4 was obtained according to Reaction Scheme 25.

Synthesis of Third Compound

Synthesis Example 22: Synthesis of Compound E-9

[Reaction Scheme 26]

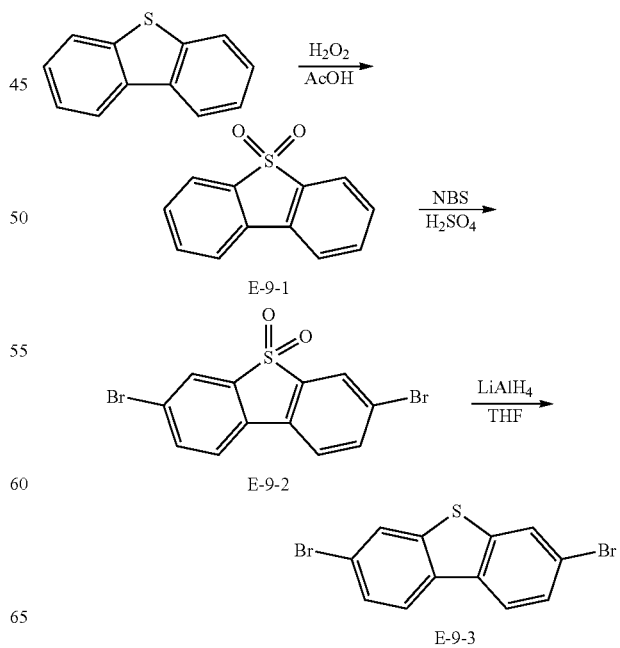

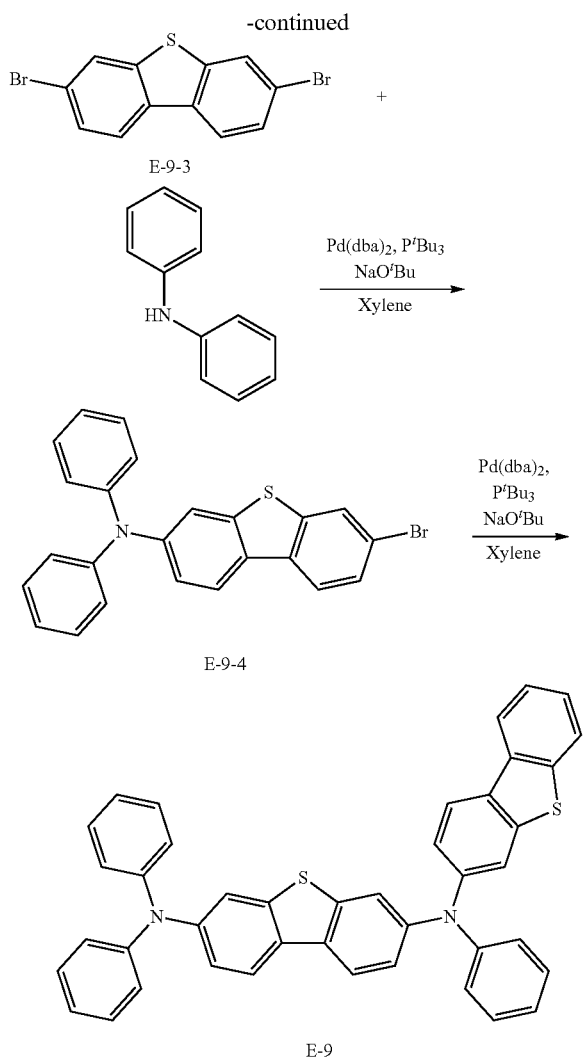

E-9

1st Step: Synthesis of Intermediate E-9-1

50 g (271.43 mmol) of dibenzothiophene was added to 500 mL of acetic acid in a 1 L round-bottomed flask, and an internal temperature thereof was set at 0° C. 117 ml (1.36 mol) of hydrogen peroxide was slowly added thereto. Herein, the internal temperature was maintained at 0° C. The obtained mixture was heated under a nitrogen atmosphere at 90° C. After 12 hours, the reaction solution was cooled down, extracted with dichloromethane (DCM), treated with magnesium sulfate anhydrous to remove moisture, filtered, and concentrated under a reduced pressure to obtain 55 g (yield: 94%) of Intermediate E-9-1.

2nd Step: Synthesis of Intermediate E-9-2

54 g (249.70 mmol) of Intermediate E-9-1 was added to 500 mL of sulfuric acid in a 1 L round-bottomed flask, and an internal temperature thereof was set at 0° C. 90.7 g (499.40 mmol) of n-bromosuccinimide (NBS) was slowly added thereto. Herein, the internal temperature was maintained at 0° C. The reaction solution was stirred under a nitrogen atmosphere at ambient temperature for 4 hours, slowly put in ice water, treated with dichloromethane (DCM) for an extraction, treated with magnesium sulfate anhydrous to remove moisture, filtered, and concentrated under a reduced pressure. The obtained residue was separated and purified with flash column chromatography to obtain 46 g (49%) of Intermediate E-9-2.

3rd Step: Synthesis of Intermediate E-9-3

45 g (120.30 mmol) of Intermediate E-9-2 was added to 500 mL of tetrahydrofuran in a 1 L round-bottomed flask, and an internal temperature thereof was set at 0° C. 10.1 g (252.64 mmol) of lithium aluminum hydride was slowly added thereto. Herein, the internal temperature was maintained at 0° C. After being stirred at 75° C. under a nitrogen atmosphere for 3 hours, the reaction solution was slowly put in ice water and then, stirred and Celite-filtered. Subsequently, the reaction solution was treated with dichloromethane (DCM) for an extraction, treated with magnesium sulfate anhydrous to remove moisture, filtered, and concentrated under a reduced pressure. The obtained residue was separated and purified through flash column chromatography to obtain 28 g (68%) of Intermediate E-9-3.

4th Step: Synthesis of Intermediate E-9-4

15.0 g (43.92 mmol) of Intermediate E-9-3, 6.69 g (39.30 mmol) of diphenylamine, 10.56 g (109.8 mmol) of sodium t-butoxide, and 1.8 g (4.38 mmol) of tri-tert-butylphosphine were dissolved in 300 ml of xylene, and 2.01 g (2.19 mmol) of Pd(dba)₂ was added thereto and then, stirred under a nitrogen atmosphere for 12 hours at 100° C. When a reaction was complete, xylene and distilled water were used for an extraction, an organic layer therefrom was dried with magnesium sulfate anhydrous and filtered, and the filtrate was concentrated under a reduced pressure. A product therefrom was purified through silica gel column chromatography with n-hexane/dichloromethane (in a volume ratio of 2:1) to obtain 10.5 g (yield: 56%) of Intermediate E-9-4 as a white solid.

5th Step: Synthesis of Compound E-9

3.5 g (8.15 mmol) of Intermediate E-9-4, 3.3 g (8.96 mmol) of 3-dibenzothiophene-phenylamine, 1.96 g (20.37 mmol) of sodium t-butoxide, and 0.3 g (0.81 mmol) of tri-tert-butylphosphine were dissolved in 50 ml of xylene, and 0.37 g (0.41 mmol) of Pd(dba)₂ was added thereto and then, refluxed and stirred under a nitrogen atmosphere for 12 hours. When a reaction was complete, the resultant was extracted with xylene and distilled water, an organic layer therefrom was dried with magnesium sulfate anhydrous and filtered, and the filtrate was concentrated under a reduced pressure. A product therefrom was purified through silica gel column chromatography with n-hexane/dichloromethane (in a volume ratio of 2:1) to obtain 3.8 g (yield: 75%) of Compound E-9 as a white solid.

Calculation value: C, 80.74; H, 4.52; N, 4.48; S, 10.26
Analyzed value: C, 80.73; H, 4.53; N, 4.48; S, 10.26

Synthesis Example 23: Synthesis of Compound E-12

[Reaction Scheme 27]

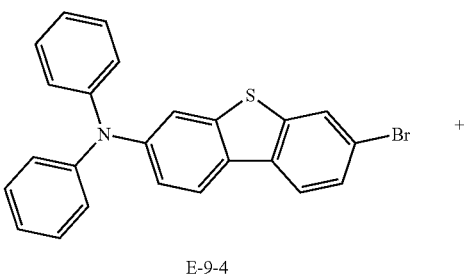

E-9-4

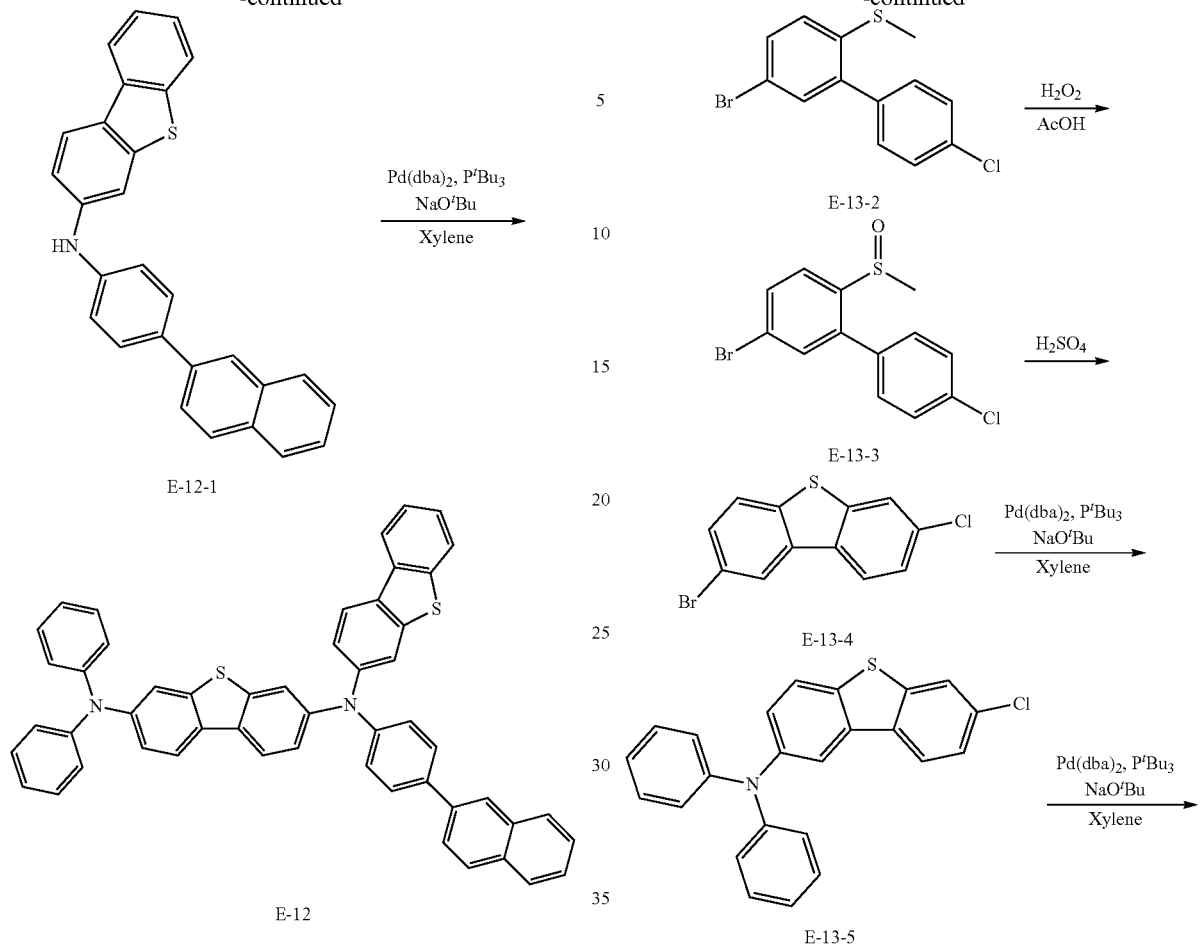

4.7 g (yield: 68%) of Compound E-12 as a white solid was obtained according to the same method as Compound E-9 according to the 5th step of Synthesis Example 22.
Calculation value: C, 83.17; H, 4.56; N, 3.73; S, 8.54
Analyzed value: C, 83.16; H, 4.56; N, 3.74; S, 8.54

Synthesis Example 24: Synthesis of Compound E-13

[Reaction Scheme 28]

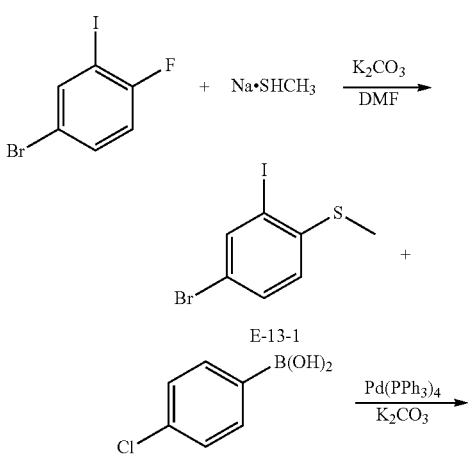

1st Step: Synthesis of Intermediate E-13-1
150 g (498.5 mmol) of 4-bromo-2-fluoro-1-iodobenzene was added to 1.5 L of N,N-dimethylformamide in a 3 L round-bottomed flask, and an internal temperature thereof was set at 0° C. 35.44 g (498.52 mmol) of sodium thiomethoxide (CAS No.: 5188-07-8), 103.19 g (747.98 mmol) of potassium carbonate were slowly added thereto. Herein, the internal temperature was set at 0° C. The obtained mixture was heated at 80° C. under a nitrogen atmosphere. After 6 hours, the reaction solution was cooled down, ethyl acetate and an aqueous layer were added thereto and stirred, and an organic layer therefrom was treated through column chromatography under a reduced pressure to obtain 106.61 g (yield: 65%) of Intermediate E-13-1.

2nd Step: Synthesis of Intermediate E-13-2

E-13-1 (106 g, 322 mmol) was dissolved in 1.0 L of tetrahydrofuran (THF), and E-13-2 (57.66 g, 322 mmol) and tetrakis(triphenylphosphine) palladium (11.2 g, 9.7 mmol) were added thereto and then, stirred. Subsequently, potassium carbonate saturated in water (111.32 g, 805 mmol) was added thereto and then, heated and refluxed at 80° C. for 12 hours. When a reaction was complete, water was added to the reaction solution, dichloromethane (DCM) was used for an extraction, magnesium sulfate anhydrous was used to remove moisture, and the residue was filtered and concentrated under a reduced pressure. The obtained residue was separated and purified through flash column chromatography to obtain 63.66 g (63%) of Intermediate E-13-2.

3rd Step: Synthesis of Intermediate E-13-3

63 g (200.87 mmol) of E-13-2 was added to 600 mL of acetic acid, and an internal temperature thereof was set at 0° C. 20.4 ml of hydrogen peroxide was slowly added thereto. Herein, the internal temperature was maintained at 0° C. The reaction solution was then stirred at ambient temperature for 6 hours, put in ice water, treated with dichloromethane (DCM) for an extraction, treated with magnesium sulfate anhydrous to remove moisture, filtered, and concentrated under a reduced pressure to obtain 61 g (yield: 92%) of Intermediate E-13-3.

4th Step: Synthesis of Intermediate E-13-4

60 g (182.12 mmol) of E-13-3 was added to 400 mL of sulfuric acid and then, stirred at ambient temperature for 6 hours, and the reaction solution was put in ice water and adjusted to have pH 9 by using a NaOH aqueous solution. The reaction solution was extracted with dichloromethane (DCM), treated with magnesium sulfate anhydrous to remove moisture, filtered, and concentrated under a reduced pressure to obtain 38 g (yield: 70%) of Intermediate E-13-4.

5th Step: Synthesis of Intermediate E-13-5

5.0 g (16.82 mmol) of Intermediate E-13-4, 2.85 g (16.82 mmol) of diphenylamine, 4.04 g (42.04 mmol) of sodium t-butoxide, and 0.7 g (1.69 mmol) of tri-tert-butylphosphine were dissolved in 100 ml of xylene, and 0.77 g (0.84 mmol) of Pd(dba)$_2$ was added thereto and then, stirred 100° C. under a nitrogen atmosphere for 12 hours. When a reaction was complete, the resultant was extracted with xylene and distilled water, an organic layer therefrom was dried with magnesium sulfate anhydrous and filtered, and the filtrate was concentrated under a reduced pressure. A product therefrom was purified through silica gel column chromatography with n-hexane/dichloromethane (in a volume ratio of 2:1) to obtain 4.7 g (yield: 72%) of Intermediate E-13-5 as a white solid.

6th Step: Synthesis of Compound E-13

4.5 g (11.68 mmol) of Intermediate E-13-5, 3.3 g (11.68 mmol) of 3-dibenzothiophene-phenylamine, 2.81 g (29.21 mmol) of sodium t-butoxide, and 1.2 g (1.17 mmol) of tri-tert-butylphosphine were dissolved in 50 ml of xylene, and 0.54 g (0.58 mmol) of Pd(dba)$_2$ was added thereto and then, refluxed and stirred under a nitrogen atmosphere for 12 hours. When a reaction was complete, the resultant was extracted with xylene and distilled water, an organic layer therefrom was dried with magnesium sulfate anhydrous and filtered, and the filtrate was concentrated under a reduced pressure. A product therefrom was purified through silica gel column chromatography with n-hexane/dichloromethane (in a volume ratio of 2:1) to obtain 5.5 g (yield: 75%) of Compound E-13 as a white solid.

Calculation value: C, 80.74; H, 4.52; N, 4.48; S, 10.26
Analyzed value: C, 80.74; H, 4.52; N, 4.48; S, 10.26

Synthesis Example 25: Synthesis of Compound E-16

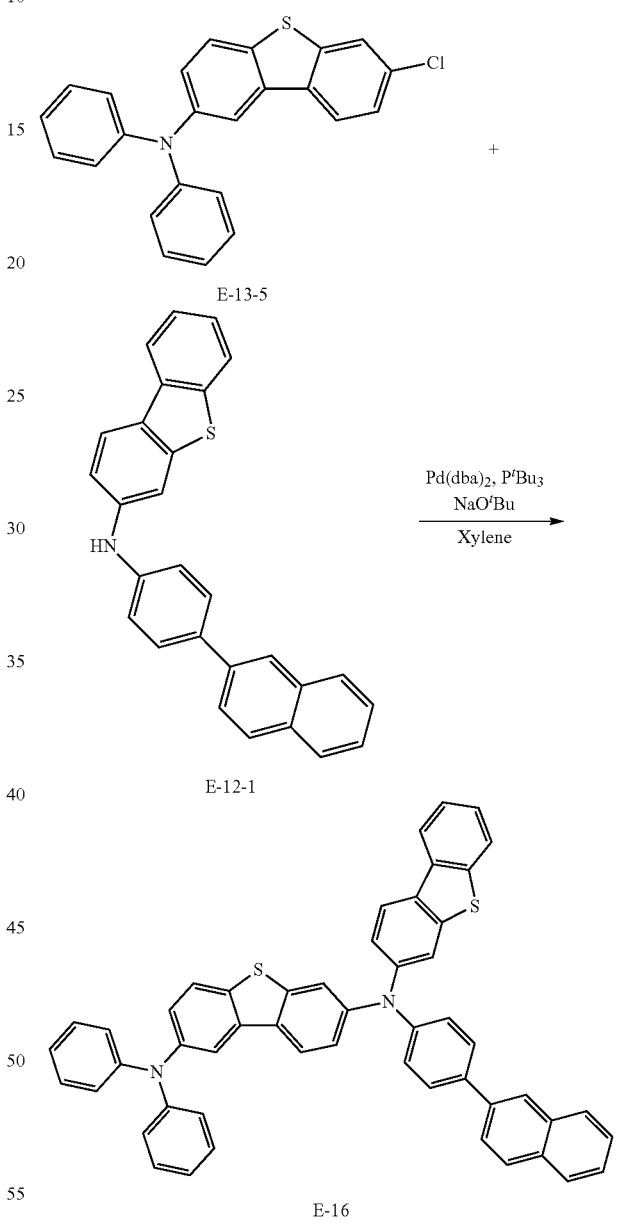

3.5 g (yield: 70%) of Compound E-16 as a white solid was obtained according to the same method as Compound E-13 according to the 6th step of Synthesis Example 24.

Calculation value: C, 83.17; H, 4.56; N, 3.73; S, 8.54
Analyzed value: C, 83.17; H, 4.56; N, 3.74; S, 8.54

Synthesis Example 26: Synthesis of Compound E-33

[Reaction Scheme 30]

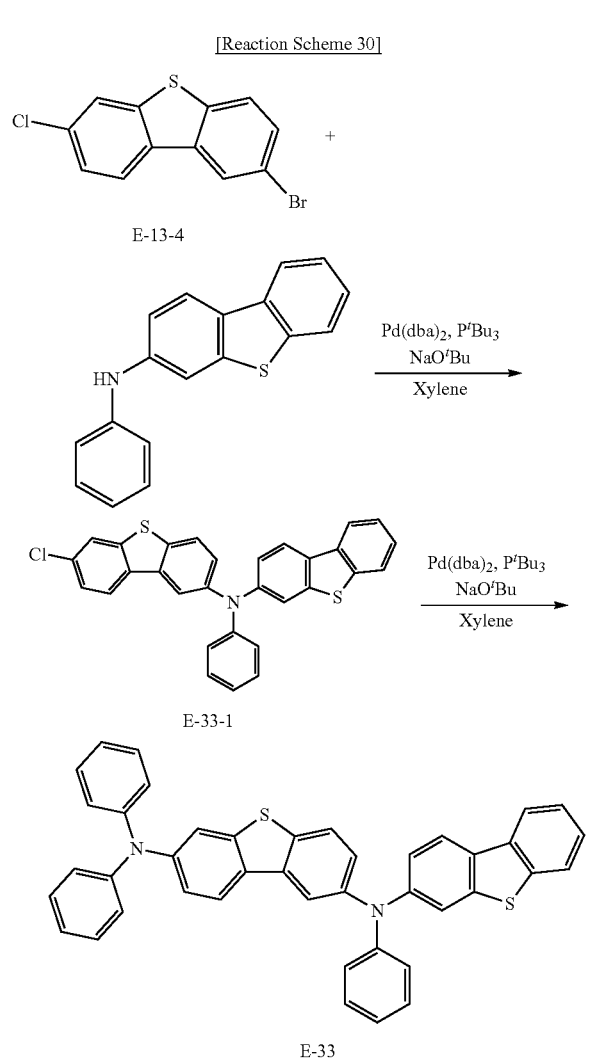

1st Step: Synthesis of Intermediate E-33-1

Intermediate E-33-1 as a white solid was obtained according to the same method as Intermediate E-13-5 according to the 5th step of Synthesis Example 24 except that 3-dibenzothiophene-phenylamine instead of the diphenylamine was used.

2nd Step: Synthesis of Compound E-33

5.1 g (yield: 62%) of Intermediate E-33 as a white solid was obtained according to the same method as Intermediate E-13 according to the 6th step of Synthesis Example 24 except that Intermediate E-33-1 instead of Intermediate E-13-5 was used.

Calculation value: C, 80.74; H, 4.52; N, 4.48; S, 10.26
Analyzed value: C, 80.72; H, 4.50; N, 4.48; S, 10.26

Synthesis Example 27: Synthesis of Compound E-65

[Reaction Scheme 31]

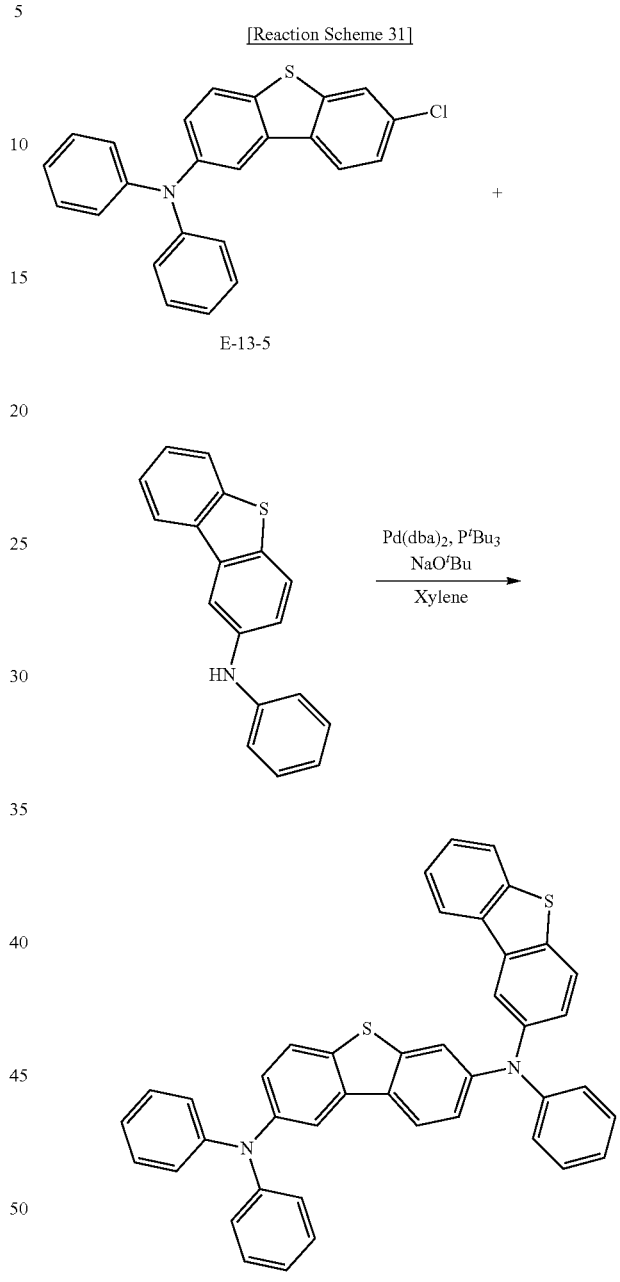

3.9 g (yield: 66%) of Intermediate E-65 as a white solid was obtained according to the same method as Intermediate E-13 according to the 6th step of Synthesis Example 24 except that 2-dibenzothiophene-phenylamine instead of the 3-dibenzothiophene-phenylamine was used.

Calculation value: C, 80.74; H, 4.52; N, 4.48; S, 10.26
Analyzed value: C, 80.74; H, 4.52; N, 4.48; S, 10.26

329
Synthesis Example 28: Synthesis of Compound E-93

330
Synthesis Example 29: Synthesis of Compound F-17

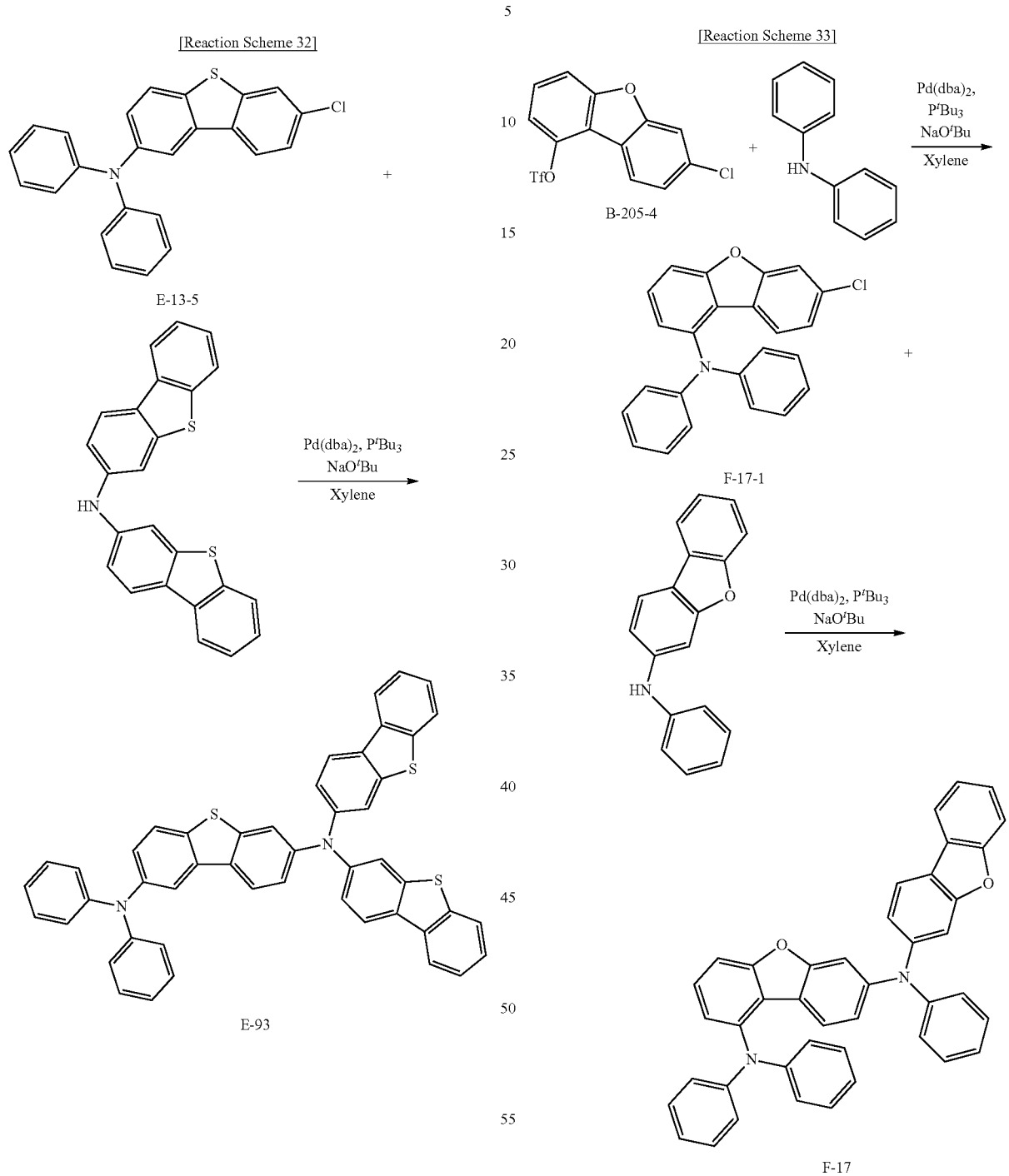

3.4 g (yield: 64%) of Intermediate E-93 as a white solid was obtained according to the same method as Intermediate E-13 according to the 6th step of Synthesis Example 23 except that N-3-dibenzothienyl-3-dibenzothiophenamine (CAS #: 1705596-48-0) instead of the 3-dibenzothiophenephenylamine was used.

Calculation value: C, 78.87; H, 4.14; N, 3.83; S, 13.16
Analyzed value: C, 78.86; H, 4.14; N, 3.84; S, 13.16

1st Step: Synthesis of Intermediate F-17-1
Intermediate F-17-1 as a white solid was obtained according to the same method as Intermediate E-13-5 according to the 5th step of Synthesis Example 24 except that Intermediate B-205-4 instead of Intermediate E-13-4 was used.

2nd Step: Synthesis of Compound F-17
6.8 g (yield: 70%) of a white solid was obtained according to the same method as Compound E-13 according to the 6th step of Synthesis Example 24 except that Intermediate F-17-1 and 3-dibenzofuran-phenylamine were used.

Calculation value: C, 85.11; H, 4.76; N, 4.73; 0, 5.40

Analyzed value: C, 85.11; H, 4.76; N, 4.73; 0, 5.40

Synthesis Example 30: Synthesis of Compound F-37

[Reaction Scheme 34]

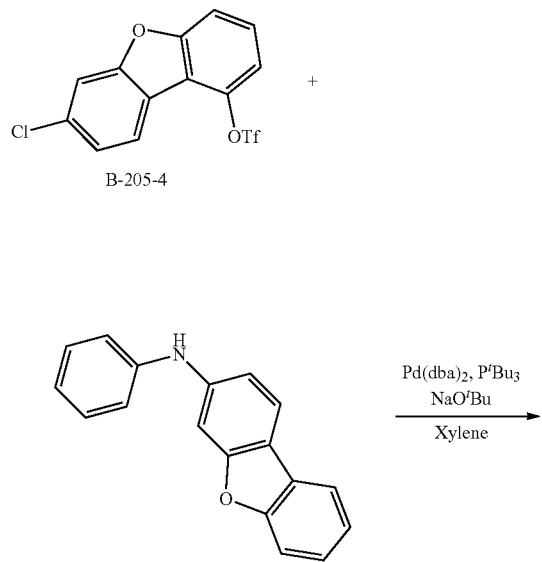

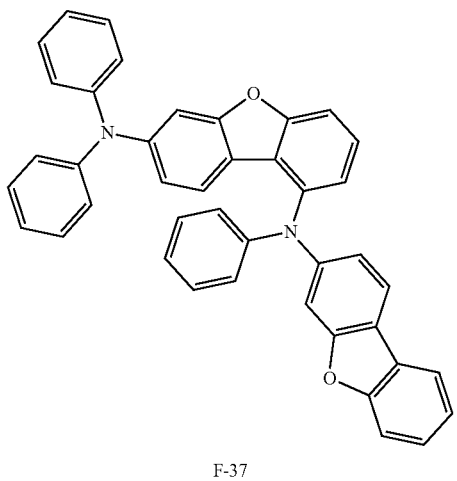

F-37

1st Step: Synthesis of Intermediate F-37-1

Intermediate F-37-1 was obtained according to the same method as Intermediate E-13-5 according to the 5th step of Synthesis Example 24 except that Intermediate B-205-4 and 3-dibenzofuran-phenylamine were used.

2nd Step: Synthesis of Compound F-37

6.2 g (yield: 69%) of Compound F-37 as a white solid was obtained according to the same method as Compound E-13 according to the 6th step of Synthesis Example 24 except that Intermediate F-37-1 and diphenylamine were used.

Calculation value: C, 85.11; H, 4.76; N, 4.73; 0, 5.40

Analyzed value: C, 85.10; H, 4.77; N, 4.73; 0, 5.40

Synthesis Example 31: Synthesis of Compound G-13

[Reaction Scheme 35]

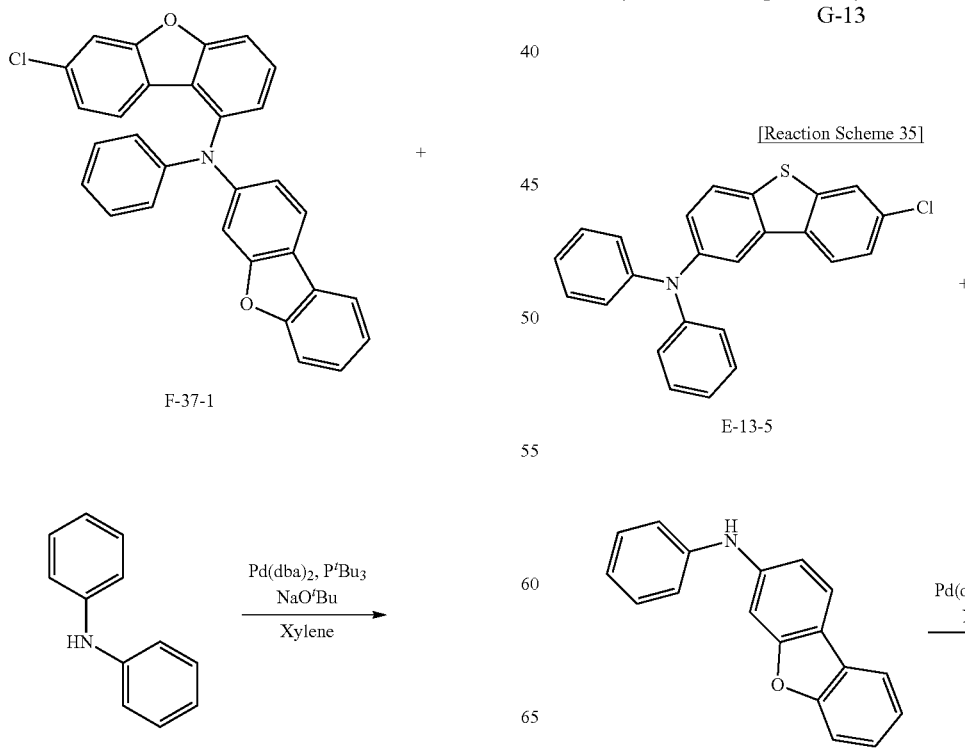

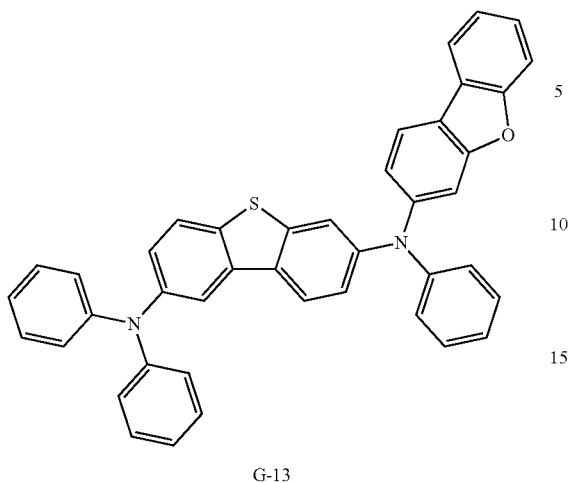

G-13

7.0 g (yield: 71%) of Compound G-13 as a white solid was obtained according to the same method as Compound E-13 according to the 6th step of Synthesis Example 24 except that Intermediate E-13-5 and 3-dibenzofuran-phenylamine were used.

LC/MS calculated for: C42H28N2OS Exact Mass: 608.19 found for 608.20 [M+H]

Synthesis Example 32: Synthesis of Compound H-17

[Reaction Scheme 36]

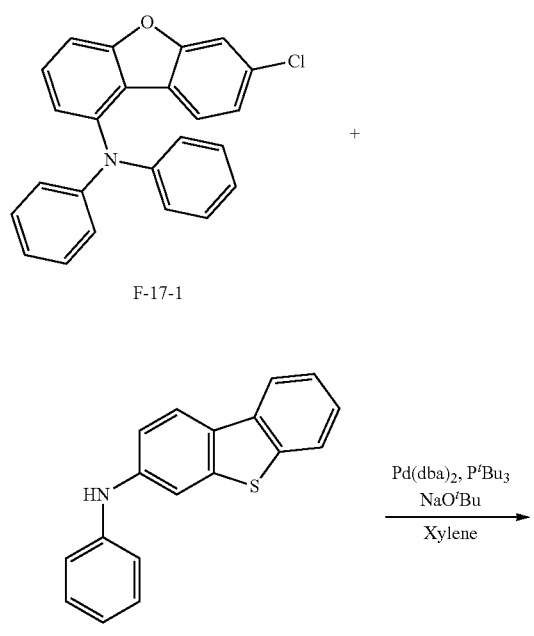

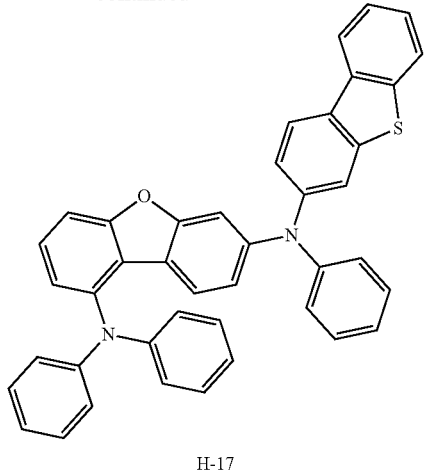

H-17

5.7 g (yield: 68%) of Compound H-17 as a white solid was obtained according to the same method as Compound E-13 according to the 6th step of Synthesis Example 24 except that Intermediate F-17-1 and 3-dibenzothiophene-phenylamine were used.

LC/MS calculated for: C42H28N2OS Exact Mass: 608.19 found for 608.21 [M+H]

Manufacture of Organic Light Emitting Diode

Example 1

A glass substrate coated with ITO (indium tin oxide) as a 1,500 Å-thick thin film was washed with distilled water. After washing with the distilled water, the glass substrate was ultrasonic wave-washed with a isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport auxiliary layer, Compound E-13 was vacuum-deposited to form a 700 Å-thick hole transport auxiliary layer. On the hole transport auxiliary layer, 400 Å-thick light emitting layer was formed by using Compounds A-2 and B-135 simultaneously as a host and doping 2 wt % of [Ir(piq)$_2$acac] as a dopant by a vacuum-deposition. In Example 1, Compound A-2 and Compound B-135 were used in a weight ratio of 6:4, and the ratios in the other Examples and in Comparative Example 1 were also 6:4. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure. ITO/Compound A (700 Å)/Compound B (50 Å)/Compound C (700 Å)/Compound E-13 (700 Å)/EML[Compound A-2: B-135: [Ir(piq)$_2$acac] (2 wt %)] (400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Examples 2 to 22

Each organic light emitting diode was manufactured according to the same method as Example 1 except for changing compositions as shown in Table 1.

Comparative Examples 1 to 3

Each organic light emitting diode was manufactured according to the same method as Example 1 except for changing compositions as shown in Table 1.

Evaluation

Driving voltages and power efficiency of the organic light emitting diodes according to Examples 1 to 22 and Comparative Examples 1 to 3 were evaluated.

Specific measurement methods are as follows, and the results are shown in Table 1.

(1) Measurement of Driving Voltage

A driving voltage of each diode was measured using a current-voltage meter (Keithley 2400) to provide the results.

(2) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(3) Measurement of Luminance Change Depending on Voltage Change

Luminance was measured by using a luminance meter (Minolta Cs-1000A), while the voltage of the organic light emitting diodes was increased from 0 V to 10 V.

(4) Measurement of Power Efficiency

Power efficiency (lm/w) was calculated by using the luminance, current density, and voltages from the items (2) and (3).

TABLE 1

| | Light emitting layer | | Hole transport auxiliary layer | Driving voltage (V) | Power efficiency ratio (%) |
|---|---|---|---|---|---|
| | First compound | Second compound | Third compound | | |
| Example 1 | A-2 | B-135 | E-13 | 3.81 | 126% |
| Example 2 | A-2 | B-135 | E-16 | 3.70 | 118% |
| Example 3 | A-2 | B-135 | E-33 | 3.79 | 131% |
| Example 4 | A-2 | B-135 | E-65 | 3.78 | 132% |
| Example 5 | A-2 | B-135 | E-93 | 3.78 | 126% |
| Example 6 | A-2 | B-135 | F-17 | 4.36 | 112% |
| Example 7 | A-2 | B-135 | F-37 | 4.21 | 119% |
| Example 8 | A-2 | B-135 | G-13 | 3.77 | 127% |
| Example 9 | A-2 | B-135 | H-17 | 4.33 | 112% |
| Example 10 | A-2 | B-17 | E-13 | 3.88 | 123% |
| Example 11 | A-2 | B-183 | E-13 | 3.69 | 128% |
| Example 12 | A-2 | B-205 | E-13 | 3.73 | 118% |
| Example 13 | A-2 | B-209 | E-13 | 4.08 | 120% |
| Example 14 | A-2 | C-23 | E-13 | 4.00 | 120% |
| Example 15 | A-2 | C-25 | E-13 | 4.00 | 122% |
| Example 16 | A-2 | D-57 | E-13 | 3.92 | 123% |
| Example 17 | A-3 | B-135 | E-13 | 4.01 | 123% |
| Example 18 | A-5 | B-135 | E-13 | 4.27 | 113% |
| Example 19 | A-11 | B-135 | E-13 | 3.82 | 136% |
| Example 20 | A-12 | B-135 | E-13 | 3.83 | 138% |
| Example 21 | A-29 | B-135 | E-13 | 3.93 | 121% |
| Example 22 | A-51 | B-135 | E-13 | 4.01 | 128% |
| Comparative Example 1 | V-1 | B-135 | E-13 | 4.62 | 77% |
| Comparative Example 2 | V-3 | | E-13 | 4.47 | 89% |
| Comparative Example 3 | V-4 | | E-13 | 4.36 | 100% |

Referring to Table 1, the organic light emitting diodes according to Examples 1 to 22 exhibited greatly reduced driving voltages and improved power efficiently, compared with the organic light emitting diodes according to Comparative Examples 1 to 3.

By way of summation and review, an organic light emitting diode converts electrical energy into light, and the performance of organic light emitting diode may be influenced by the organic materials between electrodes.

One or more embodiments may provide an organic optoelectronic device exhibiting reduced driving voltage, high efficiency, and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic optoelectronic device, comprising:

an anode and a cathode facing each other, a light emitting layer between the anode and the cathode, a hole transport layer between the anode and the light emitting layer, and a hole transport auxiliary layer between the light emitting layer and the hole transport layer, wherein:

the light emitting layer includes:

a first compound represented by a combination of Chemical Formula 1 and Chemical Formula 2, and a second compound represented by Chemical Formula 3, and the hole transport auxiliary layer includes a third compound represented by Chemical Formula 4,

[Chemical Formula 1]

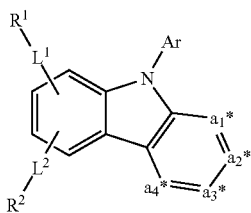

[Chemical Formula 2]

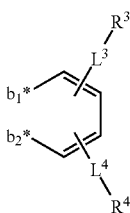

in Chemical Formula 1 and Chemical Formula 2,

Ar is a substituted or unsubstituted C6 to C30 aryl group, a substituted or unsubstituted C2 to C30 heterocyclic group, or a combination thereof, adjacent two of $a_1^*$ to $a_4^*$ are carbon (C) linked at $b_1^*$ and $b_2^*$ respectively, the other two of $a_1^*$ to $a_4^*$ not linked at $b_1^*$ and $b_2^*$ are each independently $C-L^a-R^a$, $L^a$ and $L^1$ to $L^4$ are each independently a single bond, a substituted or unsubstituted C6 to C20 arylene group, a substituted or unsubstituted C2 to C20 heterocyclic group, or a combination thereof, $R^a$ and $R^1$ to $R^4$ are each independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^4$ is a group represented by Chemical Formula a,

[Chemical Formula a]

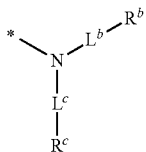

in Chemical Formula a, $L^b$ and $L^c$ are each independently a single bond, a substituted or unsubstituted C6 to C20 arylene group, a substituted or unsubstituted C2 to C20 heterocyclic group, or a combination thereof, $R^b$ and $R^c$ are each independently a substituted or unsubstituted C6 to C30 aryl group, a substituted or unsubstituted C2 to C30 heterocyclic group, or a combination thereof, and

* is a linking point with one of $L^a$ and $L^1$ to $L^4$;

[Chemical Formula 3]

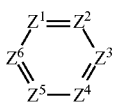

in Chemical Formula 3, $Z^1$ is N or $C-L^5-R^5$, $Z^2$ is N or $C-L^6-R^6$, $Z^3$ is N or $C-L^7-R^7$, $Z^4$ is N or $C-L^8-R^8$, $Z^5$ is N or $C-L^9-R^9$, $Z^6$ is N or $C-L^{10}-R^{10}$, at least two of $Z^1$ to $Z^6$ are N, $L^5$ to $L^{10}$ are each independently a single bond, a substituted or unsubstituted C6 to C20 arylene group, a substituted or unsubstituted C2 to C20 heterocyclic group, or a combination thereof, $R^5$ to $R^{10}$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, at least one of $R^5$ to $R^{10}$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and $R^5$ to $R^{10}$ are separately present or adjacent ones thereof are linked with each other to form a substituted or unsubstituted aliphatic, aromatic, or heteroaromatic monocyclic ring or a substituted or unsubstituted aliphatic, aromatic, or heteroaromatic polycyclic ring;

[Chemical Formula 4]

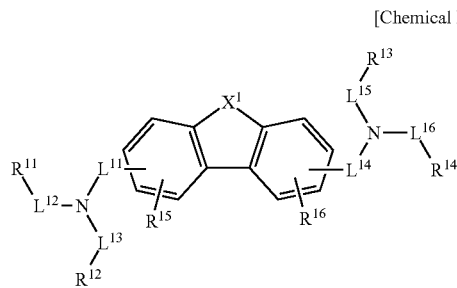

in Chemical Formula 4, $X^1$ is O or S, $L^{11}$ to $L^{16}$ are each independently a single bond, a substituted or unsubstituted C6 to C20 arylene group, a substituted or unsubstituted C2 to C20 heterocyclic group, or a combination thereof, $R^{11}$ to $R^{14}$ are each independently a substituted or unsubstituted C6 to C30 aryl group, a substituted or unsubstituted C2 to C30 heterocyclic group, or a combination thereof, and $R^{15}$ and $R^{16}$ are each independently hydrogen, deuterium, a cyano group, or a substituted or unsubstituted C1 to C10 alkyl group.

2. The organic optoelectronic device as claimed in claim 1, wherein:

the first compound is represented by Chemical Formula 1A or Chemical Formula 1C:

[Chemical Formula 1A]

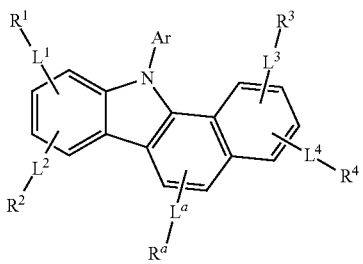

[Chemical Formula 1C]

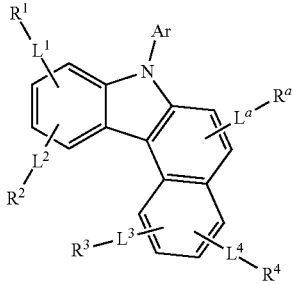

in Chemical Formula 1A and Chemical Formula 1C,

Ar is a substituted or unsubstituted C6 to C30 aryl group, a substituted or unsubstituted C2 to C30 heterocyclic group, or a combination thereof, $L^a$ and $L^1$ to $L^4$ are each independently a single bond, a substituted or unsubstituted C6 to C20 arylene group, a substituted or unsubstituted C2 to C20 heterocyclic group, or a combination thereof, $R^a$ and $R^1$ to $R^4$ are each independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^4$ is a group represented by Chemical Formula a,

[Chemical Formula a]

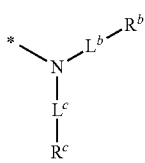

in Chemical Formula a, $L^b$ and $L^c$ are each independently a single bond, a substituted or unsubstituted C6 to C20 arylene group, a substituted or unsubstituted C2 to C20 heterocyclic group, or a combination thereof, $R^b$ and $R^c$ are each independently a substituted or unsubstituted C6 to C30 aryl group, a substituted or unsubstituted C2 to C30 heterocyclic group, or a combination thereof, and

* is a linking point with one of $L^a$ and $L^1$ to $L^4$.

3. The organic optoelectronic device as claimed in claim 1, wherein:

the first compound is represented by one of Chemical Formula 1A-1 to Chemical Formula 1A-3 and Chemical Formula 1C-1 to Chemical Formula 1C-3:

[Chemical Formula 1A-1]

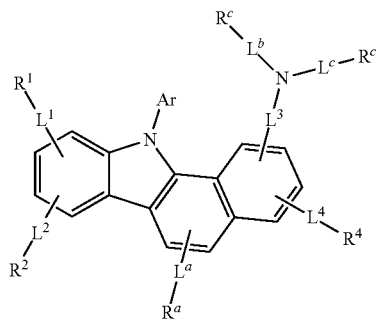

[Chemical Formula 1A-2]

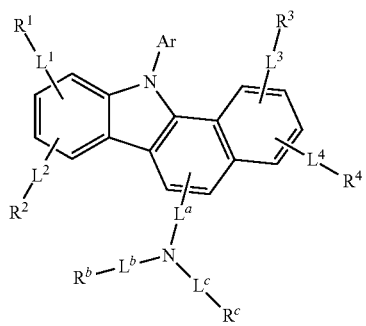

[Chemical Formula 1A-3]

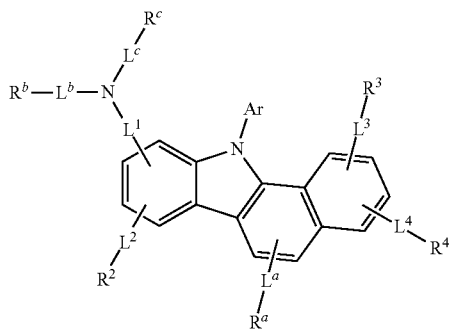

[Chemical Formula 1C-1]

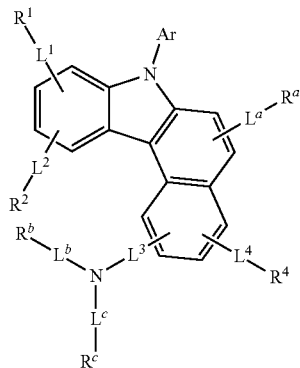

-continued

[Chemical Formula 1C-2]

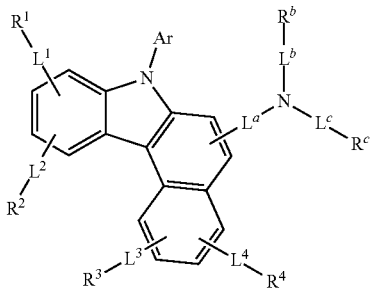

[Chemical Formula 1C-3]

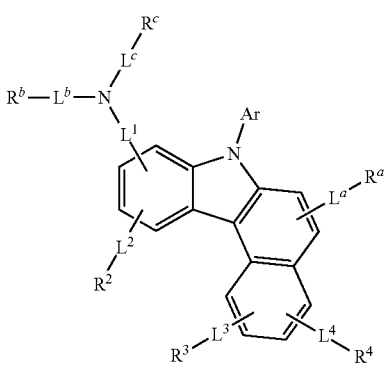

in Chemical Formula 1A-1 to Chemical Formula 1A-3 and Chemical Formula 1C-1 to Chemical Formula 1C-3, Ar is a substituted or unsubstituted C6 to C30 aryl group, a substituted or unsubstituted C2 to C30 heterocyclic group, or a combination thereof, $L^a$ and $L^1$ to $L^4$ are each independently a single bond, a substituted or unsubstituted C6 to C20 arylene group, a substituted or unsubstituted C2 to C20 heterocyclic group, or a combination thereof, $R^a$ and $R^1$ to $R^4$ are each independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, $L^b$ and $L^c$ are each independently a single bond, a substituted or unsubstituted C6 to C20 arylene group, a substituted or unsubstituted C2 to C20 heterocyclic group, or a combination thereof, and $R^b$ and $R^c$ are each independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

4. The organic optoelectronic device as claimed in claim 1, wherein:

the first compound is represented by one of Chemical Formula 1A-1-b, Chemical Formula 1A-1-c, Chemical Formula 1A-2-a, Chemical Formula 1A-3-b, and Chemical Formula 1A-3-c:

[Chemical Formula 1A-1-b]

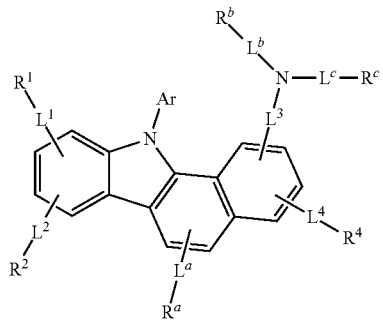

[Chemical Formula 1A-1-c]

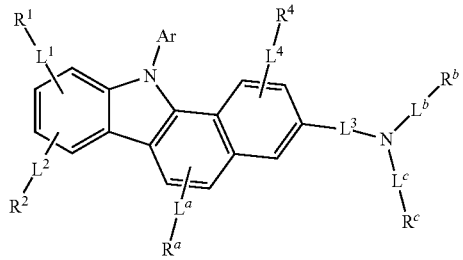

[Chemical Formula 1A-2-a]

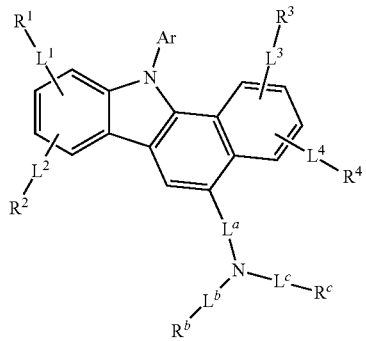

[Chemical Formula 1A-3-b]

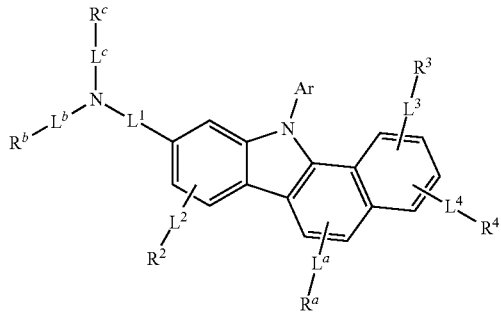

[Chemical Formula 1A-3-c]

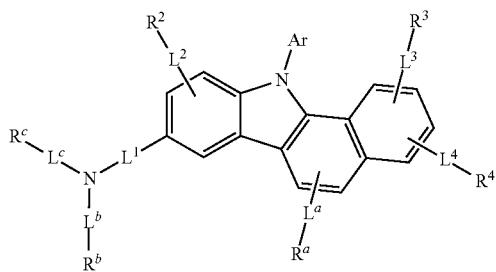

in Chemical Formula 1A-1-b, Chemical Formula 1A-1-c, Chemical Formula 1A-2-a, Chemical Formula 1A-3-b, and Chemical Formula 1A-3-c, Ar is a substituted or unsubstituted C6 to C30 aryl group, a substituted or unsubstituted C2 to C30 heterocyclic group, or a combination thereof, $L^a$ and $L^1$ to $L^4$ are each independently a single bond, a substituted or unsubstituted C6 to C20 arylene group, a substituted or unsubstituted C2 to C20 heterocyclic group, or a combination thereof, $R^a$, $R^1$, $R^2$, and $R^4$ are each independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof, $L^b$ and $L^c$ are each independently a single bond, a substituted or unsubstituted C6 to C20 arylene group, a substituted or unsubstituted C2 to C20 heterocyclic group, or a combination thereof, and $R^b$ and $R^c$ are each independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

5. The organic optoelectronic device as claimed in claim 1, wherein:

the second compound is represented by one of Chemical Formula 3-1 to Chemical Formula 3-3:

[Chemical Formula 3-1]

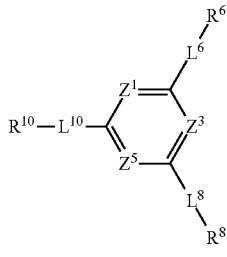

[Chemical Formula 3-2]

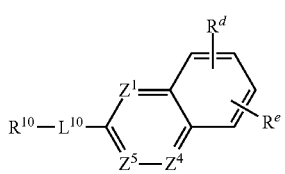

[Chemical Formula 3-3]

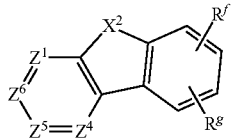

in Chemical Formula 3-1 to Chemical Formula 3-3, $Z^1$ is N or $C$-$L^5$-$R^5$,
$Z^3$ is N or $C$-$L^7$-$R^7$,
$Z^4$ is N or $C$-$L^8$-$R^8$,
$Z^5$ is N or $C$-$L^9$-$R^9$,
$Z^6$ is N or $C$-$L^{10}$-$R^{10}$, at least two of $Z^1$ and $Z^3$ to $Z^6$ are N, $L^5$ to $L^{10}$ are each independently a single bond, a substituted or unsubstituted C6 to C20 arylene group, a substituted or unsubstituted C2 to C20 heterocyclic group, or a combination thereof, $R^5$ to $R^{10}$ are each independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, at least one of $R^5$ to $R^{10}$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group, and $R^d$, $R^e$, $R^f$, and $R^g$ are each independently hydrogen, deuterium, a halogen, a cyano group, a C1 to C20 alkyl group, a C6 to C30 aryl group, a C2 to C30 heteroaryl group, or a combination thereof.

6. The organic optoelectronic device as claimed in claim 1, wherein:

$R^5$ to $R^{10}$ are each independently hydrogen, a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, a substituted or unsubstituted pyrimidinyl group, a substituted or unsubstituted triazinyl group, a substituted or unsubstituted benzofuranpyrimidinyl group, or a substituted or unsubstituted benzothiophenepyrimidinyl group, and at least one of $R^5$ to $R^{10}$ is a substituted or unsubstituted dibenzofuranyl group, a substituted or unsubstituted dibenzothiophenyl group, a substituted or unsubstituted carbazolyl group, a substituted or unsubstituted benzocarbazolyl group, a substituted or unsubstituted dibenzocarbazolyl group, or a substituted or unsubstituted triphenylene group.

7. The organic optoelectronic device as claimed in claim 6, wherein:

$R^5$ to $R^{10}$ are each independently a group of Group I or Group II, and at least one of $R^5$ to $R^{10}$ is a group of Group II

[Group I]

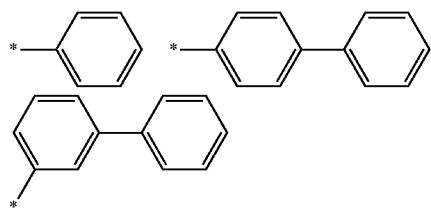

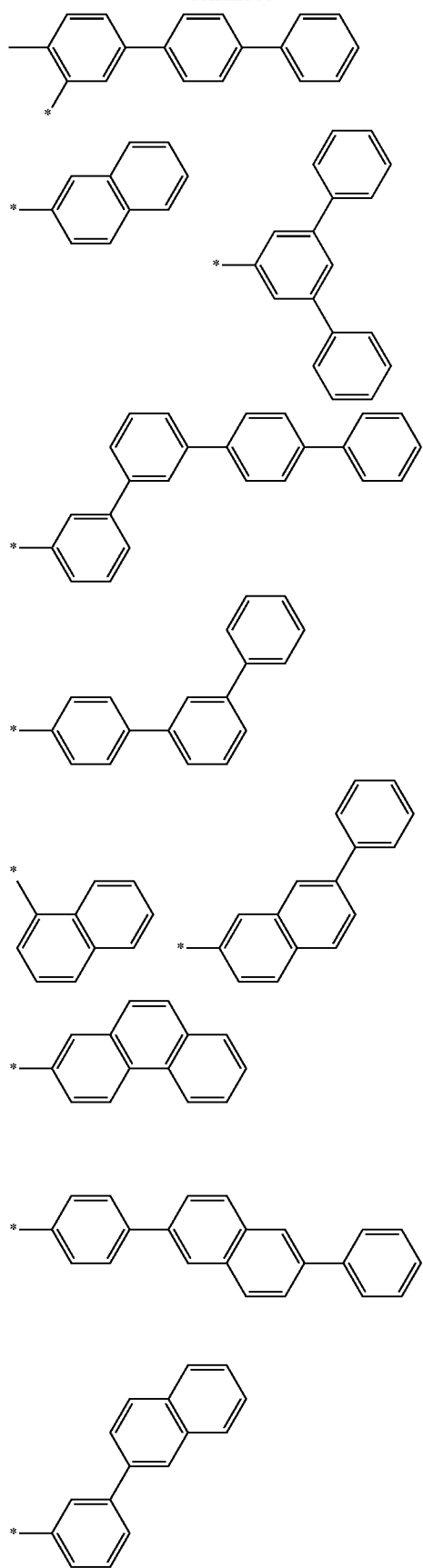
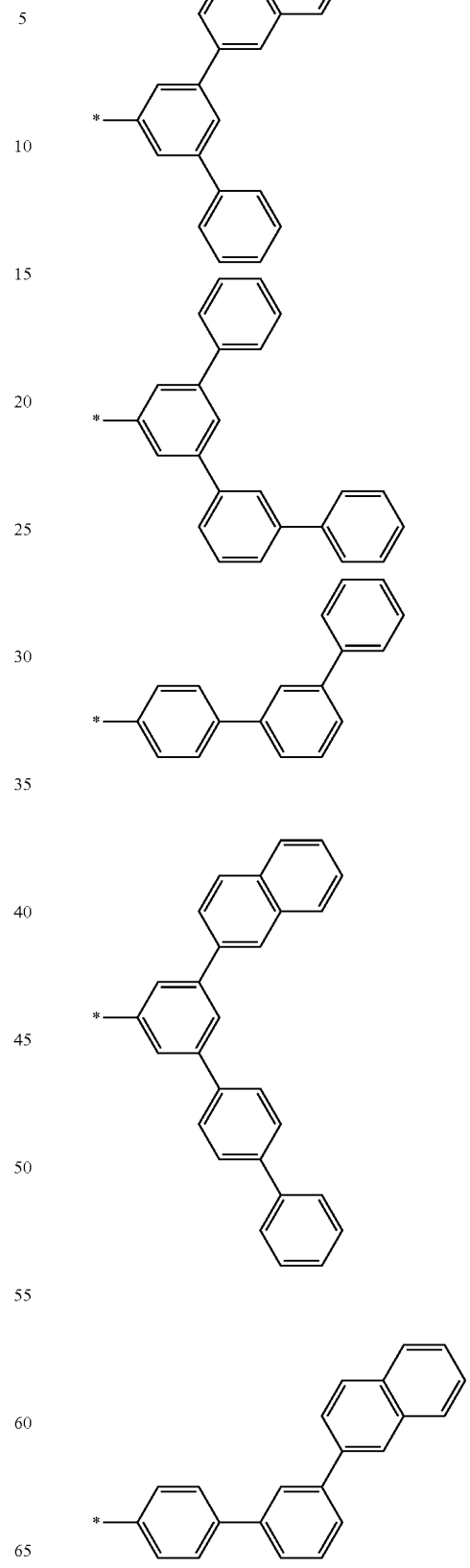

347
-continued
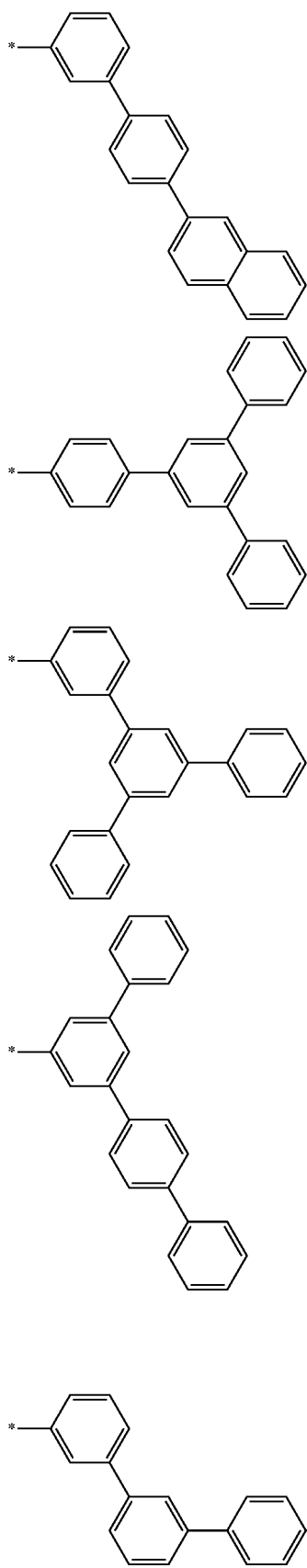
348
-continued
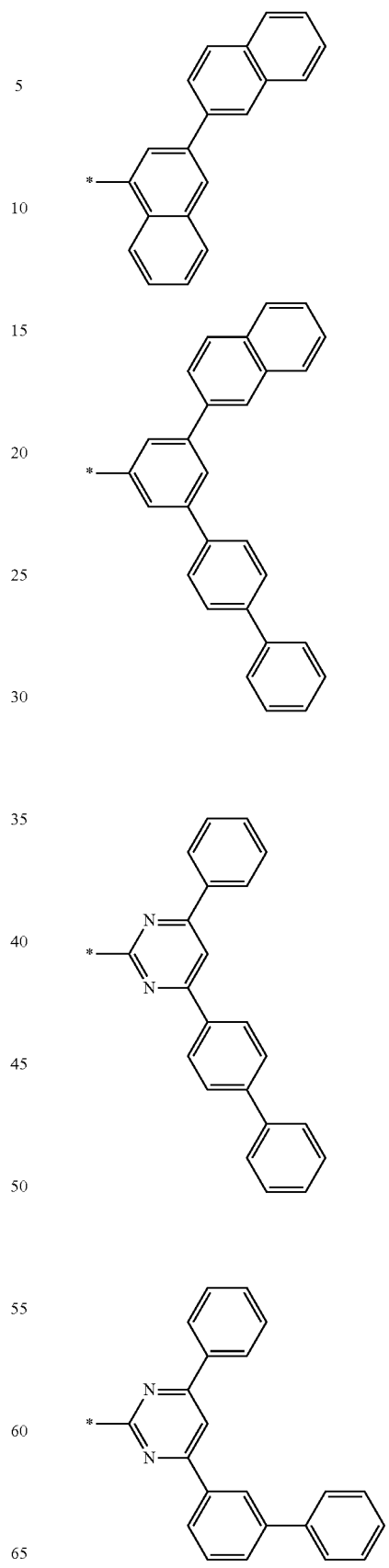

349
-continued
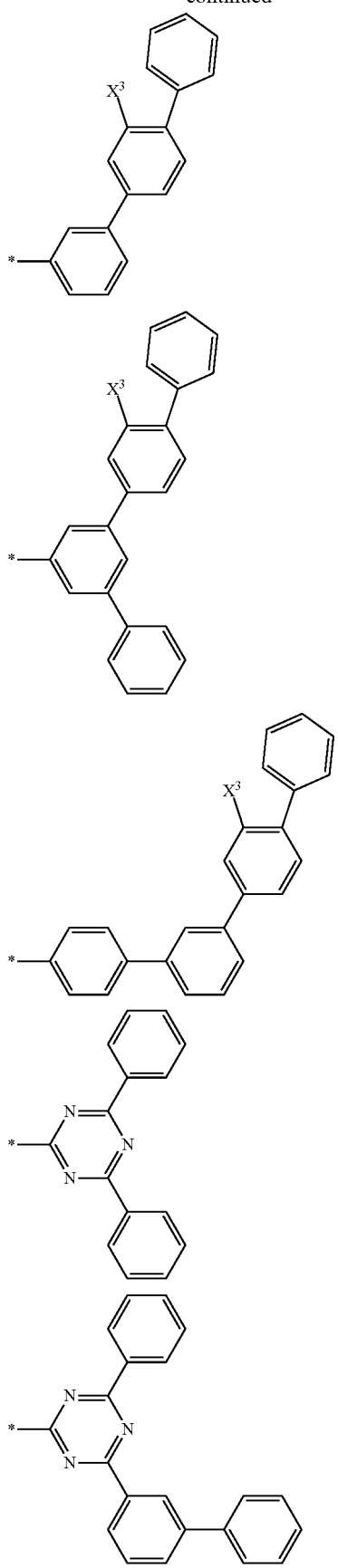
350
-continued
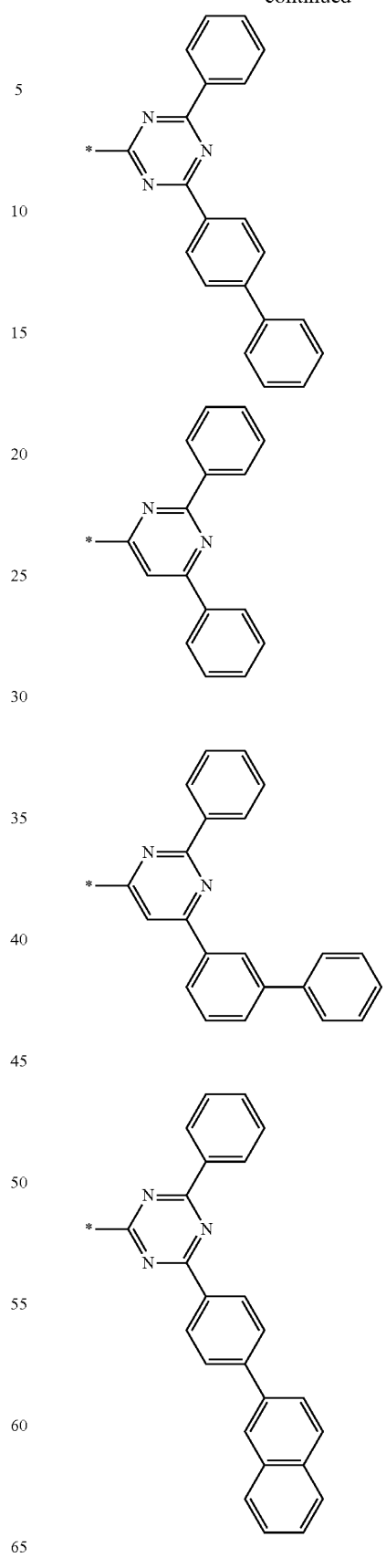

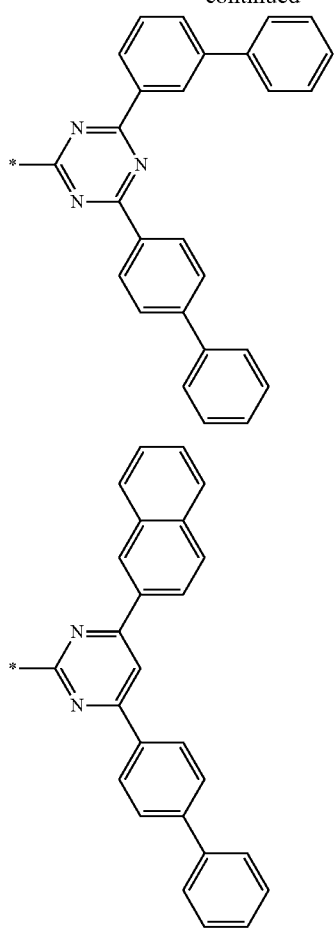
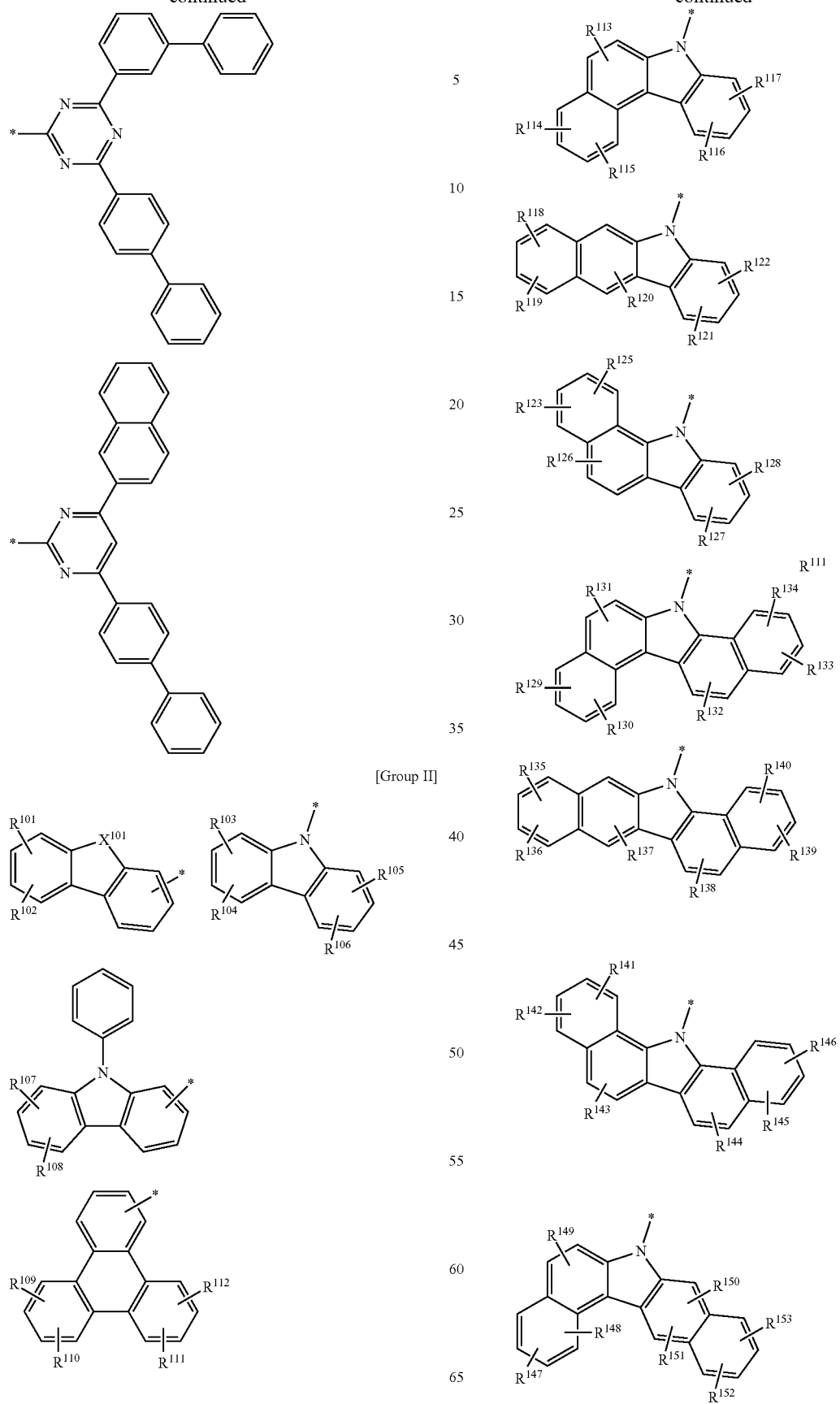
[Group II]

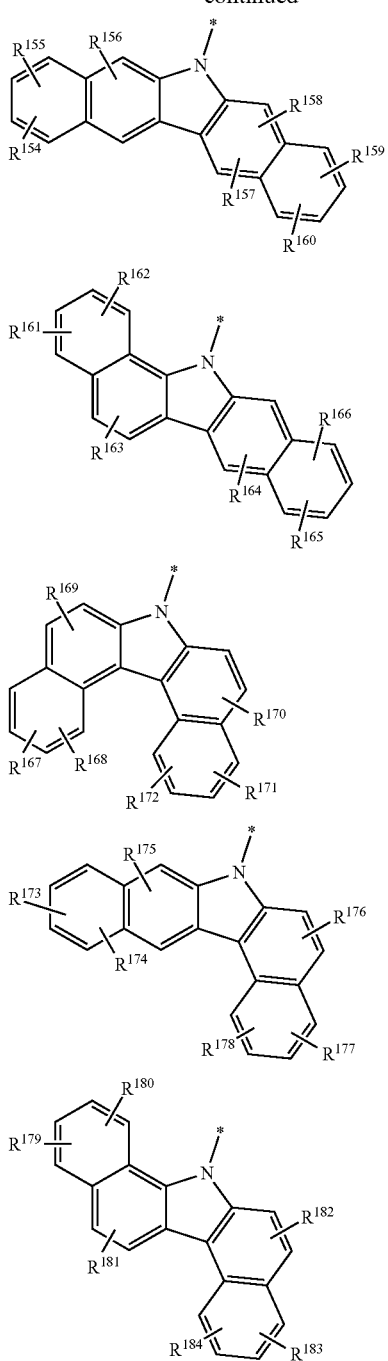

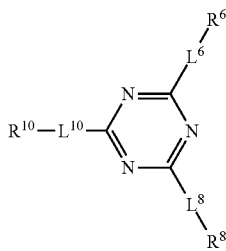

[Chemical Formula 3-1a]

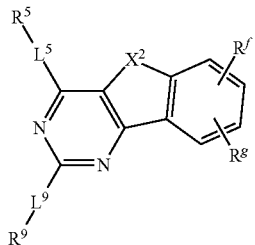

[Chemical Formula 3-3a]

wherein, in Group I and Group II, $X^3$ and $X^{101}$ is O or S, $R^{101}$ to $R^{123}$ and $R^{125}$ to $R^{184}$ are each independently hydrogen, deuterium, a halogen, a cyano group, a C1 to C20 alkyl group, a C6 to C30 aryl group, a C2 to C30 heteroaryl group, or a combination thereof, and

* is a linking point.

8. The organic optoelectronic device as claimed in claim 1, wherein:

the second compound is represented by Chemical Formula 3-1a or Chemical Formula 3-3a:

in Chemical Formula 3-1a, $L^6$, $L^8$, and $L^{10}$ are each independently a single bond or a substituted or unsubstituted phenylene group, $R^6$, $R^8$, and $R^{10}$ are each independently a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, at least one of $R^6$, $R^8$, and $R^{10}$ is a substituted or unsubstituted triphenylene group, a substituted or unsubstituted carbazolyl group, a substituted or unsubstituted dibenzofuranyl group, or a substituted or unsubstituted dibenzothiophenyl group;

in Chemical Formula 3-3a, $X^2$ is O or S, $L^5$ and $L^9$ are each independently a single bond or a substituted or unsubstituted phenylene group, $R^5$ and $R^9$ are each independently a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, at least one of $R^5$ and $R^9$ is a substituted or unsubstituted carbazolyl group, a substituted or unsubstituted dibenzofuranyl group, or a substituted or unsubstituted dibenzothiophenyl group, and $R^f$ and $R^g$ are each independently hydrogen, deuterium, a C1 to C10 alkyl group, a C6 to C12 aryl group, or a combination thereof.

9. The organic optoelectronic device as claimed in claim 8, wherein:

the first compound is represented by Chemical Formula 1A-1-b, Chemical Formula 1A-1-c, or Chemical Formula 1A-2-a:

[Chemical Formula 1A-1-b]

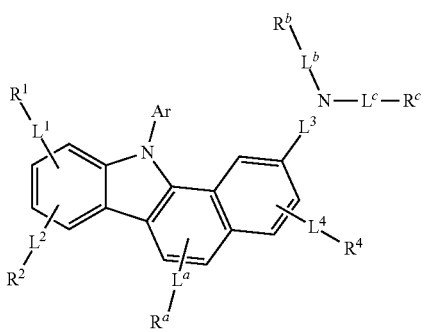

[Chemical Formula 1A-1-c]

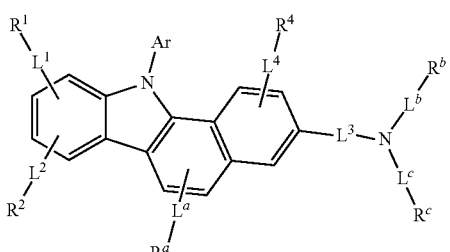

[Chemical Formula 1A-2-a]

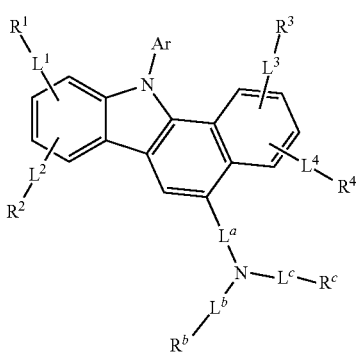

in Chemical Formula 1A-1-b, Chemical Formula 1A-1-c, and Chemical Formula 1A-2-a, Ar is a substituted or unsubstituted phenyl group, or a substituted or unsubstituted biphenyl group, $L^a$ and $L^1$ to $L^4$ are each independently a single bond or a substituted or unsubstituted phenylene group, $R^a$ and $R^1$ to $R^4$ are each independently hydrogen or the group represented by Chemical Formula a, $L^b$ and $L^c$ are each independently a single bond or a substituted or unsubstituted C6 to C12 arylene group, and $R^b$ and $R^c$ are each independently a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, or a substituted or unsubstituted dibenzothiophenyl group, in which a substituent of the substituted phenyl group, the substituted biphenyl group, the substituted naphthyl group, the substituted fluorenyl group, the substituted dibenzofuranyl group, or the substituted dibenzothiophenyl group is a phenyl group, a naphthyl group, an anthracenyl group, a phenanthrenyl group, a triphenylene group, a carbazolyl group, a dibenzofuranyl group, or a dibenzothiophenyl group.

10. The organic optoelectronic device as claimed in claim 1, wherein:
the third compound is represented by one of Chemical Formula 4-1 to Chemical Formula 4-4:

[Chemical Formula 4-1]

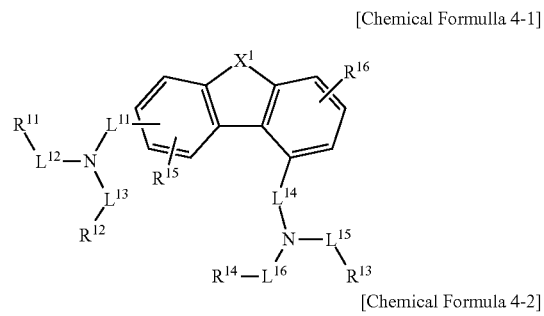

[Chemical Formula 4-2]

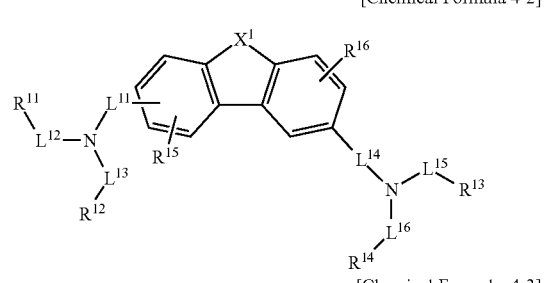

[Chemical Formula 4-3]

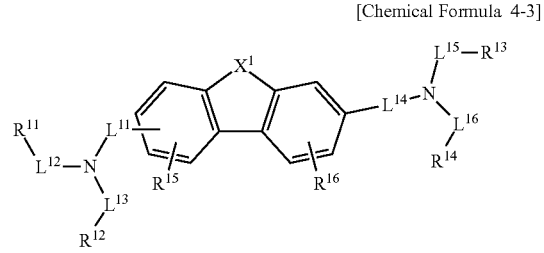

[Chemical Formula 4-4]

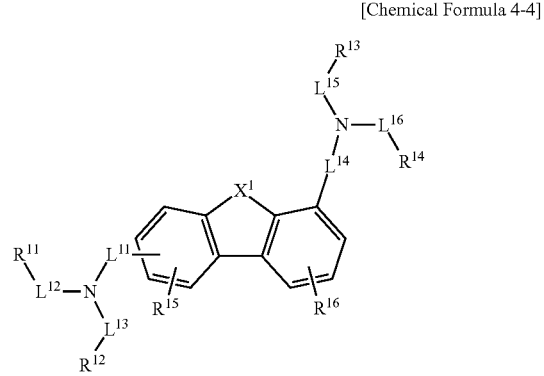

in Chemical Formula 4-1 to Chemical Formula 4-4, $X^1$ is O or S, $L^{11}$ to $L^{16}$ are each independently a single bond, a substituted or unsubstituted C6 to C20 arylene group, a substituted or unsubstituted C2 to C20 heterocyclic group, or a combination thereof, $R^{11}$ to $R^{14}$ are each independently a substituted or unsubstituted C6 to C30 aryl group, a substituted or unsubstituted C2 to C30 heterocyclic group, or a combination thereof, and $R^{15}$ and $R^{16}$ are each independently hydrogen, deuterium, a cyano group, or a substituted or unsubstituted C1 to C10 alkyl group.

11. The organic optoelectronic device as claimed in claim 1, wherein:

the third compound is represented by one of Chemical Formula 4-1b, Chemical Formula 4-2b, Chemical Formula 4-2c, Chemical Formula 4-3b, Chemical Formula 4-3c, and Chemical Formula 4-3d:

[Chemical Formula 4-1b]

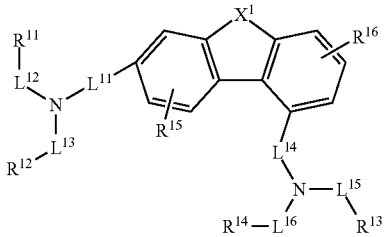

[Chemical Formula 4-2b]

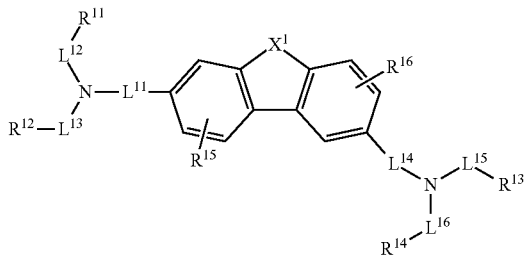

[Chemical Formula 4-2c]

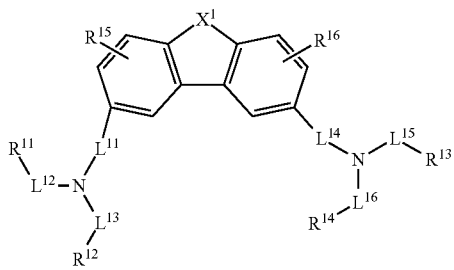

[Chemical Formula 4-3b]

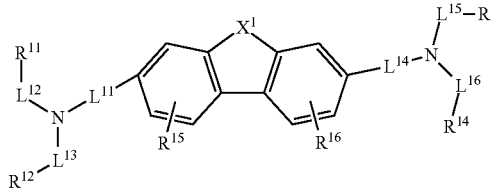

[Chemical Formula 4-3c]

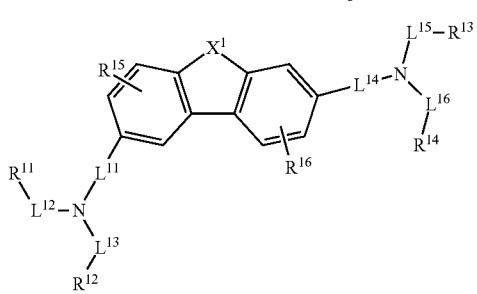

[Chemical Formula 4-3d]

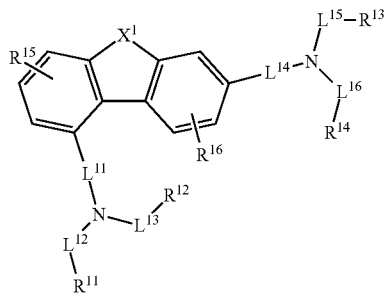

in Chemical Formula 4-1b, Chemical Formula 4-2b, Chemical Formula 4-2c, Chemical Formula 4-3b, Chemical Formula 4-3c, and Chemical Formula 4-3d, $X^1$ is O or S, $L^{11}$ to $L^{16}$ are each independently a single bond, a substituted or unsubstituted C6 to C20 arylene group, a substituted or unsubstituted C2 to C20 heterocyclic group, or a combination thereof, $R^{11}$ to $R^{14}$ are each independently a substituted or unsubstituted C6 to C30 aryl group, a substituted or unsubstituted C2 to C30 heterocyclic group, or a combination thereof, and $R^{15}$ and $R^{16}$ are each independently hydrogen, deuterium, a cyano group, or a substituted or unsubstituted C1 to C10 alkyl group.

12. The organic optoelectronic device as claimed in claim 11, wherein:

the first compound is represented by Chemical Formula 1A-1-b, Chemical Formula 1A-1-c, or Chemical Formula 1A-2-a, and the second compound is represented by Chemical Formula 3-1a or Chemical Formula 3-3a:

[Chemical Formula 1A-1-b]

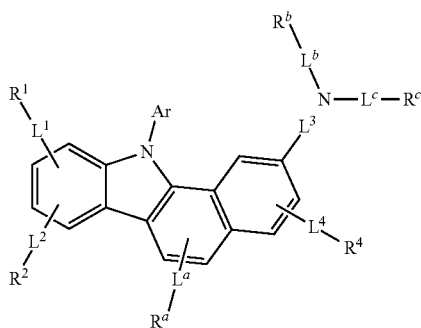

[Chemical Formula 1A-1-c]

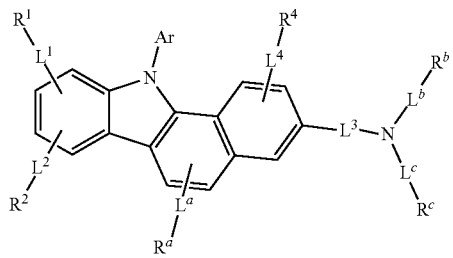

[Chemical Formula 1A-2-a]

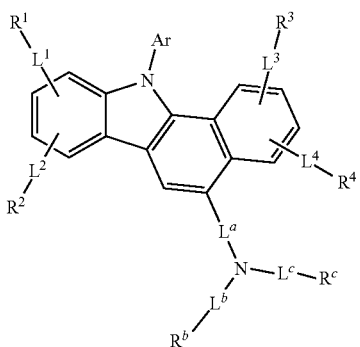

in Chemical Formula 1A-1-b, Chemical Formula 1A-1-c, or Chemical Formula 1A-2-a, Ar is a substituted or unsubstituted phenyl group, or a substituted or unsubstituted biphenyl group, $L^a$ and $L^1$ to $L^4$ are each independently a single bond or a substituted or unsubstituted phenylene group, $R^a$ and $R^1$ to $R^4$ are each independently hydrogen or the group represented by Chemical Formula a, $L^b$ and $L^c$ are each independently a single bond or a substituted or unsubstituted C6 to C12 arylene group, and $R^b$ and $R^c$ are each independently substituted or unsubstituted, phenyl group, a substituted or unsubstituted biphenyl group, substituted or naphthyl group, a substituted or unsubstituted fluorenyl group, a substituted or unsubstituted dibenzofuranyl group, or a substituted or unsubstituted dibenzothiophenyl group;

[Chemical Formula 3-1a]

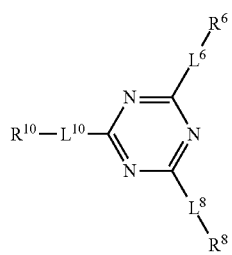

[Chemical Formula 3-3a]

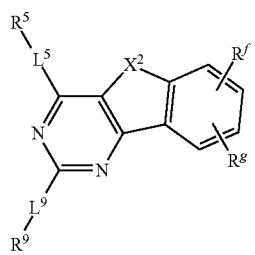

in Chemical Formula 3-1a, $L^6$, $L^8$, and $L^{10}$ are each independently a single bond or a substituted or unsubstituted phenylene group, $R^6$, $R^8$, and $R^{10}$ are each independently a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, and at least one of $R^6$, $R^8$, and $R^{10}$ is a substituted or unsubstituted triphenylene group, a substituted or unsubstituted carbazolyl group, a substituted or unsubstituted dibenzofuranyl group, or a substituted or unsubstituted dibenzothiophenyl group;

in Chemical Formula 3-3a, $X^2$ is O or S, $L^5$ and $L^9$ are each independently a single bond or a substituted or unsubstituted phenylene group, $R^5$ and $R^9$ are each independently a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted dibenzofuranyl group, a substituted or unsubstituted dibenzothiophenyl group, or a substituted or unsubstituted carbazolyl group, at least one of $R^5$ and $R^9$ is a substituted or unsubstituted carbazolyl group, a substituted or unsubstituted dibenzofuranyl group, or a substituted or unsubstituted dibenzothiophenyl group, and $R^f$ and $R^g$ are each independently hydrogen, deuterium, a C1 to C10 alkyl group, a C6 to C12 aryl group, or a combination thereof.

13. The organic optoelectronic device as claimed in claim 1, wherein at least one of $R^{11}$ to $R^{14}$ of Chemical Formula 4 is a substituted or unsubstituted dibenzofuranyl group, or a substituted or unsubstituted dibenzothiophenyl group.

14. The organic optoelectronic device as claimed in claim 1, wherein the first compound and the second compound are phosphorescent hosts of the light emitting layer.

15. The organic optoelectronic device as claimed in claim 14, wherein the light emitting layer further includes a dopant.

16. A display device comprising the organic optoelectronic device as claimed in claim 1.

* * * * *